United States Patent
Chen et al.

(10) Patent No.: US 7,449,581 B2
(45) Date of Patent: Nov. 11, 2008

(54) 6-SUBSTITUTED PYRIDO-PYRIMIDINES

(75) Inventors: Jian Jeffrey Chen, Santa Clara, CA (US); James Patrick Dunn, Los Altos, CA (US); David Michael Goldstein, San Jose, CA (US); Christoph Martin Stahl, Freiburg (DE)

(73) Assignee: Poche Palo Alto LLC, Palo Alto, CA (US)

(*) Notice: Subject to any disclaimer, the term of this patent is extended or adjusted under 35 U.S.C. 154(b) by 0 days.

(21) Appl. No.: 11/651,302

(22) Filed: Jan. 9, 2007

(65) Prior Publication Data

US 2007/0135458 A1    Jun. 14, 2007

Related U.S. Application Data

(63) Continuation of application No. 10/722,703, filed on Nov. 25, 2003, now Pat. No. 7,169,794, which is a continuation of application No. 10/073,845, filed on Feb. 11, 2002, now Pat. No. 6,696,566.

(60) Provisional application No. 60/334,654, filed on Nov. 30, 2001, provisional application No. 60/268,375, filed on Feb. 12, 2001.

(51) Int. Cl.
    *C07D 471/04*    (2006.01)
(52) U.S. Cl. .................. 546/123; 546/122
(58) Field of Classification Search ............. 546/122, 546/123; 514/300
    See application file for complete search history.

(56) References Cited

U.S. PATENT DOCUMENTS

| | | |
|---|---|---|
| 4,215,216 A | 7/1980 | Scotese et al. |
| 5,037,826 A | 8/1991 | Blythin et al. |
| 5,620,981 A | 4/1997 | Blankley et al. |
| 5,733,913 A | 3/1998 | Blankley et al. |
| 5,733,914 A | 3/1998 | Blankley et al. |
| 5,945,422 A | 8/1999 | Doherty et al. |
| 6,696,566 B2 * | 2/2004 | Chen et al. ............ 544/261 |

FOREIGN PATENT DOCUMENTS

| | | |
|---|---|---|
| EP | 0 278 686 A1 | 8/1988 |
| EP | 0 279 565 B1 | 8/1988 |
| EP | 0 790 997 B1 | 3/2000 |
| EP | 1078923 A2 | 2/2001 |
| EP | 11 361 880 B1 | 9/2005 |
| WO | WO 93/17682 | 9/1993 |
| WO | WO 96/15128 A2 | 5/1996 |
| WO | WO 96/34867 | 11/1996 |
| WO | WO 97/13771 A1 | 1/1997 |
| WO | WO 97/35539 A2 | 10/1997 |
| WO | WO 98/33798 | 8/1998 |
| WO | WO 98/46604 A1 | 10/1998 |
| WO | WO 98/46605 A1 | 10/1998 |
| WO | WO 99/61444 | 12/1999 |
| WO | WO 99/65908 | 12/1999 |

OTHER PUBLICATIONS

Daboun et al., Reactions with Activated Nitriles: Some New Approaches to the Synthesis of Pyridine Derivatives, Heterocycles 19(10):1925-29 (1982).*

Gavrin et al., Inhibition of Tp12 Kinase and TNF-alpha Production with 1,7-naphthyridine-3-carbonitriles: Synthesis and Structure-Activity Relationships, Bioorganic & Medicinal Chemistry Letters, 15:5288-5292 (2005).*

Boehm & Adams, New Inhibitors of p38 Kinase, Exp: Opin. Ther. Patents 10(1):25-37 (2000).*

Boschelli, et al, "Synthesis and Tyrosine Kinase Inhibitory Activity of a Series of 2-Amino-8H-pyrido[2,3-d]pyrimidines. Identification of Potent, Selective Platelet-Derived Growth Factor Receptor Tyrosine Kinase Inhibitors," *Journal of Med. Chem.*, (1998), pp. 4365-4377, vol. 41,.

Klutchko, et al., "2-Substituted Aminopyrido[2,3-d] Pyrimidin-7(8H)-ones. Structure-Activity Relationships Against Selected Tyrosine Kinases and in Vitro and in Vivo Anticancer Activity," *Journal of Med. Chem.*, (1998), pp. 3276-3292, vol. 41.

Barvian, et al., "Pyrido[2,3-d]pyrimidin-7-one Inhibitors of Cyclin-Dependent Kinases," *Journal of Med. Chem.*, (2000), pp. 4606-4616, vol. 43.

Hamby, et al., "Structure-Activity Relationships for a Novel Series of Pyrido[2,3-d]pyrimidine Tyrosine Kinase Inhibitors," *Journal Med. Chem.*, (1997), pp. 2296-2303, vol. 40.

* cited by examiner

*Primary Examiner*—B. Dentz
*Assistant Examiner*—David E Gallis
(74) *Attorney, Agent, or Firm*—Robert C. Hall

(57) ABSTRACT

The present invention provides compounds of the Formula I and II:

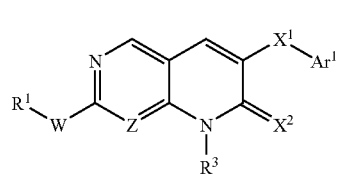

Formula I

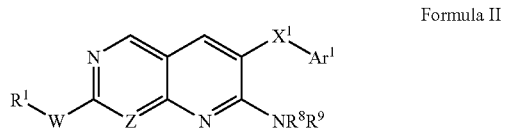

Formula II wherein $R^1$, $R^3$, W, Z, $X^1$, $X^2$, $Ar^1$, $R^8$ and $R^9$ are as defined herein, and methods and intermediates for their preparation and uses thereof.

1 Claim, No Drawings

6-SUBSTITUTED PYRIDO-PYRIMIDINES

CROSS REFERENCE TO RELATED APPLICATIONS

This Application is a continuation of U.S. patent application Ser. No. 10/722,703 filed on Nov. 25 2003, now U.S. Pat. No. 7,169,794, which is a continuation of U.S. patent application Ser. No. 10/073,845 filed on Feb. 11, 2002, now U.S. Pat. No. 6,696,566. This application claims the benefit under Title 35 U.S.C. 119(e) of U.S. Provisional Application Nos. 60/268,375 filed Feb. 12, 2001 and 60/334,654 filed Nov. 30 2001. The disclosures of the aforementioned applications are incorporated herein by reference in their entirety.

FIELD OF THE INVENTION

The present invention relates to pyridopyrimidines and derivatives thereof. In particular, the present invention provides 2,6-disubstituted-7-oxo-pyrido[2,3-d]pyrimidines, a process for their manufacture, pharmaceutical preparations comprising the same, and methods for using the same.

BACKGROUND OF THE INVENTION

Mitogen-activated protein kinases (MAP) is a family of proline-directed serine/threonine kinases that activate their substrates by dual phosphorylation. The kinases are activated by a variety of signals including nutritional and osmotic stress, UV light, growth factors, endotoxin and inflammatory cytokines. One group of MAP kinases is the p38 kinase group that includes various isoforms (e.g., p38α, p39β, p38γ and p38δ). The p38 kinases are responsible for phosphorylating and activating transcription factors as well as other kinases, and are activated by physical and chemical stress, pro-inflammatory cytokines and bacterial lipopolysaccharide.

More importantly, the products of the p38 phosphorylation have been shown to mediate the production of inflammatory cytokines, including TNF and IL-1, and cyclooxygenase-2. Each of these cytokines has been implicated in numerous disease states and conditions. For example, TNF-α is a cytokine produced primarily by activated monocytes and macrophages. Its excessive or unregulated production has been implicated as playing a causative role in the pathogenesis of rheumatoid arthritis. More recently, inhibition of TNF production has been shown to have broad application in the treatment of inflammation, inflammatory bowel disease, multiple sclerosis and asthma.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpesvirus-7 (HHV-7), human herpesvirus-8 (HHV-8), pseudorabies and rhinotracheitis, among others.

Similarly, IL-1 is produced by activated monocytes and macrophages, and plays a role in many pathophysiological responses including rheumatoid-arthritis, fever and reduction of bone resorption.

Additionally, the involvement of p38 has been implicated in stroke, Alzheimer's disease, osteoarthritis, lung injury, septic shock, angiogenesis, dermatitis, psoriasis and atopic dermatitis. *J. Exp. Opin. Ther. Patents*, (2000) 10(1).

The inhibition of these cytokines by inhibition of the p38 kinase is of benefit in controlling, reducing and alleviating many of these disease states.

Certain 6-aryl-pyrido[2,3-d]pyrimidin-7-ones, -7-imines and -7-thiones are disclosed as inhibitors of protein tyrosine kinase mediated cellular proliferation in WO 96/34867, published Nov. 7, 1996 (Warner Lambert). Other 6-aryl-pyrido[2,3-d]pyrimidines and naphthyridines are also disclosed as inhibitors of tyrosine kinase in WO 96/15128, published May 23, 1996 (Warner Lambert). 6-alkyl-pyrido[2,3-d]pyrimidin-7-ones are disclosed as inhibitors of cyclin-dependent kinases in WO 98/33798, published Aug. 6, 1998 (Warner Lambert). Certain 4-amino-pyridopyrimidines are disclosed as inhibitors of dihydrofolate reductase in EP 0 278 686A1, published Aug. 8, 1988 (Wellcome Foundation).

SUMMARY OF THE INVENTION

One aspect of the present invention provides compounds represented by Formula I and II:

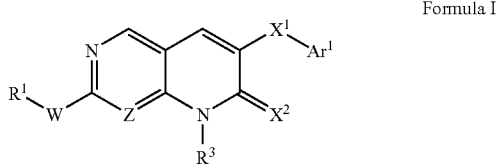

Formula I

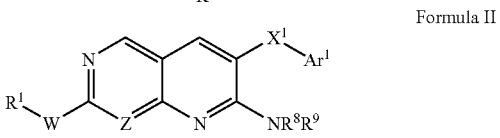

Formula II or pharmaceutically acceptable salts thereof, wherein:

Z is N or CH;

W is $NR^2$;

$X^1$ is O, $NR^4$ (where $R^4$ is hydrogen or alkyl), S, or $CR^5R^6$ (where $R^5$ and $R^6$ are independently hydrogen or alkyl) or C=O;

$X^2$ is O or $NR^7$;

$Ar^1$ is aryl or heteroaryl;

$R^2$ is hydrogen alkyl, acyl, alkoxycarbonyl, aryloxycarbonyl, heteroalkylcarbonyl, heteroalkyloxycarbonyl or —$R^{21}$—$R^{22}$ where $R^{21}$ is alkylene or —C(=O)— and $R^{22}$ is alkyl or alkoxy;

$R^1$ is hydrogen, alkyl, haloalkyl, aryl, aralkyl, heteroaryl, heteroaralkyl, cycloalkyl, cycloalkylalkyl, heteroalkylsubstituted cycloalkyl, heterosubstituted cycloalkyl, heteroalkyl, cyanoalkyl, heterocyclyl, heterocyclylalkyl, $R^{12}$—$SO_2$-heterocycloamino (where $R^{12}$ is haloalkyl, aryl, aryalkyl, heteroaryl or heteroaralkyl), —$Y^1$—C(O)—$Y^2$—$R^{11}$ (where $Y^1$ and $Y^2$ are independently either absent or an alkylene group and $R^{11}$ is hydrogen, alkyl, haloalkyl, hydroxy, alkoxy, amino, monoalkylamino or dialkylamino), (heterocyclyl)(cycloalkyl)alkyl or (heterocyclyl)(heteroaryl)alkyl;

$R^3$ is hydrogen, alkyl, cycloalkyl, cycloalkylalkyl, aryl, aralkyl, haloalkyl, heteroalkyl, cyanoalkyl, alkylene-C(O)—$R^{31}$ (where $R^{31}$ is hydrogen, alkyl, hydroxy, alkoxy, amino, monoalkylamino or dialkylamino), amino, monoalkylamino, dialkylamino or $NR^{32}$—$Y^3$—$R^{33}$ (where $Y^3$ is —C(O), —C(O)O—, —C(O)$NR^{34}$, $S(O)_2$ or $S(O)_2NR^{35}$; $R^{32}$, $R^{34}$ and $R^{35}$ are independently hydrogen or alkyl; and $R^{33}$ is hydrogen, alkyl, cycloalkyl, cycloalkylalkyl, heteroalkyl or optionally substituted phenyl) or acyl;

$R^7$ is hydrogen or alkyl; and $R^8$ and $R^9$ are independently hydrogen, alkyl, aryl, aralkyl, cycloalkyl, cycloalkylalkyl, heteroalkyl, alkylsulfonyl, arylsulfonyl, —C(O)—$R^{81}$ (where $R^{81}$ is alkyl, aryl, aralkyl, cycloalkyl, cycloalkylalkyl, heteroalkyl, alkoxy, aryloxy, amino, mono- or di-alkylamino, arylamino or aryl(alkyl) amino) or $R^8$ and $R^9$ together form =$CR^{82}R^{83}$ (where $R^{82}$ and $R^{83}$ are independently hydrogen, alkyl, cycloalkyl, cycloalkylalkyl or optionally substituted phenyl).

Another aspect of the present invention provides a pharmaceutical formulation comprising a Compound of Formula I or II and a pharmaceutically acceptable carrier, diluent, or excipient therefor.

Compounds of Formula I and II and their aforementioned salts are inhibitors of protein kinases, and exhibit effective activity against p38 in vivo. They are also surprisingly selective against p38 kinase relative to cyclin-dependent kinases and tyrosine kinases. Therefore, compounds of the present invention can be used for the treatment of diseases mediated by the pro-inflammatory cytokines such as TNF and IL-1. Thus, another aspect of the present invention provides a method for treating p38 mediated diseases or conditions in which a therapeutically effective amount of a Compound of Formula I or II is administered to a patient in need of such treatment.

Yet another aspect of the present invention provides a method for preparing the compounds described above and intermediates intermediates of Formula I' and II" useful therefor.

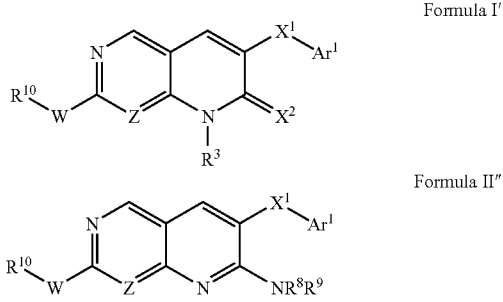

Formula I'

Formula II"

wherein:
Z is N or CH;
W is S, S(O), S(O)$_2$ or O;
$X^1$ is O, $NR^4$ (where $R^4$ is hydrogen or alkyl), S, or $CR^5R^6$ (where $R^5$ and $R^6$ are independently hydrogen or alkyl) or C=O;
$X^2$ is O or $NR^7$;
$Ar^1$ is aryl or heteroaryl;
$R^{10}$ is alkyl, aryl, aralkyl, cycloalkyl or cycloalkylalkyl, or $R^{10}W$ together form a leaving group or hydroxy;
$R^3$ is hydrogen, alkyl, cycloalkyl, cycloalkylalkyl, aryl, aralkyl, haloalkyl, heteroalkyl, cyanoalkyl, alkylene-C(O)$R^{31}$ (where $R^{31}$ is hydrogen, alkyl, hydroxy, alkoxy, amino, monoalkylamino or dialkylamino), amino, monoalkylamino, dialkylamino or $NR^{32}$—$Y^3$—$R^{33}$ (where $Y^3$ is C(O), —C(O)O—, —C(O)$NR^{34}$, S(O)$_2$, or S(O)$_2NR^{35}$; $R^{32}$, $R^{34}$ and $R^{35}$ are independently hydrogen or alkyl; and $R^{33}$ is hydrogen, alkyl, cycloalkyl, cycloalkylalkyl, heteroalkyl or optionally substituted phenyl) or acyl;
$R^7$ is hydrogen or alkyl; and
$R^8$ and $R^9$ are independently hydrogen, alkyl, aryl, aralkyl, cycloalkyl, cycloalkylalkyl, heteroalkyl, alkylsulfonyl, arylsulfonyl, —C(O)—$R^{81}$ (where $R^{81}$ is alkyl, aryl, aralkyl, cycloalkyl, cycloalkylalkyl, heteroalkyl, alkoxy, aryloxy, amino, mono- and di-alkylamino, arylamino or aryl(alkyl) amino) or $R^8$ and $R^9$ together form =$CR^{82}R^{83}$ (where $R^{82}$ and $R^{83}$ are independently hydrogen, alkyl, cycloalkyl, cycloalkylalkyl or optionally substituted phenyl).

Definitions

Unless otherwise stated, the following terms used in the specification and claims have the meanings given below:

"Acyl" means a radical-C(O)R, where R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formyl, acetyl, cylcohexylcarbonyl, cyclohexylmethylcarbonyl, benzoyl, benzylcarbonyl, and the like.

"Acylamino" means a radical-NR'C(O)R, where R' is hydrogen or alkyl, and R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formylamino, acetylamino, cylcohexylcarbonylamino, cyclohexylmethylcarbonylamino, benzoylamino, benzylcarbonylamino, and the like.

"Alkoxy" means a radical-OR where R is an alkyl as defined herein e.g., methoxy, ethoxy, propoxy, butoxy and the like.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, n-butyl, iso-butyl, tert-butyl, pentyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkylthio" means a radical-SR where R is an alkyl as defined above e.g., methylthio, ethylthio, propylthio, butylthio, and the like.

"Aryl" means a monovalent monocyclic or bicyclic aromatic hydrocarbon radical which is optionally substituted independently with one or more substituents, preferably one, two or three, substituents preferably selected from the group consisting of alkyl, hydroxy, alkoxy, haloalkyl, haloalkoxy, Y—C(O)—R (where Y is absent or an alkylene group and R is hydrogen, alkyl, haloalkyl, haloalkoxy, hydroxy, alkoxy, amino, monoalkylamino or dialkylamino), heteroalkyl, heteroalkyloxy, heteroalkylamino, halo, nitro, cyano, amino, monoalkylamino, dialkylamino, alkylsulfonylamino, heteroalkylsulfonylamino, sulfonamido, methylenedioxy ethylenedioxy, heterocyclyl or heterocyclylalkyl. More specifically the term aryl includes, but is not limited to, phenyl, chlorophenyl, methoxyphenyl, 2-fluorophenyl, 2,4-difluorophenyl, 1-naphthyl, 2-naphthyl, and the derivatives thereof.

"Aryloxy" means a radical-OR where R is an aryl as defined herein e.g. phenoxy.

"Aryloxycarbonyl" means a radical R—C(=O)— where R is aryloxy, e.g. phenoxycarbonyl.

"Cycloalkyl" refers to a saturated monovalent cyclic hydrocarbon radical of three to seven ring carbons e.g., cyclopropyl, cyclobutyl, cyclohexyl, 4-methyl-cyclohexyl, and the like.

"Cycloalkylalkyl" means a radical-$R^aR^b$ where $R^a$ is an alkylene group and $R^b$ is cycloalkyl group as defined herein, e.g., cyclohexylmethyl, and the like.

"Substituted cycloalkyl" means a cycloalkyl radical as defined herein with one, two or three (preferably one) ring hydrogen atoms independently replaced by cyano or —Y—C(O)R (where Y is absent or an alkylene group and R is hydrogen, alkyl, haloalkyl, hydroxy, alkoxy, amino, monoalkylamino, dialkylamino, or optionally substituted phenyl).

"Dialkylamino" means a radical-NRR' where R and R' independently represent an alkyl, hydroxyalkyl, cycloalkyl, or cycloalkylalkyl group as defined herein. Representative examples include, but are not limited to dimethylamino, methylethylamino, di(1-methylethyl)amino, (methyl)(hydroxymethyl)amino, (cyclohexyl)(methyl)amino, (cyclohexyl)(ethyl)amino, (cyclohexyl)(propyl)amino, (cyclohexylmethyl)(methyl)amino, (cyclohexylmethyl)(ethyl)amino, and the like.

"Halo" means fluoro, chloro, bromo, or iodo, preferably fluoro and chloro.

"Haloalkyl" means alkyl substituted with one or more same or different halo atoms, e.g., —$CH_2Cl$, —$CF_3$, —$CH_2CF_3$, —$CH_2CCl_3$, and the like.

"Heteroalkyl" means an alkyl radical as defined herein wherein one, two or three hydrogen atoms have been replaced with a substituent independently selected from the group consisting of —$R^a$, —$N(O)_nR^bR^c$ (where n is 0 or 1 if $R^b$ and $R^c$ are both independently alkyl, cycloalkyl or cycloalkylalkyl, and 0 if not) and —$S(O)_nR^d$ (where n is an integer from 0 to 2), with the understanding that the point of attachment of the heteroalkyl radical is through a carbon atom, wherein $R^a$ is hydrogen, acyl, alkoxycarbonyl, alkyl, cycloalkyl, or cycloalkylalkyl; $R^b$ and $R^c$ are independently of each other hydrogen, acyl, alkoxycarbonyl, alkyl, cycloalkyl, cycloalkylalkyl, alkylsulfonyl, aminosulfonyl, mono- or di-alkylaminosulfonyl, aminoalkyl, mono- or di-alkylaminoalkyl, hydroxyalkyl, alkoxyalkyl, hydroxyalkylsulfonyl or alkoxyalkylsulfonyl; and when n is 0, $R^d$ is hydrogen, alkyl, cycloalkyl, cycloalkylalkyl or optionally substituted phenyl, and when n is 1 or 2, $R^d$ is alkyl, cycloalkyl, cycloalkylalkyl, optionally substituted phenyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroalkylcarbonyl" means the group $R_a$—C(═O)—, where $R_a$ is a heteroalkyl group. Representative examples include acetyloxymethylcarbonyl, aminomethylcarbonyl, 4-acetyloxy-2,2-dimethyl-butan-2-oyl, 2-amino-4-methyl-pentan-2-oyl, and the like.

"Heteroalkyloxy" means the group $R_a$—O—, where $R_a$ is a heteroalkyl group. Representative examples include (Me-C(═O)—O—$CH_2$—O—, and the like "Heteroalkyloxycarbonyl" means the group $R_a$—C(═O), where $R_a$ is a heteroalkyloxy group. Representative examples include 1-acetyloxy-methoxycarbonyl (Me-C(═O)—O—$CH_2$—O—C(═O)—) and the like.

"Heteroaryl" means a monovalent monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one or more substituents, preferably one or two substituents, selected from alkyl, haloalkyl, heteroalkyl, hydroxy, alkoxy, halo, nitro or cyano. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofaranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof.

"Heteroaralkyl" means a radical-$R^aR^b$ where $R^a$ is an alkylene group and $R^b$ is a heteroaryl group as defined herein, e.g., pyridin-3-ylmethyl, imidazolylethyl, pyridinylethyl, 3-(benzofuran-2-yl)propyl, and the like.

"Heteroalkylsubstituted cycloalkyl" means a cycloalkyl radical as defined herein wherein one, two or three hydrogen atoms in the cycloalkyl radical have been replaced with a heteroalkyl group with the understanding that the heteroalkyl radical is attached to the cycloalkyl radical via a carbon-carbon bond. Representative examples include, but are not limited to, 1-hydroxymethylcyclopentyl, 2-hydroxymethylcyclohexyl, and the like.

"Heterosubstituted cycloalkyl" means a cycloalkyl radical as defined herein wherein one, two or three hydrogen atoms in the cycloalkyl radical have been replaced with a substituent independently selected from the group consisting of hydroxy, alkoxy, amino, acylamino, monoalkylamino, dialkylamino, oxo (C═O), imino, hydroximino (═NOH), NR'$SO_2R^d$ (where R' is hydrogen or alkyl and $R^d$ is alkyl, cycloalkyl, hydroxyalkyl, amino, monoalkylamino or dialkylamino), —X—Y—C(O)R (where X is O or NR', Y is alkylene or absent, R is hydrogen, alkyl, haloalkyl, alkoxy, amino, monoalkylamino, dialkylamino, or optionally substituted phenyl, and R' is H or alkyl), or —$S(O)_nR$ (where n is an integer from 0 to 2) such that when n is 0, R is hydrogen, alkyl, cycloalkyl, cycloalkylalkyl optionally substituted phenyl or thienyl, and when n is 1 or 2, R is alkyl, cycloalkyl, cycloalkylalkyl, optionally substituted phenyl, thienyl, amino, acylamino, monoalkylamino or dialkylamino. Representative examples include, but are not limited to, 2-, 3-, or 4-hydroxy-cyclohexyl, 2-, 3-, or 4-aminocyclohexyl, 2-, 3-, or 4-methanesulfonamido-cyclohexyl, and the like, preferably 4-hydroxycyclohexyl, 2-aminocyclohexyl or 4-methanesulfonamido-cyclohexyl.

"Heterosubstituted cycloalkyl-alkyl" means a radical $R^aR^b$— where $R^a$ is a heterosubstituted cycloalkyl radical and $R^b$ is an alkylene radical.

"Heterocycloamino" means a saturated monovalent cyclic group of 4 to 8 ring atoms, wherein one ring atom is N and the remaining ring atoms are C. Representative examples include piperidine and pyrrolidine.

"Heterocyclyl" means a saturated or unsaturated non-aromatic cyclic radical of 3 to 8 ring atoms in which one or two ring atoms are heteroatoms selected from N, O, or $S(O)_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, haloalkyl, heteroalkyl, halo, nitro, cyano, cyanoalkyl, hydroxy, alkoxy, amino, monoalkylamino, dialkylamino, aralkyl, —$(X)_n$—C(O)R (where X is O or NR', n is 0 or 1, R is hydrogen, alkyl, haloalkyl, hydroxy (when n is 0), alkoxy, amino, monoalkylamino, dialkylamino, or optionally substituted phenyl, and R' is H or alkyl), -alkylene-C(O)$R^a$ (where $R^a$ is alkyl, OR or NR'R" and R is hydrogen, alkyl or haloalkyl, and R' and R" are independently hydrogen or alkyl), or —$S(O)_nR$ (where n is an integer from 0 to 2) such that when n is 0, R is hydrogen, alkyl, cycloalkyl, or cycloalkylalkyl, and when n is 1 or 2, R is alkyl, cycloalkyl, cycloalkylalkyl, amino, acylamino, monoalkylamino, dialkylamino or heteroalkyl. More specifically the term heterocyclyl includes, but is not limited to, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, 4-(1,1-dioxo-tetrahydro-2H-thiopyranyl), pyrrolinyl, imidazolinyl, N-methanesulfonylpiperidin-4-yl, and the derivatives thereof.

"Heterocyclylalkyl" means a radical-$R^aR^b$ where $R^a$ is an alkylene group and $R^b$ is a heterocyclyl group as defined above, e.g., tetrahydropyran-2-ylmethyl, 2- or 3-piperidinylmethyl, 3-(4-methyl-piperazin-1-yl)propyl and the like.

"(Heterocyclyl)(cycloalkyl)alkyl" means an alkyl radical wherein two hydrogen atoms have been replaced with a heterocyclyl group and a cycloalkyl group.

"(Heterocyclyl)(heteroaryl)alkyl" means an alkyl radical wherein two hydrogen atoms have been replaced with a heterocycyl group and a heteroaryl group. "Heterocyclyl spiro cycloalkyl" means a Spiro radical consisting of a cycloalkyl ring and a heterocyclic ring with each ring having 5 to 8 ring atoms and the two rings having only one carbon atom in common, with the understanding that the point of attachment of the heterocyclyl spiro cycloalkyl radical is via the cycloalkyl ring. The spiro radical is formed when two hydrogen atoms from the same carbon atom of the cycloalkyl radical are replaced with a heterocyclyl group as defined herein, and may be optionally substituted with alkyl, hydroxy, hydroxyalkyl, or oxo. Examples include, but are not limited to, for example, 1,4-dioxaspiro[4.5]decan-8-yl, 1,3-diazaspiro[4.5]decan-8-yl, 2,4-dione-1,3-diaza-spiro [4.5]decan-8-yl, 1,5-dioxa-spiro[5.5]undecan-9-yl, (3-hydroxymethyl-3-methyl)-1,5-dioxa-spiro[5.5]undecan-9-yl, and the like.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)-2-hydroxyethyl. Accordingly, as used herein, the term "hydroxyalkyl" is used to define a subset of heteroalkyl groups.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Monoalkylamino" means a radical-NHR where R is an alkyl, hydroxyalkyl, cycloalkyl, or cycloalkylalkyl group as defined above, e.g., methylamino, (1-methylethyl)amino, hydroxymethylamino, cyclohexylamino, cyclohexylmethylamino, cyclohexylethylamino, and the like.

"Optionally substituted phenyl" means a phenyl ring which is optionally substituted independently with one or more substituents, preferably one or two substituents selected from the group consisting of alkyl, hydroxy, alkoxy, haloalkyl, haloalkoxy, heteroalkyl, halo, nitro, cyano, amino, methylenedioxy, ethylenedioxy, and acyl.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug according to Formula I or II in vivo when such prodrug is administered to a mammalian subject. Prodrugs of a compound of Formula I or II are prepared by modifying one or more functional group(s) present in the compound of Formula I or II in such a way that the modification(s) may be cleaved in vivo to release the parent compound. Prodrugs include compounds of Formula I or II wherein a hydroxy, amino, sulfhydryl, carboxy or carbonyl group in a compound of Formula I or II is bonded to any group that may be cleaved in vivo to regenerate the free hydroxyl, amino, or sulfhydryl group, respectively. Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I or II, and the like, See Bundegaard, H. "Design of Prodrugs" p 1-92, Elesevier, New York-Oxford (1985).

"Protecting group" refers to a grouping of atoms that when attached to a reactive group in a molecule masks, reduces or prevents that reactivity. Examples of protecting groups can be found in T. W. Green and P. G. Futs, *Protective Groups in Organic Chemistry*, (Wiley, $2^{nd}$ ed. 1991) and Harrison and Harrison et al., *Compendium of Synthetic Organic Methods*, Vols. 1-8 (John Wiley and Sons, 1971-1996). Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

DETAILED DESCRIPTION

Though the broadest description of the invention is set forth in the Summary of the Invention, particular aspects are set forth below.

One aspect of the present invention provides a compound of Formula I:

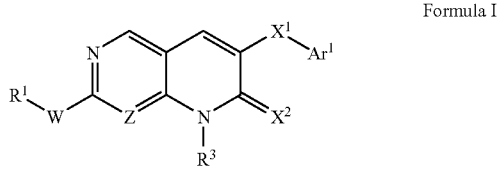

Formula I where $R^1$, $R^3$, W, Z, $X^1$ and $Ar^1$, are as defined above.

Preferably W is $NR^2$, more preferably NH.

Preferably, Z is N.

Preferably, $X^1$ is O or $CH_2$, more preferably O.

Preferably, $Ar^1$ is optionally substituted phenyl, optionally substituted furyl or optionally substituted thienyl. More preferably, $Ar^1$ is optionally substituted phenyl, particularly 2-substituted, 4-substituted or 2,4-disubstituted. Still more preferably, $Ar^1$ is monohalo-substituted phenyl (e.g. 2-chlorophenyl, 2-fluorophenyl or 4-fluorophenyl), monoalkylphenyl (e.g. 2-methylphenyl), dihalo-substituted phenyl (e.g. 2,4-difluorophenyl), dialkylphenyl (e.g. 2,4-dimethylphenyl or 2,6-dimethylphenyl), 2,4-disubstitutedphenyl (e.g. 4-fluoro-2-methylphenyl, 2-fluoro-4-methylphenyl).

Preferably, $R^1$ is aryl, aralkyl, cycloalkyl, cycloalkylalkyl, heteroalkylsubstituted cycloalkyl, heterosubstituted cycloalkyl, heteroalkyl, heterocyclyl or heterocyclylalkyl. More preferably $R^1$ is heteroalkylsubstituted cycloalkyl, heterosubstituted cycloalkyl, heteroalkyl or heterocyclyl. A particularly preferred examples of a heteroalkyl $R^1$ is hydroxyalkyl, e.g., (1-hydroxy-2-methyl)-prop-2-yl, 1-hydroxypentan-2-yl, (S)-2-hydroxy-1,2-dimethyl-propyl, (R)-2-hydroxy-1,2-dimethyl-propyl, (S)-2-hydroxy-1-methyl-ethyl, 1-hydroxymethyl-cyclopentan-1-yl and 2-hydroxy-2-methyl-propyl. Particularly preferred examples of heterocyclyl $R^1$ include tetrahydro-2H-pyran-4-yl, 1-(methylsulfonyl)piperidin-4-yl and 1,1-dioxidotetrahydro-2H-thiopyran-4-yl. Specific examples of $R^1$ include 4-hydroxycyclohexyl, tetrahydro-2H-pyran-4-yl, 1-(methylsulfonyl) piperidin-4-yl, cyclopentyl, (S)-(2-hydroxy-1,2-dimethyl) propyl, 2,2-diethoxyethyl, 2,2-dimethoxyethyl, 3-hydroxypyridin-2-yl, (S)-(1-hydroxymethyl-2-methyl) propyl, 4-(2-(N,N-diethylamino)ethoxy)phenyl, benzyl, phenyl, butyl, dodecyl, 2-hydroxyethyl, 3-methylbutyl, 2-methylpropyl, (2-hydroxy-1,1-dimethyl)ethyl, 2,3-dihydroxypropyl, 3-hydroxypropyl, hexyl, pyridin-2-yl, 2-morpholinoethyl, 2-(piperidin-1-yl)ethyl, cyclohexylmethyl, 1-(hydroxymethyl)butyl, 4-fluorophenyl, cyclopropylmethyl, 2-methoxyethyl, 3-(N,N-dimethylamino)propyl, isopropyl, methyl, 2-morpholino-2-(pyridin-4-yl)ethyl, 3-furylmethyl, 1-oxidotetrahydro-2H-thiopyran-4-yl, 1,1-dioxidotetrahydro-2H-thiopyran-4-yl, 1-phenylpropyl, phenethyl, 4-(2-hydroxyethyl)phenyl, 3-(4-methylpiperazin-1-yl)propyl, 4-hydroxybutyl, 3-morpholinopropyl, 3-(2-pyrrolidinon-1-yl)propyl, 2-acetamidoethyl, 2-(pyridin-2-yl)ethyl, pentyl, 2-(N,N-dimethylamino)ethyl, 2-(pyrrolidin-1-yl) ethyl, 3-(pyrrolidin-1-yl)propyl, ethyl, 5-methylpyridin-2-yl, propyl, methyl, cyclopropyl, (1-hydroxymethyl-3-methylthio)propyl, (1-hydroxymethyl)cyclpentyl, 1,1-dimethylpropyl, 3-ethoxy-3-oxo-propyl, (1-(piperidin-1-yl)cyclohexyl)methyl, 3-methoxypropyl, cylcobutyl, 1-(oxoethoxymethyl)piperidin-4-yl, 4-methoxycyclohexyl, 2-cyclohexylethyl, (2-methylthiazol-5-yl)methyl, imidazo[2,1-b]thiazol-6-ylmethyl, hydrogen, 4-phenylbutyl, 2-(4-aminophenyl)ethyl, pyridin-3-yl, tetrahydro-2H-thiopyran-4-yl and (1-hydroxymethyl)butyl.

Preferably, $R^3$ is alkyl, aryl, cycloalkyl or heteroalkyl, more preferably methyl.

Another aspect of the invention provides compounds of Formula II.

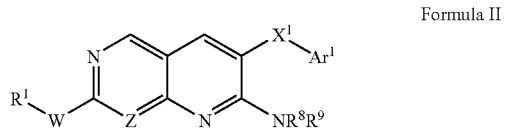

Formula II or pharmaceutically acceptable salts thereof, wherein:

Z is N or CH;

W is $NR^2$;

$X^1$ is O, $NR^4$ (where $R^4$ is hydrogen or alkyl), S, or $CR^5R^6$ (where $R^5$ and $R^6$ are independently hydrogen or alkyl) or C=O;

$Ar^1$ is aryl or heteroaryl;

$R^1$ is hydrogen, alkyl, haloalkyl, aryl, aralkyl, cycloalkyl, cycloalkylalkyl, heteroalkylsubstituted cycloalkyl, heterosubstituted cycloalkyl, heteroalkyl, cyanoalkyl, heterocyclyl, heterocyclylalkyl, —$Y^1$—C(O)—$Y^2$—$R^{11}$ (where $Y^1$ and $Y^2$ are independently either absent or an alkylene group and $R^{11}$ is hydrogen, alkyl, haloalkyl, hydroxy, alkoxy, amino, monoalkylamino or dialkylamino), (heterocyclyl)(cycloalkyl)alkyl or (heterocyclyl)(heteroaryl)alkyl;

$R^2$ is hydrogen or alkyl;

$R^7$ is hydrogen or alkyl; and $R^8$ and $R^9$ are independently hydrogen, alkyl, aryl, aralkyl, cycloalkyl, cycloalkylalkyl, heteroalkyl, alkylsulfonyl, arylsulfonyl, —C(O)—$R^{81}$ (where $R^{81}$ is alkyl, aryl, aralkyl, cycloalkyl, cycloalkylalkyl, heteroalkyl, alkoxy, aryloxy, amino, mono- and di-alkylamino, arylamino or aryl(alkyl) amino).

where $R^1$, $R^3$, W, Z, $X^1$ and $Ar^1$, are as defined above.

Preferably W is $NR^2$, more preferably NH.

Preferably, Z is N.

Preferably, $X^1$ is O or $CH_2$, more preferably 0.

Preferably, $Ar^1$ is optionally substituted phenyl, optionally substituted furyl or optionally substituted thienyl. More preferably, $Ar^1$ is optionally substituted phenyl, particularly 2-substituted, 4-substituted or 2,4-disubstituted. Still more preferably, $Ar^1$ is monohalo-substituted phenyl (e.g. 2-chlorophenyl, 2-fluorophenyl or 4-fluorophenyl), monoalkylphenyl (e.g. 2-methylphenyl), dihalo-substituted phenyl (e.g. 2,4-difluorophenyl), dialkylphenyl (e.g. 2,4-dimethylphenyl or 2,6-dimethylphenyl), 2,4-disubstitutedphenyl (e.g. 4-fluoro-2-methylphenyl, 2-fluoro-4-methylphenyl).

Preferably, $R^1$ is aryl, aralkyl, cycloalkyl, cycloalkylalkyl, heteroalkylsubstituted cycloalkyl, heterosubstituted cycloalkyl, heteroalkyl, heterocyclyl or heterocyclylalkyl. More preferably $R^1$ is heteroalkylsubstituted cycloalkyl, heterosubstituted cycloalkyl, heteroalkyl, or heterocyclyl.

Specific examples of $R^1$ include 4-hydroxycyclohexyl, tetrahydro-2H-pyran-4-yl, 1-(methylsulfonyl)piperidin-4-yl, cyclopentyl, (S)-(2-hydroxy-1,2-dimethyl)propyl, 2,2-diethoxyethyl, 2,2-dimethoxyethyl, 3-hydroxypyridin-2-yl, (S)-(1-hydroxymethyl-2-methyl)propyl, 4-(2-(N,N-diethylamino)ethoxy)phenyl, benzyl, phenyl, butyl, dodecyl, 2-hydroxyethyl, 3-methylbutyl, 2-methylpropyl, (2-hydroxy-1,1-dimethyl)ethyl, 2,3-dihydroxypropyl, 3-hydroxypropyl, hexyl, pyridin-2-yl, 2-morpholinoethyl, 2-(piperidin-1-yl) ethyl, cyclohexylmethyl, 1-(hydroxymethyl)butyl, 4-fluorophenyl, cyclopropylmethyl, 2-methoxyethyl, 3-(N,N-dimethylamino)propyl, isopropyl, methyl, 2-morpholino-2-(pyridin-4-yl)ethyl, 3-furylmethyl, 1-oxidotetrahydro-2H-thiopyran-4-yl, 1-phenylpropyl, 1,1-dioxidotetrahydro-2H-thiopyran-4-yl, phenethyl, 4-(2-hydroxyethyl)phenyl, 3-(4-methylpiperazin-1-yl)propyl, 4-hydroxybutyl, 3-morpholinopropyl, 3-(2-pyrrolidinon-1-yl)propyl, 2-acetamidoethyl, 2-(pyridin-2-yl)ethyl, pentyl, 2-(N,N-dimethylamino)ethyl, 2-(pyrrolidin-1-yl)ethyl, 3-(pyrrolidin-1-yl) propyl, ethyl, 5-methylpyridin-2-yl, propyl, methyl, cyclopropyl, (1-hydroxymethyl-3-methylthio)propyl, (1-hydroxymethyl)cyclpentyl, 1,1-dimethylpropyl, 3-ethoxy-3-oxo-propyl, (1-(piperidin-1-yl)cyclohexyl)methyl, 3-methoxypropyl, cylcobutyl, 1-(oxo-ethoxymethyl)piperidin-4-yl, 4-methoxycyclohexyl, 2-cyclohexylethyl, (2-methylthiazol-5-yl)methyl, imidazo[2,1-b]thiazol-6-ylmethyl, hydrogen, 4-phenylbutyl, 2-(4-aminophenyl)ethyl, pyridin-3-yl, tetrahydro-2H-thiopyran-4-yl and (1-hydroxymethyl)butyl.

The compounds of the present invention can exist in unsolvated forms as well as solvated forms, including hydrated forms. In general, the solvated forms, including hydrated forms, are equivalent to unsolvated forms and are intended to be encompassed within the scope of the present invention. In addition to the compounds described above, the compounds of the present invention include all tautomeric forms. Furthermore, the present invention also includes all pharmaceutically acceptable salts of those compounds along with prodrug forms of the compounds and all stereoisomers whether in a pure chiral form or a racemic mixture or other form of mixture.

The compounds of Formula I and II are capable of further forming pharmaceutically acceptable acid addition salts. All of these forms are within the scope of the present invention.

Pharmaceutically acceptable acid addition salts of the compounds of Formula I and II include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharmaceutical Science*, 1977, 66, 1-19).

The acid addition salts of the basic compounds can be prepared by contacting the free base form with a sufficient amount of the desired acid to produce the salt in the conventional manner. The free base form can be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Another aspect of the invention provides intermediates of Formula I' and II", useful in preparing compounds of Formula I and II.

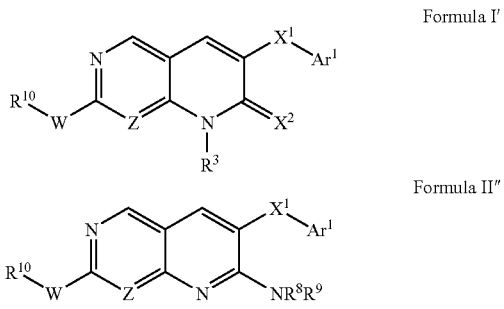

Formula I'

Formula II"

wherein:

Z is N or CH;

W is S, S(O), S(O)$_2$ or O;

$X^1$ is O, $NR^4$ (where $R^4$ is hydrogen or alkyl), S, or $CR^5R^6$ (where $R^5$ and $R^6$ are independently hydrogen or alkyl) or C=O;

$X^2$ is O or $NR^7$;

$Ar^1$ is aryl or heteroaryl;

$R^{10}$ is alkyl, aryl, aralkyl, cycloalkyl or cycloalkylalkyl, or $R^{10}W$ together form a leaving group or hydroxy;

$R^3$ is hydrogen, alkyl, cycloalkyl, cycloalkylalkyl, aryl, aralkyl, haloalkyl, heteroalkyl, cyanoalkyl, alkylene-C(O) $R^{31}$ (where $R^{31}$ is hydrogen, alkyl, hydroxy, alkoxy, amino, monoalkylamino or dialkylamino), amino, monoalkylamino, dialkylamino or $NR^{32}$—$Y^3$—$R^{33}$ (where $Y^3$ is —C(O), —C(O)O—, —C(O)NR$^{34}$, S(O)$_2$, or S(O)$_2$NR$^{35}$; $R^{32}$, $R^{34}$ and $R^{35}$ are independently hydrogen or alkyl; and $R^{33}$ is hydrogen, alkyl, cycloalkyl, cycloalkylalkyl, heteroalkyl or optionally substituted phenyl) or acyl;

$R^7$ is hydrogen or alkyl; and $R^8$ and $R^9$ are independently hydrogen, alkyl, aryl, aralkyl, cycloalkyl, cycloalkylalkyl, heteroalkyl, alkylsulfonyl, arylsulfonyl, —C(O)—$R^{81}$ (where $R^{81}$ is alkyl, aryl, aralkyl, cycloalkyl, cycloalkylalkyl, heteroalkyl, alkoxy, aryloxy, amino, mono- and di-alkylamino, arylamino or aryl(alkyl) amino) or $R^8$ and $R^9$ together form =CR$^{82}R^{83}$ (where $R^{82}$ and $R^{83}$ are independently hydrogen, alkyl, cycloalkyl, cycloalkylalkyl or optionally substituted phenyl).

Compounds of Formula I" and II" where W is O can be prepared by hydrolyzing precursor sulfones such as If, 2e, IIIg shown in the following Schemes 1-4 in refluxing aqueous acetic acid or aqueous hydroxide to provide a hydroxyl compound (i.e., compounds I' and II", wherein $R^{10}W$ is hydroxy). The resulting hydroxyl compound can be alkylated with $R^{10}$-L where L is a leaving group to provide compounds of Formula I' and II", where W is O and $R^{10}$ is as described. Alternatively, the sulfone group in the precursor sulfone may be directly displaced with an alcohol $R^{10}$—OH as described in WO 96/33798 to provide compounds of Formula I and II where W is O and $R^{10}$ is as described. Compounds of Formula I' and II" where $R^{10}W$ form a leaving group such as halo may be prepared by treating the precursor compound where $R^{10}W$ is hydroxy with a halogenating agent such as phosphorous oxychloride or phosphorous oxybromide. Compounds of Formula I' and II" where $R^{10}W$ form a leaving group such as acetoxy, tosyloxy etc. may be prepared by treating the precursor compound where $R^{10}W$ is hydroxy with an acylating or sulfonylating agent respectively.

While the forms of the invention herein constitute presently preferred embodiments, many others are possible. It is not intended herein to mention all of the possible equivalent forms or ramifications of the invention. It is understood that the terms used herein are merely descriptive rather than limiting, and that various changes can be made without departing from the spirit or scope of the invention.

Processes for Preparing the Compounds

The compounds of the present invention can be prepared by a variety of methods. In one aspect of the present invention, a method for preparing compounds of Formula I where Z is N is shown in Scheme 1 below. It should be appreciated that although the scheme often indicates exact structures, methods of the present invention apply widely to analogous compounds of Formula I or II, given appropriate consideration to protection-and deprotection of reactive functional groups by methods standard to the art of organic chemistry. For example, hydroxy groups, in order to prevent unwanted side reactions, sometimes need to be converted to ethers or esters during chemical reactions at other sites in the molecule. The hydroxy protecting group is then removed to provide the free hydroxy group. Similarly, amino groups and carboxylic acid groups can be derivatized to protect them against unwanted side reactions. Typical protecting groups, and methods for attaching and cleaving them, are described fully in the above incorporated references by T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996).

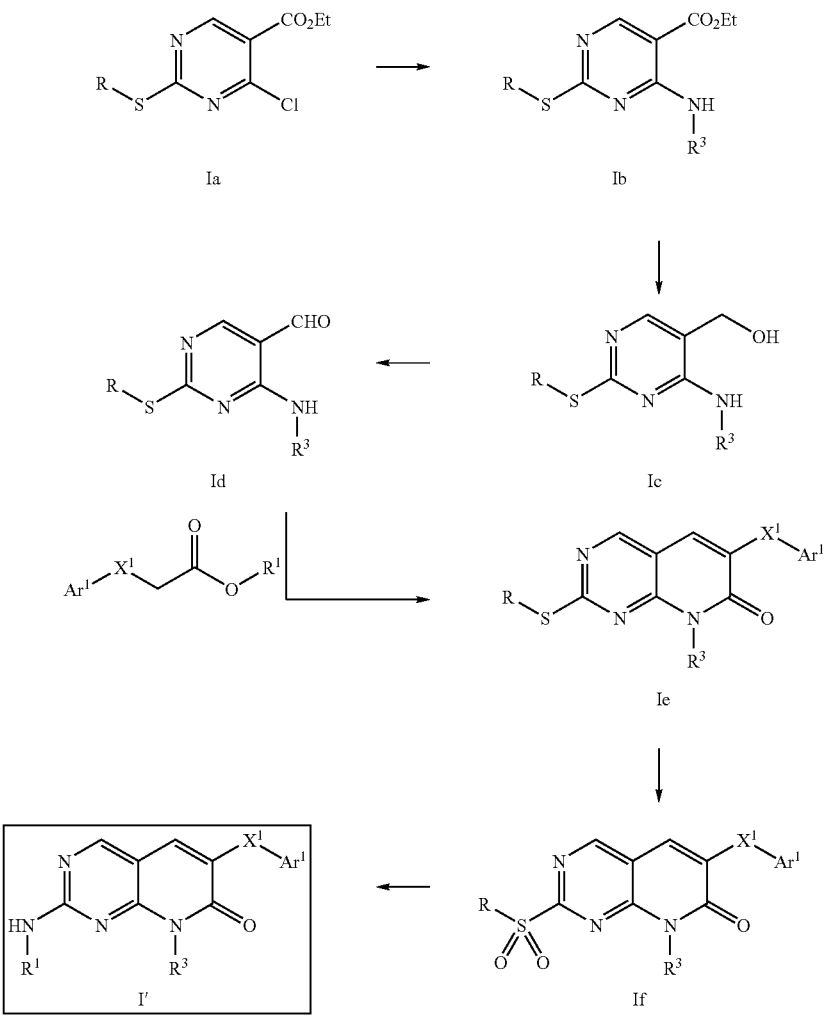

Scheme 1

Treatment of a compound of Formula Ia with a primary amine ($R^3$—$NH_2$) provides a compound of Formula Ib. This reaction is conveniently carried out in a solvent which is inert under the reaction conditions, preferably a halogenated aliphatic hydrocarbon, especially dichloromethane, an optionally halogenated aromatic hydrocarbon, or an open-chain or cyclic ether such as tetrahydrofuran, a formamide or a lower alkanol. Suitably, the reaction is carried out at about −20° C. to about 120° C.

Reduction of a compound of Formula Ib provides an alcohol of Formula Ic. This reduction is typically carried out using lithium aluminum hydride in a manner well known to those of skill in the art (e.g., in a solvent which is inert under the conditions of the reduction, preferably an open-chain or cyclic ether, especially tetrahydrofuran, at about −20° C. to about 70° C., preferably at about 0° C. to about room temperature).

Oxidation of an alcohol of Formula Ic provides a carboxaldehyde of Formula Id. The oxidation is typically carried out with manganese dioxide, although numerous other methods can also be employed (see, for example, ADVANCED ORGANIC CHEMISTRY, 4$^{TH}$ ED., March, John Wiley & Sons, New York (1992)). Depending on the oxidizing agent employed, the reaction is carried out conveniently in a solvent which is inert under the specific oxidation conditions, preferably a halogenated aliphatic hydrocarbon, especially dichloromethane, or an optionally halogenated aromatic hydrocarbon. Suitably, the oxidation is carried out at about 0° C. to about 60° C.

Reaction of a carboxaldehyde of Formula Id with an ester, $Ar^1$—$X^1CH_2$—$CO_2R'$ (where R' is an alkyl group, and $Ar^1$ and $X^1$ are those defined above) in the presence of a base provides a compound of Formula Ie. Any relatively non-nucleophilic base can be used including carbonates, such as potassium carbonate, lithium carbonate, and sodium carbonate; bicarbonates, such as potassium bicarbonate, lithium bicarbonate, and sodium bicarbonate; amines, such as secondary and tertiary amines; and resin bound amines such as 1,3,4,6,7,8-hexahydro-2H pyrimido[1,2-a]pyrimidine. Conveniently, the reaction is carried out in a solvent which is relatively polar but inert under the reaction conditions, preferably an amide such as dimethyl formamide, N-substituted pyrrolidinone, especially 1-methyl-2-pyrrolidinone, and at a temperature of about 25° C. to about 150° C.

Oxidation of Ie with an oxidizing agent, e.g. a peracid such as 3-chloroperbenzoic acid (i.e., MCPBA) or Oxone®, provides a sulfone (If) which can be converted to a variety of target compounds. Typically the oxidation of Ie is carried out in a solvent which is inert under the conditions of the oxidation. For example, when MCPBA is used as the oxidizing agent, the solvent is preferably a halogenated aliphatic hydrocarbon, especially chloroform. When Oxone® is used as the oxidizing agent, the solvent is preferably methanol, aqueous ethanol or aqueous tetrahydrofuran. The reaction temperature depends on the solvent used. For an organic solvent, the reaction temperature is generally at about −20° C. to about 50° C., preferably about 0° C. to about room temperature. When water is used as the solvent, the reaction temperature is generally from about 0° C. to about 50° C., preferably about 0° C. to about room temperature. Alternatively, the oxidation may be carried under catalytic conditions with rhenium/peroxide based reagents, see ("Oxidation of Sulfoxides by Hydrogen Peroxide, Catalyzed by Methyltrioxorhenium (VII)", Lahti, David W.; Espenson, James H, *Inorg. Chem.* (2000) 39(10) pp. 2164-2167; "Rhenium oxo complexes in catalytic oxidations, *Catal. Today* (2000) 55(4), pp 317-363 and "A Simple and Efficient Method for the Preparation of Pyridine N-Oxides", Coperet, Christophe; Adolfsson, Hans; Khuong, Tinh-Alfredo V.; Yudin, Andrei K.; Sharpless, K. Barry, J. Org. Chem. (1998) 63(5), pp 1740-1741).

Reacting the compound If with an amine ($R^1$—$NH_2$) provides the compounds of Formula I' (i.e., compounds I, wherein W is NH). Further alkylation of I' then provides compounds of Formula I, where W is $NR^2$, where $R^2$ is alkyl. The reaction can be carried out in the presence or absence of solvent. Conveniently, the reaction is carried out at temperatures of from about 0° C. to about 200° C., more preferably about room temperature to about 150° C. Alternatively, in some cases rather than using the sulfone If, the sulfide Ie or the corresponding sulfoxide can be reacted directly with an amine ($R^1$—$NH_2$) to provide the compounds of Formula I'.

Accordingly, the present invention provides a method of preparing compounds of Formula I, by treating a compound of general Formula Ie, If or the corresponding sulfoxide with an amine ($R^1$—$NH_2$) and optionally reacting the resulting product with $R^2$-L, where $R^2$ is alkyl and L is a leaving group.

Compounds of Formula I where $R^3$ is amino, monoalkylamino, dialkylamino or $NR^{32}$—$Y^3$—$R^{33}$ may be prepared as shown in Scheme 2 from the corresponding 2-alkylthio-8-amino-[2,3-d]pyridopyrimidin-7(8H)-one (IV, Z=N) or 7-alkylthio-1-amino-1,6-naphthyridin-2-one (IV, Z=CH) shown in Scheme 2 by amination with O-diphenylphosphinylhydroxylamine.

Scheme 2

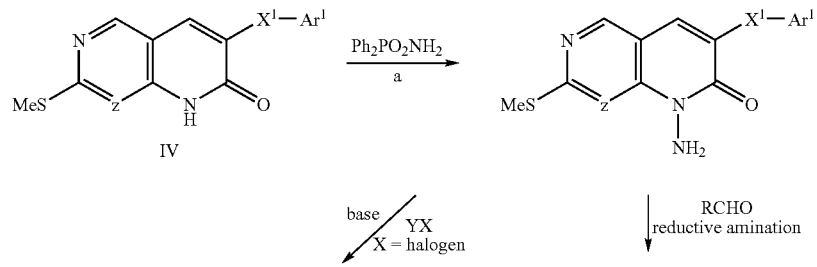

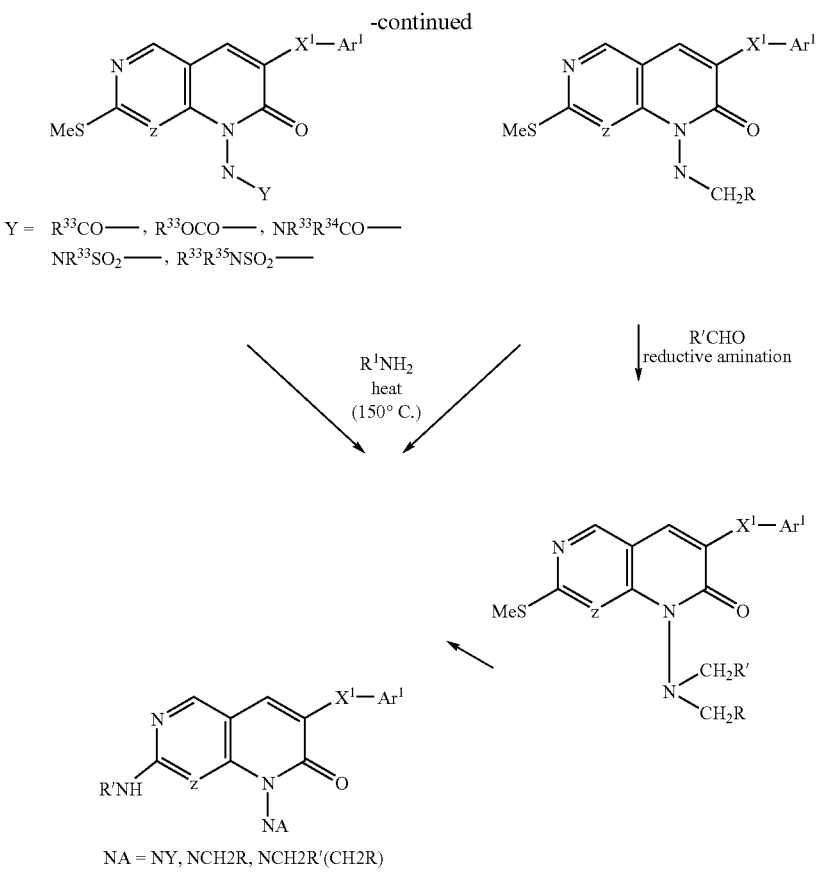

a. The aminating reagent (O-diphenylphosphinylhydroxylamine) was prepared according to literature procedure (Colvin, E.W.; Kirby, G.W.; Wilson, A.C. Tetrahedron Lett. 1982, 23, 3835. For its use see:
Klottzer, W.; Stadlwieser, J.; Raneburger, J. Org. Synth. 1986, 64, 96-03.

Displacement of the sulfide (or the corresponding sulfoxide or sulfone with an amine $R^1NH_2$ as previously described for compound Ie in Scheme 1 provides compounds of Formula I (compounds of Formula I where Z is CH and $R^2$ is H). Reacting the resulting product with $R^2$-L, where $R^2$ is alkyl and L is a leaving group gives compounds of Formula I where $R^2$ is alkyl.

Compounds of Formula I where Z is CH may be prepared as shown in Scheme 3.

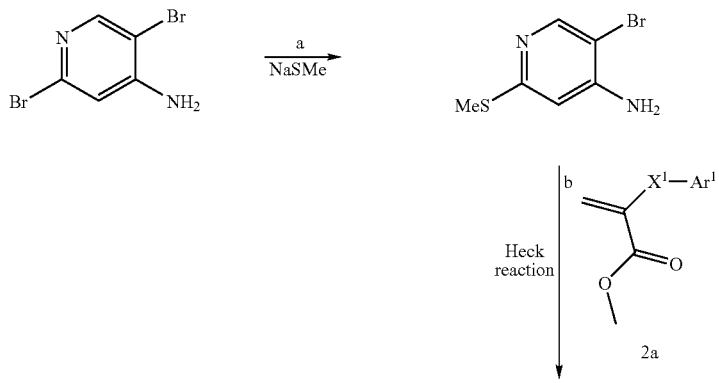

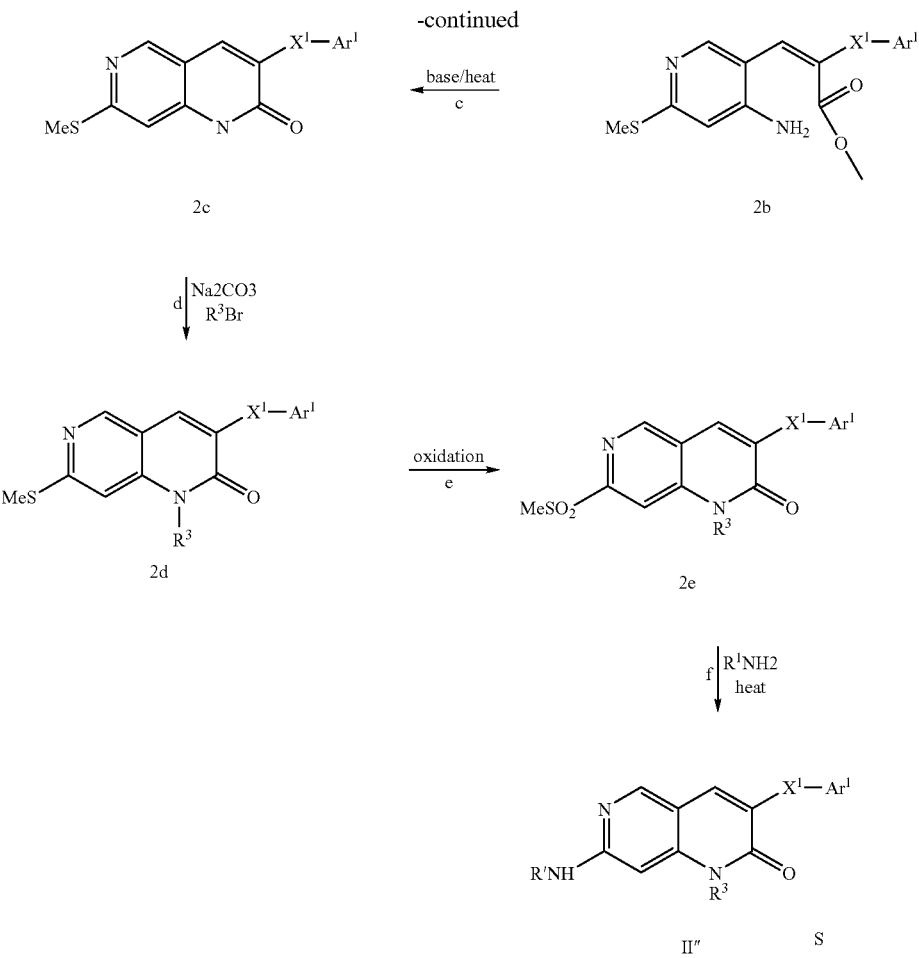

4-amino-3,6-dibromo-pyridine (Den Hertog et. al., Rec. Trav. Chim. Pays-Bas, 64 85-100 (1945) is treated with sodium methyl thiolate to give 4-amino-3-bromo-6-methylthiopyridine (Step a, see Windscheif, P; Voegtle, F.; *Synthesis,* 87092 (1994). The methylthiopyridine is coupled in a Heck reaction under palladium catalysis (e.g. palladium acetate) in the presence of base (e.g. potassium acetate or tributylamine) with the vinyl ester 2a to give a compound of Formula 2b (see Dong, Y.; Busacca, C. A. *J. Org. Chem.,* 62, 6464-65 (1997). Ring closure under basic conditions gives a 1,6-naphthyridone of Formula 2c. Alkylation of 2c with an alkyl halide (or any other alkylating agent $R^3$—X where X is a leaving group) gives a 1-alkylated naphthyridone of Formula 2d. Oxidation of 2d and displacement of the sulfone with an amine $R^1NH_2$ as previously described for compound Ie in Scheme 1 provides compounds of Formula I″ (compounds of Formula I where Z is CH and $R^2$ is H). Reacting the resulting product with $R^2$-L, where $R^2$ is alkyl and L is a leaving group gives compounds of Formula I where $R^2$ is alkyl. An alternative route is shown in Scheme 3A.

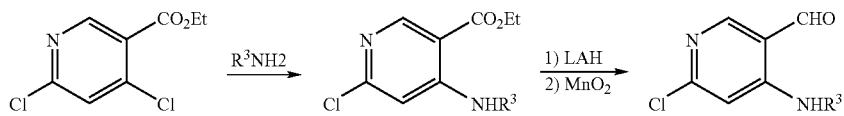

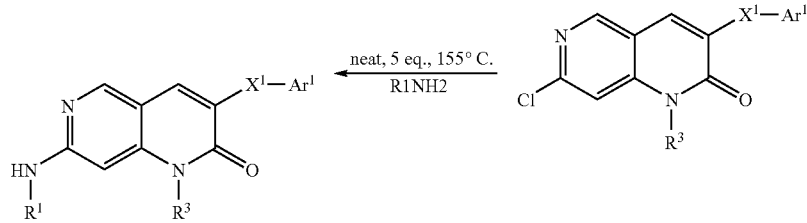

An example of this route is shown in Example 88.

Compounds of Formula II may be prepared as shown in Scheme 4.

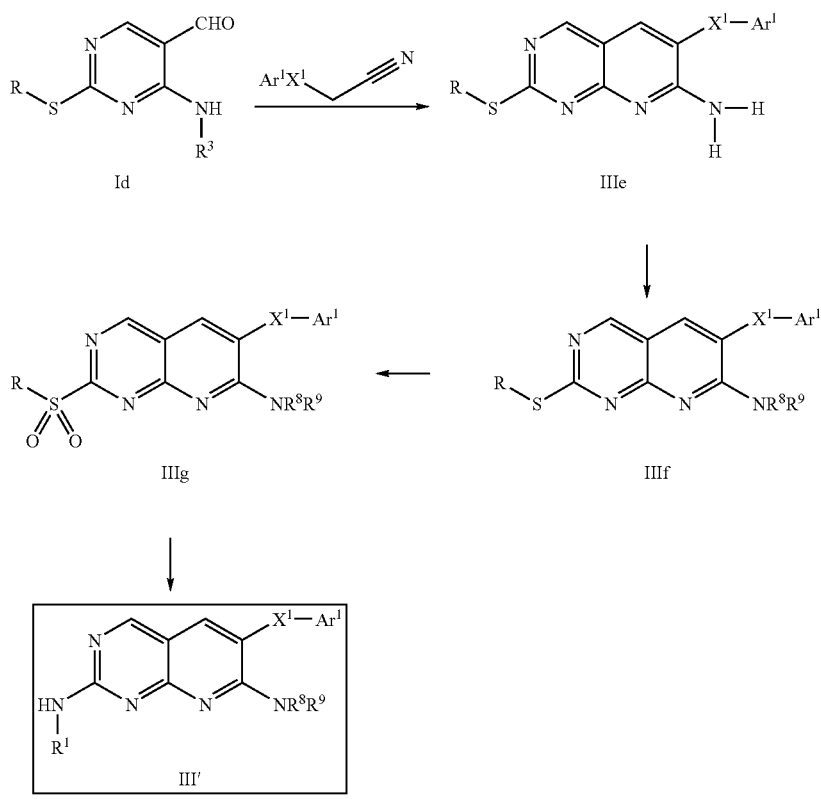

Reaction of a carboxaldehyde of Formula Id ($R^3$ is H) with a nitrile, $Ar^1$—$X^1CH_2$—CN (where $Ar^1$ and $X^1$ are those defined above) in the presence of a base under condtions similar to those described for conversion of Id to Ie in Scheme 1 provides a compound of Formula IIIe. Compounds of Formula IIIe may be sequentially alkylated, acylated or sulfonylated with alkylating agents, acyl halides, isocyanates, anhydrides and sulfonyl halides to provide compounds of Formula IIIf where $R^8$ and $R^9$ are as described in the Summary of the Invention. Subsequent oxidation of IIIf and displacement of the sulfone with an amine $R^1NH_2$ as previously described for compound Ie in Scheme 1 provides compounds of Formula III'. Further reacting the resulting product with $R^2$-L, where $R^2$ is is alkyl and L is a leaving group gives compounds of Formula II where $R^2$ is alkyl.

One of skill in the art will understand that certain modifications to the above schemes are contemplated and within the scope of the present invention. For example, certain steps will involve the use of protecting groups for functional groups that are not compatible with particular reaction conditions.

Pharmaceutical Compositions Containing the Compounds

The compounds of Formula I and II and the pharmaceutically acceptable salts of basic compounds of Formula I and II with acids can be used as medicaments, e.g., in the form of pharmaceutical preparations. The pharmaceutical preparations can be administered enterally, e.g., orally in the form of tablets, coated tablets, dragées, hard and soft gelatine capsules, solutions, emulsions or suspensions, nasally, e.g., in the form of nasal sprays, or rectally, e.g., in the form of suppositories. However, they may also be administered parenterally, e.g., in the form of injection solutions.

The compounds of Formula I and II and their aforementioned pharmaceutically acceptable salts can be processed with pharmaceutically inert, organic or inorganic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, sucrose, invert sugar, glucose and the like. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain therapeutically valuable substances other than the compounds of Formula I and II and their aforementioned pharmaceutically acceptable salts.

Medicaments which contain a compound of Formula I or II or a pharmaceutically acceptable salt of a basic compound of Formula I or II with an acid in association with a compatible pharmaceutical carrier material are also an object of the present invention, as is a process for the production of such medicaments which comprises bringing one or more of these compounds or salts and, if desired, one or more other therapeutically valuable substances into a galenical administration form together with a compatible pharmaceutical carrier.

As mentioned earlier, the compounds of Formula I and II and their aforementioned pharmaceutically acceptable salts can be used in accordance with the invention as therapeutically active substances, especially as antiinflammatory agents or for the prevention of graft rejection following transplant surgery. The dosage can vary within wide limits and will, of course, be fitted to the individual requirements in each particular case. In general, in the case of administration to adults a convenient daily dosage should be about 0.1 mg/kg to about 100 mg/kg, preferably about 0.5 mg/kg to about 5 mg/kg. The daily dosage may be administered as a single dose or in divided doses and, in addition, the upper dosage limit referred to earlier may be exceeded when this is found to be indicated.

Finally, the use of compounds of Formula I and II and their aforementioned pharmaceutically acceptable salts for the production of medicaments, especially in the treatment or prophylaxis of inflammatory, immunological, oncological, bronchopulmonary, dermatological and cardiovascular disorders, in the treatment of asthma, central nervous system disorders or diabetic complications or for the prevention of graft rejection following transplant surgery, is also an object of the invention.

Methods of Using the Compounds and Compositions

Compounds of Formula I and II would be useful for, but not limited to, the treatment of any disorder or disease state in a human, or other mammal, which is exacerbated or caused by excessive or unregulated TNF or p38 kinase production by such mammal. Accordingly, the present invention provides a method of treating a cytokine-mediated disease which comprises administering an effective cytokine-interfering amount of a compound of Formula I, or a pharmaceutically acceptable salt or tautomer thereof.

Compounds of Formula I and II would be useful for, but not limited to, the treatment of inflammation in a subject, and for use as antipyretics for the treatment of fever. Compounds of the invention would be useful to treat arthritis, including but not limited to, rheurmatoid arthritis, spondyloarthropathies, gouty arthritis, osteoarthritis, systemic lupus erythematosus and juvenile arthritis, osteoarthritis, gouty arthritis and other arthritic conditions. Such compounds would be useful for the treatment of pulmonary disorders or lung inflammation, including adult respiratory distress syndrome, pulmonary sarcoidosis, asthma, silicosis, and chronic pulmonary inflammatory disease. The compounds are also useful for the treatment of viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpes virus. The compounds are also useful for the treatment of bone resorption diseases, such as osteoporosis, endotoxic shock, toxic shock syndrome, reperfusion injury,autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection.

The compounds are also useful for the treatment of Alzheimer's disease, influenza, multiple sclerosis, cancer, diabetes, systemic lupus erthrematosis (SLE), skin-related conditions such as psoriasis, eczema, burns, dermatitis, keloid formation, and scar tissue formation. In addition, compounds of the invention are useful in treating gastrointestinal conditions such as inflammatory bowel disease, Crohn's disease, gastritis, irritable bowel syndrome and ulcerative colitis. The compounds are also useful in the treatment of ophthalmic diseases, such as retinitis, retinopathies, uveitis, ocular photophobia, and of acute injury to the eye tissue. The compounds can also be used in treating angiogenesis, including neoplasia; metastasis; ophthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemangiomas, including infantile hemangiomas, angiofibroma of the nasopharynx and avascular necrosis of bone; diabetic nephropathy and cardiomyopathy; and disorders of the female reproductive system such as endometriosis. The compounds can further be used for preventing the production of cyclooxygenase-2.

Besides being useful for human treatment, these compounds are also useful for veterinary treatment of companion animals, exotic animals and farm animals, including mammals, rodents, and the like. More preferred animals include horses, dogs, and cats.

The present compounds can also be used in co-therapies, partially or completely, in place of other conventional antiinflammatories, such as together with steroids, cyclooxygenase-2 inhibitors, NSAIDs, DMARDS, immunosuppressive agents, 5-lipoxygenase inhibitors, $LTB_4$ antagonists and $LTA_4$ hydrolase inhibitors.

As used herein, the term "TNF mediated disorder" refers to any and all disorders and disease states in which TNF plays a role, either by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-β has close structural homology with TNF-α (also known as cachectin), and since each induces similar biologic responses and binds to the same cellular receptor, the synthesis of both TNF-α and TNF-β are inhibited by the compounds of the present invention and thus are herein referred to collectively as "TNF" unless specifically delineated otherwise.

EXAMPLES

Additional objects, advantages, and novel features of this invention will become apparent to those skilled in the art upon examination of the following illustrative examples thereof, which are not intended to be limiting.

Unless otherwise stated, all temperatures including melting points (i.e., Mpt.) are in degrees celsius (° C.).

Example 1

Preparation of 4-methylamino-2-methylthiopyrimidine-5-carboxaldehyde

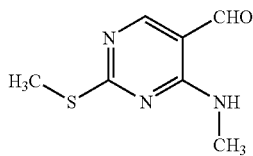

Step A: Preparation of ethyl 4-methylamino-2-methyl-thiopyrimidine-5-carboxylate

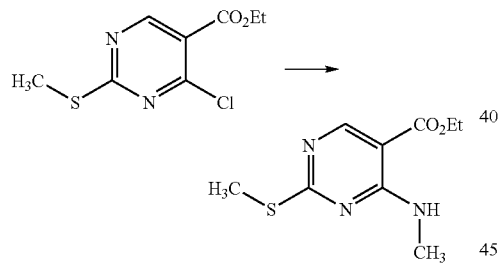

To a solution of ethyl 4-chloro-2-methylthiopyrimidine-5-carboxylate (Aldrich, 20 g, 86 mmol) in 250 mL of dichloromethane at 0° C. was added slowly solution of methylamine in ethanol (33%, 35 mL 281 mmol). After stirring for 30 minutes, water (150 mL) was added and the phases were separated. The organic phase was dried (MgSO₄) and filtered. The filtrate was evaporated under reduced pressure to give 19 g of the ethyl 4-methylamino-2-methylthiopyrimidine-5-carboxylate as a white solid.

Step B: Preparation of 4-methylamino-2-methylthiopyrimidine-5-methanol

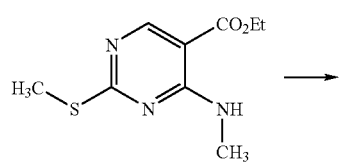

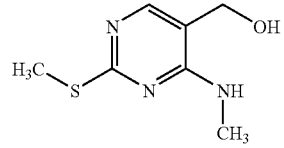

Lithium aluminum hydride (8.2 g, 215 mmol) was stirred in dry tetrahydrofuran (300 mL) at 5° C. and treated dropwise with a solution of ethyl 4-methylamino-2-methylthiopyrimidine-5-carboxylate (46 g, 215 mmol) in dry tetrahydrofuran (450 mL). The reaction mixture was stirred for 15 minutes and then water (18 mL) was added dropwise with caution. The reaction was stirred for 30 minutes and then an aqueous solution of sodium hydroxide (15%, 8.5 mL) was added dropwise, followed by water (25.5 mL). The resulting suspension was stirred for 17 hours at room temperature and then filtered. The filter residue was washed with tetrahydrofuran (2×, 100 mL) and the combined filtrate and washings were evaporated under reduced pressure. The residue was suspended in ethyl acetate/hexane—1/2 (200 mL) and the solid was filtered and dried to provide 32.7 g of 4-methylamino-2-methylthiopyrimidine-5-methanol as a yellow solid.

Step C: Preparation of 4-methylamino-2-methylthiopyrimidine-5-carboxaldehyde

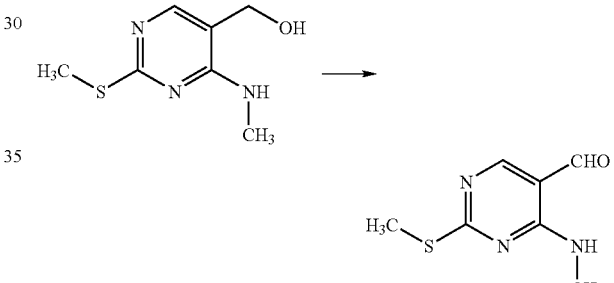

4-Methylamino-2-methylthiopyrimidine-5-methanol (20 g, 108 mmol) and 1 L of dichloromethane were combined with stirring and treated with manganese dioxide (87 g, 1 mol). The resulting suspension was stirred for 24 hours and then filtered through celite. The filter residue was washed with dichloromethane (100 mL) and the combined filtrate and washings were evaporated under reduced pressure to give 15.8 g of the 4-methylamino-2-methylthiopyrimidine-5-carboxaldehyde as a white solid.

Example 2

Preparation of 4-(cyclopropylamino)-2-(methylthio)pyrimidine-5-carboxaldehyde

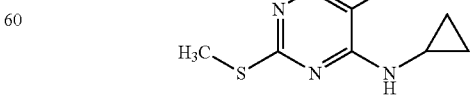

The 4-cyclopropylamino-2-methylthiopyrimidine-5-carboxaldehyde was prepared as described in Example 1 (steps A through C) starting with ethyl 4-chloro-2-methylthiopyrimidine-5-carboxylate (Aldrich Chemical Co.) and cyclopropyl amine (Aldrich Chemical Co.).

Example 3

Preparation of 4-[(4-fluorophenyl)amino]-2-(methylthio)pyrimidine-5-carboxaldehyde

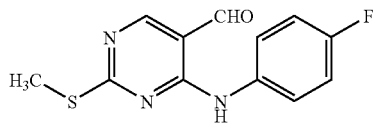

The 4-[(4-fluorophenyl)amino]-2-(methylthio)pyrimidine-5-carbaldehyde was prepared as described in Example 1 (steps A through C) starting with ethyl 4-chloro-2-methylthiopyrimidine-5-carboxylate (Aldrich Chemical Co.) and 4-fluoroaniline (Aldrich Chemical Co.).

Example 4

Preparation of methyl 2-fluorophenoxyacetate

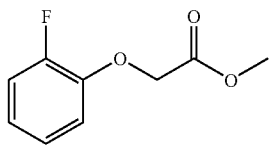

To a solution of 2-fluorophenol (6.72 g, 60 mmol) in 50 mL of 1-methyl-2-pyrrolidinone was added methyl bromoacetate (6.24 mL, 65.92 mmol) and potassium carbonate (9.9 g, 72 mmol). The reaction was stirred for 12 hours at room temperature and then poured into water. The aqueous solution was extracted with ethyl acetate, washed with water and dried (brine, $Na_2SO_4$). Evaporation of organic solvents yielded 10.5 g of the respective acetate (spectral data matched that of known literature compound).

Example 5

Preparation of methyl(phenylthio)acetate

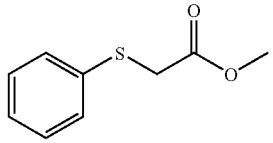

To a solution of thiophenol (1.09 g, 9.9 mmol) in 25 mL of 1-methyl-2-pyrrolidinone was added methyl bromoacetate (1.1 mL, 12 mmol) and potassium carbonate (2.0 g, 14.5 mmol). The reaction was stirred for 12 hours at room temperature and then poured into water. The aqueous solution was extracted with ethyl acetate, washed with water and dried (brine, $Na_2SO_4$). Evaporation of organic solvents yielded 1.2 g of the respective acetate (spectral data matched that of known literature compound).

Example 6

Preparation of ethyl 3-(2-fluorophenyl)propanoate

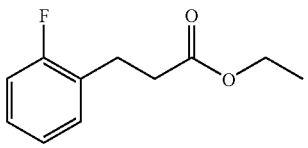

Step A:
To a solution of (2E)-3-(2-fluorophenyl)prop-2-enoic acid (10.0 g, 9.9 mmol) in 100 mL of EtOH was added sulfuric acid (0.2 mL). The reaction was refluxed for 5 hours and then cooled to room temperature. The reaction solution was evaporated to ¼ of the original volume and poured into water. Extraction of the mixture with ethyl acetate followed by drying (brine, $Na_2SO_4$) and complete evaporation yielded the ester which was taken on the Step B.

Step B:
The ester (Step A) was dissolved in 50 mL of ethanol and a catalytic amount of palladium on carbon was added. The reaction was hydrogenated in a Parr hydrogenator for 6 hours at room temperature. Filtration of the reaction mixture through a celite pad, followed by evaporation of the solvent under reduced pressure yielded 9.8 g of the fluoropropanoate (spectral data matched that of known literature compound).

Example 7

Preparation of 6-phenoxy-8-methyl-2-(methylsulfonyl)pyrido[2,3-d]pyrimidin-7(8H)-one (Sulfone 1)

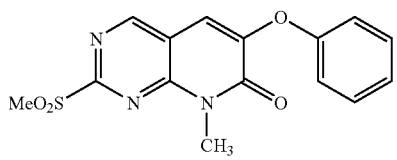

Sulfone I

Step A: Preparation of 6-phenoxy-8-methyl-2-(thiomethyl)pyrido[2,3-d]pyrimidin-7(8H)-one

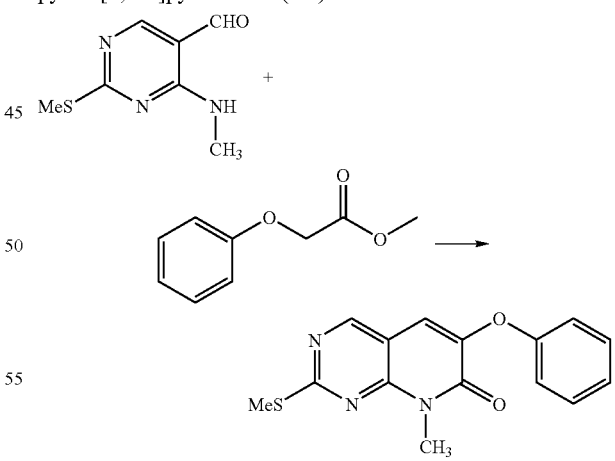

To a mixture of 4-methylamino-2-methylthiopyrimidine-5-carboxaldehyde (10 g, 54.6 mmol) and methyl phenoxyacetate (Aldrich, 11.4 g, 68.6 mmol) in 150 mL of 1-methyl-2-pyrrolidinone was added potassium carbonate (14 g, 101.4 mmol). The reaction mixture was heated to 120° C. and after 12 hours, additional phenoxyacetate (3×, 6.0 g, 36.1 mmol) and potassium carbonate (6.0 g, 44 mmol) was added. After 6 hours of stirring at 120° C., the reaction was cooled to room temperature and water (300 mL) was added. The solution was stirred for 1 hour and filtered. The resultant solid was chromatographed (SiO₂, EtOAC/Hexane—50/50 to EtOAc 100%) and then isolated via evaporation of solvents yielding 5 g of the sulfide (mass spec. M+1=300).

Step B: Preparation of 6-phenoxy-8-methyl-2-(methylsulfonyl)pyrido[2,3-d]pyrimidin-7(8H)-one (Sulfone 1)

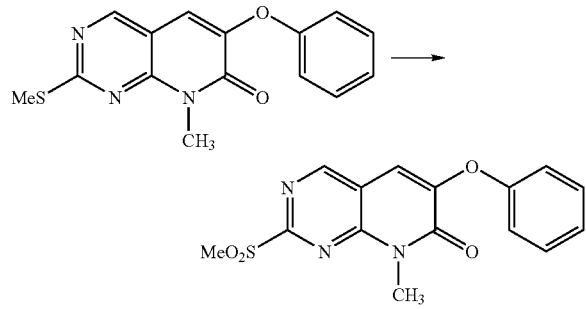

The sulfide (5.07 g, 17.8 mmol) was dissolved in 100 mL of methylene chloride and 3-chloroperbenzoic acid (77%, 5.9 g, 24 mmol) was added. The mixture was stirred at room temperature for 12 to 16 hours, filtered and then washed with aqueous sodium sulfite solution (2×, 75 mL) followed by saturated aqueous sodium bicarbonate solution (2×, 75 mL). The organic solution was then dried (brine, Na₂SO₄) and evaporated under reduced pressure. The resultant solid was chromatographed (SiO₂, EtOAc/Hexane—80/20) and then isolated via evaporation of solvents yielding 3.0 g of the sulfone (mass spec. M+1=332).

Example 8

Preparation of 6-(2-fluorophenoxy)-8-methyl-2-(methylsulfonyl)pyrido[2,3-d]pyrimidin-7(8H)-one (Sulfone 2)

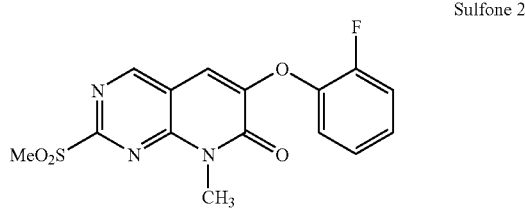

Step A: Preparation of 6-(2-fluorophenoxy)-8-methyl-2-(methylthio)pyrido[2,3-d]pyrimidin-7(8H)-one

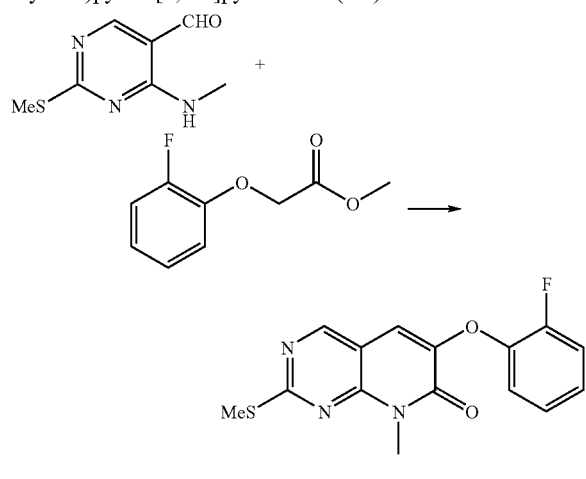

To a mixture of 4-methylamino-2-methylthiopyrimidine-5-carboxaldehyde (4.8 g, 26.2 mmol) and methyl 2-fluorophenoxyacetate (5.9 g, 32 mmol) in 50 mL of 1-methyl-2-pyrrolidinone was added potassium carbonate (6.0 g, 43.5 mmol). The reaction mixture was heated to 120° C. and after 12 hours, additional phenoxyacetate (2.0 g, 10.8 mmol) and potassium carbonate (2.0 g, 15 mmol) was added. After 6 hours of stirring at 120° C., the reaction was cooled to room temperature and water (700 mL) was added. The solution was stirred for 45 minutes and filtered. The resultant solid was washed with water (2×, 100 mL) and added to ethyl acetate (100 mL) and stirred for 1 hour. The solid was then isolated via filtration and dried yielding 6.4 g of the sulfide (mass spec. M+1=318, MP=234-236° C.).

Step B: Preparation of 6-(2-fluorophenoxy)-8-methyl-2-(methylsulfonyl)pyrido[2,3-d]pyrimidin-7(8H)-one (Sulfone 2)

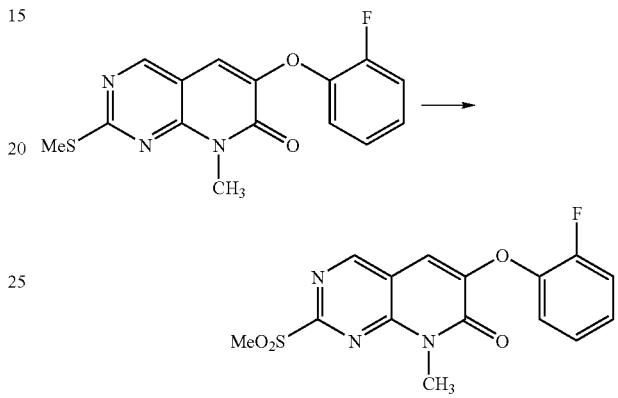

The sulfide (6.3 g, 20.5 mmol) was dissolved in 50 mL of methylene chloride and 3-chloroperbenzoic acid (77%, 9.9 g, 44.2 mmol) was added. The mixture was stirred at room temperature for 12 to 16 hours, then washed with aqueous sodium sulfite solution (2×, 75 mL) followed by saturated aqueous sodium bicarbonate solution (3×, 75 mL). The organic solution was then dried (brine, Na₂SO₄) and evaporated. The resultant solid was stirred with ether for 1 hour and filtered to yield the sulfone (mass spec. M+1=350, MP=158-162° C.).

Example 9

Preparation of 6-(3-fluorophenoxy)-8-methyl-2-(methylsulfonyl)pyrido[2,3-d]pyrimidin-7(8H)-one (Sulfone 3)

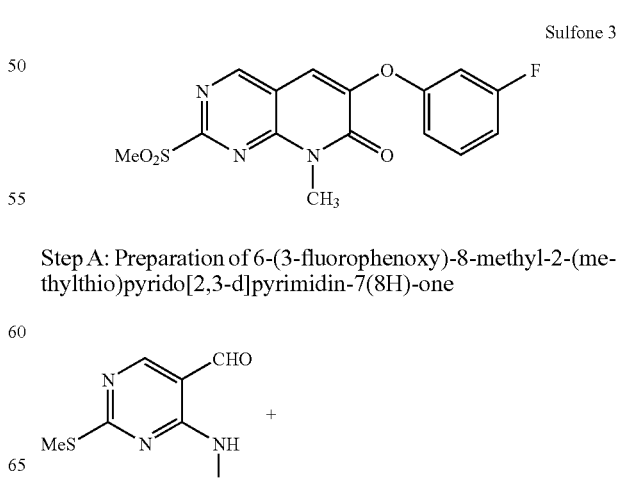

Step A: Preparation of 6-(3-fluorophenoxy)-8-methyl-2-(methylthio)pyrido[2,3-d]pyrimidin-7(8H)-one -continued

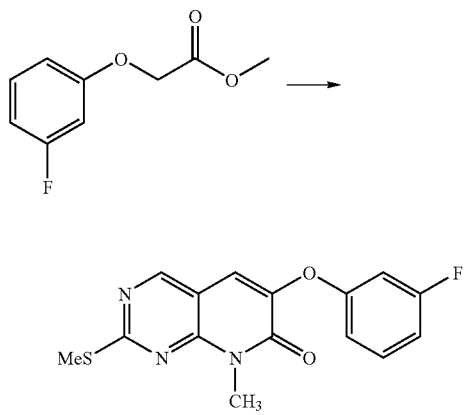

To a mixture of 4-methylamino-2-methylthiopyrimidine-5-carboxaldehyde (0.55 g, 26.2 mmol) and methyl 3-fluorophenoxyacetate (0.61 g, 3.3 mmol) in 5 mL of 1-methyl-2-pyrrolidinone was added potassium carbonate (0.6 g, 4.3 mmol). The reaction mixture was heated to 120° C. and after 12 hours, additional phenoxyacetate (0.3 g, 1.5 mmol) and potassium carbonate (0.4 g, 2.9 mmol) was added. After 6 hours of stirring at 120° C., the reaction was cooled to room temperature and water (100 mL) was added. The reaction mixture was extracted with ethyl acetate (2×, 75 mL) and the resultant organic solution was washed with water (5×, 50 mL) then dried (brine, MgSO$_4$). Evaporation of the solution yielded a solid which was recrystalized (EtOAc/Hexane) yielding 1.0 g of the sulfide (mass spec. M+1=317).

Step B: Preparation of 6-(3-fluorophenoxy)-8-methyl-2-(methylsulfonyl)pyrido[2,3-d]pyrimidin-7(8H)-one (Sulfone 3)

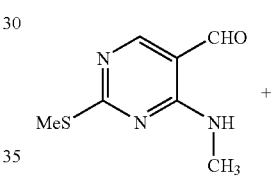

The sulfide (1.02 g, 3.2 mmol) was dissolved in 25 mL of methylene chloride and 3-chloroperbenzoic acid (77%, 1.7 g, 9.6 mmol) was added. The mixture was stirred at room temperature for 16 hours, diluted with methylene chloride (25 mL) then washed with aqueous sodium sulfite solution (3×, 50 mL) followed by saturated aqueous sodium bicarbonate solution (3×, 50 mL). The organic solution was then dried (brine, MgSO$_4$) and evaporated to yield 0.64 g of the sulfone (mass spec. M+1=349).

Example 10

Preparation of 6-(2,6-difluorophenoxy)-8-methyl-2-(methylsulfonyl)pyrido[2,3-d]pyrimidin-7(8H)-one (Sulfone 4)

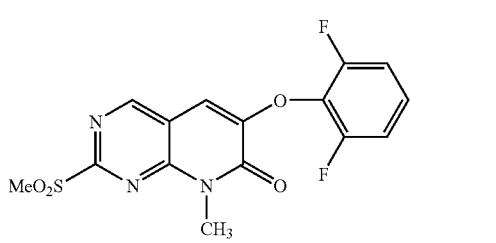

Sulfone 4

Step A: Preparation of 6-(2,6-difluorophenoxy)-8-methyl-2-(methylthio)pyrido[2,3-d]pyrimidin-7(8H)-one

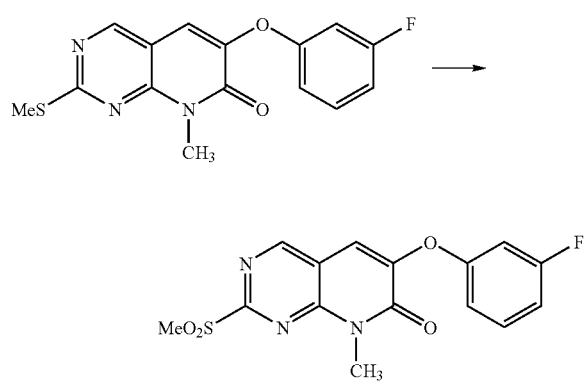

To a mixture of 4-methylamino-2-methylthiopyrimidine-5-carboxaldehyde (4.8 g, 26.2 mmol) and methyl 2,6-difluorophenoxyacetate (prepared as in Example 4 using 2,6-difluorophenol, 5.9 g, 32 mmol) in 50 mL of 1-methyl-2-pyrrolidinone was added potassium carbonate (6.0 g, 43.5 mmol). The reaction mixture was heated to 120° C. and after 12 hours, additional phenoxyacetate (2×, 2.0 g, 10.8 mmol) and potassium carbonate (2.0 g, 15 mmol) was added. After 6 hours of stirring at 120° C., the reaction was cooled to room temperature and water (70 mL) was added. The solution was stirred for 30 minutes and filtered. The resultant solid was washed with water (2×), ethyl acetate and ether. The solid was then dried yielding 7.0 g of the sulfide (mass spec. M+1=336, MP=247-250.7° C.).

Step B: Preparation of 6-(2,6-difluorophenoxy)-8-methyl-2-(methylsulfonyl)pyrido[2,3-d]pyrimidin-7(8H)-one (Sulfone 4)

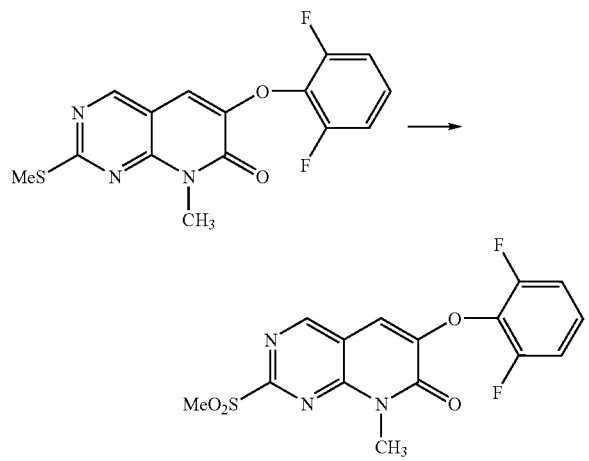

The sulfide (7.0 g, 20.8 mmol) was dissolved in 50 mL of methylene chloride and 3-chloroperbenzoic acid (77%, 11.5 g, 51.5 mmol) was added. The mixture was stirred at room temperature for 16 hours, filtered then washed with aqueous sodium sulfite solution (2×, 75 mL) followed by saturated aqueous sodium bicarbonate solution (3×, 75 mL). The organic solution was then dried (brine, $Na_2SO_4$) and evaporated. The resultant solid was stirred with ether for 1 hour and filtered to yield 5.5 g of the sulfone (mass spec. M+1=368, MP=215.2-216.4° C.).

Example 11

Preparation of 6-(2,4-difluorophenoxy)-8-methyl-2-(methylsulfonyl)pyrido[2,3-d]pyrimidin-7(8H)-one (Sulfone 5)

Sulfone 5

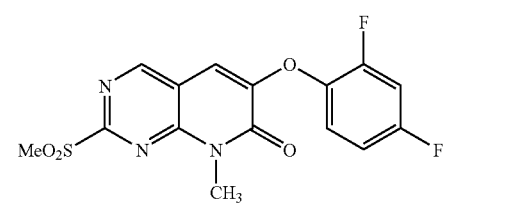

Step A: Preparation of 6-(2,4-difluorophenoxy)-8-methyl-2-methylthio)pyrido[2,3-d]pyrimidin-7(8H)-one

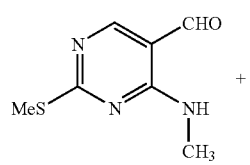

+

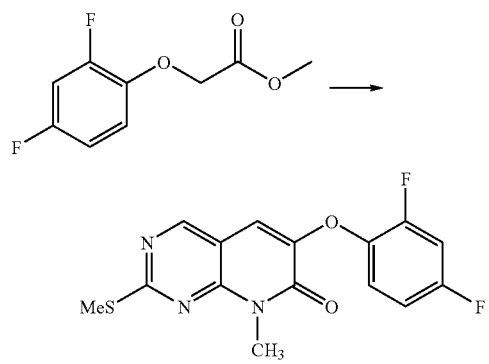

To a mixture of 4-methylamino-2-methylthiopyrimidine-5-carboxaldehyde (4.8 g, 26.2 mmol) and methyl 2,4-difluorophenoxyacetate (prepared as in Example 4 using 2,4-difluorophenol, 5.4 g, 29 mmol) in 50 mL of 1-methyl-2-pyrrolidinone was added potassium carbonate (6.0 g, 43.5 mmol). The reaction mixture was heated to 120° C. and after 12 hours, additional phenoxyacetate (2.5 g, 13.4 mmol) and potassium carbonate (2.5 g, 18 mmol) was added. After 6 hours of stirring at 120° C., the reaction was cooled to room temperature and water (100 mL) was added. The solution was stirred for 45 minutes and filtered. The resultant solid was washed with water (3×) and added to ethyl acetate (75 mL) and stirred for 1 hour. The solid was then isolated via filtration and dried yielding 6.1 g of the sulfide (mass spec. M+1=336, MP=175.2-176.9° C.).

Step B: Preparation of 6-(2,4-difluorophenoxy)-8-methyl-2-(methylsulfonyl)pyrido[2,3-d]pyrimidin-7(8H)-one (Sulfone 5)

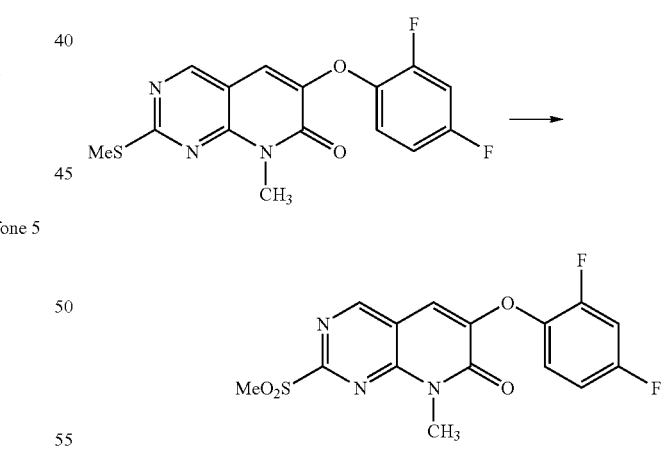

The sulfide (6.0 g, 20.5 mmol) was dissolved in 50 mL of methylene chloride and 3-chloroperbenzoic acid (77%, 9.3 g, 41.5 mmol) was added. The mixture was stirred at room temperature for 16 hours, then washed with aqueous sodium sulfite solution (2×, 75 mL) followed by saturated aqueous sodium bicarbonate solution (3×, 75 mL). The organic solution was then dried (brine, $Na_2SO_4$) and evaporated. The resultant solid was stirred with ether for 1 hour and filtered to yield the sulfone (mass spec. M+1=368, MP=177.2-178.5° C.).

Example 12

Preparation of 6-(2-chlorophenoxy)-8-methyl-2-(methylsulfonyl)pyrido[2,3-d]pyrimidin-7(8H)-one (Sulfone 6)

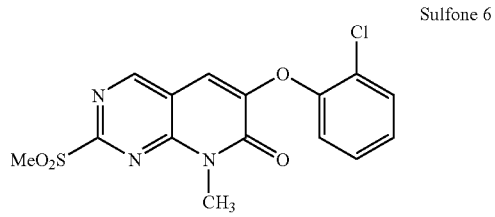
Sulfone 6

Step A: Preparation of 6-(2-chlorophenoxy)-8-methyl-2-(methylthio)pyrido[2,3-d]pyrimidin-7(8H)-one

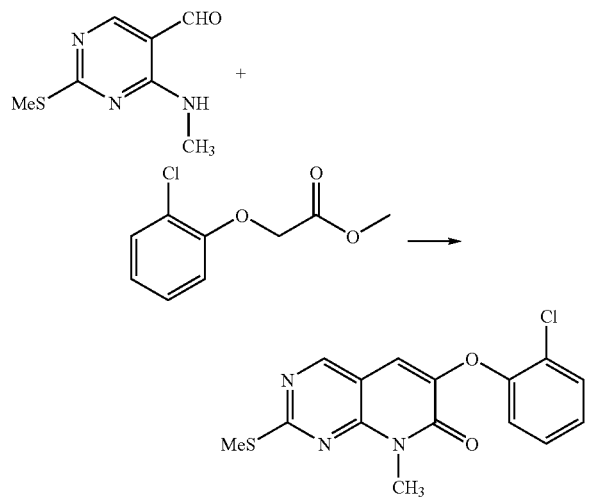

To a mixture of 4-methylamino-2-methylthiopyrimidine-5-carboxaldehyde (5.5 g, 30 mmol) and methyl 2-chlorophenoxyacetate (prepared as in Example 4 using 2-chlorophenol, 7.0 g, 35 mmol) in 80 mL of 1-methyl-2-pyrrolidinone was added potassium carbonate (9.0 g, 65.2 mmol). The reaction mixture was heated to 120° C. and after 12 hours, additional phenoxyacetate (2×, 0.5 g, 2.5 mmol) and potassium carbonate (2×, 2.0 g, 15 mmol) was added. After 6 hours of stirring at 120° C., the reaction was cooled to room temperature and water (100 mL) was added. The solution was stirred for 45 minutes and filtered. The resultant solid was filtered and washed with water (2×) and ether (2×). Drying of the product via vacuum oven yielded 9.0 g of the sulfide (mass spec. M+1=334).

Step B: Preparation of 6-(2-chlorophenoxy)-8-methyl-2-(methylsulfonyl)pyrido[2,3-d]pyrimidin-7(8H)-one (Sulfone 6)

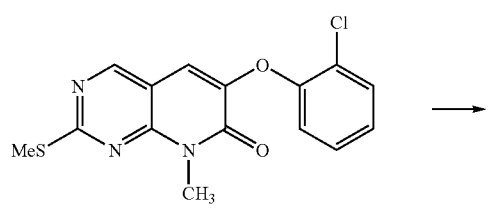

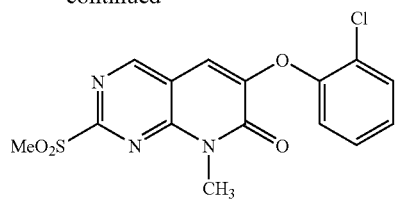

The sulfide (8.9 g, 26.7 mmol) was dissolved in 70 mL of methylene chloride and 3-chloroperbenzoic acid (77%, 13 g, 58 mmol) was added. The mixture was stirred at room temperature for 16 hours, filtered then washed with aqueous sodium sulfite solution (2×, 75 mL) followed by saturated aqueous sodium bicarbonate solution (3×, 75 mL). The organic solution was then dried (brine, Na$_2$SO$_4$) and evaporated. The resultant solid was stirred with ether for 18 hours and filtered to yield 8.5 g of the sulfone (mass spec. M+1=366).

Example 13

Preparation of 6-(4-chlorophenoxy)-8-methyl-2-(methylsulfonyl)pyrido[2,3-d]pyrimidin-7(8H)-one (Sulfone 7)

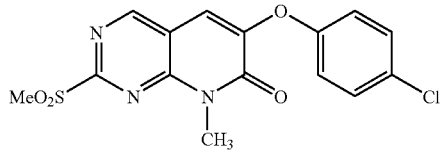
Sulfone 7

Step A: Preparation of 6-(4-chlorophenoxy)-8-methyl-2-(methylthio)pyrido[2,3-d]pyrimidin-7(8H)-one

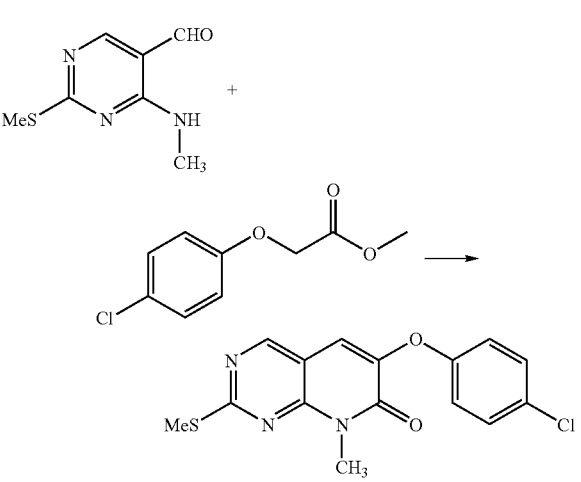

To a mixture of 4-methylamino-2-methylthiopyrimidine-5-carboxaldehyde (0.55 g, 3.0 mmol) and methyl 4-chlorophenoxyacetate (prepared as in Example 4 using 4-chlorophenol, 0.66 g, 3.3 mmol) in 5 mL of 1-methyl-2-pyrrolidinone was added potassium carbonate (0.5 g, 3.6 mmol). The reaction mixture was heated to 120° C. and after 12 hours, additional phenoxyacetate (0.3 g, 1.5 mmol) and potassium carbonate (0.4 g, 2.9 mmol) was added. After 6 hours of stirring at 120° C., the reaction was cooled to room temperature and poured into water (100 mL). The reaction mixture was extracted with ethyl acetate (2×, 75 mL) and the resultant organic solution was washed with water (5×, 50 mL) then dried (brine, MgSO$_4$). Evaporation of the solution yielded a solid which was recrystalized (EtOAc/Hexane) yielding 0.55 g of the sulfide (mass spec. M+1=334).

Step B: Preparation of 6-(4-chlorophenoxy)-8-methyl-2-(methylsulfonyl)pyrido[2,3-d]pyrimidin-7(8H)-one (Sulfone 7)

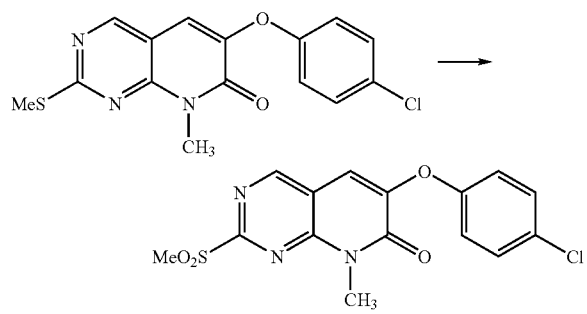

The sulfide (1.44 g, 4.3 mmol) was dissolved in 50 mL of methylene chloride and 3-chloroperbenzoic acid (77%, 2.2 g, 12.8 mmol) was added. The mixture was stirred at room temperature for 16 hours, filtered then washed with aqueous sodium sulfite solution (3×, 75 mL) followed by saturated aqueous sodium bicarbonate solution (3×, 50 mL). The organic solution was then dried (brine, MgSO$_4$) and evaporated. The resultant solid was stirred with ether for 18 hours and filtered to yield 0.7 g of the sulfone (mass spec. M+1=366).

Example 14

Preparation of 8-methyl-2-(methylthio)-6-(phenylthio)pyrido[2,3-d]pyrimidin-7(8H)-one (Sulfide 1)

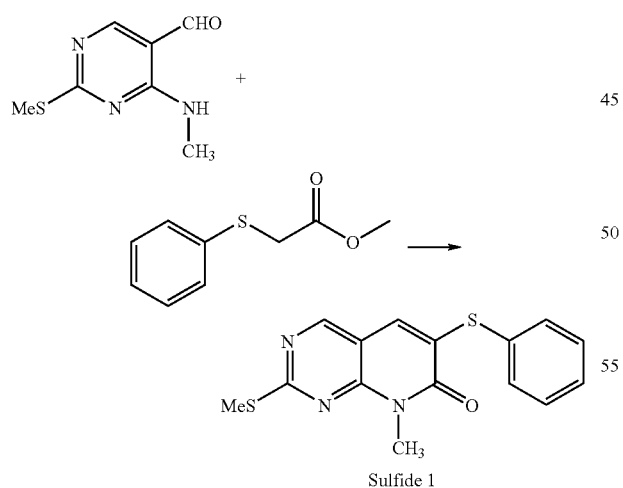

Sulfide 1

To a mixture of 4-methylamino-2-methylthiopyrimidine-5-carboxaldehyde (549 mg, 3 mmol) and methyl(phenylthio)acetate (600 mg, 3.3 mmol) in 25 mL of 1-methyl-2-pyrrolidinone was added potassium carbonate (750 mg, 5.4 mmol). The reaction mixture was heated to 120° C. and after 12 hours, it was cooled to room temperature and water (50 mL) was added. The aqueous mixture was extracted with ethyl acetate (75 mL) yielding a organic solution which was washed with water (2×, 50 mL) and dried (brine, Na$_2$SO$_4$). Evaporation of the solvent yielded a solid which was stirred with ether and hexane for 1 hour. Filtration of the solid yielded 0.67 g of the sulfide (mass spec. M+1=316).

Example 15

Preparation of 6-[(4-fluorophenyl)thio]-8-methyl-2-(methylthio)pyrido[2,3-d]pyrimidin-7(8H)-one (Sulfide 2)

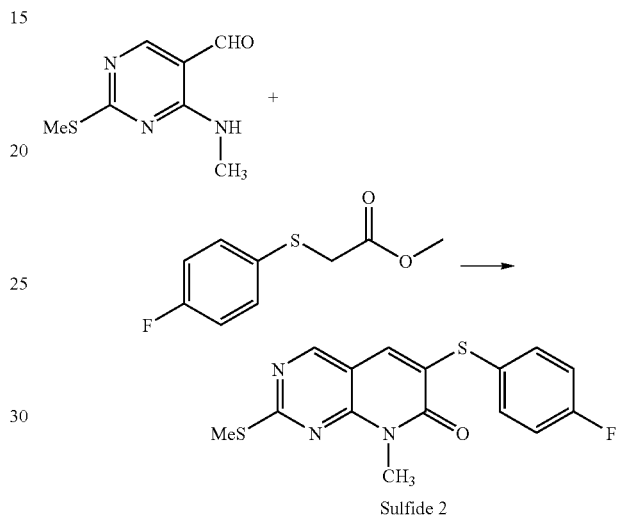

Sulfide 2

To a mixture of 4-methylamino-2-methylthiopyrimidine-5-carboxaldehyde (0.55 g, 3 mmol) and methyl(4-fluorophenylthio)acetate (prepared as in Example 5 using 4-fluorothiophenol, 0.65 g, 3.3 mmol) in 25 mL of 1-methyl-2-pyrrolidinone was added 1,3,4,6,7,8-hexahydro-2H-pyrimido(1,2-a)pyrimidine polymer bound resin base (Aldrich, 200 mg). The reaction mixture was heated to 120° C. After 12 hours it was cooled to room temperature and added to water (50 mL). The aqueous mixture was extracted with ethyl acetate (75 mL) yielding a organic solution which was washed with water (2×, 50 mL) and dried (brine, Na$_2$SO$_4$). Evaporation of the solvent yielded 0.95 g of the sulfide (mass spec. M+1=334).

Example 16

Preparation of 6-(2-fluorobenzyl)-8-methyl-2-(methylsulfonyl)pyrido[2,3-d]pyrimidin-7(8H)-one (Sulfone 8)

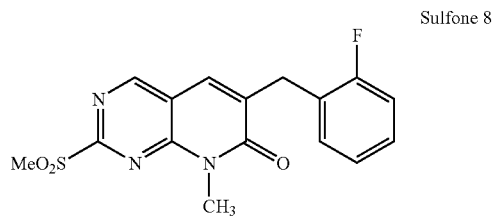

Sulfone 8

Step A: Preparation of 6-(2-fluorobenzyl)-8-methyl-2-(methylthio)pyrido[2,3-d]pyrimidin-7(8H)-one

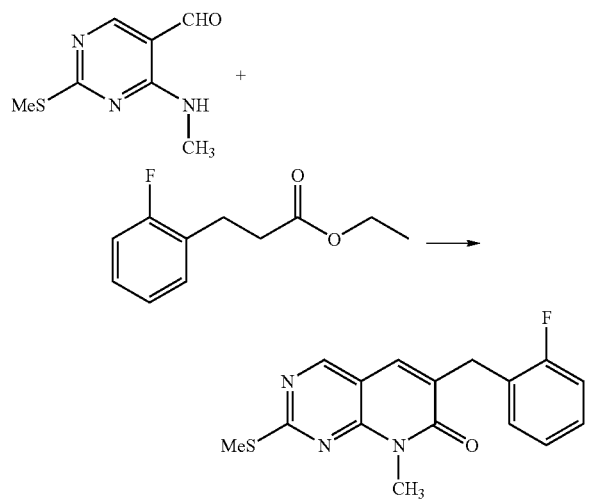

To a mixture of 4-methylamino-2-methylthiopyrimidine-5-carboxaldehyde (4.8 g, 26.2 mmol) and ethyl 3-(2-fluorophenyl)propanoate (5.7 g, 29 mmol) in 50 mL of 1-methyl-2-pyrrolidinone was added potassium carbonate (6.0 g, 43.5 mmol). The reaction mixture was heated to 120° C. and after 12 hours, additional propanoate (1.5 g, 7.6 mmol) and potassium carbonate (3.0 g, 22 mmol) was added. After 6 hours of stirring at 120° C., the reaction was cooled to room temperature and water (700 mL) was added. The solution was stirred for 45 minutes and filtered. The resultant solid was washed with water (3×, 50 mL) and added to ethyl acetate (75 mL) and stirred for 1 hour. The solid was then isolated via filtration and dried yielding 7.5 g of the sulfide (mass spec. M+1=316, MP=156-159° C.).

Step B: Preparation of 6-(2-fluorobenzyl)-8-methyl-2-(methylsulfonyl)pyrido[2,3-d]pyrimidin-7(8H)-one (Sulfone 8)

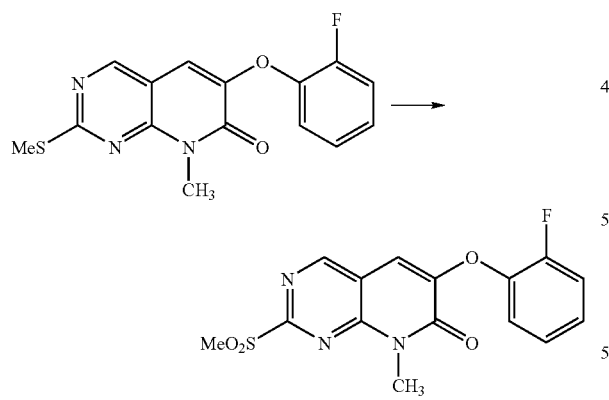

The sulfide (7.4 g, 23.5 mmol) was dissolved in 50 mL of methylene chloride and 3-chloroperbenzoic acid (77%, 11.5 g, 51 mmol) was added. The mixture was stirred at room temperature for 16 hours, filtered and then washed with aqueous sodium sulfite solution (2×, 75 mL) followed by saturated aqueous sodium bicarbonate solution (3×, 75 mL). The organic solution was then dried (brine, Na₂SO₄) and evaporated. The resultant solid was stirred with ether for 1 hour and filtered to yield the sulfone (mass spec. M+1=348, MP=153.8-154.4° C.).

Example 17

Preparation of 6-(4-fluorobenzyl)-8-methyl-2-(methylsulfonyl)pyrido[2,3-d]pyrimidin-7(8H)-one (Sulfone 9)

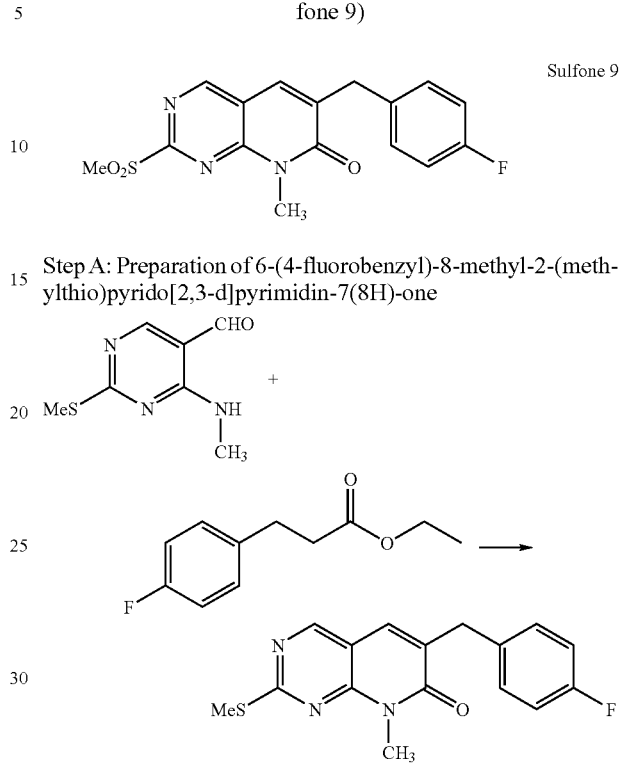

Step A: Preparation of 6-(4-fluorobenzyl)-8-methyl-2-(methylthio)pyrido[2,3-d]pyrimidin-7(8H)-one To a mixture of 4-methylamino-2-methylthiopyrimidine-5-carboxaldehyde (4.8 g, 26.2 mmol) and ethyl 3-(4-fluorophenyl)propanoate (prepared as in Example 6, 5.7 g, 29 mmol) in 50 mL of 1-methyl-2-pyrrolidinone was added potassium carbonate (6.0 g, 43.5 mmol). The reaction mixture was heated to 120° C. and after 12 hours, additional propanoate (1.5 g, 7.6 mmol) and potassium carbonate (3.0 g, 22 mmol) was added. After 6 hours of stirring at 120° C., the reaction was cooled to room temperature and water (100 mL) was added. The solution was stirred for 45 minutes and filtered. The resultant solid was washed with water (2×) and then isolated via filtration and dried yielding 6.5 g of the sulfide (mass spec. M+1=316).

Step B: Preparation of 6-(4-fluorobenzyl)-8-methyl-2-(methylsulfonyl)pyrido[2,3-d]pyrimidin-7(8H)-one (Sulfone 9)

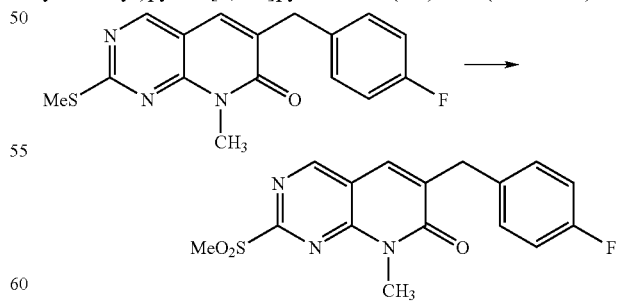

The sulfide (6.5 g, 20.6 mmol) was dissolved in 50 mL of methylene chloride and 3-chloroperbenzoic acid (77%, 10.1 g, 45 mmol) was added. The mixture was stirred at room temperature for 16 hours, filtered and then washed with aqueous sodium sulfite solution (2×, 75 mL) followed by saturated aqueous sodium bicarbonate solution (3×, 75 mL). The organic solution was then dried (brine, Na$_2$SO$_4$) and evaporated. The resultant solid was stirred with ether for 1 hour and filtered to yield 6.7 g of the sulfone (mass spec. M+1=348).

Example 18

Preparation of 8-cyclopropyl-6-(2-fluorophenoxy)-2-(methylsulfonyl)pyrido[2,3-d]pyrimidin-7(8H)-one (Sulfone 10)

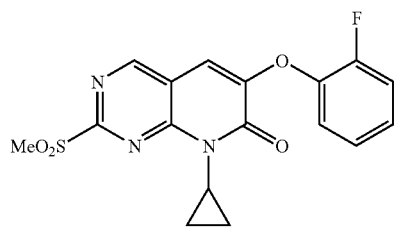

Sulfone 10

Step A: Preparation of 8-cyclopropyl-6-(2-fluorophenoxy)-2-(methylthio)pyrido[2,3-d]pyrimidin-7(8H)-one

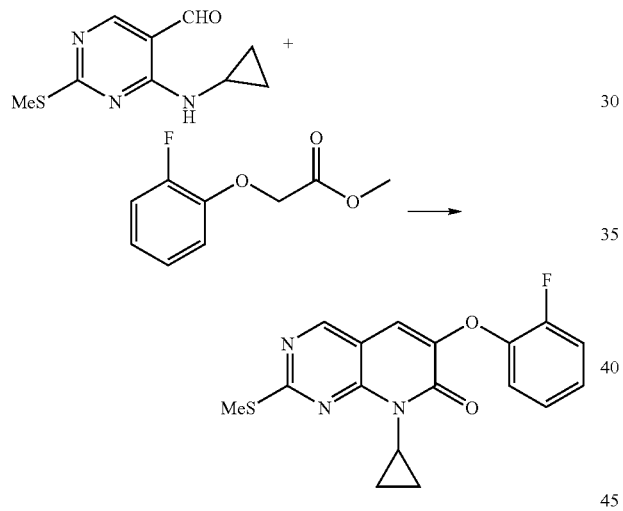

The cyclopropyl sulfide was prepared using the procedure described in Example 8 (step A) starting with 4-(cyclopropylamino)-2-(methylthio)pyrimidine-5-carboxaldehyde (Example 2, 1.814 g, 8.67 mmol) and methyl 2-fluorophenoxyacetate (Example 4, 1.756 g, 9.53 mmol). It was taken directly on to Step B.

Step B: Preparation of 8-cyclopropyl-6-(2-fluorophenoxy)-2-(methylsulfonyl)pyrido[2,3-d]pyrimidin-7(8H)-one (Sulfone 10)

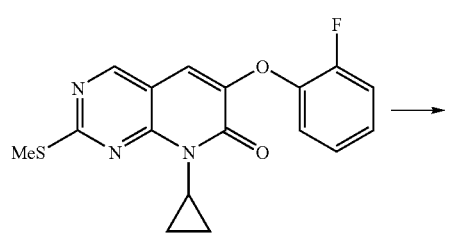

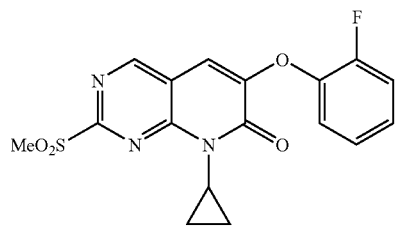

The sulfide (3.02 g, 8.8 mmol) was dissolved in 50 mL of tetrahydrofuran, cooled to 0° C. and oxone (Aldrich, 10.8 g, 17.6 mmol) in 50 mL of water was added dropwise holding the temperature constant. After the addition was completed, the reaction mixture was allowed to warm to room temperature and stir for 4 hours. Water (50 mL) and ethyl acetate (75 mL) were then added and the reaction was partitioned between the two phases. The organic layer was dried (brine, MgSO$_4$) and evaporation of the solvent yielded 2.26 g of the sulfone (mass spec. M+1=376).

Example 19

Preparation of 6-(2-fluorophenoxy)-8-(4-fluorophenyl)-2-(methylsulfonyl)pyrido[2,3-d]pyrimidin-7(8H)-one (Sulfone 11)

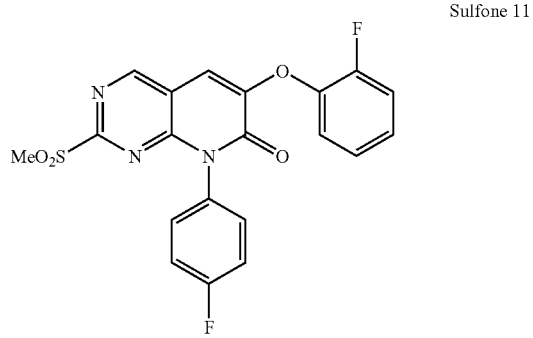

Sulfone 11

Step A: Preparation of 6-(2-fluorophenoxy)-8-(4-fluorophenyl)-2-(methylthio)pyrido[2,3-d]pyrimidin-7(8H)-one

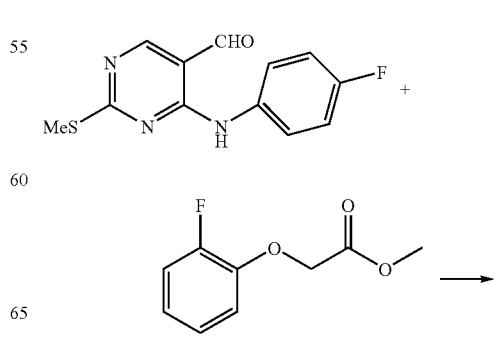

-continued

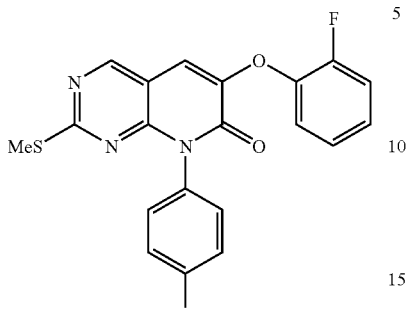

The fluorophenyl sulfide was prepared using the procedure described in Example 8 (step A) starting with 4-[(4-fluorophenyl)amino]-2-(methylthio)pyrimidine-5-carbaldehyde (Example 3, 1.22 g, 4.6 mmol) and methyl 2-fluorophenoxyacetate (Example 4, 0.93 g, 5.7 mmol). It was taken directly on to Step B.

Step B: Preparation of 6-(2-fluorophenoxy)-8-(4-fluorophenyl)-2-(methylsulfonyl)pyrido[2,3-d]pyrimidin-7(8H)-one (Sulfone 11)

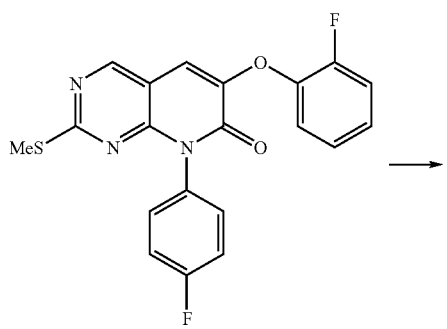

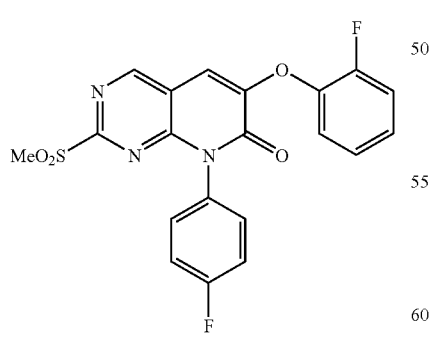

The sulfide (0.75 g, 1.88 mmol) was dissolved in 20 mL of tetrahydrofuran, cooled to 0° C. and oxone (Aldrich, 2.38 g, 3.88 mmol) in 20 mL of water was added dropwise holding the temperature constant. After the addition was completed, the reaction mixture was allowed to warm to room temperature and stir for 4 hours. Water (100 mL) and ethyl acetate (100 mL) were then added and the reaction was partitioned between the two phases. The organic layer was dried (brine, MgSO$_4$) and evaporation of the solvent yielded 0.77 g of the sulfone (mass spec. M+1=414, MP=82.3-91.5° C.).

Example 20

Preparation of 2-amino-6-(2-fluorophenoxy)-8-methyl-pyrido[2,3-d]pyrimidin-7(8H)-one

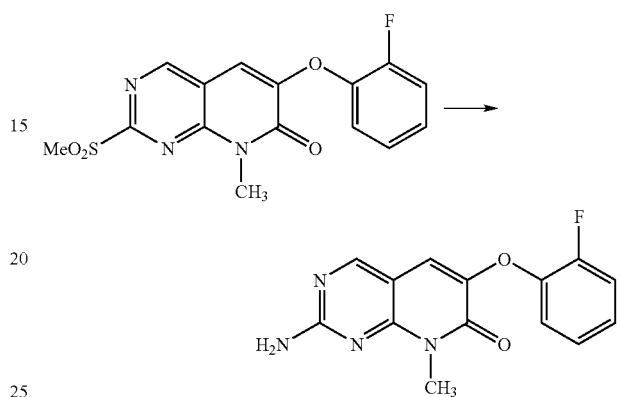

A mixture of sulfone 2 (0.315 g, 0.9 mmol) and ammonia (0.5M in 1,4-dioxane, 2 mL, 1 mmole) in 1 mL of 1-methyl-2-pyrrolidinone was heated to 80° C. for 4 hours under a nitrogen atmosphere. The reaction mixture was cooled, evaporated under reduced pressure and purified via column chromatography (SiO$_2$, CH$_2$Cl$_2$/MeOH—99/1). Isolation of the product via evaporation of solvents and drying provided 0.33 g of the amine (Mass spec. M+1=287, MP=240.8-242.6° C.).

Example 21

Preparation of 6-(phenoxy)-8-methyl-2-(tetrahydro-2H-pyran-4-ylamino)pyrido[2,3-d]pyrimidin-7(8H)-one

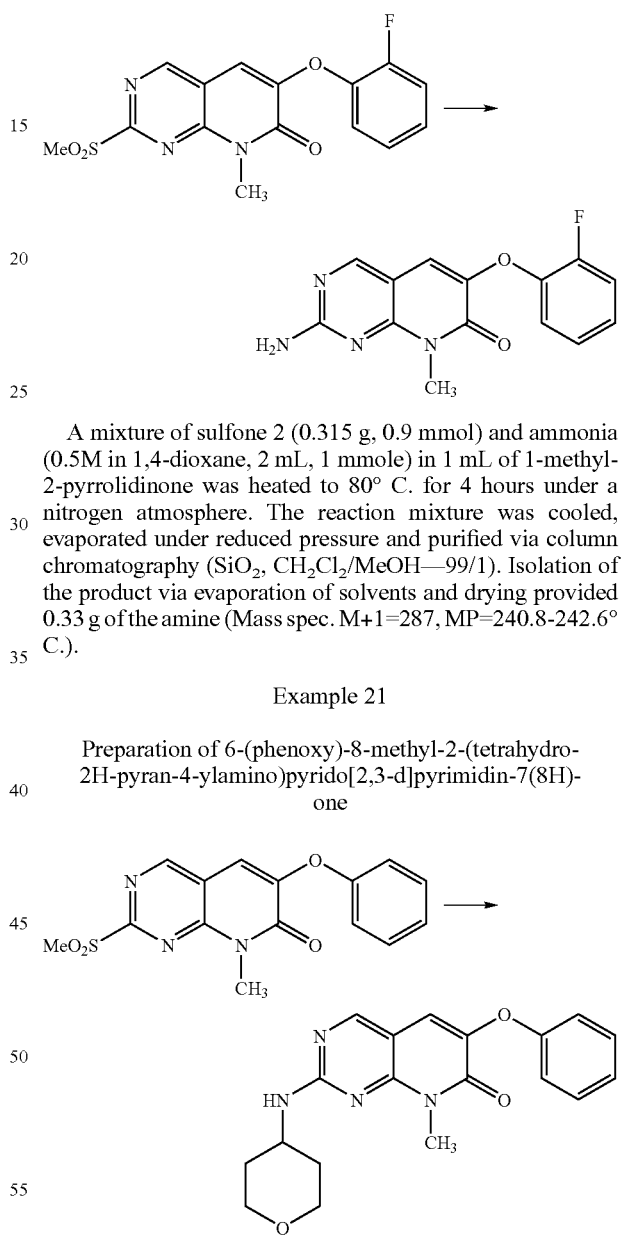

A mixture of sulfone 1 (0.20 g, 0.6 mmol) and 4-aminotetrahydropyran (Combi-Blocks—vendor, 0.183 g, 1.81 mmol) in 0.2 mL of 1-methyl-2-pyrrolidinone was heated to 80° C. for 3 hours. The reaction mixture was cooled, poured into water and extracted with ethyl acetate (2×, 50 mL). The organic solution was washed with water (5×, 50 mL) and dried (brine, MgSO$_4$). Evaporation of the solvent and addition of methanol followed by acidification (1M, HCL/Et$_2$O, 1.5 eq) yielded the hydrochloride salt which was isolated as a solid via filtration (0.166 g, mass spec. M+1=353).

Example 22

Preparation of 6-(3-fluorophenoxy)-8-methyl-2-(tetrahydro-2H-pyran-4-ylamino)pyrido[2,3-d]pyrimidin-7(8H)-one

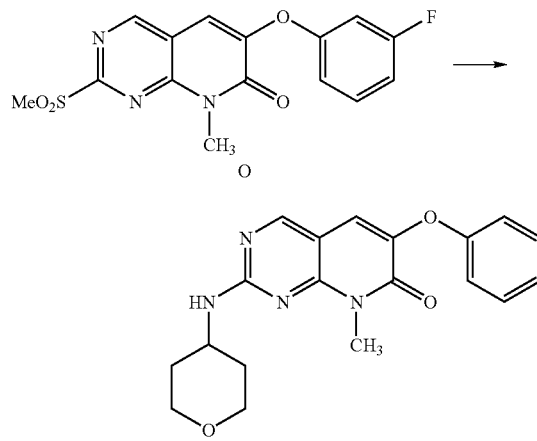

A mixture of sulfone 3 (0.20 g, 0.57 mmol) and 4-aminotetrahydropyran (Combi-Blocks—vendor, 0.173 g, 1.72 mmol) in 0.2 mL of 1-methyl-2-pyrrolidinone was heated to 80° C. for 3 hours. The reaction mixture was cooled and methanol (0.2-0.5 mL) was added. The product precipitated and was isolated via filtration. The yellow solid was transferred to a flask with methanol (5 mL). Dropwise addition of hydrochloric acid in ether (1M, 1.5 eq) followed by stirring for 15 hours yielded the hydrochloride salt which was isolated as a solid (0.129 g, mass spec. M+1=371).

Example 23

Preparation of 6-(2,4-difluorophenoxy)-8-methyl-2-(tetrahydro-2H-pyran-4-ylamino)pyrido[2,3-d]pyrimidin-7(8H)-one

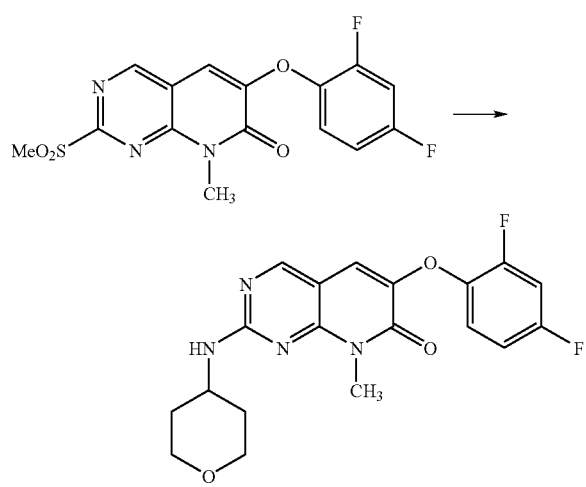

A mixture of sulfone 5 (0.20 g, 0.54 mmol) and 4-aminotetrahydropyran (Combi-Blocks—vendor, 0.165 g, 1.63 mmol) in 0.3 mL of 1-methyl-2-pyrrolidinone was heated to 80° C. for 3 hours. The reaction mixture was cooled, poured into water and extracted with ethyl acetate (2×, 50 mL). The organic solution was washed with water (5×, 25 mL) and dried (brine, MgSO$_4$). Evaporation of the solvent and addition of methanol followed by hydrochloric acid in ether (1M, 1.5 eq) yielded the hydrochloride salt which was isolated as a solid via filtration (0.180 g, mass spec. M+1=389).

Example 24

Preparation of 6-(2-fluorobenzyl)-8-methyl-2-(tetrahydro-2H-pyran-4-ylamino)pyrido[2,3-d]pyrimidin-7(8H)-one

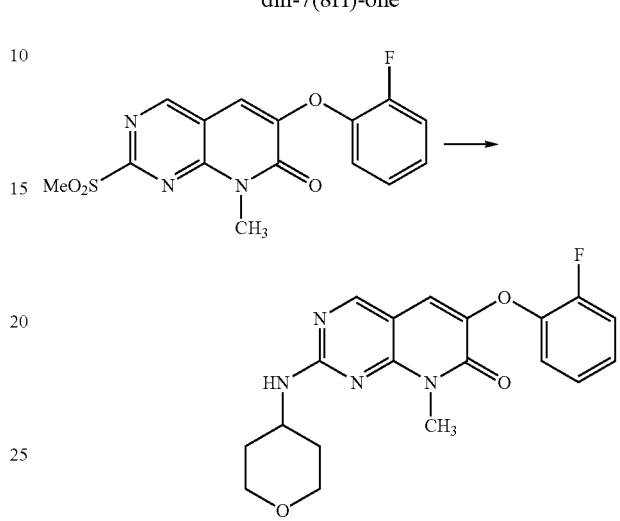

A mixture of sulfone 8 (0.35 g, 1.01 mmol) and 4-aminotetrahydropyran (Combi-Blocks—vendor, 0.35 g, 3.47 mmol) in 0.3 mL of 1-methyl-2-pyrrolidinone was heated to 80° C. for 3 hours. The reaction mixture was cooled, poured into water and extracted with ethyl acetate (2×, 50 mL). The organic solution was washed with water (5×, 25 mL) and dried (brine, MgSO$_4$). Evaporation of the solvent and column chromatography (SiO$_2$, CH$_2$Cl$_2$/MeOH—95/5) provided the product which was transferred to a flask with methanol (5 mL). Dropwise addition of hydrochloric acid in ether (1M, 1.5 eq) followed by stirring for 1 hour yielded the hydrochloride salt which was isolated as a solid via filtration (0.299 g, mass spec. M+=369, MP=198.4-201.6° C.).

Example 25

Preparation of 6-[(4-fluorophenyl)thio]-2-[(4-hydroxycyclohexyl)amino]-8-methylpyrido[2,3-d]pyrimidin-7(8H)-one

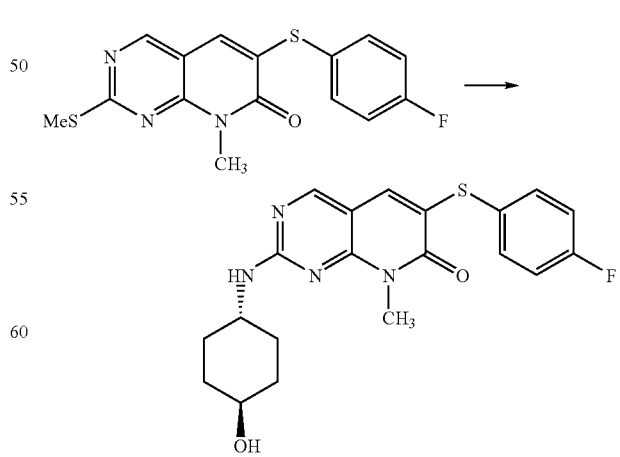

A mixture of sulfide 2 (0.333 g, 1.0 mmol) and trans-4-aminocyclohexanol (0.345 g, 3.0 mmol) in 0.3 mL of 1-methyl-2-pyrrolidinone was heated to 120° C. for 24 hours. The reaction mixture was cooled, poured into water and stirred for 2 hours. The resultant solid was filtered, rinsed with water (2×) and dried. The product was transferred to a flask with methanol (5 mL) and hydrochloric acid in ether (1M, 1.5 eq) was added dropwise. The organic solvents were evaporated under reduced pressure and ether/methanol was added. Stirring for 2 hours followed by filtration and drying yielded the hydrochloride salt which was isolated as a solid (0.286 g, mass spec. M+1=401, MP=246.2-247.5° C.).

Example 26

Preparation of 6-(4-fluorophenoxy)-2-[(4-hydroxy-cyclohexyl)amino]-8-methylpyrido[2,3-d]pyrimidin-7(8H)-one

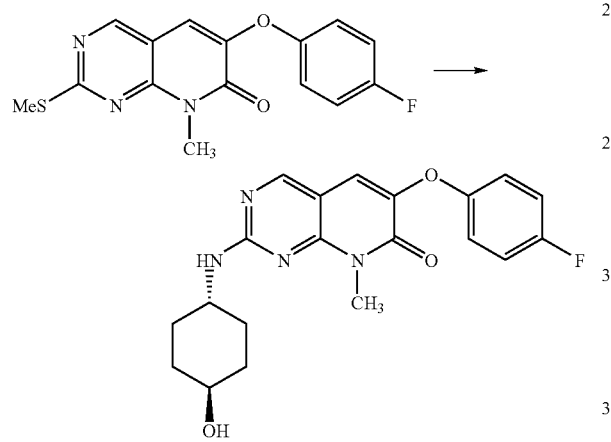

A mixture of 4-fluorophenoxy sulfide (see Example 8-Step A, 0.4 g, 1.26 mmol) and trans-4-aminocyclohexanol (0.7 g, 6.0 mmol) in 0.5 mL of 1-methyl-2-pyrrolidinone was heated to 120° C. for 24 hours. The reaction mixture was cooled, poured into water and extracted with ethyl acetate (2×, 50 mL). The organic solution was washed with water (5×, 25 mL) and dried (brine, MgSO$_4$). Evaporation of the solvent and chromatography (SiO$_2$, CH$_2$Cl$_2$/MeOH—95/5) provided the product which was transferred to a flask with methanol (5 mL). Dropwise addition of hydrochloric acid in ether (1M, 1.5 eq) followed by stirring for 1 hour yielded the hydrochloride salt which was isolated as a solid via filtration (0.286 g, mass spec. M+1=385, MP=253.2-253.9° C.).

Example 27

Preparation of 6-(2-fluorobenzyl)-2-[(4-hydroxycyclohexyl)amino]-8-methylpyrido[2,3-d]pyrimidin-7(8H)-one

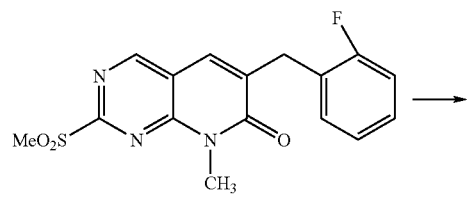

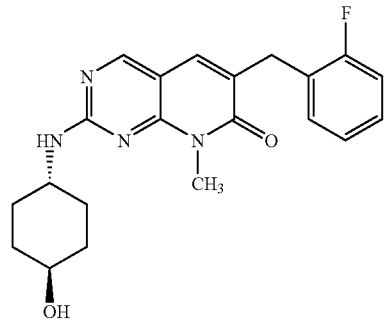

A mixture of sulfone 8 (0.348 g, 1.0 mmol) and trans-4-aminocyclohexanol (0.35 g, 3.0 mmol) in 0.35 mL of 1-methyl-2-pyrrolidinone was heated to 80° C. for 30 minutes. The reaction mixture was cooled and methanol (0.2-0.5 mL) was added with stirring. The product precipitated and was isolated via filtration. The solid was transferred to a flask with methanol (5 mL). Dropwise addition of hydrochloric acid in ether (1M, 1.5 eq) followed by stirring for 30 minutes yielded the hydrochloride salt which was isolated as a solid (0.233 g, mass spec. M+1=383, MP=229.5-230.2° C.).

Example 28

Preparation of 6-(2-fluorophenoxy)-2-[(4-methoxy-cyclohexyl)amino]-8-methylpyrido[2,3-d]pyrimidin-7(8H)-one

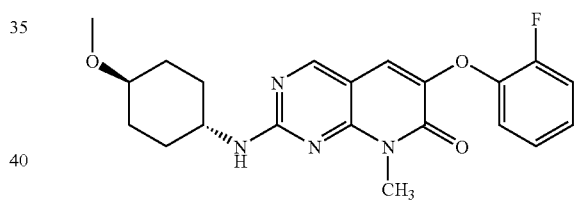

Step A: Preparation of 6-(2-fluorophenoxy)-2-[(4-hydroxy-cyclohexyl)amino]-8-methylpyrido[2,3-d]pyrimidin-7(8H)-one

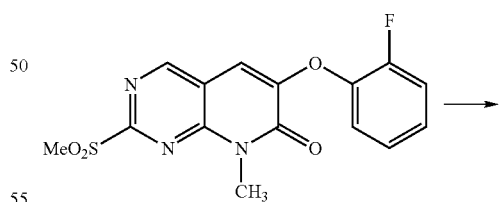

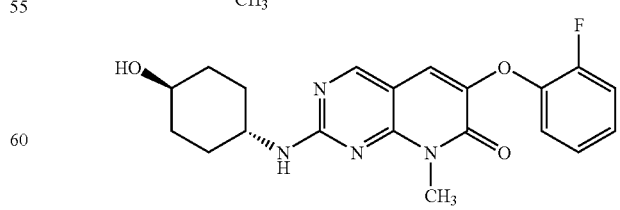

A mixture of sulfone 2 (0.20 g, 1.15 mmol) and trans-4-aminocyclohexanol (0.123 g, 1.15 mmol) in 2 mL of 1-methyl-2-pyrrolidinone was heated to 120° C. for 17 hours. The reaction mixture was cooled to room temperature, evaporated

49 under reduced pressure and purified by column chromatography (SiO$_2$, CH$_2$Cl$_2$/MeOH—95/5). Fractions containing product were combined and evaporated to yield 0.20 g of the product. This was taken directly on to Step B.

Step B: Preparation of 6-(2-fluorophenoxy)-2-[(4-methoxycyclohexyl)amino]-8-methylpyrido[2,3-d]pyrimidin-7(8H)-one

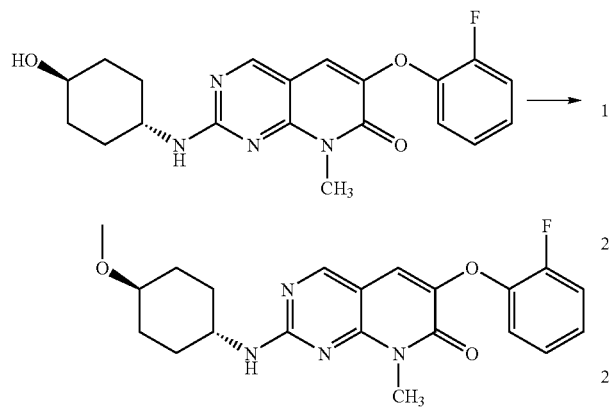

To a slurry of freshly prepared silver oxide (filtered/dried from an aqueous mixture of silver nitrate, 0.44 g, 2.70 mmol) and sodium hydroxide (0.21 g, 5.20 mmol)) in 2 mL tetrahydrofuran was added pyrimidin-7(8H)-one (Step A, 0.20 g, 0.52 mmol) and methyl iodide (0.065 mL, 1.04 mmol). After stirring at 50° C. for three days, additional silver oxide and methyl iodide (0.98 mL, 15.7 mmol) were added; the temperature was increased to reflux and the reaction continued for 2 weeks. Following this time period, the mixture was cooled to room temperature, evaporated and purified by column chromatography (SiO$_2$, CH$_2$Cl$_2$/MeOH/NH$_4$OH—90/9/1). Fractions containing product were combined and evaporated under reduced pressure to provide the free amine. This was dissolved in methanol (1-2 mL) and hydrochloric acid in ether (1M, 1.0 eq) was added. Isolation of the solid via filtration, rinsing with ether and drying provided 0.030 g of the hydrochloride salt (Mass spec. M+1=399, MP=135.0-145.0° C.).

Example 29

Preparation of 6-(2-fluorophenoxy)-8-methyl-2-{[1-(methylsulfonyl)piperidin-4-yl]amino}pyrido[2,3-d]pyrimidin-7(8H)-one

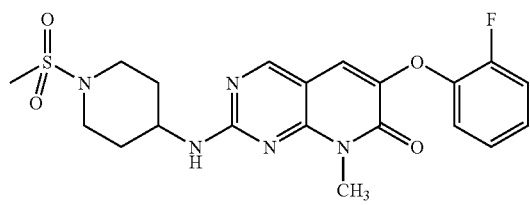

50

Step A: Preparation of benzyl 1-benzylpiperidin-4-ylcarbamate

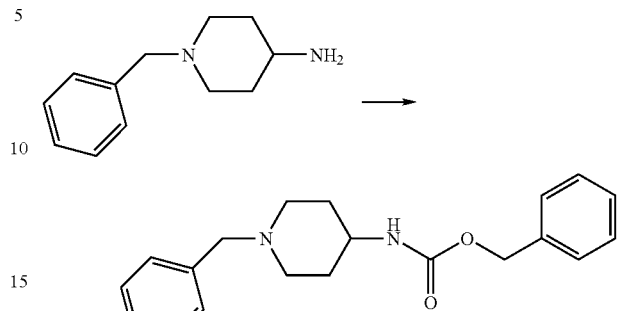

To a 0° C. solution of 4-amino-1-benzylpiperidine (41.2 g, 216.5 mmol) and triethylamine (51.3 mL, 369 mmol) in 600 mL of tetrahydrofuran was added benzyl chloroformate (31 mL, 217 mmol) dropwise over a period of 30 to 45 min. at such a rate that the reaction temperature was kept between 5° C. and 10° C. After the addition was complete, the reaction mixture was allowed to warm to room temperature and stir for 12 hours. The solvent and volatiles were removed under reduced pressure. Water (500 mL) and ethyl acetate (1.2 L) were then added and the reaction was partitioned between the two phases. The organic layer was washed with saturated aqueous sodium bicarbonate solution (2×, 150 mL) and then dried (brine, MgSO$_4$). Evaporation of the solvent yielded a tan liquid which was purified via column chromatography (SiO$_2$, EtOAc/Hexane—30/70 to EtOAc—100) to provide 27.8 g of the amine as a white solid (mass spec. M+=324, MP=79.1-79.6° C.).

Step B: Preparation of benzylpiperidin-4-ylcarbamate

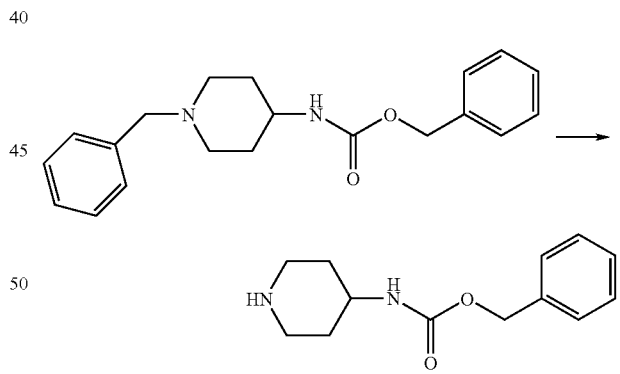

The benzyl amine (27.8 g, 85.7 mmol) was dissolved in 400 mL of methylene chloride at room temperature and 1-chloroethylchloroformate (25.4 g, 178 mmol) in 50 mL of methylene chloride was added dropwise via addition funnel. After addition was complete, the reaction mixture was stirred at room temperature for 3 hours. The solvent and volatiles were removed under reduced pressure and methanol 500 mL) was added. The reaction was heated to reflux with stirring for 1 hour and then cooled to room temperature. Removal of the reaction solution via evaporation yielded 26.3 g of the piperidine as an off-white solid (mass spec. M+1=235, MP=190.7-192.2° C.).

Step C: Preparation of benzyl 1-(methylsulfonyl)piperidin-4-ylcarbamate

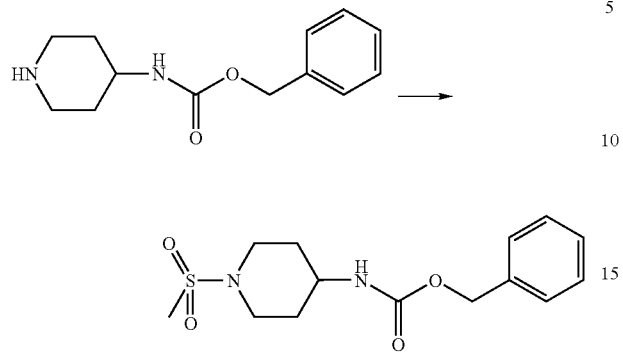

The protected piperidine (10 g, 42.7 mmol) and triethylamine (12 mL, 86.7 mmol) was dissolved in 500 mL of methylene chloride at room temperature. Methane sulfonylchloride (4.3 mL, 55.5 mmol) in 20 mL of methylene chloride was added dropwise via addition funnel. After addition was complete, the reaction mixture was stirred at room temperature for 3 hours. The solvent and volatiles were removed under reduced pressure. Ethyl acetate (500 mL) and an aqueous solution of hydrochloric acid (0.5M, 350 mL) was added. The reaction was partitioned between the two phases and the aqueous layer was removed. The organic layer was washed again with an aqueous solution of hydrochloric acid (0.5M, 2×, 100 mL) and then with saturated aqueous sodium bicarbonate solution (3×, 100 mL). The reaction solvent was then dried (brine, MgSO$_4$) and evaporated at reduced pressure to provide 9.2 g of the methane sulfonamide (MP=148.6-152.8° C.).

Step D: Preparation of 1-(methylsulfonyl)piperidin-4-amine

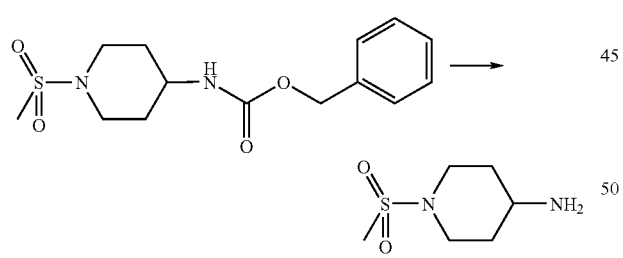

The methane sulfonamide (9.2 g, 29.5 mmol) was dissolved in 200 mL of tetrahydrofuran at room temperature in a 500 mL round-bottomed flask under a nitrogen atmosphere. Palladium on Carbon (10%, 2-3 g) was then added and the reaction vessel was flushed with hydrogen gas (3×). A balloon of hydrogen gas was put on the reaction flask and the solution was stirred for 15 hours (more catalyst added and hydrogen balloon filled if necessary). Methylene chloride (100 mL) was added to the reaction and it was filtered through a celite pad. Evaporation of the solvents under reduced pressure provided 4.63 g of the desired amine (mass spec. M+1=179, MP=65.3-65.7° C.).

Step E: Preparation of 6-(2-fluorophenoxy)-8-methyl-2-{[1-(methylsulfonyl)piperidin-4-yl]amino}pyrido[2,3-d]pyrimidin-7(8H)-one

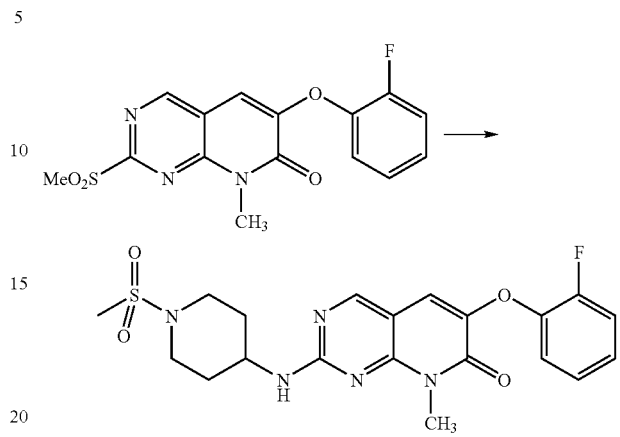

A mixture of sulfone 2 (0.2 g, 0.57 mmol) and 1-(methylsulfonyl)piperidin-4-amine (Example 29-Steps A-D, 0.243 g, 1.36 mmol) in 0.45 mL of 1-methyl-2-pyrrolidinone was heated to 80° C. for 3 hours. The reaction mixture was cooled and methanol (0.2-0.5 mL) was added. The product precipitated and was isolated via filtration. The solid was transferred to a flask with methanol (5 mL). Dropwise addition of hydrochloric acid in ether (1M, 1.5 eq) followed by stirring yielded the hydrochloride salt which was isolated as a solid (0.143 g, mass spec. M+1=448).

Example 30

Preparation of 6-(2-fluorophenoxy)-8-(4-fluorophenyl)-2-{[1-(methylsulfonyl)piperidin-4-yl]amino}pyrido[2,3-d]pyrimidin-7(8H)-one

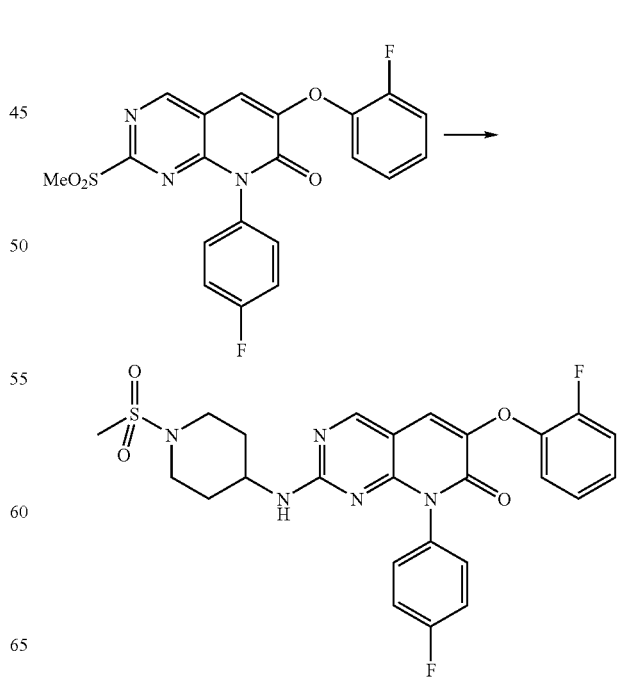

A mixture of sulfone 11 (0.2 g, 0.46 mmol) and 1-(methylsulfonyl)piperidin-4-amine (Example 29-Steps A-D, 0.112 g, 0.62 mmol) in 0.2 mL of 1-methyl-2-pyrrolidinone was heated to 110° C. for 1 hour. The reaction mixture was cooled and ethyl acetate (40 mL) was added. The reaction was transferred, dried (brine, MgSO₄) and evaporated to provide a crude product. Purification of this via chromatography (SiO₂, prep. TLC plate, EtOAc/Hexane—80/20) followed by isolation and evaporation under reduced pressure yielded the free amine. This product was dissolved in methylene chloride and hydrochloric acid in ether (1M, 0.4 mL) was added followed by stirring. The hydrochloride salt was isolated as a solid via filtration and drying (0.13 g, mass spec. M+1=528, MP=223.4-225° C.).

Example 31

Preparation of 8-cyclopropyl-6-(2-fluorophenoxy)-2-{[1-(methylsulfonyl)piperidin-4-yl]amino}pyrido[2,3-d]pyrimidin-7(8H)-one

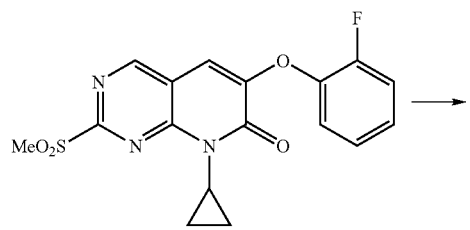

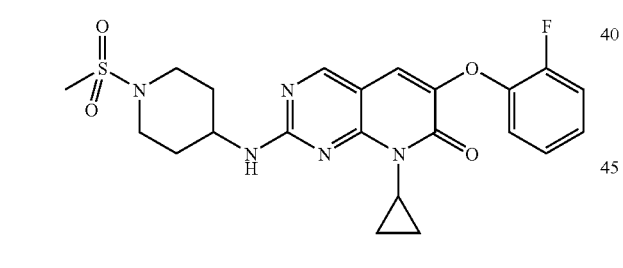

A mixture of sulfone 10 (0.361 g, 0.97 mmol) and 1-(methylsulfonyl)piperidin-4-amine (Example 29-Steps A-D, 0.262 g, 1.47 mmol) in 0.4 mL of 1-methyl-2-pyrrolidinone was heated to 110° C. for 2 hours. The reaction mixture was cooled and ethyl acetate (40 mL) and water (40 mL) were added. The reaction mixture was partitioned between the two layers and the aqueous layer was discarded. The organic layer was then dried (brine, MgSO₄) and evaporated to provide a crude product. Purification of this with chromatography (SiO₂, prep. TLC plate, EtOAc/Hexane—80/20) followed by isolation and evaporation under reduced pressure yielded the free amine. This product was dissolved in methylene chloride and hydrochloric acid in ether (1M, 1.5 eq) was added followed by stirring. The hydrochloride salt was isolated as a solid via filtration and drying (0.27 g, mass spec. M+1=474).

Example 32

Preparation of 6-(2-chlorophenoxy)-8-methyl-2-{[1-(methylsulfonyl)piperidin-4-yl]amino}pyrido[2,3-d]pyrimidin-7(8H)-one

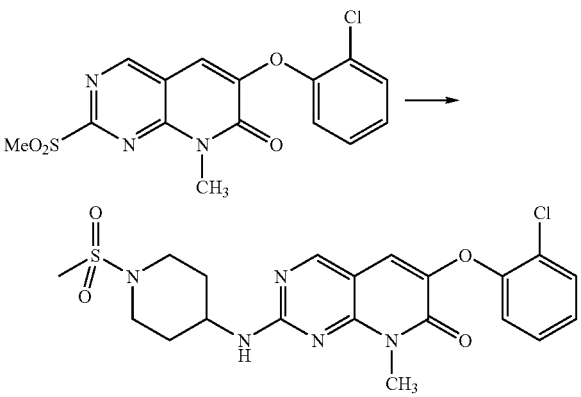

A mixture of sulfone 6 (0.2 g, 0.55 mmol) and 1-(methylsulfonyl)piperidin-4-amine (Example 29-Steps A-D, 0.195 g, 1.09 mmol) in 0.2 mL of 1-methyl-2-pyrrolidinone was heated to 80° C. for 3 hours. The reaction mixture was cooled and methanol (1 mL) was added. The product precipitated and was isolated via filtration. The solid was transferred to a flask with methanol (5 mL). Dropwise addition of hydrochloric acid in ether (1M, 1.5 eq) followed by stirring yielded the hydrochloride salt which was isolated as a solid (0.145 g, mass spec. M+1=465).

Example 33

Preparation of 6-(4-chlorophenoxy)-8-methyl-2-{[1-(methylsulfonyl)piperidin-4-yl]amino}pyrido[2,3-d]pyrimidin-7(8H)-one A mixture of sulfone 7 (0.17 g, 0.46 mmol) and 1-(methylsulfonyl)piperidin-4-amine (Example 29-Steps A-D, 0.164 g, 0.92 mmol) in 0.2 mL of 1-methyl-2-pyrrolidinone was heated to 80° C. for 3 hours. The reaction mixture was cooled and methanol (1 mL) was added. The product precipitated (3 days) and was isolated via filtration. The solid was transferred to a flask with methanol (5 mL). Dropwise addition of hydrochloric acid in ether (1M, 1.5 eq) followed by stirring yielded the hydrochloride salt (0.2 g, mass spec. M+1=465).

Example 34

Preparation of 2-(cyclopropylamino)-6-(2-fluorophenoxy)-8-methylpyrido[2,3-d]pyrimidin-7(8H)-one

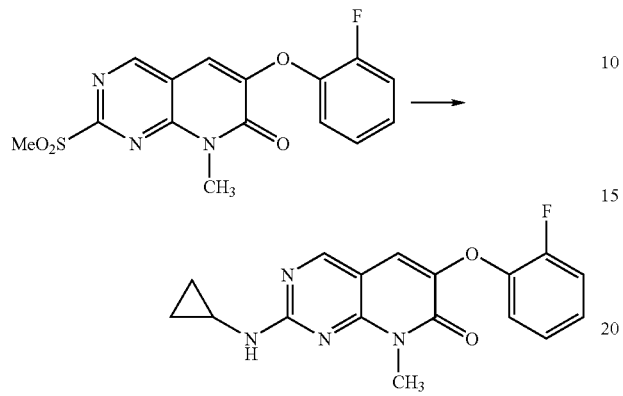

A mixture of sulfone 2 (0.35 g, 1.0 mmol) and cyclopropylamine (1 mL, 14 mmole) was heated to 60° C. for 8 hours under a nitrogen atmosphere. The reaction mixture was cooled, evaporated under reduced pressure and purified via column chromatography (SiO$_2$, Hexane/EtOAc—3/2). The product was suspended in methanol, hydrochloric acid in ether (1M, 1.5 eq) was added and the reaction was stirred for 30 minutes. Isolation of the solid via filtration and drying provided the hydrochloride salt (Mass spec. M+1=327, MP=178.2-179.6° C.).

Example 35

Preparation of 2-(cyclopentylamino)-6-(4-fluorophenoxy)-8-methylpyrido[2,3-d]pyrimidin-7(8H)-one

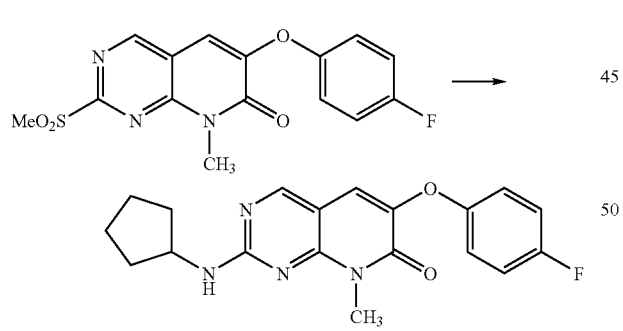

A mixture of 4-fluorophenoxy sulfone (see Example 8, substituting methyl 4-fluorophenoxyacetate for methyl 2-fluorophenoxyacetate-Step A-B, 0.4 g, 1.26 mmol) and cyclopentylamine (Aldrich, 0.146 g, 1.71 mmol) in 0.3 mL of 1-methyl-2-pyrrolidinone was heated to 80° C. for 3 hours. The reaction mixture was cooled and methanol (1 mL) was added. The product precipitated and was isolated via filtration. The solid was transferred to a flask with methanol (5 mL). Dropwise addition of hydrochloric acid in ether (1M, 1.5 eq) followed by stirring yielded the hydrochloride salt (0.165 g, mass spec. M+1=355).

Example 36

Preparation of 2-(cyclopentylamino)-6-(3-fluorophenoxy)-8-methylpyrido[2,3-d]pyrimidin-7(8H)-one

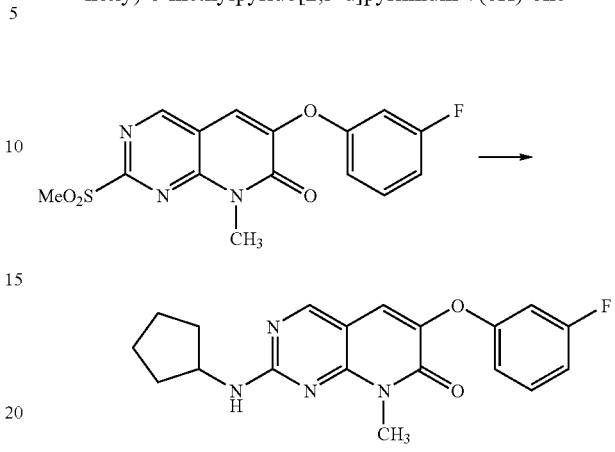

A mixture of sulfone 3 (0.2 g, 0.57 mmol) and cyclopentylamine (0.146 g, 1.71 mmol) in 0.3 mL of 1-methyl-2-pyrrolidinone was heated to 80° C. for 4 hours under a nitrogen atmosphere. The reaction mixture was cooled and methanol (1 mL) was added. The product precipitated and was isolated via filtration. The solid was transferred to a flask with methanol (5 mL). Dropwise addition of hydrochloric acid in ether (1M, 1.5 eq) followed by stirring yielded the hydrochloride salt (0.105 g, mass spec. M+1=355).

Example 37

Preparation of 2-(butylamino)-6-(2-fluorophenoxy)-8-methylpyrido[2,3-d]pyrimidin-7(8H)-one

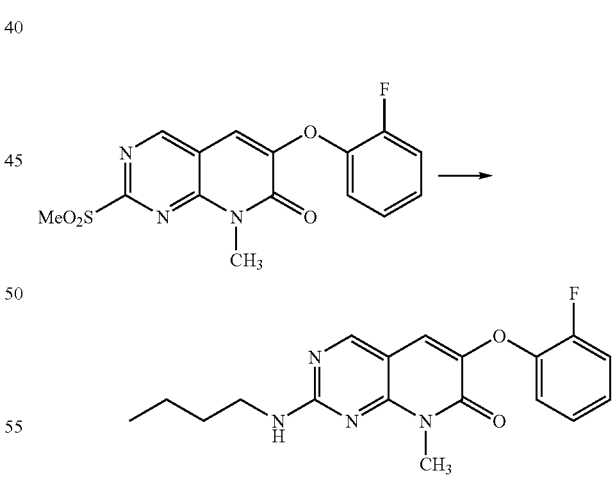

A mixture of sulfone 2 (0.05 g, 0.143 mmol) and butylamine (0.017 g, 0.17 mmol) in 0.2 mL of 1-methyl-2-pyrrolidinone was heated to 65° C. for 12 hours. The reaction mixture was cooled, methanol/water (90/10, 1 mL) was added and a precipitate formed. The product was washed with water, dissolved in methylene chloride and evaporated under reduced pressure to yield the amine (0.019 g, mass spec. M+1=343).

Example 38

Preparation of 6-(2-fluorophenoxy)-2-[(2-hydroxyethyl)amino]-8-methylpyrido[2,3-d]pyrimidin-7(8H)-one

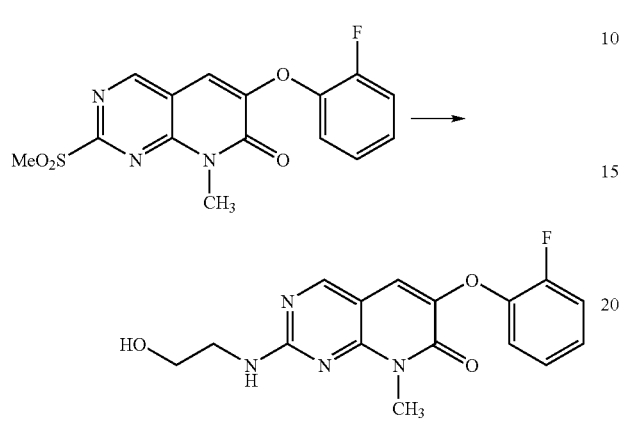

A mixture of sulfone 2 (0.05 g, 0.143 mmol), 2-aminoethanol (0.015 g, 0.2 mmol) in 0.2 mL of chloroform was heated to 65° C. for 12 hours. The reaction mixture was cooled and the chloroform was removed via evaporation. Methanol/water (90/10, 1 mL) was added and a precipitate formed. The product was washed with water, dissolved in methylene chloride and evaporated under reduced pressure to yield the amine (0.027 g, mass spec. M+1=331).

Example 39

Preparation of 6-(2-fluorophenoxy)-2-(isobutylamino)-8-methylpyrido[2,3-d]pyrimidin-7(8H)-one

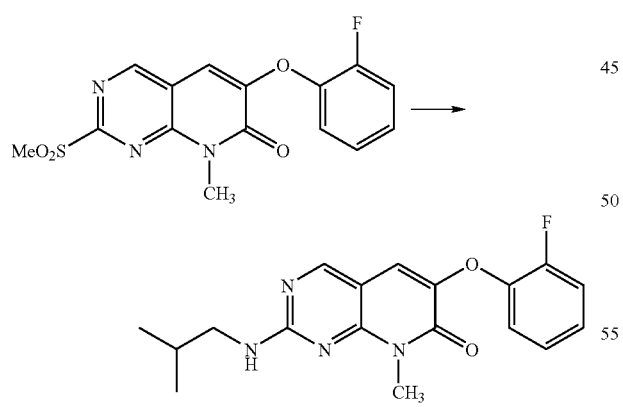

A mixture of sulfone 2 (0.05 g, 0.143 mmol), isobutylamine (0.013 g, 0.18 mmol) in 0.2 mL of chloroform was heated to 65° C. for 12 hours. The reaction mixture was cooled and the chloroform was removed via evaporation. Methanol/water (90/10, 1 mL) was added and a precipitate formed. The product was washed with water, dissolved in methylene chloride and evaporated under reduced pressure to yield the amine (0.038 g, mass spec. M+1=343).

Example 40

Preparation of 6-(2-fluorophenoxy)-2-{[(1S)-1-(hydroxymethyl)-2-methylpropyl]amino}-8-methylpyrido[2,3-d]pyrimidin-7(8H)-one

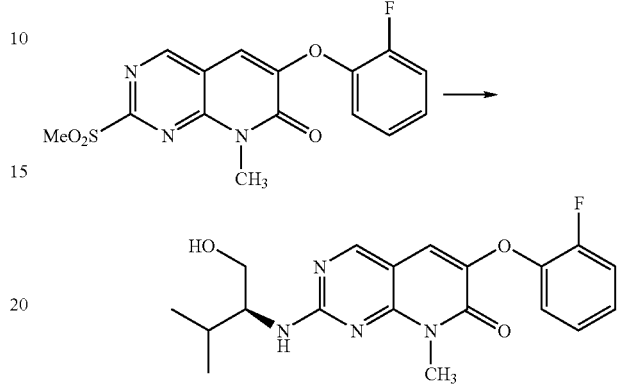

A mixture of sulfone 2 (0.05 g, 0.143 mmol) and (2S)-2-amino-3-methylbutan-1-ol (0.044 g, 0.43 mmol) in 0.1 mL of 1-methyl-2-pyrrolidinone was heated to 80° C. for 3 hours. The reaction mixture was cooled, methanol/water (90/10, 1 mL) was added and a precipitate formed. The product was washed with water, dissolved in methylene chloride, filtered through a drying agent (MgSO$_4$) and evaporated under reduced pressure to yield the amine (0.047 g, mass spec. M+1=373).

Example 41

Preparation of 2-[(2,3-dihydroxypropyl)amino]-6-(2-fluorophenoxy)-8-methylpyrido[2,3-d]pyrimidin-7(8H)-one

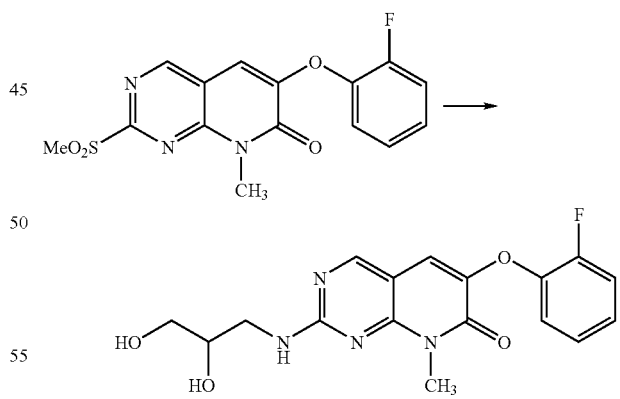

A mixture of sulfone 2 (0.05 g, 0.143 mmol) and 3-aminopropane-1,2-diol (0.016 g, 0.18 mmol) in 0.1 mL of 1-methyl-2-pyrrolidinone was heated to 65° C. for 3 hours. The reaction mixture was cooled, methanol/water (90/10, 1 mL) was added but no precipitate formed. Therefore removed all solvents via evaporation under reduced pressure, added water (1 mL) and ethyl acetate (1 mL) and partitioned product into the organic layer. The aqueous layer was removed; the ethyl acetate was dried (MgSO$_4$) and evaporated to provide the amine (0.034 g, mass spec. M+1=361).

Example 42

Preparation of 6-(2-fluorophenoxy)-8-methyl-2-[(2-piperidin-1-ylethyl)amino]pyrido[2,3-d]pyrimidin-7(8H)-one

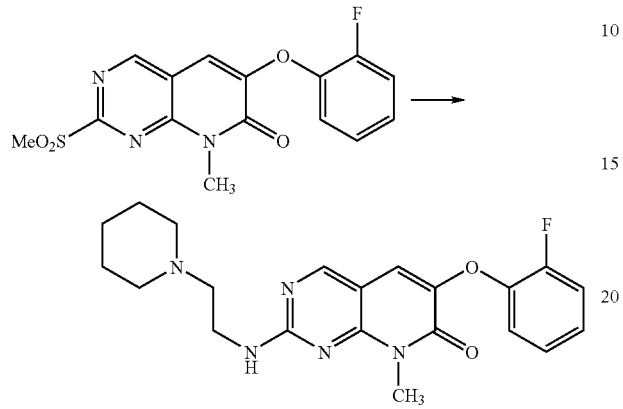

A mixture of sulfone 2 (0.05 g, 0.143 mmol), 2-piperidin-1-ylethylamine (0.022 g, 0.17) mmol in 0.2 mL of chloroform was heated to 65° C. for 12 hours. The reaction mixture was cooled and the solvents were removed via evaporation. Methanol/water (90/10, 1 mL) was added and a precipitate formed. The product was washed with water, dissolved in methylene chloride and evaporated to yield the amine (0.041 g, mass spec. M+1=398).

Example 43

Preparation of 2-[(cyclohexylmethyl)amino]-6-(2-fluorophenoxy)-8-methylpyrido[2,3-d]pyrimidin-7(8H)-one

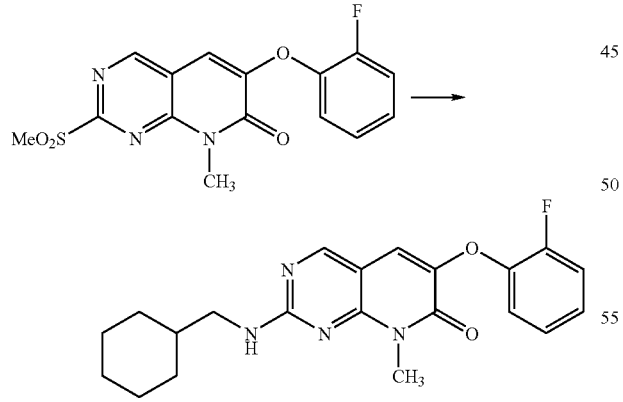

A mixture of sulfone 2 (0.05 g, 0.143 mmol), cyclohexylmethylamine (0.019 g, 0.17 mmol) in 0.2 mL of chloroform was heated to 65° C. for 12 hours. The reaction mixture was cooled and the solvents were removed via evaporation. Methanol/water (90/10, 1 mL) was added and a precipitate formed. The product was washed with water, dissolved in methylene chloride and evaporated to yield the amine (0.045 g, mass spec. M+1=383).

Example 44

Preparation of 2-[(cyclopropylmethyl)amino]-6-(2-fluorophenoxy)-8-methylpyrido[2,3-d]pyrimidin-7(8H)-one

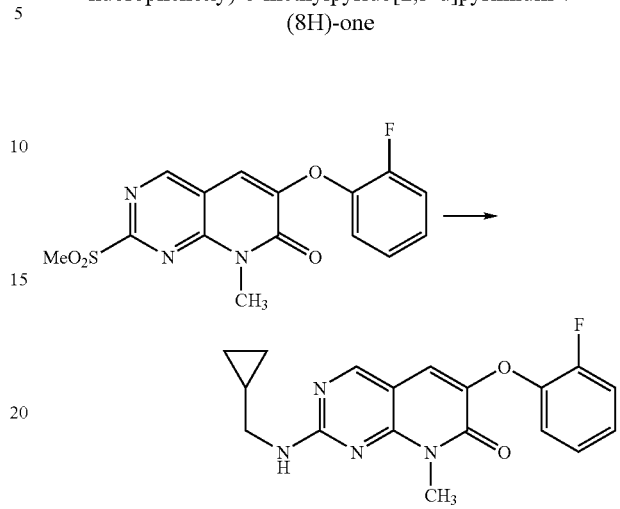

A mixture of sulfone 2 (0.05 g, 0.143 mmol), cyclopropylmethylamine (0.02 g, 0.28 mmol) in 0.2 mL of chloroform was heated to 65° C. for 12 hours. The reaction mixture was cooled and the solvents were removed via evaporation. Methanol/water (90/10, 1 mL) was added and a precipitate formed. The product was washed with water, dissolved in methylene chloride and evaporated under reduced pressure to yield the amine (0.03 g, mass spec. M+1=341).

Example 45

Preparation of 6-(2-fluorophenoxy)-2-[(2-methoxyethyl)amino]-8-methylpyrido[2,3-d]pyrimidin-7(8H)-one

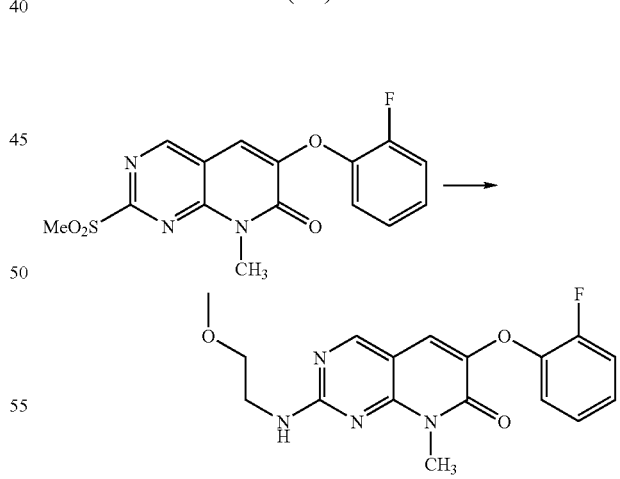

A mixture of sulfone 2 (0.05 g, 0.143 mmol), 2-methoxyethylamine (0.02 g, 0.27 mmol) in 0.2 mL of chloroform was heated to 65° C. for 12 hours. The reaction mixture was cooled and the solvents were removed via evaporation. Methanol/water (90/10, 1 mL) was added and a precipitate formed. The product was washed with water, dissolved in methylene chloride and evaporated under reduced pressure to yield the amine (0.04 g, mass spec. M+1=345).

Example 46

Preparation of 2-{[3-(dimethylamino)propyl]amino}-6-(2-fluorophenoxy)-8-methylpyrido[2,3-d]pyrimidin-7(8H)-one

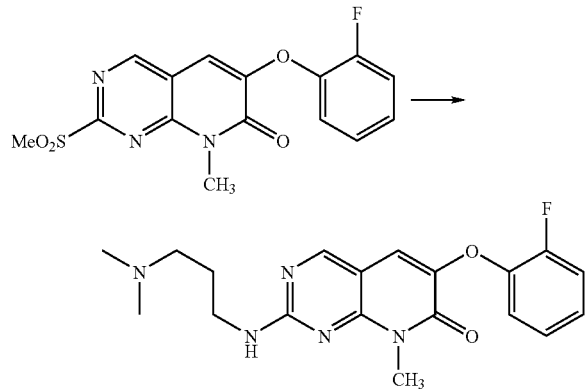

A mixture of sulfone 2 (0.05 g, 0.143 mmol), N,N-dimethylpropane-1,3-diamine (0.018 g, 0.18 mmol) in 0.2 mL of chloroform was heated to 65° C. for 12 hours. The reaction mixture was cooled and the solvents were removed via evaporation. Methanol/water (90/10, 1 mL) was added and a precipitate formed. The product was washed with water, dissolved in methylene chloride and evaporated to yield the amine (0.045 g, mass spec. M+1=372).

Example 47

Preparation of 6-(2-fluorolphenoxy)-8-methyl-2-{[3-(2-oxopyrrolidin-1-yl)propyl]amino}pyrido[2,3-d]pyrimidin-7(8H)-one

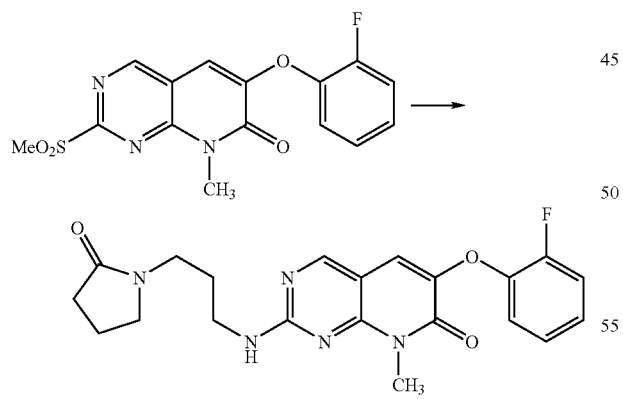

A mixture of sulfone 2 (0.05 g, 0.143 mmol), 1-(3-aminopropyl)pyrimidin-2-one (0.024 g, 0.17 mmol) in 0.2 mL of chloroform was heated to 65° C. for 12 hours. The reaction mixture was cooled and the solvents were removed via evaporation. Methanol/water (90/10, 1 mL) was added and a precipitate formed. The product was washed with water, dissolved in methylene chloride and evaporated to yield the amine (0.033 g, mass spec. M+1=412).

Example 48

Preparation of N-(2-{[6-(2-fluorophenoxy)-8-methyl-7-oxo-7,8-dihydropyrido[2,3-d]pyrimidin-2-yl]amino}ethyl)acetamide

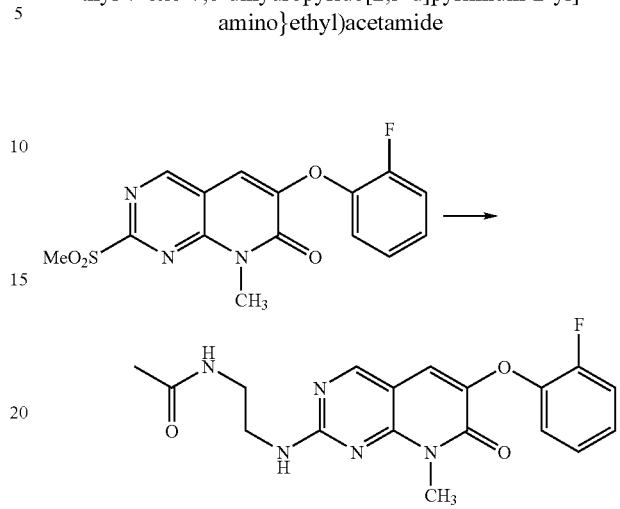

A mixture of sulfone 2 (0.05 g, 0.143 mmol), N-(2-aminoethyl)acetamide (0.024 g, 0.18 mmol) in 0.2 mL of chloroform was heated to 65° C. for 12 hours. The reaction mixture was cooled and the solvents were removed via evaporation. Methanol/water (90/10, 1 mL) was added and a precipitate formed. The product was washed with water, dissolved in methylene chloride and evaporated to yield the amine (0.035 g, mass spec. M+1=373).

Example 49

Preparation of 6-(2-fluorophenoxy)-8-methyl-2-[(2-pyridin-3-ylethyl)amino]pyrido[2,3-d]pyrimidin-7(8H)-one

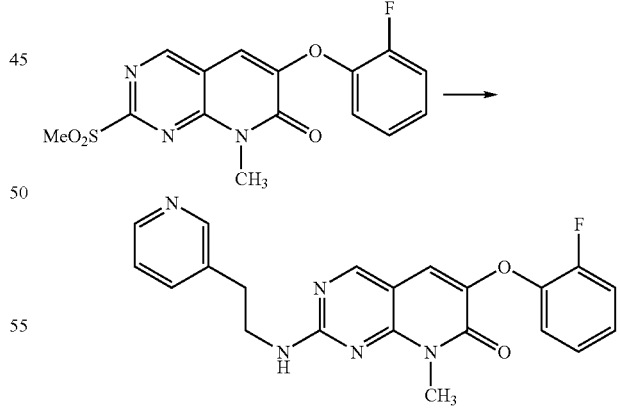

A mixture of sulfone 2 (0.05 g, 0.143 mmol), 2-pyridin-3-ylethylamine (0.021 g, 0.17 mmol) in 0.2 mL of chloroform was heated to 65° C. for 12 hours. The reaction mixture was cooled and the solvents were removed via evaporation. Methanol/water (90/10, 1 mL) was added and a precipitate formed. The product was washed with water, dissolved in methylene chloride and evaporated to yield the amine (0.039 g, mass spec. M+1=392).

Example 50

Preparation of ethyl N-[6-(2-fluorophenoxy)-8-methyl-7-oxo-7,8-dihydropyrido[2,3-d]pyrimidin-2-yl]-β-alaninate

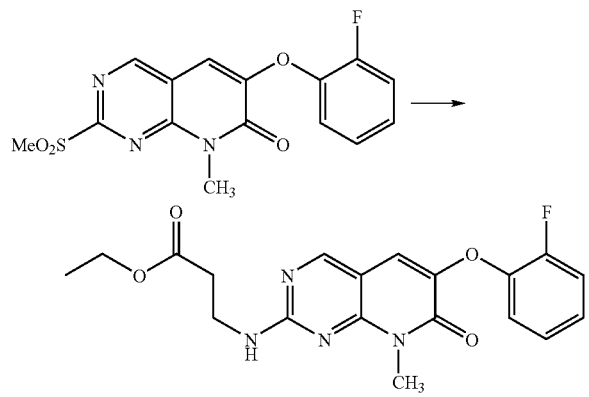

To a solution of ethyl β-alaninate hydrochloride salt (0.053 g, 0.34 mmol) in 3 mL of chloroform at room temperature was added MP Carbonate Resin (Argonaut Technologies Inc., 0.45 g). This was allowed to stir for 1 hour and then Sulfone 2 (0.05 g, 0.143 mmol) was added. The reaction was brought to 65° C. and stirred for 24 hours. The mixture was then cooled and the resin was removed via filtration. Evaporation of the solvent and chromatography (SiO$_2$, CH$_2$Cl$_2$/MeOH—95/5) and subsequent evaporation of appropriate fractions provided the amine (0.027 g, mass spec. M+1=387).

Example 51

Preparation of 6-(2-fluorophenoxy)-2-[(3-methoxypropyl)amino]-8-methylpyrido[2,3-d]pyrimidin-7(8H)-one

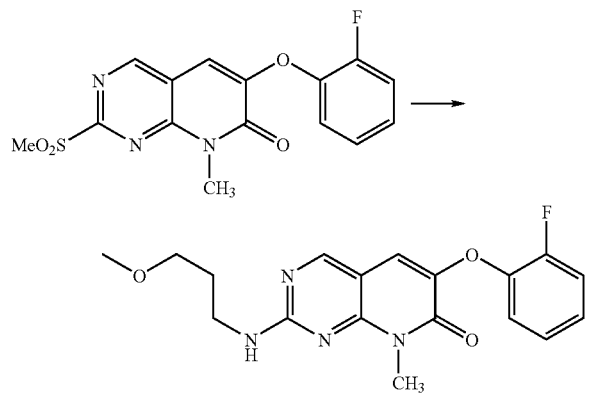

A mixture of sulfone 2 (0.05 g, 0.143 mmol), 3-methoxypropylamine (0.015 g, 0.17 mmol) in 1.5 mL of chloroform was heated to 65° C. for 12 hours. The reaction mixture was cooled and the solvents were removed via evaporation. The crude reaction mixture was purified via column chromatography (Supelco 3 mL plug, SiO$_2$, CH$_2$Cl$_2$/MeOH—95/5) and subsequent evaporation to provide the amine (0.027 g, mass spec. M+1=359).

Example 52

Preparation of 6-(4-chlorophenoxy)-2-{[(1S)-2-hydroxy-1,2-dimethylpropyl]amino}-8-methylpyrido[2,3-d]pyrimidin-7(8H)-one

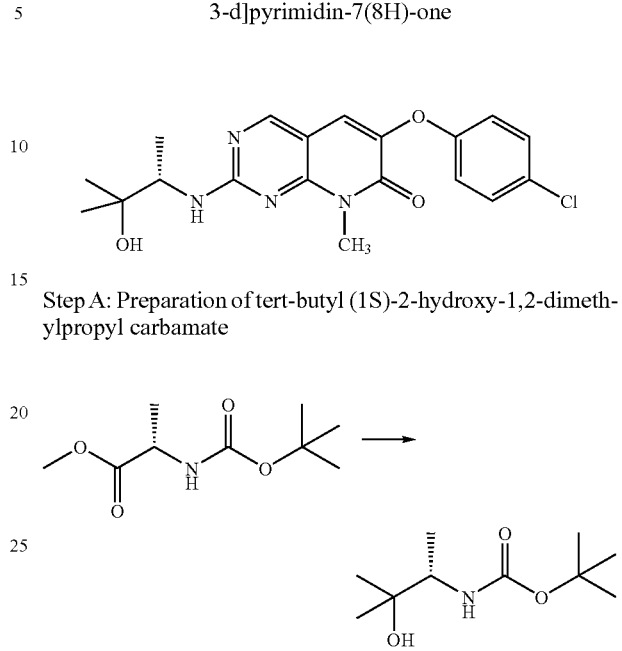

Step A: Preparation of tert-butyl (1S)-2-hydroxy-1,2-dimethylpropyl carbamate

To a 0° C. solution of methyl N-(tert-butoxycarbonyl)-L-alaninate (10.0 g, 49.3 mmol) in 70 mL of tetrahydrofuran under a nitrogen atmosphere was added methylmagnesium chloride (3.0M in THF, 70 mL, 210 mmol) dropwise over a period of 30 to 45 min. After the addition was completed, the reaction mixture was allowed to warm to room temperature and stir for 2 hours. The solvent and volatiles were removed under reduced pressure. Water (500 mL) and ethyl acetate (1.2 L) were then added and the reaction was partitioned between the two phases. The organic layer was dried (brine, MgSO$_4$) and evaporation of the solvent yielded a liquid which was chromatographed (SiO$_2$, CH$_2$Cl$_2$/MeOH—90/10) providing 9.6 g of the protected amine as a liquid (mass spec. M+1=204).

Step B: Preparation of (3S)-3-amino-2-methylbutan-2-ol

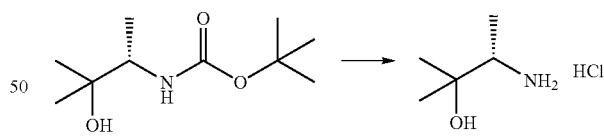

To a 0° C. solution of the carbamate (9.6 g, 47.3 mmol) in 96 mL of methylene chloride under a nitrogen atmosphere was added trifluoroacetic acid (4 mL, 51.9 mmol) dropwise. After the addition was completed, the reaction mixture was allowed to warm to room temperature and stir for 2 hours. t-Butanol (2-3 mL) was added to the reaction and the solvent/volatiles were removed under reduced pressure. Addition of toluene (3×, 75 mL) with evaporation followed by drying in a vacuum oven provided the crude amine which was a solid. This material was transferred to a flask and methanol (10 mL) and hydrochloric acid (12M, 5-7 mL) were then added with stirring. After 30 minutes, the hydrochloride salt of the amine formed as a precipitate and this was rinsed with toluene (50 mL) and Et$_2$O (2×, 150 mL) and then dried under reduced pressure (mass spec. M+1=104, MP=128.1-130.1° C.). Note:

This amine is hydroscopic and care was taken to not allow extensive exposure to air/water during isolation.

Step C: Preparation of 6-(4-chlorophenoxy)-2-{[(1S)-2-hydroxy-1,2-dimethylpropyl]amino}-8-methylpyrido[2,3-d]pyrimidin-7(8H)-one

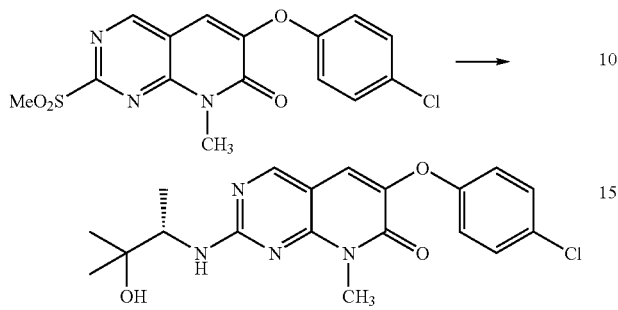

To a solution of (3S)-3-amino-2-methylbutan-2-ol hydrochloride salt (0.077 g, 0.55 mmol) in 3 mL of chloroform at room temperature was added MP Carbonate Resin (Argonaut Technologies Inc., Foster City, Calif., 0.75 g). This was allowed to stir for 1 hour and then Sulfone 7 (0.1 g, 0.28 mmol) was added. The reaction was brought to 60° C. and stirred for 24 hours. The mixture was then cooled and the resin was removed via filtration. Evaporation of the solvent and column chromatography (SiO$_2$, CH$_2$Cl$_2$) provided a crude product which was chromatographed a second time (SiO$_2$, CH$_2$Cl$_2$/Hexane—1/1 gradient to CH$_2$Cl$_2$/MeOH—99/1). Isolation of the appropriate fractions followed by solvent evaporation at reduced pressure yielded the amine (0.032 g, mass spec. M+1=389).

Example 53

Preparation of 6-(2,4-difluorophenoxy)-2-{[(1S)-2-hydroxy-1,2-dimethylpropyl]amino}-8-methylpyrido[2,3-d]pyrimidin-7(8H)-one

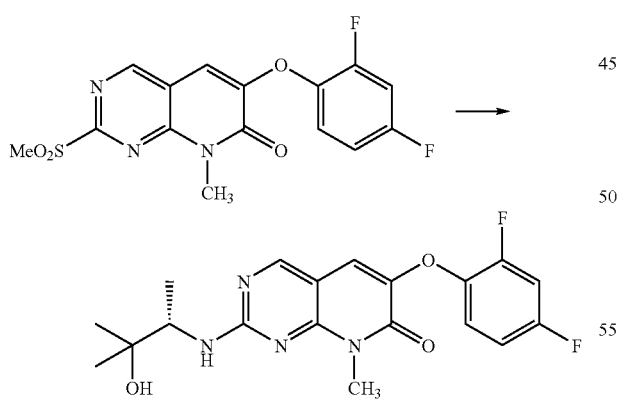

To a solution of (3S)-3-amino-2-methylbutan-2-ol hydrochloride salt (0.24 g, 1.77 mmol) in 3 mL of acetonitrile at room temperature was added trimethylsilyl cyanide (Aldrich, 0.7 mL, 5.2 mmol). This was refluxed for 30 minutes, cooled to room temperature and then Sulfone 5 (0.367 g, 1.0 mmol) was added. The reaction was refluxed for 2 hours and cooled to room temperature. Methanol (2 mL) and aqueous sodium hydroxide solution (2N, 1-3 mL) was added and the mixture was refluxed for 30 minutes. The reaction was evaporated and ethyl acetate (25 mL) was added. Drying of the organic solution (brine, 3×), followed by evaporation under reduced pressure and chromatography (SiO$_2$, prep. TLC plate, EtOAc/Hexane—75/25) provided the crude product. This was dissolved in methylene chloride (1-2 mL) and hydrochloric acid in ether (1M, X's) was added. Isolation of the solid via filtration and drying provided 0.16 g of the hydrochloride salt (Mass spec. M+1=391, MP=104.3-107.5° C.).

Example 54

Preparation of 6-(2-fluorobenzyl)-2-{[(1S)-2-hydroxy-1,2-dimethylpropyl]amino}-8-methylpyrido[2,3-d]pyrimidin-7(8H)-one

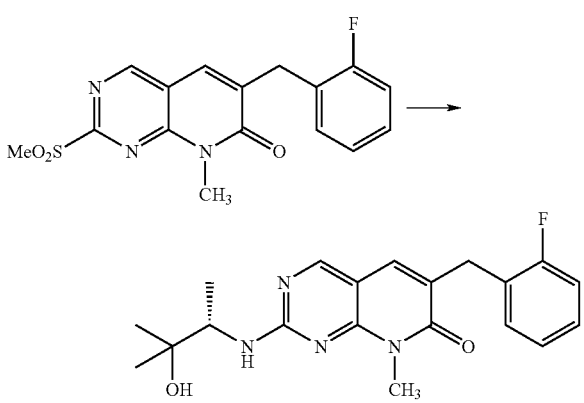

To a solution of (3S)-3-amino-2-methylbutan-2-ol hydrochloride salt (0.31 g, 2.21 mmol) in 3 mL of acetonitrile at room temperature was added N,N-diisopropylethylamine (0.7 mL, 4 mmol). This was refluxed for 30 minutes, cooled to room temperature and then Sulfone 8 (0.4 g, 1.15 mmol) was added. The reaction was refluxed for 2 hours and cooled to room temperature. Ethyl acetate (25 mL) was added and this solution was dryed (brine—3×, MgSO$_4$). Evaporation under reduced pressure and chromatography (SiO$_2$, prep. TLC plate, EtOAc/Hexane—75/25) provided the crude product. This was dissolved in methylene chloride (1-2 mL) and hydrochloric acid in ether (1M, X's) was added. Isolation of the solid via filtration and drying provided 0.25 g of the hydrochloride salt (Mass spec. M+1=371, MP=162.9-170.5° C.).

Example 55

Preparation of 6-(2-fluorophenoxy)-8-methyl-2-[(1-oxidotetrahydro-2H-thiopyran-4-yl)amino]pyrido[2,3-d]pyrimidin-7(8H)-one

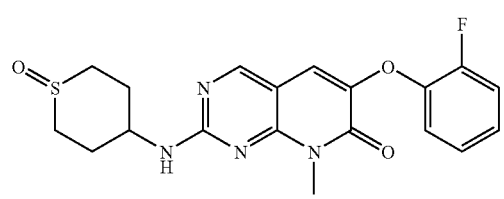

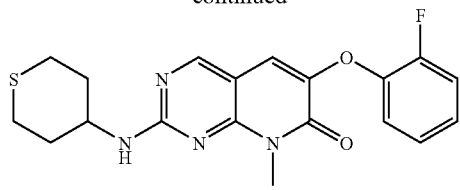

Step A: Preparation tetrahydro-4H-thiopyran-4-one oxime:

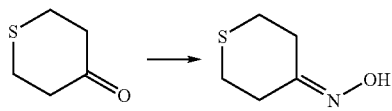

A suspension mixture of tetrahydrothiopyran-4-one (5 g, 43 mmol), sodium acetate trihydrate (29.26 g, 215 mmol) and hydroxylamine hydrochloride (14.9 g, 215 mmol) in 200 mL of ethanol were heated to reflux for 6 hours. The reaction mixture was cooled and solvent/volatiles were removed under reduced pressure. The residue was diluted with ice water (400 mL) and extracted with ethyl acetate (3×, 150 mL). The organic solution was dried (brine, MgSO$_4$) and evaporated affording 5.6 g of the thianone oxime as a white solid (mass spec. M+=131).

Step B: Preparation 4-aminotetrahydrothiopyran:

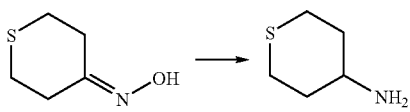

To a solution of lithium aluminum hydride (1M, 76 mL, 76 mmol) in tetrahydrofuran at room temperature under a nitrogen atmosphere (1M, 76 mL, 76 mmole) was added dropwise the thianone oxime (2 g, 15 mmol) in 30 mL of tetrahydrofuran. After addition was completed, the mixture was stirred at reflux for 7 hours and then room temperature for 12 hours. Water (2.9 mL) was added slowly (dropwise) to the suspension, followed by an aqueous solution of sodium hydroxide (15%, 2.9 mL). Additional water (8.7 mL) was then added and the reaction mixture was stirred for 30 minutes, filtered through a celite pad and rinsed with ethyl acetate (200 mL). The filtrate was dried (brine, MgSO$_4$) and evaporated under reduced pressure affording 1.62 g of the 4-aminotetrahydropyran (mass spec. M+1=118).

Step C: Preparation 6-(2-fluorophenoxy)-8-methyl-2-(tetrahydro-2H-thiopyran-4-ylamino)pyrido[2,3-d]pyrimidin-7(8H)-one:

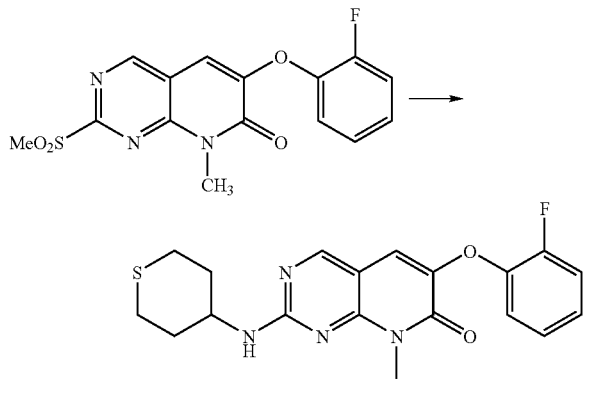

A mixture of sulfone 2 (1.0 g, 2.9 mmol) and 4-aminotetrahydrothiopyran (0.67 g, 5.8 mmol) in 1 mL of 1-methyl-2-pyrrolidinone was heated at 80° C. for 1 hour. The reaction mixture was cooled, ethyl acetate (100 mL) was added and the organic solution was washed with water (3×, 75 mL) and then dried (brine, MgSO$_4$). Evaporation of the solvent under reduced pressure and column chromatography (SiO$_2$, EtOAc/Hexane—40/60) afforded 0.84 g of the sulfide as a white solid which was taken on to Step D.

Step D: Preparation 6-(2-fluorophenoxy)-8-methyl-2-[(1-oxidotetrahydro-2H-thiopyran-4-yl)amino]pyrido[2,3-d]pyrimidin-7(8H)-one:

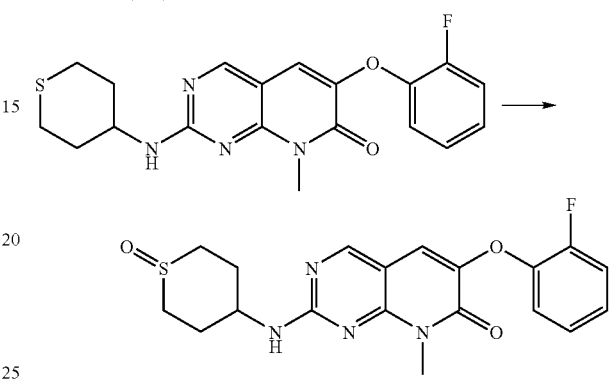

The sulfide (0.84 g, 2.2 mmol) was dissolved in 80 mL of dichloromethane and was cooled to 5° C. as 3-chloroperbenzoic acid (77%, 0.5 g, 2.2 mmol) was added in three portions over a period of 30 minutes. Reaction was completed in 30 minutes and the mixture was washed with aqueous sodium sulfite solution (10%, 100 mL) followed by cold saturated aqueous sodium bicarbonate solution. The solution was dried (brine, Na$_2$SO$_4$) and evaporated under reduced pressure. The product was purified by column chromatography (SiO$_2$, CH$_2$Cl$_2$/MeOH—95/5) yielding the amine sulfoxide. This product (0.4 g) was dissolved in ethyl acetate/dichloromethane (1/1, 1 mL) and hydrochloric acid in ether (1M, 1.2 mL 1.2 eq) was added. A white suspension formed and this was stirred for 15 minutes. Filtration of the solid and rinsing with ether yielded 385 mg of the hydrochloride salt (mass spec. M+1=403, MP=188.8-189.7° C.).

Example 56

Preparation of 2-[(1,1-dioxidotetrahydro-2H-thiopyran-4-yl)amino]-6-(2-fluorophenoxy)-8-methylpyrido[2,3-d]pyrimidin-7(8H)-one

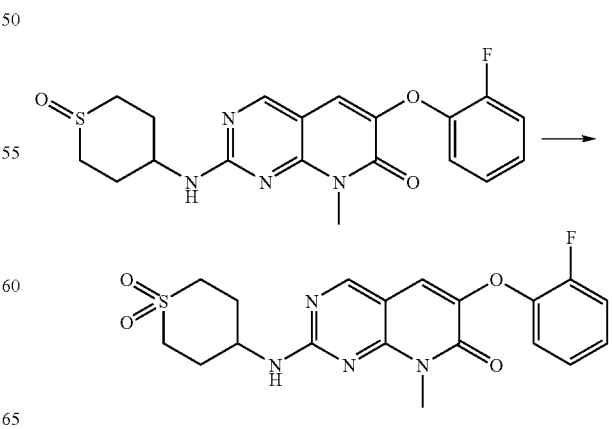

A mixture of the sulfoxide (0.47 g, 1.2 mmol) and 3-chloroperbenzoic acid (0.26 g, 1.2 mmol) in 50 mL of dichloromethane was stirred at room temperature for 2 hours under a nitrogen atmosphere. The reaction was then quenched with an aqueous sodium sulfite solution (10%, 100 mL), then washed with cold saturated aqueous sodium bicarbonate solution (100 mL). The organic solution was dried (brine, Na$_2$SO$_4$), evaporated under reduced pressure, and purified via column chromatography (SiO$_2$, CH$_2$Cl$_2$/MeOH—97/3) affording 0.45 g of the sulfone. This was dissolved in methanol/dichloromethane (5/95, 1 mL) and hydrochloric acid in ether (1M, 1.3 mL) was added. A suspension formed and this was stirred for 30 minutes. Filtration of the solid and rinsing with ether yielded 413 mg of the hydrochloride salt (mass spec. M+1=419, MP=186.2-230.7° C., sample partially melted throughout the range).

Example 57

Preparation of 6-(2,4-difluorophenoxy)-8-methyl-2-[(1-oxidotetrahydro-2H-thiopyran-4-yl)amino]pyrido[2,3-d]pyrimidin-7(8H)-one

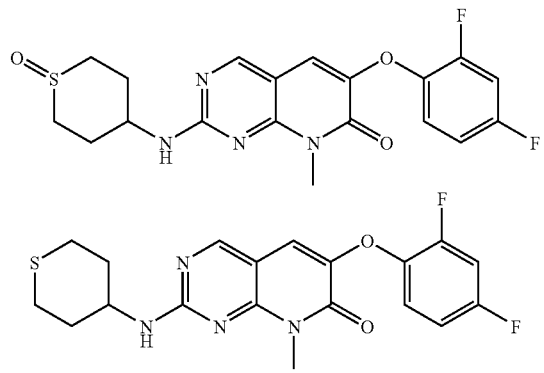

Step A: Preparation 6-(2,4-difluorophenoxy)-8-methyl-2-(tetrahydro-2H-thiopyran-4-ylamino)pyrido[2,3-d]pyrimidin-7(8H)-one:

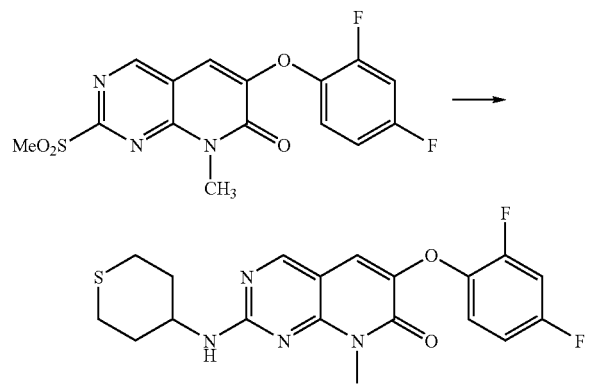

A mixture of sulfone 5 (1.14 g, 3.1 mmol) and 4-aminotetrahydrothiopyran (0.73 g, 6.2 mmol) in 2 ml of 1-methyl-2-pyrrolidinone was heated at 70° C. for 15 minutes. The reaction mixture was cooled, ethyl acetate (100 mL) was added. The organic solution was then washed with water (3×, 75 mL) and dried (brine, MgSO$_4$). Evaporation of the solvent and column chromatography (SiO$_2$, CH$_2$Cl$_2$/EtOAc—90/10) afforded 0.9 g of the sulfide (mpt. 230.7-232.8, MS (M+H)=405) which was taken on to Step B.

Step B: Preparation 6-(2,4-difluorophenoxy)-8-methyl-2-[(1-oxidotetrahydro-2H-thiopyran-4-yl)amino]pyrido[2,3-d]pyrimidin-7(8H)-one:

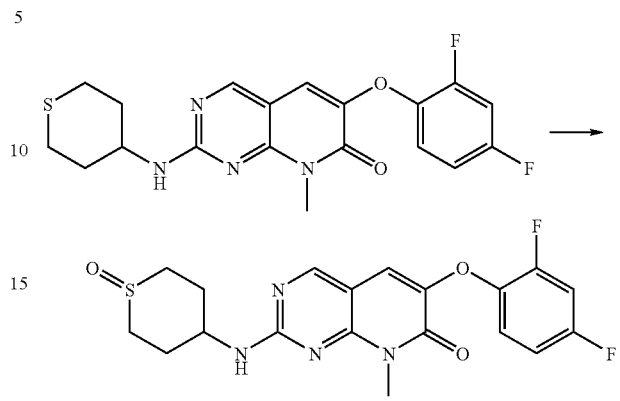

The sulfide (0.9 g, 2.2 mmol) was dissolved in 80 mL of dichloromethane and was cooled to 5° C. as 3-chloroperbenzoic acid (77%, 0.5 g, 2.2 mmol) was added in three portions over a period of 30 minutes. Reaction was completed in 20 minutes and the mixture was quenched with aqueous sodium sulfite solution (10%, 100 mL) followed by cold saturated aqueous sodium bicarbonate solution. The solution was dried (brine, MgSO$_4$) and evaporated under reduced pressure. The product was purified by column chromatography (SiO$_2$, CH$_2$Cl$_2$/MeOH—95/5) yielding the amine sulfoxide. This product (0.35 g, 0.8 mmol) was dissolved in 1 ml of dichloromethane and hydrochloric acid in ether (1M, 1.0 mL) was added. A suspension formed and this was stirred for 15 minutes. Dilution of the solid with ether (10 mL), filtration and rinsing with ether yielded 344 mg of the hydrochloride salt (mass spec. M+1=421, MP=201.8-202.5° C.).

Example 58

Preparation of 2-[(1,1-dioxidotetrahydro-2H-thiopyran-4-yl)amino]-6-(2,4-difluorophenoxy)-8-methylpyrido[2,3-d]pyrimidin-7(8H)-one

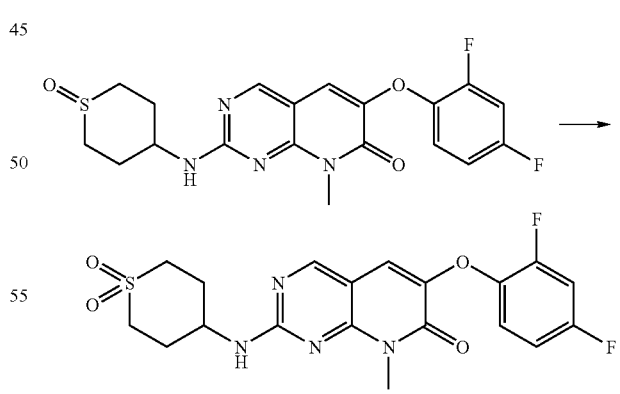

A mixture of the sulfoxide (0.6 g, 1.4 mmol) and 3-chloroperbenzoic acid (0.48 g, 1.5 mmol) in 50 mL of dichloromethane was stirred at room temperature for 12 hours under a nitrogen atmosphere. The reaction was then quenched with an aqueous sodium sulfite solution (10%, 100 mL), then washed with cold saturated aqueous sodium bicarbonate solution (100 mL). The organic solution was dried (brine, Na$_2$SO$_4$), evaporated under reduced pressure, and purified via column chromatography (SiO₂, CH₂Cl₂/MeOH—95/5) affording 0.41 g of the sulfone. This was dissolved in methanol/dichloromethane (5/95, 1 mL), hydrochloric acid in ether (1M, 1.1 mL) was added and the solution was stirred for 15 minutes. Evaporation under reduced pressure followed by addition of ether (10 mL) and stirring provided a solid. Filtration of the precipitate and rinsing with ether yielded 382 mg of the hydrochloride salt (mass spec. M+1=437, MP=251.7-254.9° C.).

Example 59

Preparation of 6-(2,6-difluorophenoxy)-2-{[1-(hydroxymethyl)butyl]amino}-8-methylpyrido[2,3-d]pyrimidin-7(8H)-one

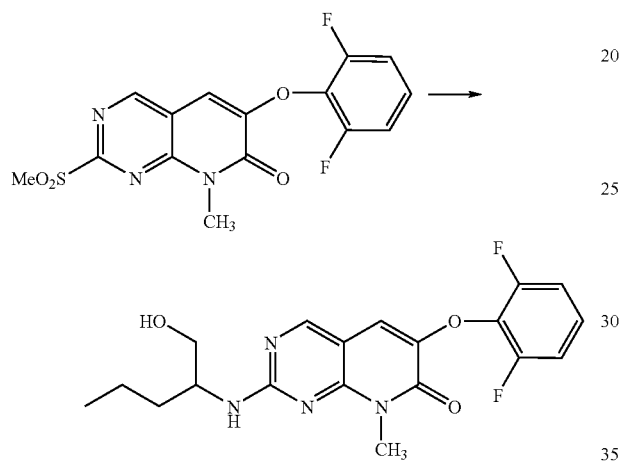

A mixture of sulfone 4 (0.38 g, 1 mmol) and 2-aminopentan-1-ol (0.35 g, 3.4 mmol) in 0.5 mL 1-methyl-2-pyrrolidinone was stirred at 80° C. for 1 hour and then cooled to room temperature. Methanol/water (9/1, 1-2 mL) was added and the suspension was stirred for 30 minutes. Filtration and washing of the precipitate thoroughly with ether then water followed by drying provided the free amine. This was dissolved in methanol (1-2 mL), hydrochloric acid in ether (1M, X's) was added and the reaction was stirred for 30 minutes. Evaporation of the organics, followed by addition of ether/methanol (1-2 mL) yielded a precipitate. Isolation of this solid via filtration and drying provided 0.28 g of the hydrochloride salt (Mass spec. M+1=391, MP=176.7-177.7° C.).

Example 60

Preparation of 6-(2,6-difluorophenoxy)-2-[(2-hydroxy-1,1-dimethylethyl)amino]-8-methylpyrido[2,3-d]pyrimidin-7(8H)-one

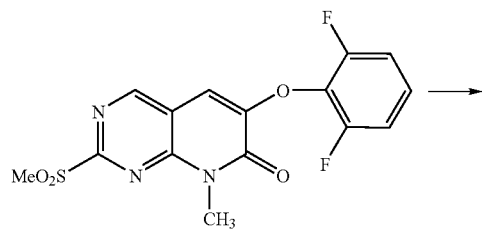

-continued

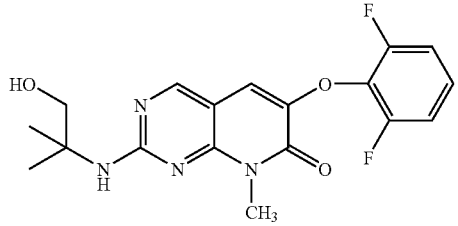

A mixture of sulfone 4 (0.38 g, 1 mmol) and 2-amino-2-methylpropan-1-ol (0.35 g, 3.4 mmol) in 0.4 mL 1-methyl-2-pyrrolidinone was stirred at 80° C. for 1 hour and then cooled to room temperature. Methanol/water (9/1, 1-2 mL) was added and the suspension was stirred for 30 minutes. Filtration and washing of the precipitate thoroughly with ether then water followed by drying provided the free amine. This was dissolved in methanol (1-2 mL), hydrochloric acid in ether (1M) was added and the reaction was stirred for 30 minutes. Evaporation of the organics, followed by addition of ether/methanol (1-2 mL) yielded a precipitate. Isolation of this solid via filtration and drying provided 0.212 g of the hydrochloride salt (Mass spec. M+1=377, MP=212.8-213.5° C.).

Example 61

Preparation of 6-(2-fluorophenoxy)-2-{[1-(hydroxymethyl)cyclopentyl]amino}-8-methylpyrido[2,3-d]pyrimidin-7(8H)-one

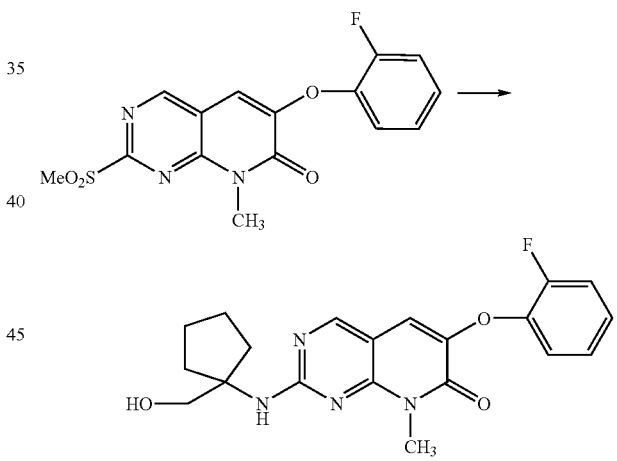

A mixture of sulfone 2 (0.353 g, 1 mmol), (1-aminocyclopentyl)methanol (0.154 g, 1.42 mmol) in 0.4 mL of 1-methyl-2-pyrrolidinone was heated to 80° C. for 1 hour. The reaction mixture was cooled, water (50 mL) and ethyl acetate (50 mL) were then added and the reaction was partitioned between the two phases. The organic layer was dried (brine, MgSO₄) and evaporation of the solvent yielded a residue which was purified via column chromatography (SiO₂, CH₂Cl₂/MeOH—90/10). The column fractions were combined and concentrated under reduced pressure to provide the free amine. This was suspended in methanol (1-2 mL), hydrochloric acid in ether (1M, X's) was added and the reaction was stirred for 30 minutes. Evaporation of the organics, followed by addition of ether/methanol (1-2 mL) yielded a precipitate. Isolation of this solid via filtration and drying provided 0.279 g of the hydrochloride salt (Mass spec. M+1=385, MP=198.6-200.3° C.).

Example 62

Preparation of 6-(2-fluorophenoxy)-2-{[1-(hydroxymethyl)-3-(methylthio)propyl]amino}-8-methylpyrido[2,3-d]pyrimidin-7(8H)-one

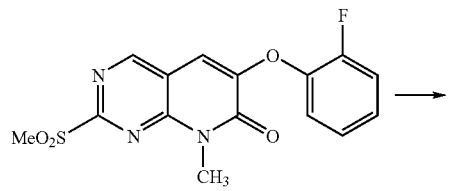

A mixture of sulfone 2 (1.04 g, 2.94 mmol), 2-amino-4-(methylthio)butan-1-ol (1.0 g, 9.7 mmol) in 1.0 mL of 1-methyl-2-pyrrolidinone was heated to 80° C. for 1 hour. The reaction mixture was cooled and methanol/water (9/1, 5-7 mL) was added but no precipitate formed. Therefore all solvents were removed via evaporation under reduced pressure, water (25 mL) and ethyl acetate (25 mL) were added. The reaction mixture was partitioned between the two layers and the aqueous layer was removed. The ethyl acetate solution was dried (brine, MgSO$_4$) and evaporated under reduced pressure. The crude reaction mixture was purified via column chromatography (SiO$_2$, CH$_2$Cl$_2$/MeOH—95/5) and the column fractions were combined and concentrated under reduced pressure to provide 0.8 g of the free amine. This product (0.2 g) was suspended in methanol (1-3 mL), hydrochloric acid in ether (1M, X's) was added and the reaction was stirred for 30 minutes. Evaporation of the organics, followed by addition of ether/methanol (1-2 mL) yielded a precipitate. Isolation of this solid via filtration and drying provided 0.125 g of the hydrochloride salt (Mass spec. M+1=405, MP=130.6-132.2° C.).

Example 63

Preparation of 2-(benzylamino)-6-(4-fluorophenoxy)-8-methylpyrido[2,3-d]pyrimidin-7(8H)-one

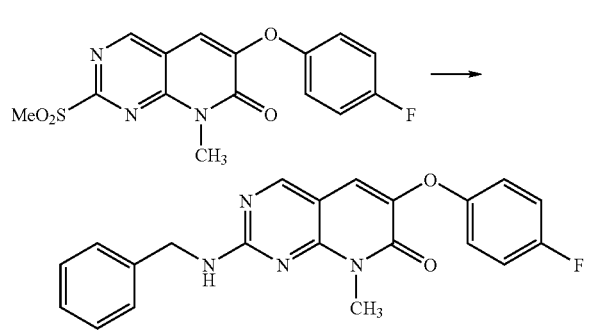

A mixture of 6-(4-fluorophenoxy)-8-methyl-2-(methylsulfonyl)pyrido[2,3-d]pyrimidin-7(8H)-one (see Example 8 made by replacing methyl 2-fluorophenoxyacetate with methyl 4-fluorophenoxyacetate-Steps A and B, 0.35 g, 1.0 mmol) and benzylamine (0.33 mL, 3 mmol) in 0.5 mL of 1-methyl-2-pyrrolidinone was stirred at 110° C. for 12 hours and then cooled to room temperature. Methanol (2 mL) was added and the suspension was stirred for 30 minutes. Filtration and washing of the precipitate thoroughly with methanol followed by drying provided the free amine. This was dissolved in ethyl acetate (1-2 mL) and hydrochloric acid in ether (1M, 1.5 eq) was added. Isolation of the solid via filtration and drying provided 0.317 g of the hydrochloride salt (Mass spec. M+1=377, MP=203.2-204° C.).

Example 64

Preparation of 2-(benzylamino)-6-(4-fluorobenzyl)-8-methylpyrido[2,3-d]pyrimidin-7(8H)-one

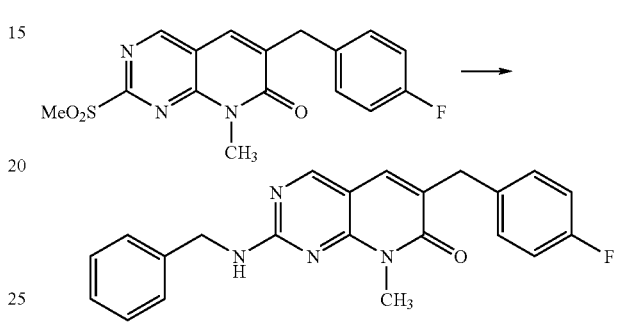

A mixture of sulfone 9 (0.36 g, 1.03 mmol) and benzylamine (0.35 mL, 3 mmol) in 0.3 mL of 1-methyl-2-pyrrolidinone was stirred at 80° C. for 1 hour and then cooled to room temperature. Ether (2 mL) was added and the suspension was stirred for 30 minutes. Filtration and washing of the precipitate thoroughly with ether followed by drying provided the free amine. This was dissolved in methanol (1-2 mL) and hydrochloric acid in ether (1M, X's) was added. Evaporation under reduced pressure, followed by stirring with ether/methanol (1-3 mL) yielded a precipitate. Isolation of the this solid via filtration and drying provided 0.193 g of the hydrochloride salt (Mass spec. M+1=375).

Example 65

Preparation of 6-(2-fluorophenoxy)-8-methyl-2-[(1-phenylpropyl)amino]pyrido[2,3-d]pyrimidin-7(8H)-one

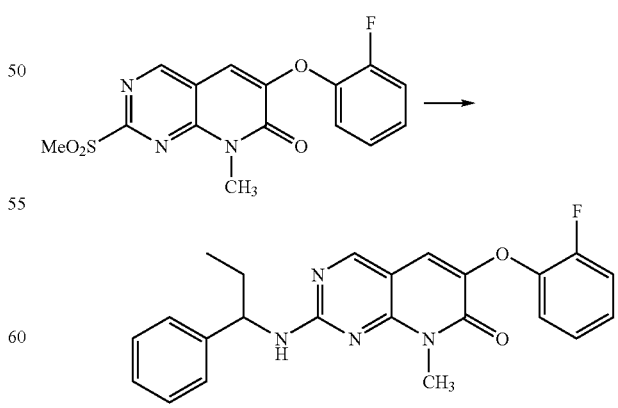

A mixture of sulfone 2 (0.1 g, 0.286 mmol), α-ethylbenzylamine (0.088 mL, 0.573 mmole) in 2 mL of 1-methyl-2-pyrrolidinone was heated to 120° C. for 12 hours. The reaction mixture was cooled and purified by column chromatography (SiO$_2$, Hexane/Acetone—80/20). The column fractions were combined and concentrated under reduced pressure to provide the free amine. This product was taken up in methanol (1-3 mL), hydrochloric acid in ether (1M, 1 eq) was added and the reaction was stirred for 30 minutes. Isolation of this solid via filtration, rinsing with ether and drying provided 0.084 g of the hydrochloride salt (Mass spec. M+1=405, MP=109.4-111.3° C.).

Example 66

Preparation of 6-(2-fluorophenoxy)-8-methyl-2-[(pyridin-2-ylmethyl)amino]pyrido[2,3-d]pyrimidin-7(8H)-one

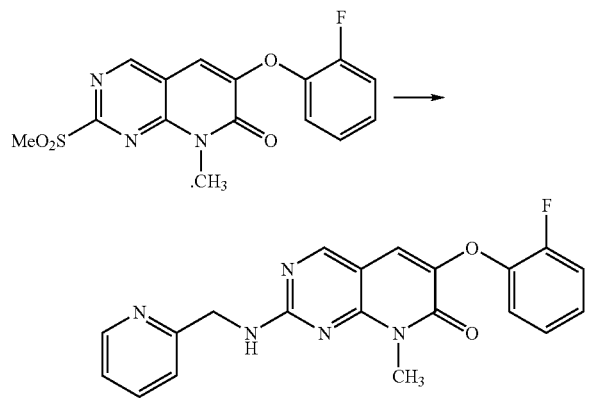

A mixture of sulfone 2 (0.05 g, 0.143 mmol), pyridin-2-ylmethylamine (0.154 g, 1.42 mmol) in 0.2 mL of chloroform was heated to 65° C. for 12 hours. The reaction mixture was cooled and the solvents were removed via evaporation. Methanol/water (90/10, 1 mL) was added and a precipitate formed. The product was washed with water, dissolved in methylene chloride and evaporated to yield the amine (0.035 g, mass spec. M+1=378).

Example 67

Preparation of 6-(2-fluorophenoxy)-2-[(3-furylmethyl)amino]-8-methylpyrido[2,3-d]pyrimidin-7(8H)-one

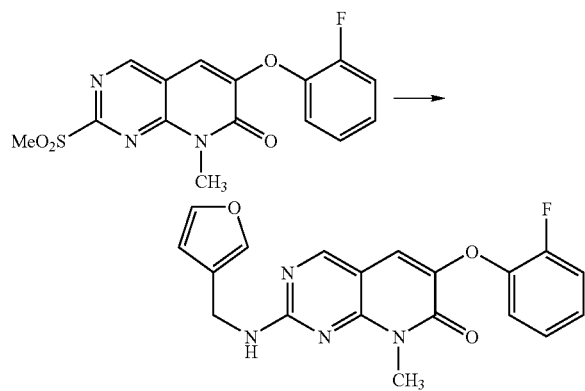

A mixture of sulfone 2 (0.05 g, 0.143 mmol), 3-furylmethylamine (0.023 g, 0.23 mmol) in 0.2 mL of chloroform was heated to 65° C. for 12 hours. The reaction mixture was cooled and the solvents were removed via evaporation. Methanol/water (90/10, 1 mL) was added and a precipitate formed. The product was washed with water, dissolved in methylene chloride and evaporated to yield the amine (0.042 g, mass spec. M+1=367).

Example 68

Preparation of 8-methyl-6-phenoxy-2-[(2-phenylethyl)amino]pyrido[2,3-d]pyrimidin-7(8H)-one

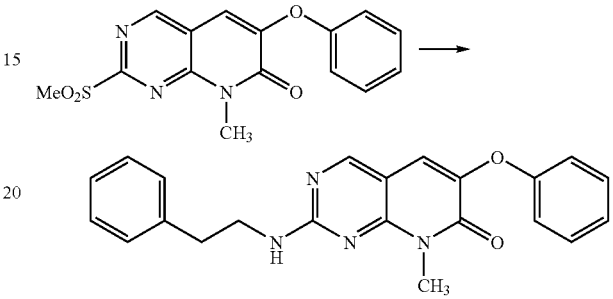

A mixture of sulfone 1 (0.33 g, 1 mmol) and phenethylamine (0.380 mL, 3 mmol) in 0.5 mL of 1-methyl-2-pyrrolidinone was stirred at 110° C. for 12 hours and then cooled to room temperature. Methanol (2 mL) was added and the suspension was stirred for 30 minutes. Filtration and washing of the precipitate thoroughly with methanol followed by drying provided the free amine. This was suspended in methanol (1-2 mL) and hydrochloric acid in ether (1M, 2 mL) was added. Isolation of the solid via filtration and drying provided 0.127 g of the hydrochloride salt (Mass spec. M+1=373, MP=211.8-213° C.).

Example 69

Preparation of 6-(2-chlorophenoxy)-8-methyl-2-[(2-phenylethyl)amino]pyrido[2,3-d]pyrimidin-7(8H)-one

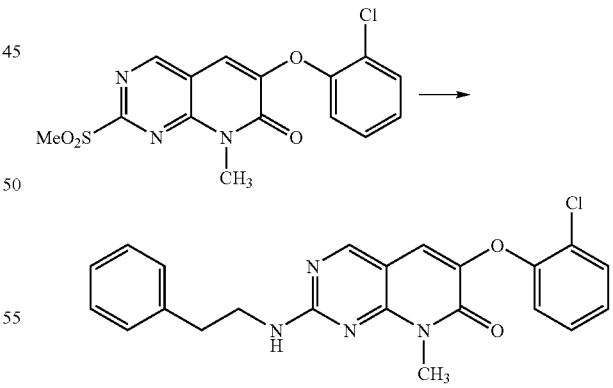

A mixture of sulfone 6 (0.365 g, 1 mmol) and phenethylamine (0.4 mL, 3.3 mmol) in 0.4 mL of 1-methyl-2-pyrrolidinone was stirred at 80° C. for 1 hour and then cooled to room temperature. Ether (2-3 mL) was added but no precipitate formed. Therefore the solvents were removed via evaporation under reduced pressure, water (5 mL) and ethyl acetate (5 mL) were added. The reaction was partitioned between the two layers and the aqueous layer was removed. The ethyl acetate solution was dried (brine, MgSO$_4$) and evaporated to provide a residue. Ether (2-3 mL was added to this and a precipitate formed. Filtration, rinsing with additional ether and drying provided the free amine. This solid was suspended in methanol (1-3 mL), hydrochloric acid in ether (1M, X's) was added and the reaction was stirred for 30 minutes. Filtration, washing with ether and drying provided 0.321 g of the hydrochloride salt (Mass spec. M+1=407, MP=210-211° C.).

Example 70

Preparation of ethyl 4-{[6-(2,4-difluorophenoxy)-8-methyl-7-oxo-7,8-dihydropyrido[2,3-d]pyrimidin-2-yl]amino}piperidine-1-carboxylate

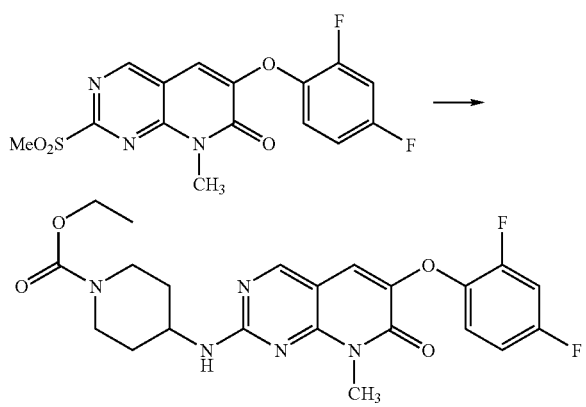

A mixture of sulfone 5 (1.0 g, 2.72 mmol) and ethyl 4-amino-1-piperidinecarboxylate (0.93 mL, 5.44 mmol) in 5 mL of 1-methyl-2-pyrrolidinone was stirred at 80° C. for 17 hours and then cooled to room temperature. Water (200 mL) was added and the suspension was stirred overnight. Filtration and washing of the precipitate thoroughly with methanol followed by drying provided the free amine. A portion of this product (0.100 g, 0.216 mmol) was dissolved in methanol (1-2 mL) and hydrochloric acid in ether (1M, 1 eq) was added. Isolation of the solid via filtration, followed by rinsing with ether and drying provided 0.317 g of the hydrochloride salt (Mass spec. M+1=462, MP=197.0-204.0° C.).

Example 71

Preparation of 8-methyl-2-{[3-(4-methylpiperazin-1-yl)propyl]amino}-6-phenoxypyrido[2,3-d]pyrimidin-7(8H)-one

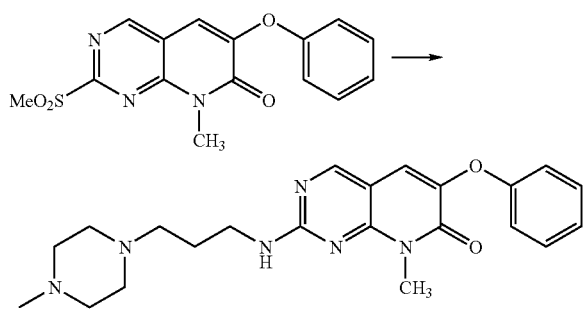

A mixture of sulfone 1 (0.33 g, 1 mmol) and 1-(3-aminopropyl)-4-methylpiperazine (0.51 mL, 3 mmol) in 0.5 mL 1-methyl-2-pyrrolidinone was stirred at 110° C. for 12 hours and then cooled to room temperature. Methanol (2 mL) was added and the suspension was stirred for 30 minutes. Filtration and washing of the precipitate thoroughly with methanol followed by drying provided the free amine. This was suspended in methanol (1-2 mL) and hydrochloric acid in ether (1M, 2 mL) was added. Isolation of the solid via filtration and drying provided 0.183 g of the hydrochloride salt (Mass spec. M+1=409, MP=180.2-182.2° C.).

Example 72

Preparation of 6-(2-chlorophenoxy)-8-methyl-2-{[3-(4-methylpiperazin-1-yl)propyl]amino}pyrido[2,3-d]pyrimidin-7(8H)-one

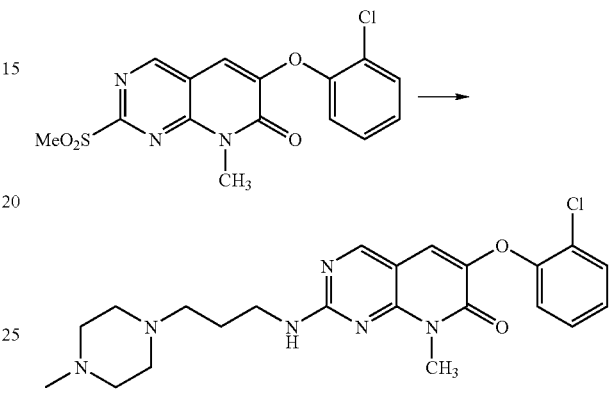

A mixture of sulfone 6 (0.38 g, 1 mmol) and 1-(3-aminopropyl)-4-methylpiperazine (0.46 mL, 2.9 mmol) in 0.4 mL 1-methyl-2-pyrrolidinone was stirred at 80° C. for 1 hour and then cooled to room temperature. Ether (2 mL) was added and the suspension was stirred for 2 hours. Filtration and washing of the precipitate thoroughly with ether followed by drying provided the free amine. This was suspended in methanol (1-2 mL), hydrochloric acid in ether (1M, X's) was added and the reaction was stirred for 30 minutes. Evaporation of the organics, followed by addition of ether/methanol (1-2 mL) yielded a precipitate. Isolation of this solid via filtration and drying provided 0.44 g of the hydrochloride salt (Mass spec. M+1=443, MP=233.9-235.5° C.).

Example 73

Preparation of 2-anilino-6-(4-fluorobenzyl)-8-methylpyrido[2,3-d]pyrimidin-7(8H)-one

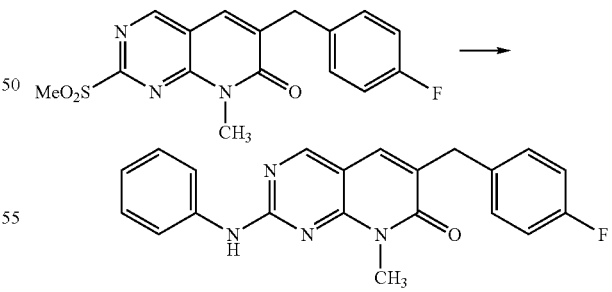

A mixture of sulfone 9 (0.4 g, 1.15 mmol) and aniline (0.4 mL, 4.3 mmol) in 0.4 mL 1-methyl-2-pyrrolidinone was stirred at 110° C. for 12 hours and then cooled to room temperature. Methanol (2 mL) was added and the suspension was stirred for 30 minutes. Filtration and washing of the precipitate thoroughly with methanol followed by drying provided the free amine. This was suspended in methanol (1-2 mL), hydrochloric acid in ether (1M, X's) was added and the reaction was stirred for 30 minutes. Isolation of the solid via filtration, rinsing with ether and drying provided 0.167 g of the hydrochloride salt (Mass spec. M+1=361, MP=243.1-246.3° C.).

Example 74

Preparation of 6-(4-fluorophenoxy)-2-[(4-fluorophenyl)amino]-8-methylpyrido[2,3-d]pyrimidin-7(8H)-one

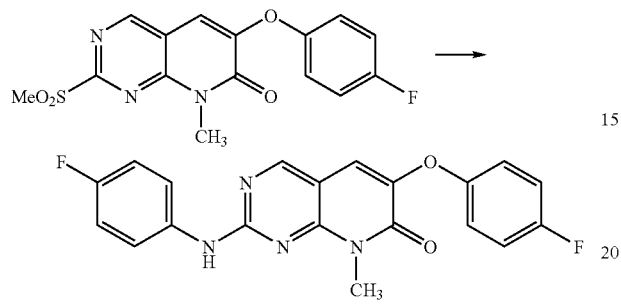

A mixture of 6-(4-fluorophenoxy)-8-methyl-2-(methylsulfonyl)pyrido[2,3-d]pyrimidin-7(8H)-one (see Example 8 replacing methyl 2-fluorophenoxyacetate with methyl 4-fluorophenoxyacetate-Step A-B, 0.35 g, 1 mmol) and 4-fluoroaniline (0.284 mL, 3 mmol) in 0.5 mL 1-methyl-2-pyrrolidinone was stirred at 110° C. for 12 hours and then cooled to room temperature. Methanol (2 mL) was added and the suspension was stirred for 30 minutes. Filtration and washing of the precipitate thoroughly with methanol followed by drying provided the crude product which was purified by column chromatography (SiO$_2$, CH$_2$Cl$_2$/MeOH—95/5). The column fractions were combined and concentrated under reduced pressure to provide the free amine. This was suspended in ethyl acetate (1-2 mL) and hydrochloric acid in ether (1M, 1.2 eq) was added. Isolation of the solid via filtration and drying provided 0.101 g of the hydrochloride salt (Mass spec. M+1=381, MP=242.3-242.6° C.).

Example 75

Preparation of 6-(2,6-dichlorophenoxy)-2-[(4-fluorophenyl)amino]-8-methylpyrido[2,3-d]pyrimidin-7(8H)-one

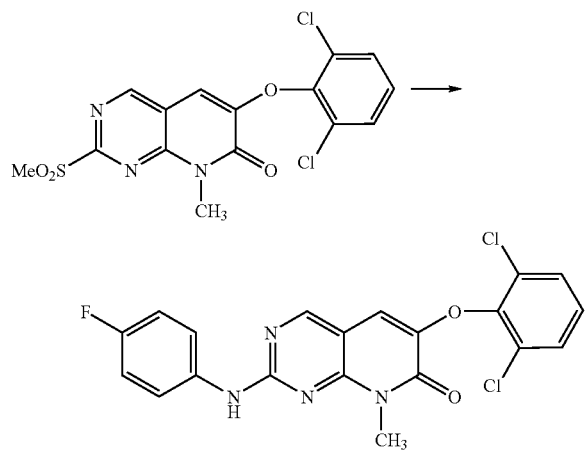

A mixture of 6-(2,6-dichlorophenoxy)-8-methyl-2-(methylsulfonyl)pyrido[2,3-d]pyrimidin-7(8H)-one (see Example 12-Step A-B, (replacing methyl 2-fluorophenoxyacetate with methyl 2,6-dichlorophenoxyacetate) 0.35 g, 1 mmol) and 4-fluoroaniline (0.284 mL, 3 mmol) in 0.5 mL 1-methyl-2-pyrrolidinone was stirred at 110° C. for 12 hours and then cooled to room temperature. Methanol (2 mL) was added and the suspension was stirred for 30 minutes. Filtration and washing of the precipitate thoroughly with methanol followed by drying provided the crude product which was purified by column chromatography (SiO$_2$, CH$_2$Cl$_2$/MeOH—95/5). The column fractions were combined and concentrated under reduced pressure to provide the free amine. This was suspended in ethyl acetate (1-2 mL) and hydrochloric acid in ether (1M, 1.2 eq) was added. Isolation of the solid via filtration and drying provided 0.131 g of the hydrochloride salt (Mass spec. M+1=430, MP=248.2-249.1° C.).

Example 76

Preparation of 6-(4-fluorobenzyl)-2-[(4-fluorophenyl)amino]-8-methylpyrido[2,3-d]pyrimidin-7(8H)-one

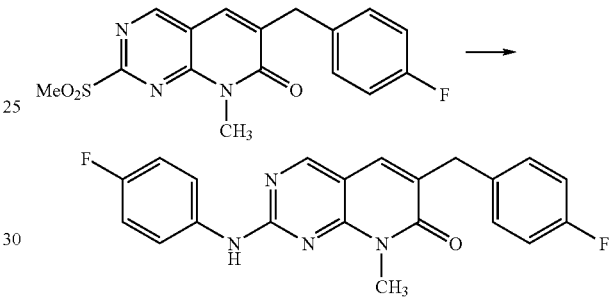

A mixture of sulfone 9 (0.36 g, 1 mmol) and 4-fluoroaniline (0.8 mL, 7.2 mmol) in 0.4 mL 1-methyl-2-pyrrolidinone was stirred at 110° C. for 12 hours and then cooled to room temperature. Methanol (2 mL) was added and the suspension was stirred for 30 minutes. Filtration and washing of the precipitate thoroughly with methanol followed by drying provided the crude product. This was suspended in methanol (1-2 mL), hydrochloric acid in ether (1M, X's) was added and the reaction was stirred for 1 hour. Isolation of the solid via filtration, rinsing with ether and drying provided 0.207 g of the hydrochloride salt (Mass spec. M+1=379, MP=246-250° C.).

Example 77

Preparation of 2-{[4-(2-hydroxyethyl)phenyl]amino}-8-methyl-6-phenoxypyrido[2,3-d]pyrimidin-7(8H)-one

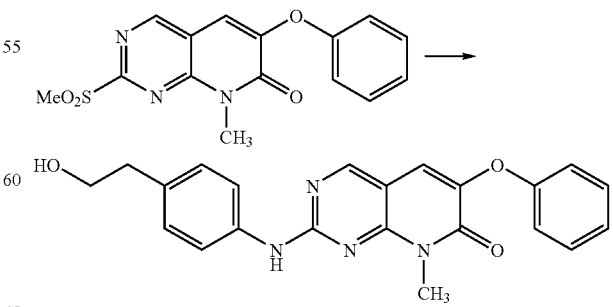

A mixture of sulfone 1 (0.331 g, 1 mmol) and 2-(4-aminophenyl)ethanol (0.411 g, 3 mmol) in 0.5 mL 1-methyl-2- pyrrolidinone was stirred at 110° C. for 12 hours and then cooled to room temperature. Methanol (2 mL) was added and the suspension was stirred for 30 minutes. Filtration and washing of the precipitate thoroughly with methanol followed by drying provided the free amine. This was suspended in methanol (1-2 mL), hydrochloric acid in ether (1M, 1.5 mL) was added and the reaction was stirred for 30 minutes. Isolation of the solid via filtration and drying provided 0.127 g of the hydrochloride salt (Mass spec. M+1=389).

Example 78

Preparation of 6-(2-chlorophenoxy)-2-({4-[2-(diethylamino)ethoxy]phenyl}amino)-8-methylpyrido[2,3-d]pyrimidin-7(8H)-one

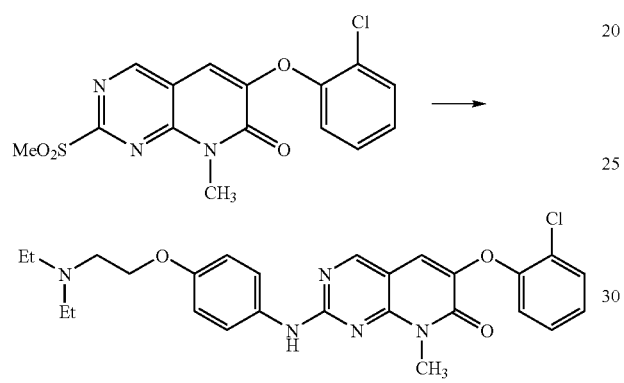

A mixture of sulfone 6 (0.4 g, 1.1 mmol) and 4-(2-diethylaminoethoxy)aniline (0.8 g, 3.8 mmol) in 0.5 mL 1-methyl-2-pyrrolidinone was stirred at 110° C. for 12 hours and then cooled to room temperature. Methanol/water (9/1, 1-2 mL) was added and the suspension was stirred for 30 minutes. Filtration and washing of the precipitate thoroughly with water followed by drying provided the crude product which was purified by column chromatography (SiO₂, CH₂Cl₂/MeOH—95/5). The column fractions were combined and concentrated under reduced pressure to provide the free amine. This was suspended in methanol (1-2 mL), hydrochloric acid in ether (1M, X's) was added and the reaction was stirred for 30 minutes. Evaporation of the organics, followed by addition of ether/methanol (1-2 mL) yielded a precipitate. Isolation of this solid via filtration and drying provided 0.16 g of the hydrochloride salt (Mass spec. M+1=494, MP=255.5-261.4° C.).

Example 79

Preparation of 2-({4-[2-(diethylamino)ethoxy]phenyl}amino)-6-(4-fluorophenoxy)-8-methylpyrido[2,3-d]pyrimidin-7(8H)-one

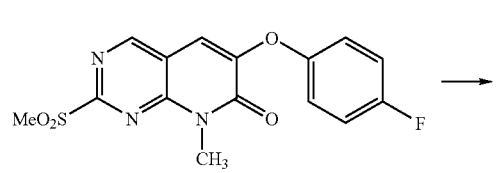

-continued

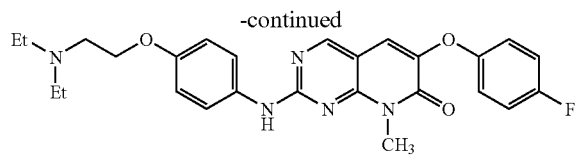

A mixture of 6-(4-fluorophenoxy)-8-methyl-2-(methylsulfonyl)pyrido[2,3-d]pyrimidin-7(8H)-one (see Example 8-Step A-B, 0.35 g, 1 mmol) and 4-(2-diethylaminoethoxy)aniline (0.625 g, 3 mmol) in 0.5 mL 1-methyl-2-pyrrolidinone was stirred at 110° C. for 12 hours and then cooled to room temperature. Methanol (2 mL) was added and the suspension was stirred for 30 minutes. Filtration and washing of the precipitate thoroughly with methanol followed by drying provided the free amine. This was suspended in ethyl acetate (1-2 mL), hydrochloric acid in ether (1M, 1.2 eq) was added and the reaction was stirred for 30 minutes. Isolation of the solid via filtration and drying provided 0.085 g of the hydrochloride salt (Mass spec. M+1=478, MP=245.2-246.1° C.).

Example 80

Preparation of 6-(2-fluorophenoxy)-2-[(3-hydroxypyridin-2-yl)amino]-8-methylpyrido[2,3-d]pyrimidin-7(8H)-one

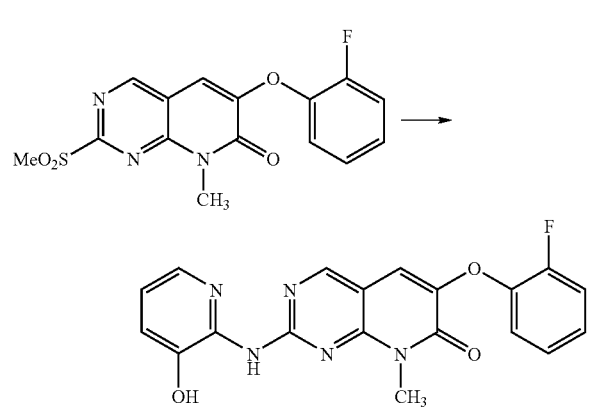

A mixture of sulfone 2 (0.05 g, 0.143 mmol), 2-aminopyridin-3-ol (0.047 g, 0.43 mmol) in 0.1 mL of 1-methyl-2-pyrrolidinone was heated to 80° C. for 3 hours. The reaction mixture was cooled, methanol/water (90/10, 1 mL) was added and a precipitate formed. The product was washed with water, dissolved in methylene chloride, filtered through a drying agent (MgSO₄) and evaporated to yield the amine (0.040 g, mass spec. M+1=380).

Example 81

Preparation of 6-(2-fluorophenoxy)-8-methyl-2-[(5-methylpyridin-2-yl)amino]pyrido[2,3-d]pyrimidin-7(8H)-one

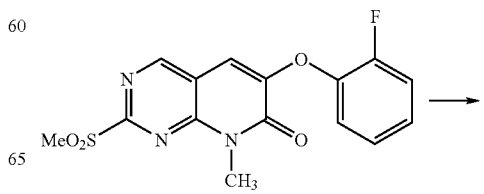

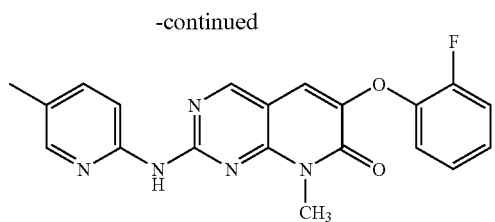

To a solution of 5-methylpyridin-2-amine hydrochloride salt (0.025 g, 0.17 mmol) in 2 mL of chloroform at room temperature was added barium hydroxide monohydrate (0.16 g, 0.86 mmol). This was allowed to stir for 1 hour, filtered and evaporated under reduced pressure. Sulfone 2 (0.05 g, 0.143 mmol) in 1 mL of chloroform was added to the residue, the reaction was brought to 65° C. and stirred for 24 hours. The mixture was cooled and the solvents were removed via evaporation. Methanol/water (90/10, 1 mL) was added and a precipitate formed. The product was washed with methanol/water, dissolved in methylene chloride and evaporated to yield the amine (0.034 g, mass spec. M+1=378).

Example 82

Preparation of 2-(benzylthio)-6-(4-fluorophenoxy) pyrido[2,3-d]pyrimidin-7-amine Step A: Preparation of 4-fluorophenoxy)acetonitrile:

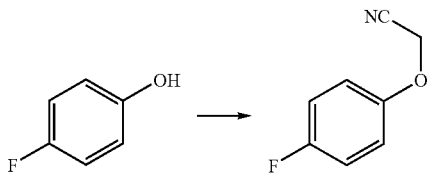

Iodoacetonitrile (2.14 mL, 29 mmol) was added to a suspension of 4-fluorophenol (3.0 g, 27 mmol) and K$_2$CO$_3$ (4.85 g, 35 mmol) in 10 mL of DMF. The reaction was heated to 60° C. for 15 hours then the mixture was cooled, diluted with water and extracted with ethyl acetate-hexane (1:1, 150 mL, 3×). The organic solution was combined and washed with water (200 mL, 2×), and dried (brine, MgSO$_4$). The solvent was removed under reduced pressure affording 4.1 g of the product.

Step B: Preparation of 2-(benzylthio)-6-(4-fluorophenoxy) pyrido[2,3-d]pyrimidin-7-amine:

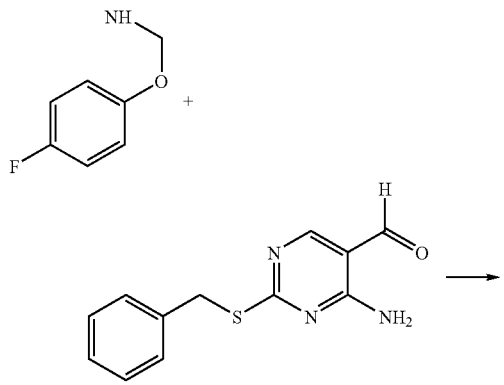

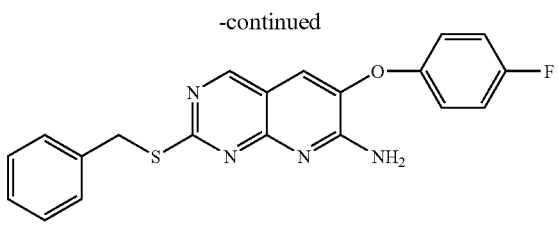

A mixture of the nitrile (prepared in Step A, 1.83 g, 12 mmol), the amino-pyrimidine aldehyde (2.48 g, 10 mmol) and K$_2$CO$_3$ (7.0 g, 50 mmol) in 30 mL of dimethylformamide was heated in an oil bath at 120° C. for 4 hours. The mixture was cooled, diluted with water and extracted with ethyl acetate (125 mL, 3×). The organic solution was combined and washed with water (120 mL, 3×), dried (brine, MgSO$_4$) and filtered through a short column filled with silica. The solvent was removed under reduced pressure and the crude material was purified by column chromatography (SiO2, MeOH/CH$_2$Cl$_2$, 80/20 to 95/5) affording 1.3 g of the product (mass spec. M+1=379, MP=186.2-192.2° C.).

Displacement of the benzylthio group (or the corresponding sulfoxide or sulfone) with an amine R$^1$NH$_2$ as described earlier provides compounds of Formula II where R$^8$ and R$^9$ are both hydrogen. Further alkylation, acylation, sulfonylation, reductive amination etc. provides compounds of Formula II where R$^8$ and R$^9$ are as described in the Summary of the Invention.

Example 83

Preparation of 6-(2,4-difluorophenoxy)-2-(benzylthio)pyrido[2,3-d]pyrimidin-7(8H)-one

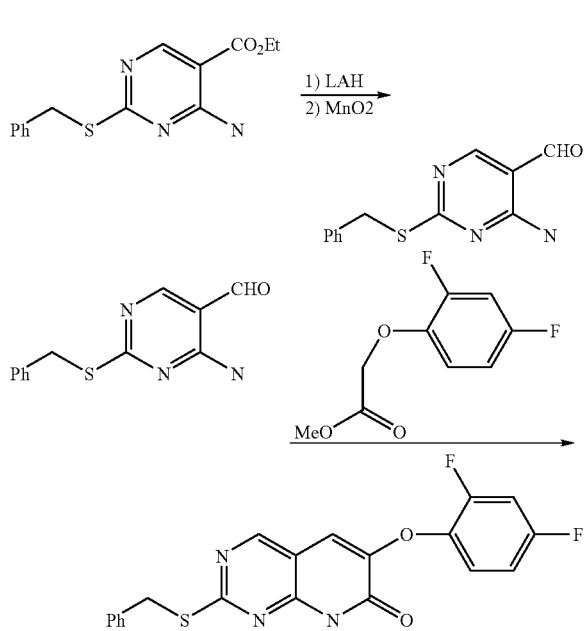

Step A: Preparation of 4-Amino-2-benzylthiopyrimidine-5-carbaldehyde

To a 1M solution of lithium aluminum hydride (185 mL, 185 mmol) in diethyl ether was added a solution of 4-amino-2-benzylthiopyrimidine-5-carboxylate (46 g, 159 mmol) in 500 mL of dry tetrahydrofuran dropwise over a period of 1.5 hours at 0° C. The reaction mixture was slowly-warmed to ambient temperature and then cooled back to 0° C. before carefully quenching with 7 mL of water, 7 mL of 2 M sodium hydroxide solution, followed by 14 mL of water. The resulting suspension was filtered and the filter residue was washed with 2×300 mL of ethyl acetate. The collected fractions were concentrated to give 45.7 g of 4-amino-2-benzylthiopyrimidine-5-methanol as a white solid.

A suspension of 4-amino-2-benzylthiopyrimidine-5-methanol (45.7 g) obtained above in 800 mL of methylene chloride was treated with activated manganese oxide powder (87 g). The reaction mixture was stirred for 18 hours, then filtered through a pad of celite. The filter residue was repeatedly washed with a solution of hot methylene chloride and methanol. The combined fractions were concentrated to give 25 g of 4-amino-2-benzylthiopyrimidine-5-carboxaldehyde as a white solid.

Step B: Preparation of 6-(2,4-difluorophenoxy)-2-(benzylthio)pyrido[2,3-d]pyrimidin-7(8H)-one:

To a mixture of 4-amino-2-benzylthiopyrimidine-5-carboxaldehyde (19.5 g, 80 mmol) and methyl 2,4-difluorophenoxyacetate (25.6 g, 119 mmol) in NMP (50 mL) was added potassium carbonate (16.5 g, 119 mmol). The mixture was heated at 80-90° C. for two days and cooled to room temperature. It was added to ice-water (1000 g) and stirred for 1 hour. The solids were filtered, washed with water and ether, and dried to give 27 g of the sulfide (Mass spec. M+1=398, MP=240-244° C.).

Example 84

Preparation of 1-tert-Butyl-3-[6-(2,4-difluoro-phenoxy)-2-(tetrahydro-pyran-4-ylamino)pyrido[2,3-d]pyrimidin-7-yl]-urea Step A: Preparation of 1-tert-Butyl-3-[6-(2,4-difluoro-phenoxy)-2-methylsulfanylpyrido[2,3-d]pyrimidin-7-yl]-urea:

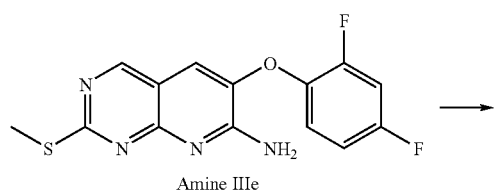

Amine IIIe

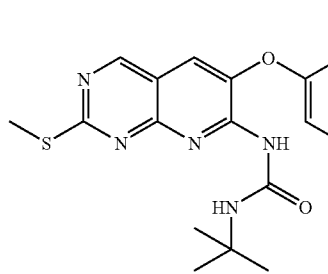

To a solution of the amine IIIe (prepared in similar fashion as described in example 82) (0.32 g, 1.0 mmol) in 5 mL of 1-methyl-2-pyrrolidinone at room temperature was added the sodium hydride (60%, 0.04 g, 1.0 mmol). The mixture was stirred at room temperature for 1 hour. t-Butylisocyanate (0.01 g, 0.11 mL, 1.0 mmol) was added by dropwise over a period of three minutes. The dark brown solution was then stirred for two more hours and poured into 50 mL of 1M HCl and extracted with ethyl acetate (2×, 50 mL). The combined ethyl acetate solution was washed with water (3×, 75 mL) and dried (brine, MgSO₄). Evaporation of solvent and purification of product via column chromatography with silica gel eluting with 10% ethyl acetate in dichloromethane gave 0.164 g of desired sulfide.

Step B: Preparation of 1-tert-Butyl-3-[6-(2,4-difluoro-phenoxy)-2-methanesulfonyl-pyrido[2,3-d]pyrimidin-7-yl]-urea:

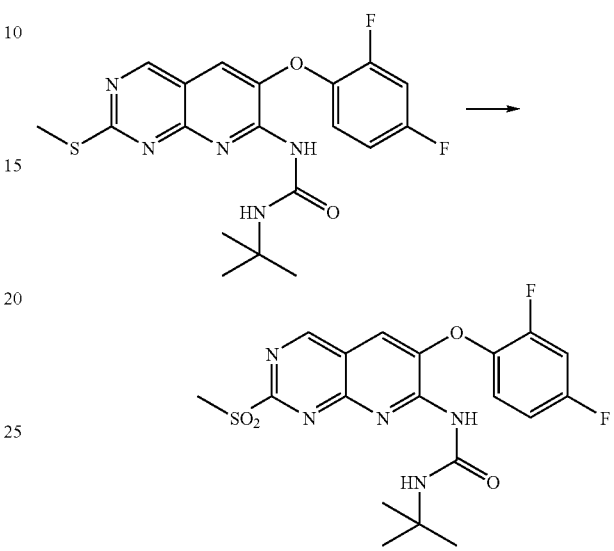

To a solution the sulfide (0.164 g, 0.4 mmol) in dichloromethane (50 mL) was added the meta-chloroperbenzoic acid (77% max, 0.19 g, 0.88 mmol) at 5° C. The mixture was then stirred at room temperature for 15 hours and was poured into 10% aqueous NaHSO₃. The organic solution was then washed with 10% aqueous NaHCO₃ and dried (brine, MgSO₄). Evaporation of solvent gave 0.176 g of the sulfone (mass spec. M+1=452).

Step C: Preparation of 1-tert-Butyl-3-[6-(2,4-difluoro-phenoxy)-2-(tetrahydro-pyran-4-ylamino)-pyrido[2,3-d]pyrimidin-7-yl]-urea:

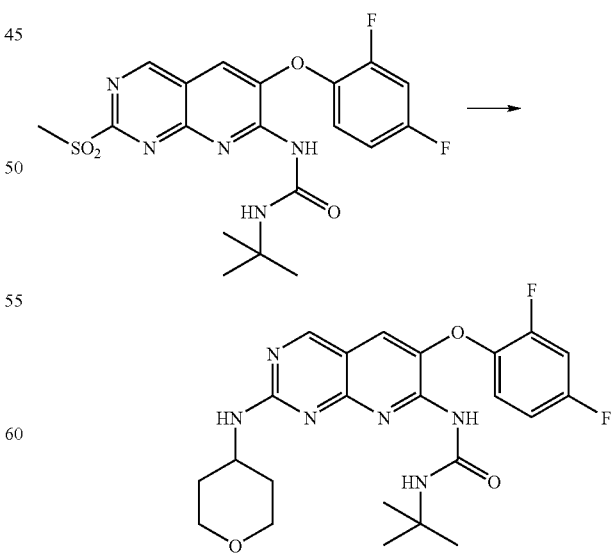

A solution of the sulfone (0.17 g, 0.4 mmol) and 4-aminotetrahydropyran (0.24 g, 2.3 mmol) in 2 mL of 1-methyl-2- pyrrolidinone was heated to 80° C. for 3 hours. The reaction mixture was cooled, poured into water and extracted with ethyl acetate (2×, 50 mL). The organic solution was washed with water (5×, 50 mL) and dried (brine, MgSO$_4$). Evaporation of the solvent under reduced pressure and purified via column chromatography (SiO$_2$, CH$_2$Cl$_2$/ethyl acetate—50/50) yielded 0.123 g of the desired product (Mass spec. M+1=473, MP=195-201° C.).

Example 85

Preparation of N-[6-(2,4-Difluoro-phenoxy)-2-(tetrahydro-pyran-4-ylamino)-pyrido[2,3-d]pyrimidin-7-yl]-methanesulfonamide Step A: Preparation of N-[6-(2,4-Difluoro-phenoxy)-2-methylsulfanyl-pyrido[2,3-d]pyrimidin-7-yl]-methanesulfonamide

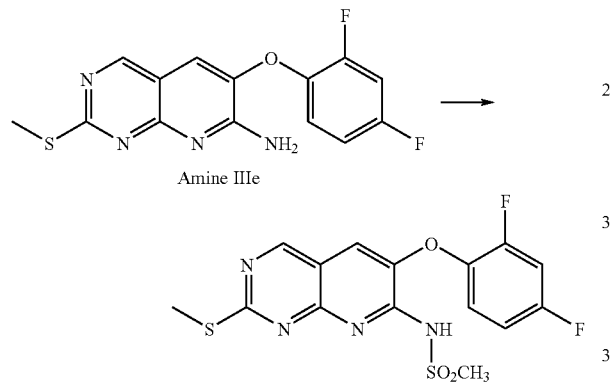

Amine IIIe

To a suspension of the amine IIIe (prepared in similar fashion as described in example 82) (0.32 g, 1.0 mmol) in 10 mL of dichloromethane at 5° C. was added the trimethylaluminum reagent (2M in Toluene, 0.5 mL, 1.0 mmol) dropwise. The dark solution was stirred for 30 minutes at ambient temperature. Methanesulfonic anhydride (0.174 g, 1.0 mmol) was added and the solution was heated to reflux. Course of reaction was followed by TLC and adddition of more methanesulfonic anhydride was required until completion of reaction. A total of 3.6 equivalents of the anhydride was added and after 5 hours of reflux, the reaction mixture was poured into aqueous 1M HCl (50 mL) and was extracted with ethyl acetate. (2×, 50 mL). The solvent was dried (brine, MgSO$_4$) and after evaporation the compound was purified via column chromatography (SiO$_2$, CH$_2$Cl$_2$/MeOH—97/3), providing 0.164 g of the sulfonamide-sulfide (Mass spec. M+1=399).

Step B: N-[6-(2,4-Difluoro-phenoxy)-2-(tetrahydro-pyran-4-ylamino)-pyrido[2,3-d]pyrimidin-7-yl]-methanesulfonamide

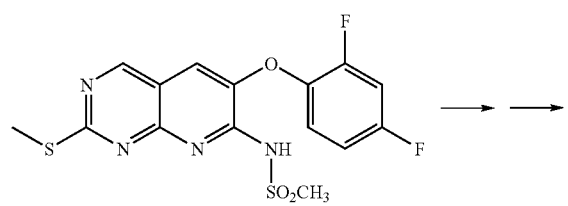

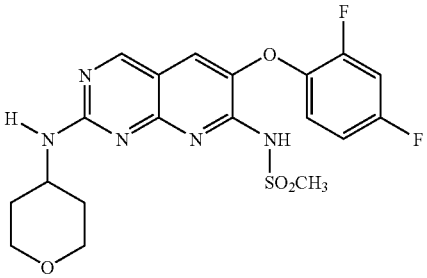

To a solution of the sulfonamide-sulfide (0.164 g, 0.4 mmol) in 20 mL of dichloromethane was added the meta-chloroperbenzoic acid (0.2 g, 0.9 mmol). The reaction mixture was stirred at room temperature for 15 hours and was washed with 10% aqueous NaHSO$_3$ and dried (brine and MgSO$_4$). (Note: do not wash with NaHCO$_3$, the sulfone is base sensitive). The solvent was evaporated under reduced pressure and this sulfonamide-sulfone (0.4 mmol) and 4-amino-tetrahydropyran (0.5 g,) in 1.0 mL of 1-methyl-2-pyrrolidinone was heated to 100° C. for 12 hours after which the solvent was evaporated under high vacuum and the compound was purified via column chromatography (SiO$_2$, CH$_2$Cl$_2$/MeOH—97/3), providing 90 mg of desired product (Mass spec. M+H=452, MP=199-204° C.).

Example 86

Preparation of 6-(2,4-difluorophenoxy)-2-{[(1S)-2-fluoro-1,2-dimethylpropyl]amino}-8-methylpyrido[2,3-d]pyrimidin-7(8H)-one

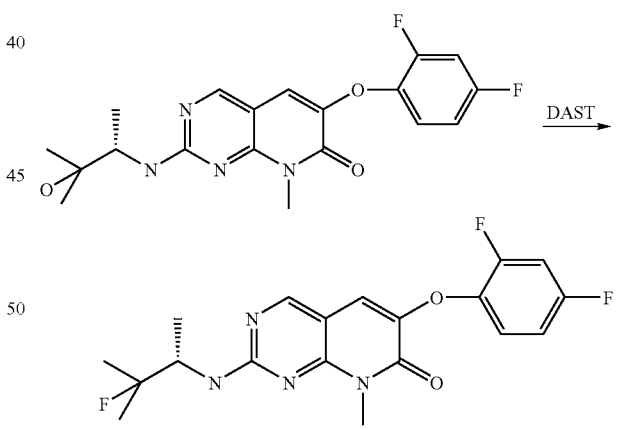

To the compound obtained in the Example 53 (free base, 0.28 g) in methylene chloride (5 mL) at −78° C. was added DAST (Aldrich, 0.14 mL). The reaction mixture was slowly warmed up to room temperature. It was partitioned between methylene chloride and water. The organic layer was separated and washed with saturated aqueous sodium carbonate, dried, and concentrated to give the crude product. Preparative TLC (silica gel, 45% EtOAc/hexanes) gave the pure product (0.16 g). It was converted to the hydrochloride salt by treatment with 1M HCl in ether to give R03310297-001 (Mass spec. M+1=393, MP=196-197.2° C.).

Example 87

Preparation of 6-(2,4-Difluoro-phenoxy)-2-{[(1S)-2-hydroxy-1,2-dimethylpropyl]amino}-8-isopropylpyrido[2,3-d]pyrimidin-7(8H)-one Step A: Preparation of 6-(2,4-Difluoro-phenoxy)-8-isopropyl-2-phenylmethanesulfonyl-8H-pyrido[2,3-d]pyrimidin-7-one

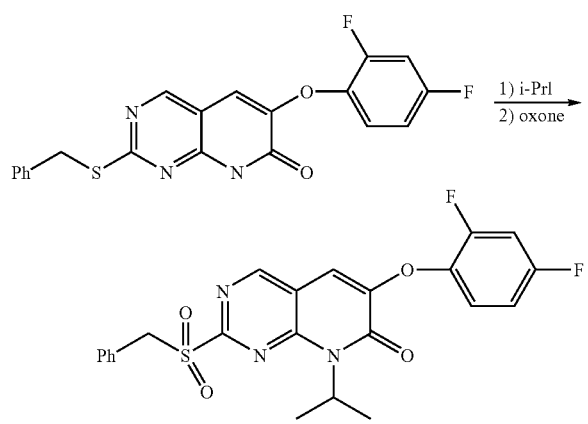

The above sulfide (2.2 g, 5.5 mmol), potassium carbonate (0.84 g, 6.1 mmol), and 2-iodopropane (0.58 mL, 5.8 mmol) in dry DMF (5 mL) were stirred at room temperature overnight. Aqueous work up gave the crude sulfide. It was dissolved in THF (50 mL) and treated with oxone™ (8 g) in water (50 mL) at 0-5. The mixture was then slowly warmed to room temperature and stirred for additional 5 hours. Aqueous work up gave the crude sulfone.

Step B: Preparation of 6-(2,4-Difluoro-phenoxy)-2-{[(1S)-2-dimethylpropyl]amino}-8-isopropylpyrido[2,3-d]pyrimidin-7(8H)-one

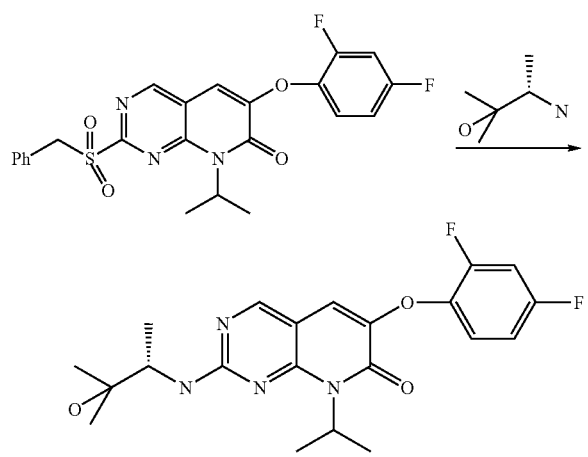

The above sulfone (0.93 g, 2.05 mmol), (3S)-3-amino-2-methylbutan-2-ol hydrochloride salt (0.54 g, 4 mmol) and triethylamine (1 mL) in isopropyl alcohol (10 mL) were refluxed for 10 hours. Aqueous work up gave the crude product. After column chromatography (silica gel, 35%-45% EtOAc/hexanes) the pure product (0.386 g) was obtained. It was converted to its hydrochloride salt by the treatment with 1M HCl (in ether) and recrystallized from isopropyl alcohol to gave R03310294-001 (0.29 g) (Mass spec. M+1=419, MP=200-202° C.).

Example 88

Preparation of 6-(2,4-difluorophenoxy)-8-methyl-2-(tetrahydro-2H-pyran-4-ylamino)pyrido[2,3-d]pyrimidin-7(8H)-one Step A: Preparation of 6-Chloro-4-methylamino-nicotinic acid ethyl ester

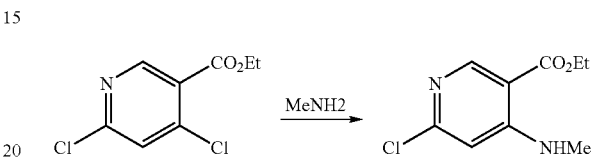

4,6-dichloro-3-nicotinic acid ethyl ester (Specs, 7.37 g, 33.5 mmol) was stirred with aqueous methyl amine (40%, 14.5 mL) in acetonitrile (50 mL) at 0-5° C. and then room temperature for 6 hours. The mixture was concentrated and added EtOAc. The organic layer was washed with brine (2×), dried and evaporated to give the desired product (7.12 g; MP=61.4-63.1° C.).

Step B: Preparation of 6-Chloro-4-methylamino-pyridine-3-carbaldehyde

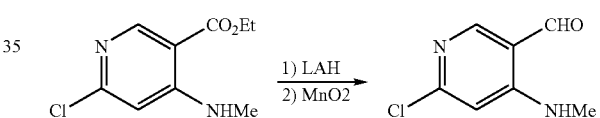

Step B: To the above ester (7.1 g, 33.2 mmol) in THF (100 mL) was slowly added LAH (1.0 M in THF, 70 mL) at −78° C. and stirred for 3 hours. The temperature was slowly raised to −10° C. and TLC indicated that the ester was consumed. MeOH/EtOAc (5 ml each) was added to destroy excess LAH and the mixture was warmed to room temperature. Water (50 mL) and EtOAc (500 mL) were added and filtered through a pad of celite. The filtrate was separated and dried. The crude product was further purified by column chromatography (silica gel, 40-75% EtOAc/hexanes and then 5% MeOH/CH$_2$Cl$_2$) to give 3.3 g of solids (Mass spec. M+1=173.1, MP=168.8-169.6° C.).

The alcohol obtained (3.2 g) was stirred with MnO2 (16.2 g) in methylene chloride (800 mL) at room temperature for two hours. The mixture was filtered through a pad of celite and washed with EtOAc. The filtrate was concentrated to give the aldehyde (2.8 g, MP=77.2-80.8° C.).

Step C: Preparation of 7-Chloro-3-(2,4-difluoro-phenoxy)-1-methyl-1H-[1,6]naphthyridin-2-one

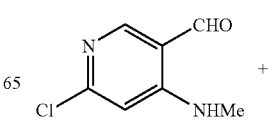

+

-continued

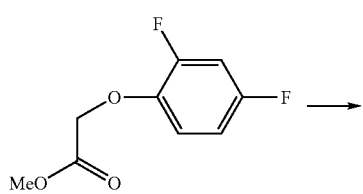

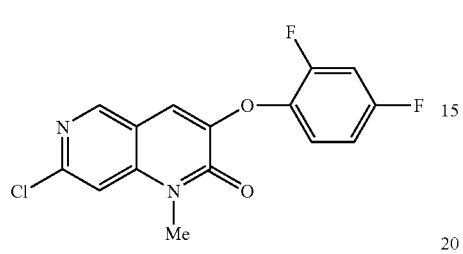

The aldehyde obtained above (1.8 g) was heated with methyl 2,4-difluorophenoxyacetate (4.1 g) and potassium carbonate (4.1 g) in NMP (20 mL) at 70° C. for two days. EtOAc (200 mL) was added and washed with brine (3×), dried and concentrated to give the crude product. Tituration with hexanes gave 3.07 g of white solids (Mass spec. M+1=323, MP=168-170.5° C.

Step D: Preparation of 6-(2,4-difluorophenoxy)-8-methyl-2-(tetrahydro-2H-pyran-4-ylamino)pyrido[2,3-d]pyridin-7(8H)-one

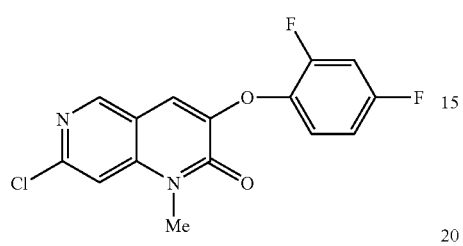

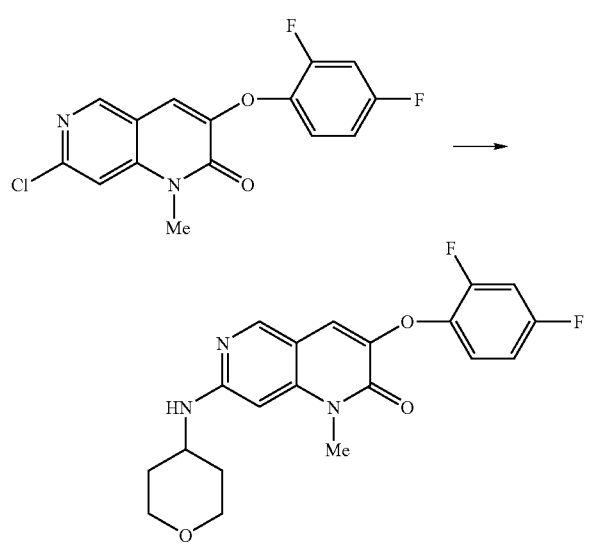

The product obtained above (2.06 g, 6.4 mmol) was heated with 4-amino-tetrahydropyran (3.4 g, 33.6 mmol) at 150-160° C. for three days. The mixture was cooled to room temperature and stirred with EtOAc (200 mL) and brine (50 mL). The organic layer was separated, dried, and concentrated. The crude product obtained was purified by column chromatography (40-60% EtOAc/hexanes) to 1.65 g of solids. They were dissolved in CH$_2$Cl$_2$/MeOH (5 mL each) and treated with 4.5 mL of 1M HCl in ether. The solvents were removed and the resulting solids were recrystallized from isopropyl alcohol to 1.3 g of white crystals (Mass spec. M+1=388.2, MP=237.5-239° C.).

Example 89

Preparation of 8-Amino-6-(2,4-difluoro-phenoxy)-2-(tetrahydro-pyran-4-ylamino)-8H-pyrido[2,3-d]pyrimidin-7-one Step A: Preparation of 8-Amino-2-benzylsulfanyl-6-(2,4-difluoro-phenoxy)-8H-pyrido[2,3-d]pyrimidin-7-one:

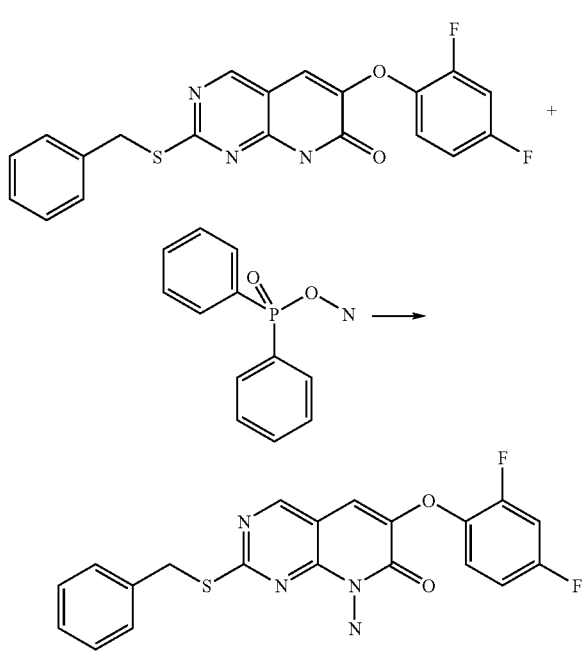

To a solution of the sulfide (see Example 83 for preparation) (2.67 g, 6.72 mmol) in DMF (120 mL) at 0° C. with stirring was added 60% NaH (375 mg, 1.4 eq) in one portion. The resulting mixture was stirred at 0° C. for 30 minutes. Then diphenyl phosphinyl-O-hydroxylamine (Tet. Let., vol. 23, No. 37, 3835-3836, 1982) (2.34 g, 1.5 eq) was added in one portion. After about one minute, the mixture became very thick and difficult to stir. TLC analysis indicated that all of the starting NH sulfide was consumed. Added ethyl acetate (650 mL) and water (250 mL) to the reaction, partitioned and separated the layers. The ethyl acetate layer was further washed with water (4×200 mL) and then finally washed with brine (1×200 mL). The organic layer was dried over magnesium sulfate, filtered and concentrated. Pumped under high vacuum to give the hydrazido sulfide as a dark tan powder (2.683 g, (M+H)$^+$=413, m.p.=179.3-182.3° C.).

Step B: Preparation of 8-Amino-6-(2,4-difluoro-phenoxy)-2-(tetrahydro-pyran-4-ylamino)-8H-pyrido[2,3-d]pyrimidin-7-one:

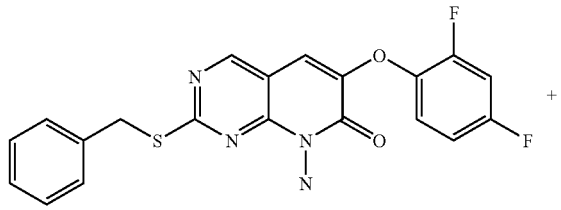

-continued

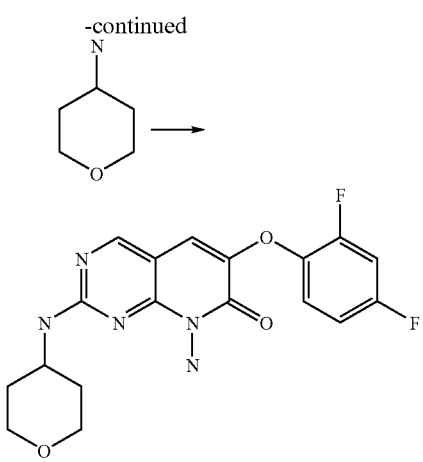

To the sulfide (820 mg, 1.99 mmol) and 4-aminotetrahydropyran (500 mg, 2.5 eq) was added NMP (0.8 mL) and the resulting mixture was heated with stirring at 150° C. for 24 hours. By TLC, the starting hydrazido sulfide was consumed. Ethyl acetate (175 mL) and water (50 mL) were added and the layers were partitioned and then separated. The aqueous layer was further extracted with ethyl acetate (100 mL) and the combined ethyl acetate layers were washed with water (2×200 mL). Finally, the organic layer was washed with brine (1×150 mL) and then the ethyl acetate layer was dried over magnesium sulfate, filtered and concentrated to give 882 mg of the crude product. Purification by Preparative Thin Layer Chromatography eluting with 6% methanol in dichloromethane gave the free amine as a dark tan powder (44 mg). The free amine was taken up in dichloromethane (15 mL) and then 1M HCl in diethyl ether (0.17 mL, 1.5 eq) was added with stirring. Stirred for 5 minutes and then the solvent was removed under reduced pressure at 50° C. Dried under high vacuum at 56° C. for 24 hours to give the desired product (43 mg, (M+H)$^+$=390) as a tan powder.

Example 90

Preparation of 6-(2,4-Difluoro-phenoxy)-8-isopropylamino-2-(tetrahydro-pyran-4-ylamino)-8H-pyrido[2, 3-d]pyrimidin-7-one Step A: Preparation of 2-Benzylsulfanyl-6-(2,4-difluoro-phenoxy)-8-isopropylamino-8H-pyrido[2,3-d]pyrimidin-7-one:

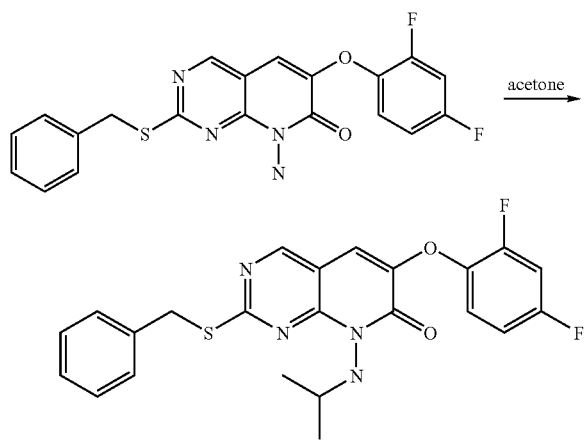

To the hydrazido sulfide (300 mg, 0.73 mmol) in methanol (70 mL) and acetic acid (16 mL) was added acetone (0.16 mL) followed by sodium cyanoborohydride (55 mg, 1.2 eq). The resulting mixture was stirred at room temperature for 24 hours. The next day the reaction mixture was poured in to saturated sodium bicarbonate (100 mL) and then extracted with ethyl acetate (2×100 mL). The ethyl acetate extracts were washed with brine (1×50 mL) and then dried over magnesium sulfate, filtered and concentrated to give 323 mg of crude product. Purification by Preparative Thin Layer Chromatography eluting with 30% ethyl acetate in hexanes gave the desired compound (64 mg, (M+H)$^+$=455).

Step B: Preparation of 2-Benzylsulfinyl-6-(2,4-difluoro-phenoxy)-8-isopropylamino-8H-pyrido[2,3-d]pyrimidin-7-one

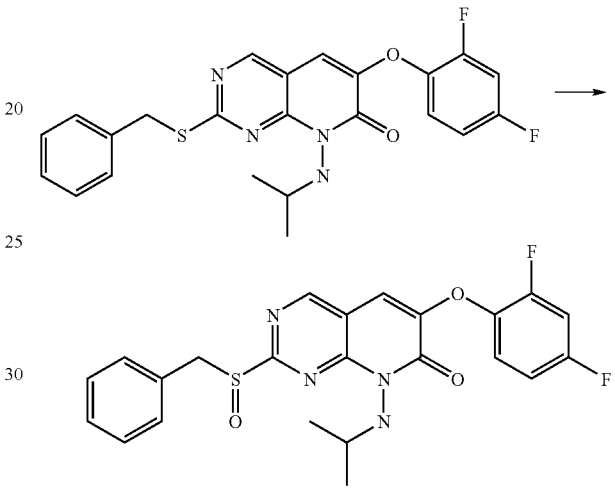

To the N-isopropyl hydrazido sulfide (64 mg, 0.141 mmol) in THF (10 mL) at 0° C. with stirring was added a solution of oxone (130 mg, 1.5 eq) in water (10 mL) dropwise. After the addition was complete, the resulting mixture was stirred from 0° C. to room temperature overnight. The next day the reaction was complete by TLC. Ethyl acetate (75 mL) and water (25 mL) were added and then partitioned and separated the layers. Washed further with water (2×25 mL) and finally washed with brine (1×75 mL). The organic layer was dried over magnesium sulfate, filtered, concentrated and pumped to give the N-isopropyl hydrazido sulfoxide (74 mg, (M+H)$^+$=471).

Step C: Preparation of 6-(2,4-Difluoro-phenoxy)-8-isopropylamino-2-(tetrahydro-pyran-4-ylamino)-8H-pyrido[2,3-d]pyrimidin-7-one:

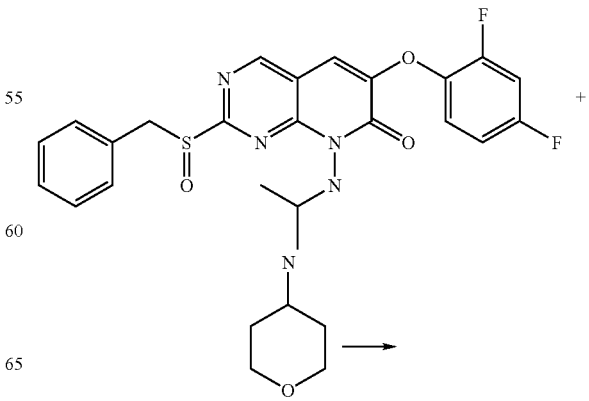

-continued

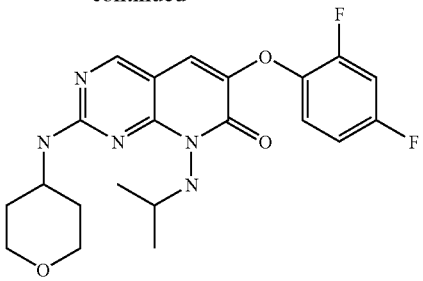

The sulfoxide (74 mg, 0.157 mmol), 4-aminotetrahydropyran (80 mg, 5 eq) and NMP (0.1 mL) were mixed together and heated ad 80° C. with stirring for 30 minutes. By TLC the reaction was complete and was cooled to room temperature. Ethyl acetate (35 mL) and water (25 mL) were added and then partitioned and separated the layers. The organic layer was further washed with water (2×25 mL) and finally with brine (1×25 mL). Then dried the ethyl acetate layer over magnesium sulfate, filtered and concentrated. Pumped under high vacuum to give 75 mg of crude product. Purification by Preparative Thin Layer Chromatography eluting with 75% ethyl acetate in hexanes gave the desired compound as the free amine (39 mg). The free amine was taken up in dichloromethane (5 mL) and with stirring was added 1M HCl in diethyl ether (0.14 mL, 1.2 eq). The resulting mixture was stirred for 5 minutes. Then the solvent was removed under reduced pressure at 50° C. Dried under high vacuum at 56° C. for 24 hours to give the title compound as an off-white powder (39 mg, (M+H)$^+$=432).

Example 91

Preparation of 6-(2,4-Difluoro-phenoxy)-8-[N-methyl-(N-3-methyl-butyl)-amino]-2-(tetrahydro-pyran-4-ylamino)-8H-pyrido[2,3-d]pyrimidin-7-one Step A: Preparation of 2-Benzylsulfanyl-6-(2,4-difluoro-phenoxy)-8-N-isobutylamino-8H-pyrido[2,3-d]pyrimidin-7-one

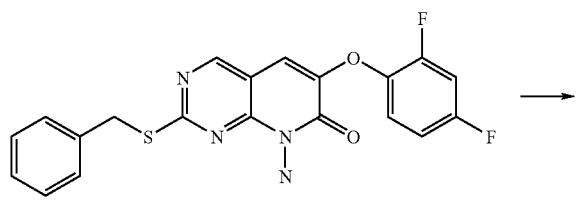

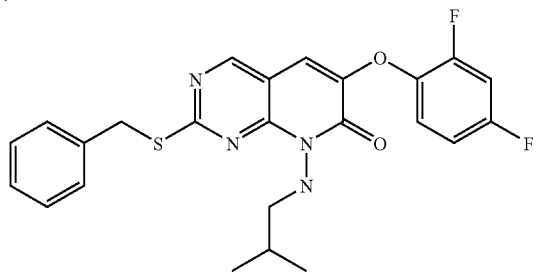

To a mixture of the hydrazido sulfide (1 g, 2.52 mmol) in methanol (200 ml) and acetic acid was added isobutyraldehyde (0.3 mL, 1.3 eq) followed by sodium cyanoborohydride (159 mg, 1 eq). The resulting mixture was stirred at room temperature for 3.5 hours. Then added ethyl acetate (500 mL) and washed with saturated sodium bicarbonate (5×200 mL) until slightly basic. Finally washed with brine (1×150 mL) and the organic layer was dried over magnesium sulfate, filtered, concentrated and pumped to give the crude product (1.083 g) as a tan solid. Purification by Flash Column Chromatography on silica gel eluting with 15% ethyl acetate in hexanes gave the desired product as a foamy solid (487 mg, (M+H)$^+$=469, m.p.=132.1-133.9° C.).

Step B: Preparation of 2-Benzylsulfanyl-6-(2,4-difluoro-phenoxy)-8-(N-isobutyl-N-methyl-amino)-8H-pyrido[2,3-d]pyrimidin-7-one

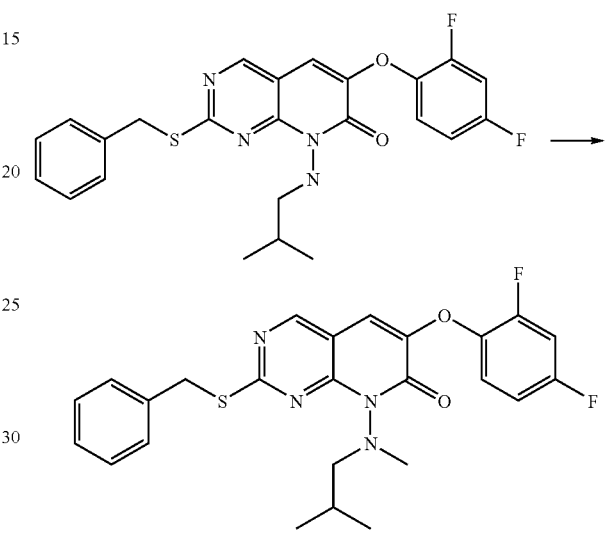

To the N-isobutyl hydrazido sulfide (100 mg, 0.213 mmol) in methanol (10.5 mL) at 0° C. was added acetic acid (3 mL) followed by 37% formaldehyde$_{(aq)}$ (25 μL, 1.6 eq) and then sodium cyanoborohydride (20 mg, 1.4 eq). The resulting mixture was stirred from 0° C. to room temperature overnight. The next day there was only a trace of starting material by TLC. The reaction was poured into saturated sodium bicarbonate (150 mL) and then extracted with ethyl acetate (3×75 mL). The combined ethyl acetate layers were washed with brine (1×50 mL) and then dried over magnesium sulfate, filtered and concentrated. This crude material was purified by Preparative Thin Layer Chromatography eluting with 20% ethyl acetate in hexanes to afford the desired compound as a white foamy solid (96 mg, (M+H)$^+$=483).

Step C: Preparation of 2-Benzylsulfinyl-6-(2,4-difluoro-phenoxy)-8-(N-isobutyl-N-methyl-amino)-8H-pyrido[2,3-d]pyrimidin-7-one

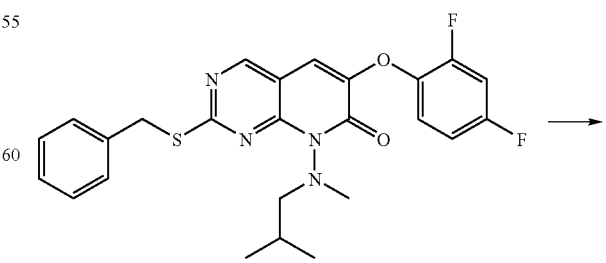

-continued

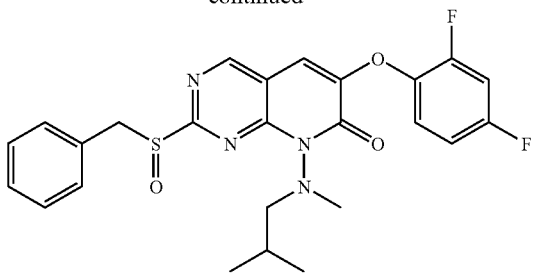

To the sulfide (96 mg, 0.199 mmol) in THF (10 mL) at 0° C. with stirring was added dropwise a solution of oxone (185 mg, 1.5 eq) in water (10 mL). After addition was complete, the resulting mixture was stirred from 0° C. to room temperature overnight. By TLC the reaction was complete the next day. Added ethyl acetate (75 mL) and washed with water (4×30 mL) and finally washed with brine (1×30 mL). The organic layer was dried over magnesium sulfate, filtered and concentrated to give the desired compound as a white foamy solid (95 mg, (M+H)$^+$=499).

Step D: Preparation of 6-(2,4-Difluoro-phenoxy)-8-[N-methyl-(N-3-methyl-butyl)-amino]-2-(tetrahydro-pyran-4-ylamino)-8H-pyrido[2,3-d]pyrimidin-7-one:

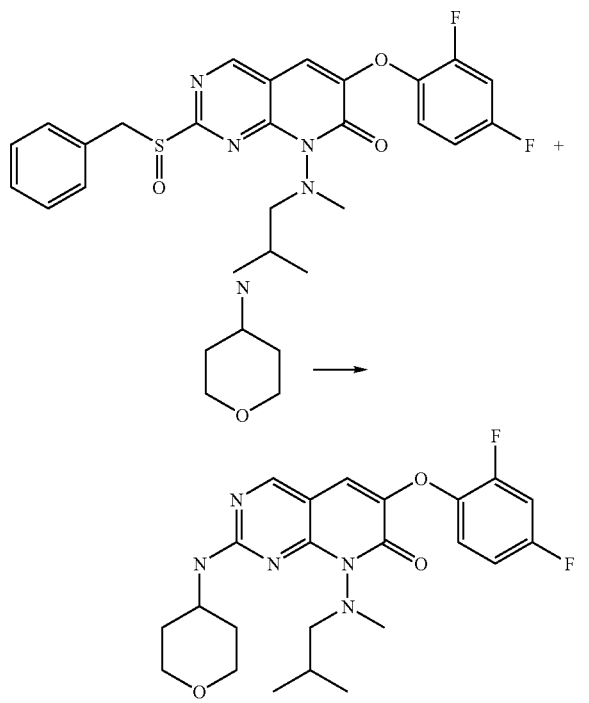

The N-isobutyl, N-methyl hydrazido sulfoxide (95 mg, 0.191 mmol), 4-amino tetrahydropyran (97 mg, 5 eq) and NMP (0.1 mL) were mixed together and heated at 80° C. with stirring for 30 minutes. By TLC, all of the starting sulfoxide was consumed. Cooled to room temperature and added ethyl acetate (35 mL) and water (25 mL). Partitioned and separated the layers and subsequently washed with water (2×25 mL) followed with brine (1×25 mL). The organic layer was dried over magnesium sulfate, filtered concentrated and pumped. Purification by Preparative Thin Layer Chromatography eluting with 40% ethyl acetate in hexanes gave the desired product as the free amine (82 mg). The free amine (82 mg) was taken up in dichloromethane (5 mL) and then added 1M HCl in diethyl ether (0.2 mL, 1.2 eq). The resulting mixture was stirred for 5 minutes and then the solvent was removed under reduced pressure at 50° C. Dried under high vacuum at 56° C. for 24 hours to give the title compound (60 mg, (M+H)$^+$=460) as an off-white powder.

Example 92

Preparation of 6-(2,4-Difluoro-phenoxy)-8-N,N-dimethylamino-2-(tetrahydro-pyran-4-ylamino)-8H-pyrido[2,3-d]pyrimidin-7-one Step A: Preparation of 2-Benzylsulfanyl-6-(2,4-difluoro-phenoxy)-8-N,N-dimethylamino-8H-pyrido[2,3-d]pyrimidin-7-one:

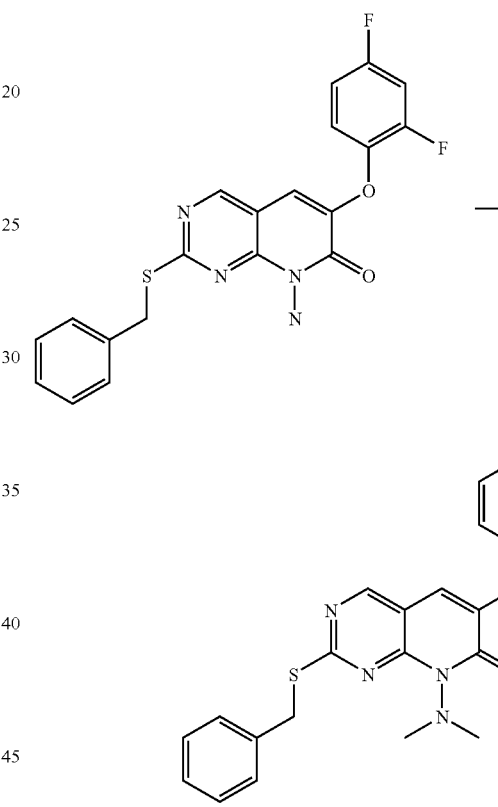

The hydrazido sulfide (1.5 g, 3.64 mmol) was taken up in methanol (200 mL) and acetic acid (60 mL) and then added 37% formaldehyde$_{(aq)}$ (0.5 mL, 4 eq) followed by sodium cyanoborohydride (458 mg, 2 eq). The resulting mixture was stirred at room temperature overnight. The next day there was still some starting sulfide remaining, so additional 37% formaldehyde$_{(aq)}$ (0.5 mL, 4 eq) was added and the reaction was stirred at room temperature for one more day. On the second day, the reaction was complete by TLC. Added ethyl acetate (300 mL) and saturated sodium bicarbonate (150 mL) and partitioned. Then separated the layers and washed with more saturated sodium bicarbonate (3×150 mL) until slightly basic. Finally washed with brine (1×150 mL) and the organic layer was dried over magnesium sulfate, filtered, concentrated and pumped to give crude product (1.93 g). Purification by Flash Column Chromatography on silica gel eluting with 15% ethyl acetate in hexanes afforded the desired product as a foamy off-white solid (740 mg, (M+H)$^+$=441, m.p.=63.0-66.0° C.).

Step B: Preparation of 2-Benzylsulfinyl-6-(2,4-difluoro-phenoxy)-8-N,N-dimethylamino-8H-pyrido[2,3-d]pyrimidin-7-one:

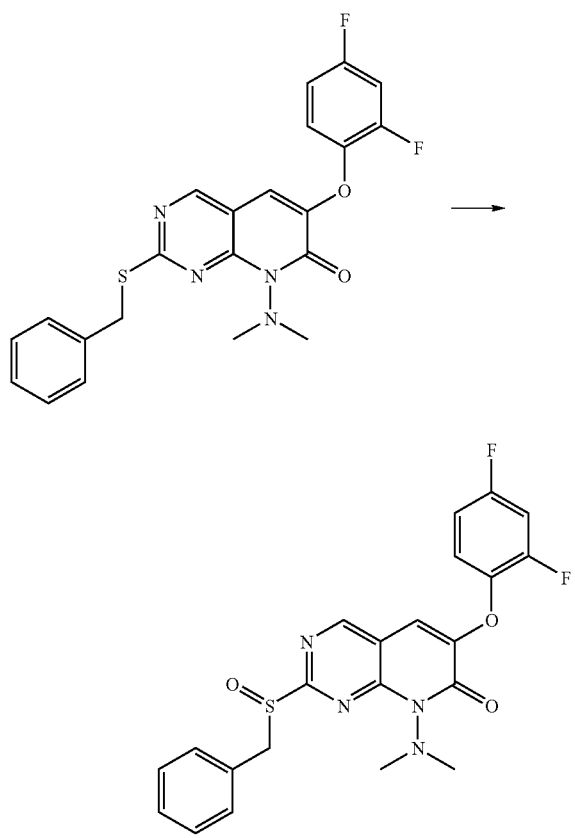

To the sulfide (725 mg, 1.65 mmol) in THF (30 mL) at 0° C. with stirring was added dropwise a solution of oxone (1.01 g, 1 eq) in water (20 mL). After addition was complete, the resulting mixture was stirred from 0° C. to room temperature for 6 hours. Then added ethyl acetate (100 ml) and washed with water (3×50 mL) followed by brine (1×50 mL). The organic layer was dried over magnesium sulfate, filtered, concentrated and pumped the give the desired compound as a foamy white solid (727 mg, (M+H)+=457, m.p.=80.5-89.9° C.).

Step C: Preparation of 6-(2,4-Difluoro-phenoxy)-8-N,N-dimethylamino-2-(tetrahydro-pyran-4-ylamino)-8H-pyrido[2,3-d]pyrimidin-7-one:

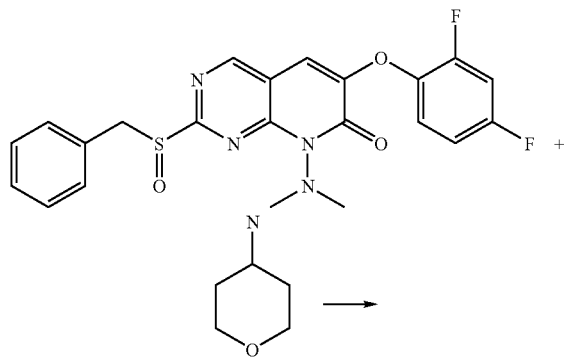

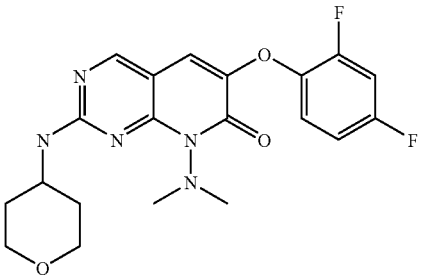

The sulfoxide (308 mg, 0.675 mmol), 4-amino tetrahydropyran (205 mg, 3 eq) and NMP (0.3 mL) were mixed together and heated at 80° C. with stirring for 30 minutes. By TLC, the reaction was complete. Ethyl acetate (35 mL) and water (25 ml) were added, partitioned and separated the layers. The organic layer was washed with water (2×25 mL) and finally with brine (1×25 mL). Dried the ethyl acetate layer over magnesium sulfate, filtered, concentrated and pumped to give the crude product (571 mg). Purification by Preparative Thin Layer Chromatography eluting with 70% ethyl acetate in hexanes afforded the product as the free amine (185 mg). The free amine was taken up in dichloromethane (20 mL) and then 1M HCl in diethyl ether (1.2 eq, 0.5 mL) was added. The resulting mixture was stirred for 5 minutes and then the solvent was removed under reduced pressure at 50° C. Dried under high vacuum at 56° C. for 24 hours to give the title compound as an off-white powder (195 mg, (M+H)+=418, m.p.=126.4-131.0° C.).

Example 93

Preparation of 6-(2,4-Difluoro-phenylamino)-2-(2-hydroxy-1,1-dimethyl-ethylamino)-8-methyl-8H-pyrido[2,3-d]pyrimidin-7-one Step A: Preparation of (2,4-Difluoro-phenyl)-carbamic acid benzyl ester

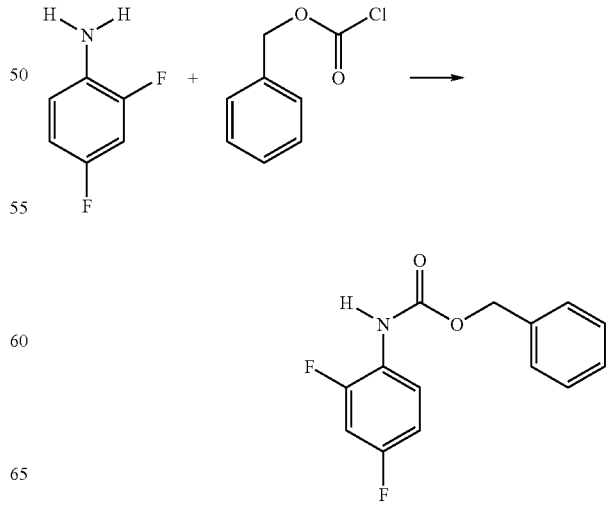

The 2,4 difluoro aniline (5.06 ml, 49.6 mmole) put into a solution of 10% NaOH (76 ml). Cooled in an ice bath and added benzyl chloroformate (7.85 ml, 55 mmole). After stirring for 2 hours the product was filtered, stirred with hexane, dried. Yield 9.4 g Step B: Preparation of [Benzyloxycarbonyl-(2,4-difluorophenyl)-amino]-acetic acid methyl ester

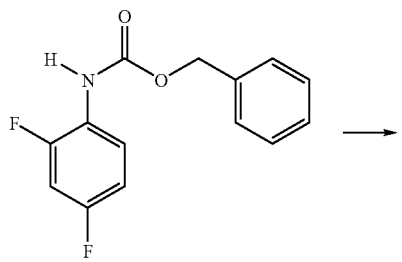

The CBZ protected aniline (7.89 g 30 mmole) dissolved in 1-methyl-2-pyrrolidinone (NMP) and cooled in an ice bath to 0°. To this solution was added sodium hydride (1.3 g 60% oil dispersion, 32.5 mmole), this was stirred at for 30 minutes. To this solution was added methyl bromoacetate (3.0 ml, 31 mmole), this-solution was allowed to warm to room temperature and stirred for 12 hours. Added to water and extracted with ethyl acetate, washed 5 times with water, dried (magnesium sulfate) and evaporated to dryness. The product was purified by column chromatography (80:20 hexane:ethyl acetate) to give the product. Yield 8.2 g Step C: Preparation of (2,4-Difluoro-phenyl)-(8-methyl-2-methylsulfanyl-7-oxo-7,8-dihydro-pyrido[2,3-d]pyrimidin-6-yl)-carbamic acid benzyl ester

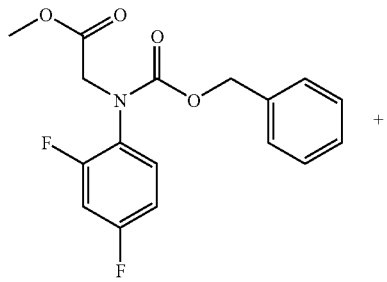

+

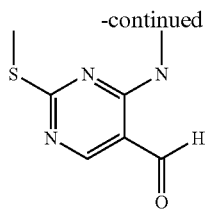

→

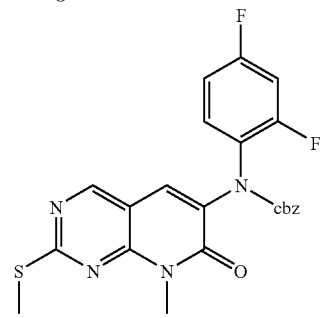

To a solution of the aldehyde (1.69 g, 10 mmole) in NMP and the CBZ protected aniline (3.5 g, 10.5 mmole) was added potassium carbonate (2.0 g, 14.5 mmole) and heated at 120° for 12 hours. Reaction mixture cooled to room temperature and added to water. Extracted with ethyl acetate and washed 5 times with water, dried (MgSO$_4$) and evaporated to dryness. Product purified by column chromatography (75:25 EtOAc: Hexane).
Yield 1.9 g (M+H)$^+$ 469

Step D: Preparation of (2,4-Difluoro-phenyl)-(8-methyl-2-methylsulfonyl-7-oxo-7,8-dihydro-pyrido[2,3-d]pyrimidin-6-yl)-carbamic acid benzyl ester

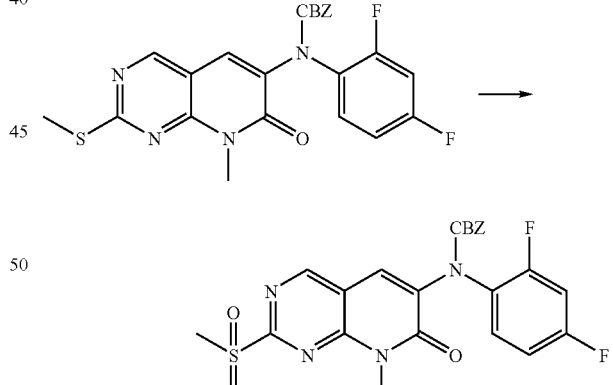

To a solution of the sulfide (8.5 g, 18 mmole) in CH$_2$Cl$_2$ (100 ml) was added meta chloro perbenzoic acid (9.0 g ~75%, 39 mmole), and stirred at room temperature for 12 hours. The reaction solution was washed with a 10% solution of NaSO$_3$, then three time with a 10% solution of NaHCO$_3$, dried (MgSO$_4$), and evaporated to dryness. The crude product was stirred with ethyl ether (100 ml) for an hour, filtered, and dried. Yield 7.9 g

103

Step E: Preparation of (2,4-Difluoro-phenyl)-[2-(2-hydroxy-1,1-dimethyl-ethylamino)-8-methyl-7-oxo-7,8-dihydro-pyrido[2,3-d]pyrimidin-6-yl]-carbamic acid benzyl ester

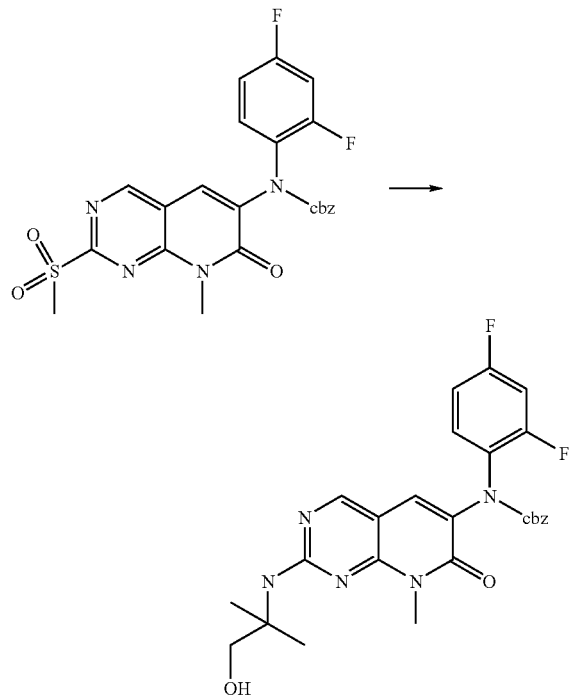

The sulfone (0.5 g 1 mmole) was combined with the 2-amino-2-methyl-1-propanol (0.5 g, 5.5 mmole) and 0.5 ml NMP, this solution was heated at 80° for 1 hour. Cooled to room temperature, added MeOH (2 ml) and water (4 ml), stirred for one hour, filtered to give the product as a solid. Yield 450 mg, (M+H)+ 510

Step F: Preparation of 6-(2,4-Difluoro-phenylamino)-2-(2-hydroxy-1,1-dimethyl-ethylamino)-8-methyl-8H-pyrido[2,3-d]pyrimidin-7-one

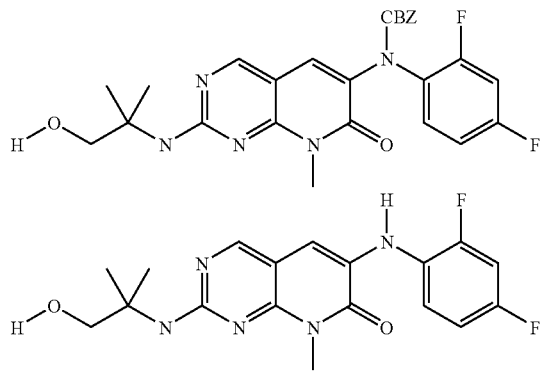

The CBZ protected amine (450 mg, 0.8 mmole) dissolved in EtOH (20 ml) to this added 5% Pd/carbon (50 mg) and hygrogenated at atmospheric pressure. After 12 hours filtered through celite, evaporated to dryness. This material suspended in MeOH, and acidified with hydrochloric acid (1.0M/Et₂O, 1 equivalent), stirred for 20 minutes, evaporated under reduced pressure, stirred with a mixture of Et₂O/MeOH, for 2 hours, filtered to give the hydrochloride salt. Yield 140 mg MP216-217.9°. MS (M+H)+ 376.

104

Example 94

Preparation of 6-[(2,4-Difluoro-phenyl)-methyl-amino]-8-methyl-2-(tetrahydro-pyran-4-ylamino)-8H-pyrido[2,3-d]pyrimidin-7-one Step A: Preparation of [(2,4-Difluoro-phenyl)-methyl-amino]-acetic acid methyl ester

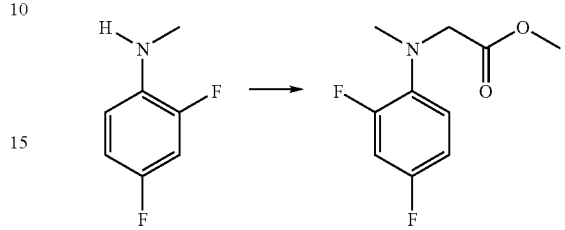

To a mixture of the 2,4-Difluoro-N-methylaniline (Avacado Research Chemical, Heysham UK) (1.43 g, 10 mmole) in NMP, and K₂CO₃, was added methyl bromoacetate (0.945 ml, 10 mmole) and stirred at room temperature for 24 hours. The reaction mixture was added to water and extracted with ethyl acetate (3×50 ml), the organic extracts were washed 6× with water, dried (MgSO₄) and evaporated to give the product as a oil.

Yield 2.0 g

Step B: Preparation of 6-[(2,4-Difluoro-phenyl)-methyl-amino]-8-methyl-2-methylsulfanyl-8H-pyrido[2,3-d]pyrimidin-7-one

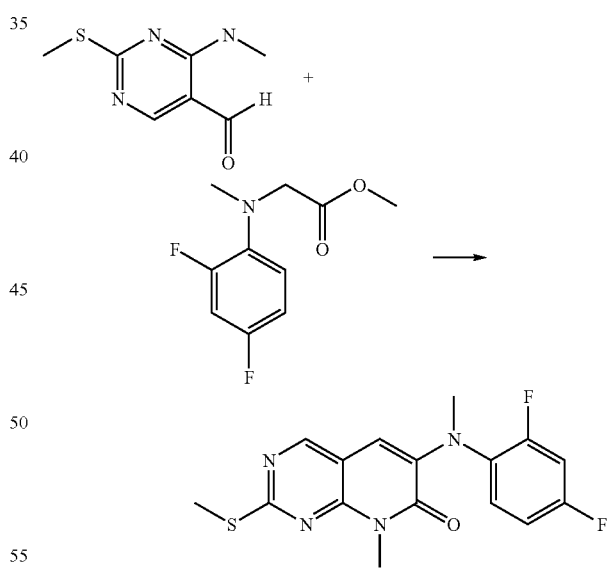

A mixture of 4-methylamino-2 methylthiopyrimidine-5-carboxaldehyde (915 mg, 5 mmole) and the aniline (1.1 g, 5.1 mmole) and K₂CO₃ (1.5 g, 10.8 mmole) in 10 ml of NMP was heated at 120°. After 12 hours the reaction mixture was cooled to room temperature and added to 100 ml of water. The resultant mixture was extracted with EtOAc, (3×, 100 ml), and the organic layer was with water 6×, dried (MgSO₄) and evaporated under reduced pressure. The product residue was stirred with ether (50 ml) for 1 hour, filtered to yield the product as a solid. Yield 1.07 g MS (M+H)+ 349

Step C: Preparation of 6-[(2,4-Difluoro-phenyl)-methyl-amino]-8-methyl-2-methylsulfonyl-8H-pyrido[2,3-d]pyrimidin-7-one

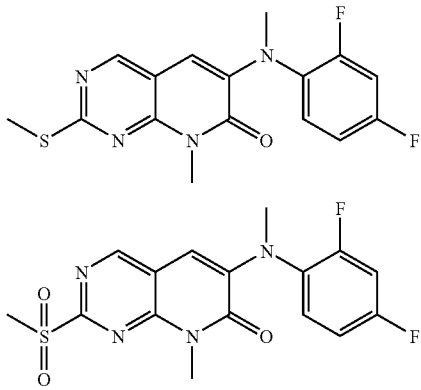

The sulfide (1.0 g, 2.8 mmole) was disolved in 25 ml of dichloromethane, to this solution was added 3-chloroperbenzoic acid (77%, 1.4 g, 6.2 mmole). This solution was stirred at room temperature for 6 hours, then washed with an aqueous sodium sulfite solution (2×, 10 ml) and with a saturated solution of sodium bicarbonate (3×, 10 ml). The organic solution then dried (MgSO$_4$), and evaporated to a solid residue. This residue was stirred with ether (25 ml), filtered and dried to give the sulfone as a solid. Yield 870 mg MS (M+H)$^+$ 381

Step D: Preparation of 6-[(2,4-Difluoro-phenyl)-methyl-amino]-8-methyl-2-(tetrahydro-pyran-4-ylamino)-8H-pyrido[2,3-d]pyrimidin-7-one

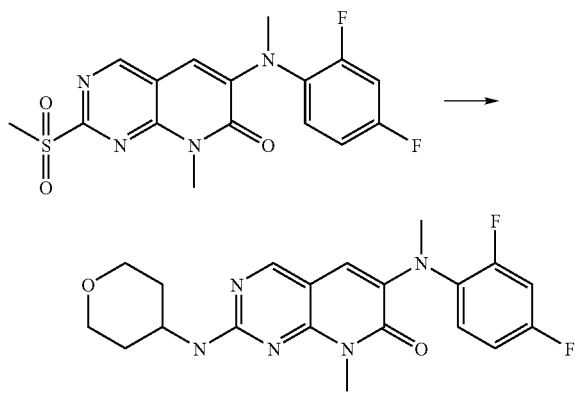

A mixture of the sulfone (0.4 g, 1.05 mmole) and 4-amino-tetrahydropyran (0.35 g, 3.47 mmole) and 0.3 ml of NMP heated at 80° for 1 hour. Cooled to room temperature, added 1.0 ml MeOH, and 2.0 ml of water, stirred at room temperature for 1 hour, and filtered, washed with water and dried, to give the product as a solid. The product was suspended in MeOH, and made acidic with hydrochloric acid (1.0M/Et$_2$O 1 equivalent) and stirred for an hour. The organic solvent was evaporated, the residue was stirred with a mixture of MeOH/Et$_2$O for an hour, filtered to give the product as a hydrochloride salt. Yield 0.358 g MP197-198.5° MS (M+H)$^+$ 402

Example 95

Preparation of 6-(2,4-Difluorophenoxy)-8-ethyl-2-(tetrahydro-2H-pyran-4-ylamino)pyrido[2,3-d]pyrimidin-7(8H)-one Step A: Preparation of ethyl 4-ethylamino-2-methyl-thiopyrimidine-5-carboxylate

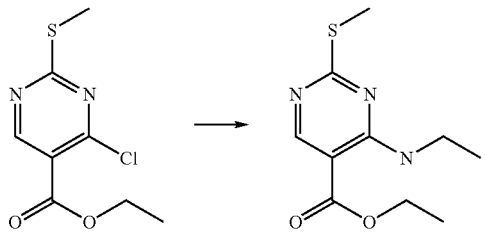

To a solution of 25 g (107 mmole) ethyl 4-chloro-2-methylthio-5-pyrimiinecarboxylate in 250 ml of tetrahydrofuran was added 47 ml (337 mmole) and 43 ml of 70% ethylamine solution (668 mmole). The mixture was stirred at room temperature for 4 hours. Evaporated to dryness, this material dissolve in a mixture of ethyl acetate/water, washed twice with 10% NaHCO$_3$ solution, dried (MgSO$_4$), evaporated to dryness to give the product as a solid. Yield 24.1 g Step B: Preparation 4-ethylamino-2-methylthiopyrimidine-5-methanol

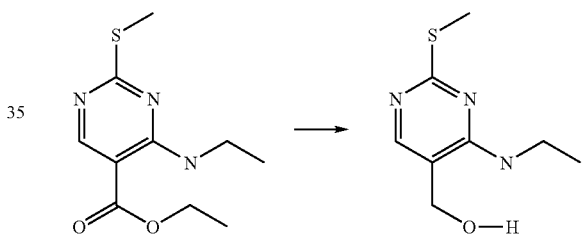

A solution of the ethyl 4-ethylamino-2-methylthio-pyrimidinecarboxylate (24.1 g, 100 mmole) in tetrahydrofuran (250 ml) was cooled in an ice bath to 0°. To this solution was carefully added 1 small portions over an hour lithium aluminum hydride (4.3 g, 113 mmole), one hour after addition is complete water is slowly added (4.3 ml), then a solution of NaOH (4.3 ml, 15%), then an additional 13 ml of water added, stirred for 1 hour. The resulting suspension was filtered, the filter residue washed twice with 100 ml of tetrahydrfuran. This solution was evaporated under reduced pressure. The residue stirred with 150 ml Et$_2$O, filtered, dried. Yield 19.1 g.

Step C: Preparation of 4-ethylamino-2-methylthiopyrimidine-5-carboxaldehyde

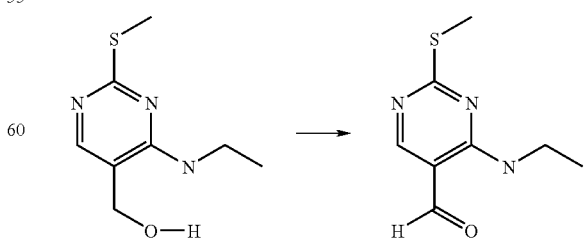

To a solution of 4-ethylamino-2-methylthiopyrimidine-5-methanol (19.1 g, 96 mmole) in 1000 ml of dichloromethane was added 87 g of manganese dioxide. The resulting suspension was stirred for 20 hours, filtered through celite. The residue was washed twice with 100 ml of dichloromethane, the combined filtrate and washings was evaporated under reduced pressure to give the product as a solid. Yield 12.8 g Step D: Preparation of 6-(2,4-difluorophenoxy)-8-ethyl-2-methylthio)pyrido[2,3-d]pyrimidin-7(8H)-one

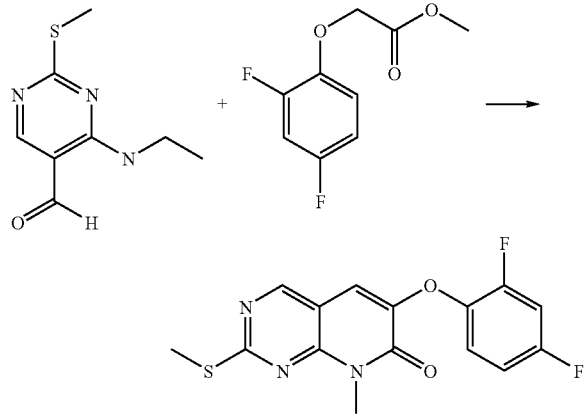

To a mixture of 4-ethylamino-2-methylthiopyrimidine-5-carboxalehyde (5.0 g, 25.5 mmole) and the phenoxy acetate (6.0 g, 29.7 mmole) in 50 ml of NMP was added K₂CO₃ (6.0 g, 43.4 mmole) and heated at 120°. After 2 hours an additional 1.5 g of the ester was added and heated an additional 2 hours. At this time and additional 1.5 g of the ester and 2.0 g K₂CO₃ was added to the reaction, after an additional 2 hours the reaction was cooled to room temperature. The reaction mixture was added to water (300 ml) and stirred for 2 hours. Filtered, and washed with ethyl ether, dried.

Yield 8.7 g MP 122-127.9° MS (M+H)⁺ 350

Step E: Preparation of 6-(2,4-difluorophenoxy)-8-ethyl-2-(methylsulfonyl)pyrido[2,3-d]pyrimidin-7(8H)-one

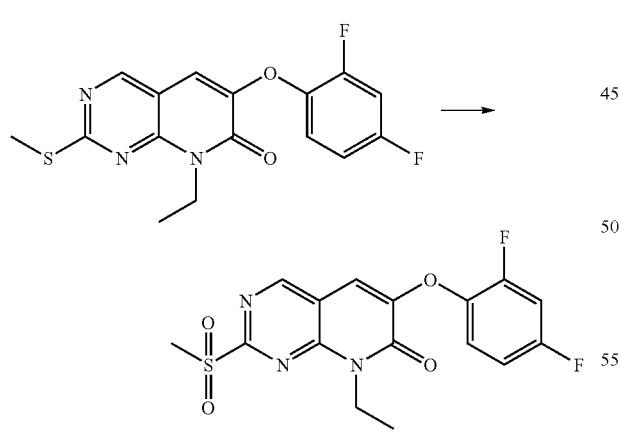

The sulfide (8.7 g, 24.9 mmole) was dissolved in 100 ml of dichloromethane and 3-chloroperbenzoic acid (77% 11.5 g 50 mmole) was added. The mixture was stirred at room temperature for 8 hours, then washed with sodium sulfite solution (2×, 75 ml) followed by saturated aqueous sodium bicarbonate (3×, 75 ml). The organic solution was then dried (MgSO₄) and evaporated. The resultant solid was stirred with ether for 1 hour, and filtered to yield the sulfone as a white solid. Yield 6.9 g MP 128-129.1° MS (M+H)⁺ 381

Step F: Preparation of 6-(2,4-difluorophenoxy)-8-ethyl-2-(tetrahydro-2H-pyran-4-ylamino)pyrido[2,3-d]pyrimidin-7(8H)-one

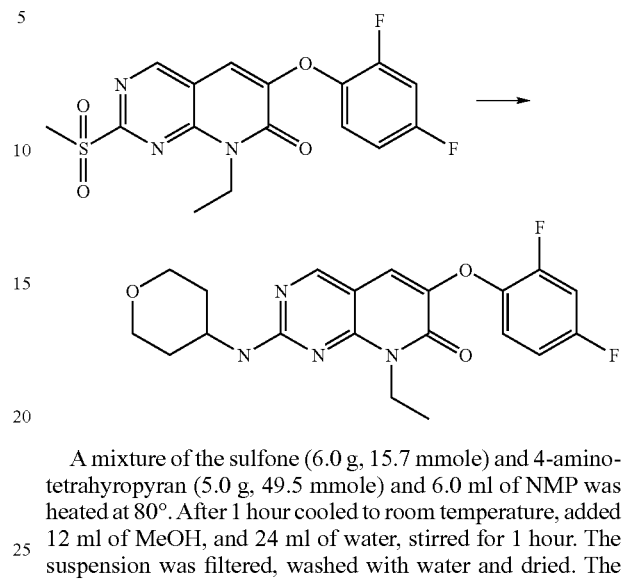

A mixture of the sulfone (6.0 g, 15.7 mmole) and 4-amino-tetrahyropyran (5.0 g, 49.5 mmole) and 6.0 ml of NMP was heated at 80°. After 1 hour cooled to room temperature, added 12 ml of MeOH, and 24 ml of water, stirred for 1 hour. The suspension was filtered, washed with water and dried. The solid residue was suspended in MeOH (60 ml) and hydrochloric acid was added (1.0M/Et₂O 1 equivalent), the mixture was stirred for 1 hour and evaporated. The solid residue was stirred with a mixture of MeOH/Et₂O for one hour, filtered, washed with ether, and dried. Yield 5.9 g MP199.1-205.9° MS (M+H)⁺ 403

Example 96

Preparation of 6-(2,4-difluorophenoxy)-8-ethyl-2-(3-hydroxy-tetrahydro-pyran-4-ylamino)pyrido[2,3-d]pyrimidin-7(8H)-one

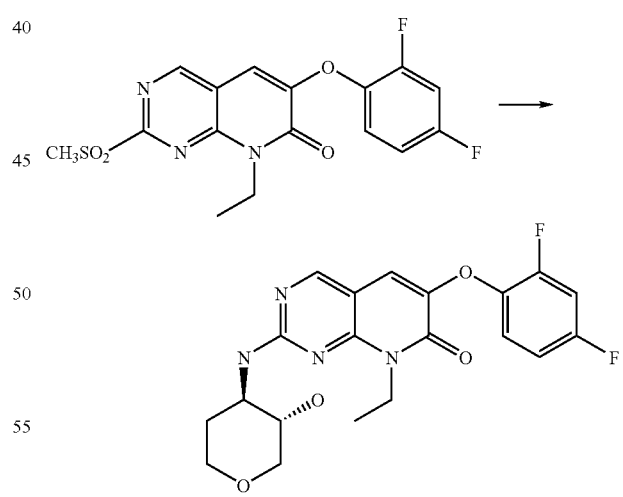

A mixture of the sulfone (see example 95 for preparation) (0.50 g, 1.31 mmol) and trans-4-amino-3-hydroxy-tetrahydropyran (0.23 g, 1.97 mmol) (see following ref for preparation: (a) Marquis, Robert W et al J. Med. Chem. (2001), 44(5), 725-736. (b) Gribble, Andrew D et al PCT Int. Appl. (1998), 74 pp. (c) Mochalin, V. B et al Zh. Org. Khim. (1971), 7(4), 825-8). in 2 mL of 1-methyl-2-pyrrolidinone was heated at 100° C. for 12 h. The reaction mixture was cooled, ethyl acetate (15 mL) was added and the organic solution was washed with water (3×, 15 mL), brine and then dried (MgSO₄). Evaporation of the solvent under reduced pressure and column chromatography (CH₂Cl₂/methanol—97/3) afforded 120 mg of product (mpt. 174.9-176.3° C., MS (M+H)=419)

Example 97

Preparation of 6-(2,4-Difluoro-phenoxy)-2-(3-hydroxy-1,3-dimethyl-butylamino)-8-methyl-8H-pyrido[2,3-d]pyrimidin-7-one Step A: Preparation of 4-Hydroxy-4-methyl-pentan-2-one oxime

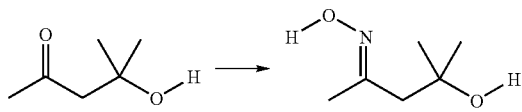

A mixture of 4-hydroxy-4-methyl-2-pentanone (10.0 g, 85.7 mmole) and hydroxylamine hydrochloride (22.17 g, 343 mmole) in 90 ml of water was stirred vigorously at room temperature. To this solution was added slowly over a period of an hour solid sodium bicarbonate (26.8 g, 343 mmole). After 3 hours the reaction mixture was extracted with ethyl acetate (3×, 100 ml), dried (MgSO₄) and evaporated under reduced pressure, to give the product as an oil. Yield 11.2 g Step B: Preparation of 4-Amino-2-methyl-pentan-2-ol

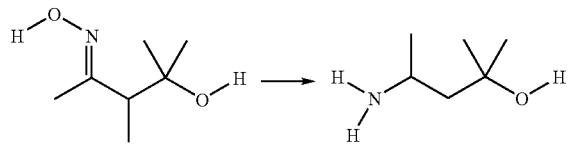

The oxime (11.2 g, 85 mmole) was dissolved in 150 ml of ethanol, to this was added a slurry of 20 ml of 50% Raney Nickel/water, and put onto a Parr hydrogenator at 50 psi. After 6 hours the reaction mixture was filtered through celite, and evaporated to give the amine as an oil. Yield 9.9 g Step C: Preparation of 6-(2,4-Difluoro-phenoxy)-2-(3-hydroxy-1,3-dimethyl-butylamino)-8-methyl-8H-pyrido[2,3-d]pyrimidin-7-one

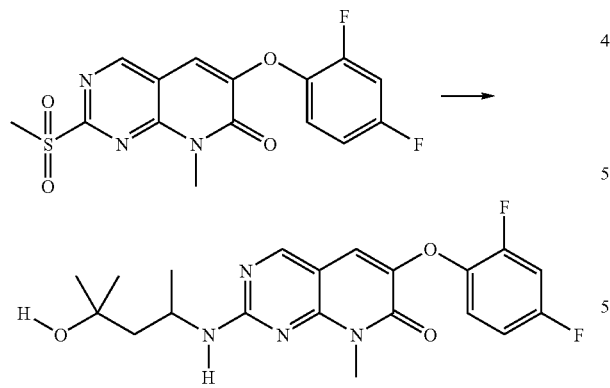

A mixture of the sulfone (1.0 g, 2.7 mmole), the 4-amino-2-hydroxy-2 methyl pentane (1.0 g, 8.5 mmole) and 1.0 ml of NMP heated at 80° for 2 hours. The reaction mixture was cooled, and added to water, extracted with ethyl acetate (3×, 75 ml), washed with water (6×, 75 ml), dried (MgSO₄), and evaporated. The residue was purified by column chromatography (SiO₂, CH₂Cl₂/MeOH—95/5) to give the pure product. The residue was suspended in MeOH and acidified with hydrochloric acid (Et₂O/HCl, 1.0M, 1 equivalent), stirred for 30 minutes, then evaporated. The residue was stirred in a mixture of methanol/ether for 1 hour, filtered and dried to give the product as a white solid. Yield 818 mg MP 158.9-161°, MS (M+H)⁺ 405

By following the above procedure and resolving the amino alcohol in step B prior to use in step C may also be prepared:
6-(2,4-Difluoro-phenoxy)-2-(3-hydroxy-1(S),3-dimethyl-butylamino)-8-methyl-8H-pyrido[2,3-d]pyrimidin-7-one, and
6-(2,4-Difluoro-phenoxy)-2-(3-hydroxy-1 (R),3-dimethyl-butylamino)-8-methyl-8H-pyrido[2,3-d]pyrimidin-7-one.

Example 98

Preparation of 6-(2,4-difluorophenoxy)-8-methyl-2-(3-hydroxy-tetrahydro-pyran-4-ylamino)pyrido[2,3-d]pyrimidin-7(8H)-one

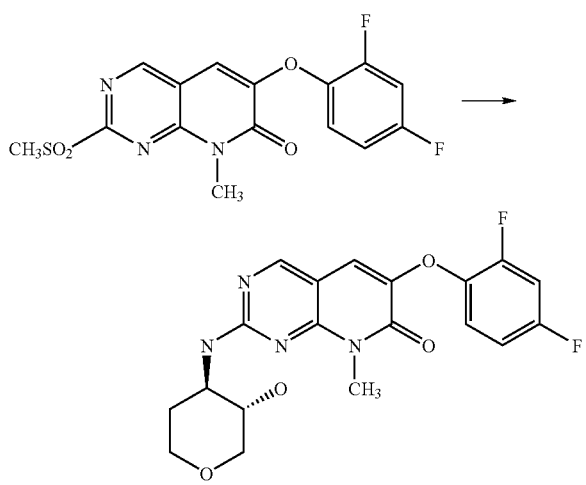

A mixture of sulfone 5 (0.70 g, 1.4 mmol) and trans-4-amino-3-hydroxy-tetrahydropyran (0.33 g, 2.85 mmol) (see following ref for preparation: (a) Marquis, Robert W et al J. Med. Chem. (2001), 44(5), 725-736. (b) Gribble, Andrew D et al PCT Int. Appl. (1998), 74 pp. (c) Mochalin, V. B et al Zh. Org. Khim. (1971), 7(4), 825-8). in 2 mL of 1-methyl-2-pyrrolidinone was heated at 100° C. for 12 h. The reaction mixture was cooled, ethyl acetate (20 mL) was added. The organic solution was then washed with water (3×, 30 mL) and dried (MgSO₄). Evaporation of the solvent and thin layer chromatography (CH₂Cl₂/EtOAc—95/5) afforded 0.25 g of the product. Addition of hydrochloric acid (1.0M/Et₂O, 1.2 equivalents) gave the salt which was filtered and dried to give 185 mg of desired product (mpt. 226.4-227.7° C., MS (M+H) =405)

Example 99

Preparation of 6-(2-fluorophenoxy)-2-[(5-hydroxy-pyrazol-3-yl)amino]-8-methylpyrido[2,3-d]pyrimidin-7(8H)-one

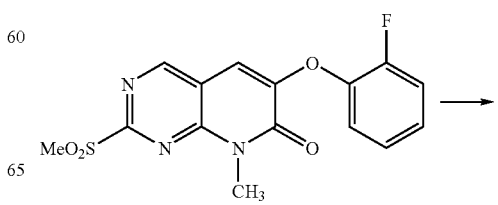

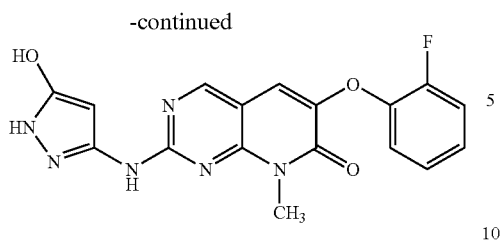

A mixture of sulfone 2 (0.05 g, 0.142 mmol), 3-amino-5-hydroxy pyrazole (0.017 g, 0.0172 mmol) in 1.0 ml DMF was heated to 65° C. for 42 hours and cooled Evaporation of the solvents yielded a residue which was purified via chromatography (Supelco Supelclean™, Sigma Aldrich, St. Louis, Mo., LC-Si SPE tube, 6 mL/1 g—$CH_2Cl_2$ to 4% $MeOH/CH_2Cl_2$ and MS/HPLC—(0.0013 g, mass spec. M+1=369)

Example 100

Preparation of 6-(2-fluorophenoxy)-2-[(pyridin-2-yl-methyl)amino]-8-methylpyrido[2,3-d]pyrimidin-7(8H)-one

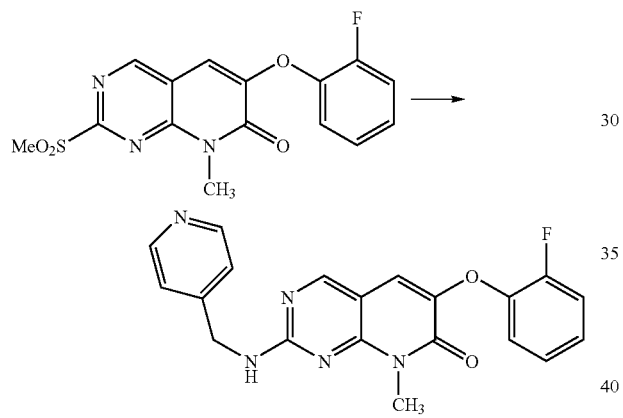

A mixture of sulfone 2 (0.05 g, 0.142 mmol), 4-(aminomethyl)pyridine, (0.019 g, 0.0172 mmol) in 1 ml DMF was heated to 65° C. for 18 hours. The cooled reaction mixture was diluted with 2 mL each $H_2O$ and EtOAc and partitioned between the two phases. The EtOAc was filtered through a plug of 0.5 g of $MgSO_4$, evaporated and purified via Supelco Supelclean™ LC-Si SPE tube, 6 mL (1 g) ($CH_2Cl_2$ to 2% $MeOH/CH_2Cl_2$) and MS/HPLC (0.0068 g, mass spec. M+1=378).

Example 101

Preparation of 2-{[(1,5-Dimethyl-1H-pyrazol-4-yl)methyl]amino}-6-(2-fluorophenoxy)-8-methylpyrido[2,3-d]pyrimidin-7(8H)-one

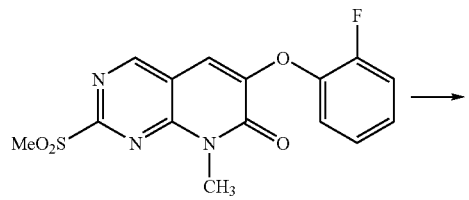

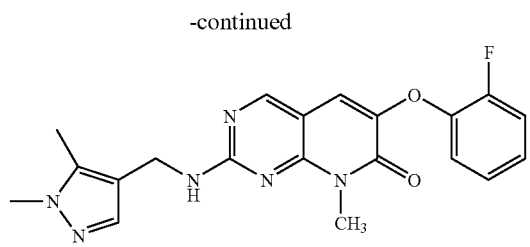

(1,5-Dimethyl-1H-pyrazol-4-yl)methylamine HCl.$H_2O$ (0.031 g, 0.172 mmol) was treated with 0.0172 ml 1M KOH/MeOH and evaporated. The amine was mixed with sulfone 2 (0.05 g, 0.142 mmol) in 1 ml DMF at 65° C. for 18 hours. The cooled reaction mixture was diluted with 2 mL each $H_2O$ and EtOAc and partitioned between the two phases. The EtOAc was filtered through a plug of 0.5 g $MgSO_4$, evaporated and the resulting mixture was chromatographed via Supelco Supelclean™ LC-Si SPE tube 6 mL (1 g) ($CH_2Cl_2$ to 2% $MeOH/CH_2Cl_2$). (0.005 g, mass spec. M+1=395)

Example 102

Preparation of 2-{[(1,3-Dimethyl-1H-pyrazol-4-yl)methyl]amino}-6-(2-fluorophenoxy-8-methylpyrido[2,3-d]pyrimidin-7(8H)-one

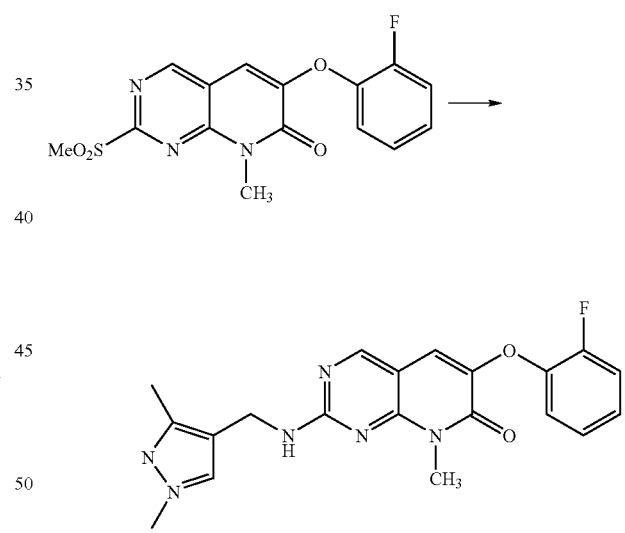

(1,3-Dimethyl-1H-pyrazol-4-yl)methylamine 1.8HCl.1.5$H_2O$ (0.037 g, 0.172 mmol) was treated with 0.0172 ml 1M KOH/MeOH and evaporated. The free amine was mixed with sulfone 2 (0.05 g, 0.142 mmol) in 1 ml DMF at 65° C. for 18 hours. The cooled reaction mixture was diluted with 2 mL each $H_2O$ and EtOAc and partitioned between the two phases. The organic phase was filtered through a plug of 0.5 g $MgSO_4$ and evaporated. The resulting mixture was chromatographed via Supelco Supelclean™ LC-Si SPE tube 6 mL (1 g) ($CH_2Cl_2$ to 2% $MeOH/CH_2Cl_2$). (0.0266 g mass spec. M+1=395)

Example 103

Preparation of 6-(2-fluorophenoxy)-2-{[(3-methyl-isoxazol-5-yl)methyl]amino}-8-methylpyrido[2,3-d]pyrimidin-7(8H)-one

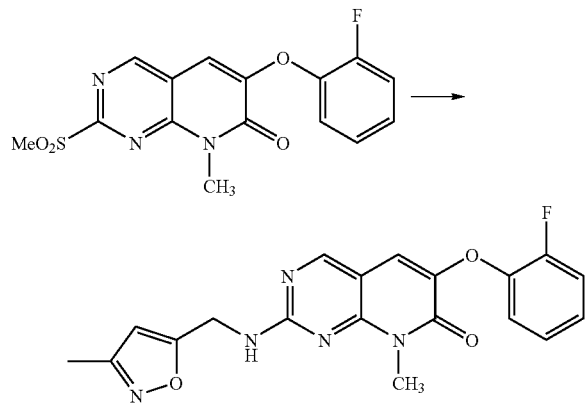

(3-Methyl-isoxazol-5-yl)methylamine HCl (0.026 g, 0.172 mmol) was treated with 0.0172 ml 1M KOH/MeOH and evaporated. The free amine was mixed with sulfone 2 (0.05 g, 0.142 mmol) in 1 ml DMF at 65° C. for 18 hours. The cooled reaction mixture was diluted with 2 mL each $H_2O$ and EtOAc and partitioned between the two phases. The EtOAc was evaporated and the resulting mixture was chromatographed via Supelco Supelclean™ LC-Si SPE tube 6 mL (1 g) ($CH_2Cl_2$ to 2% MeOH/$CH_2Cl_2$). (0.0094 g mass spec. M+1=382)

Example 104

2-{[1-(Hydroxymethyl)cyclohexyl]amino}-6-(2-methylbenzyl)-8-methylpyrido[2,3-d]pyrimidin-7(8H)-one

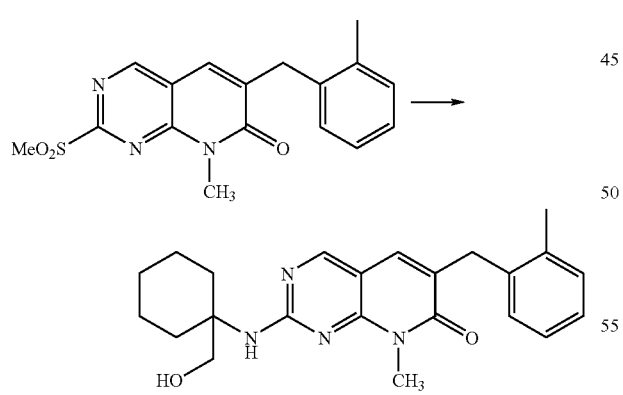

A mixture of sulfone (prepared in similar fashion to sulfone 8) (0.05 g, 0.146 mmol), (1-aminocyclohexyl)methanol (0.038 g, 0.291 mmol) in 2 ml $CHCl_3$ was heated to 65° C. for 18 hours. The cooled reaction mixture was evaporated, followed by addition of 1 mL MeOH. The resulting precipitate was collected and purified via Supelco Supelclean™ LC-Si SPE tube, 6 mL (1 g) ($CH_2Cl_2$ to 4% MeOH/$CH_2Cl_2$) and MS/HPLC (0.0249 g, mass spec. M+1=393).

Example 105

2-{[1-(Hydroxymethyl)cyclopentyl]amino}-6-(2-methylbenzyl)-8-methylpyrido[2,3-d]pyrimidin-7(8H)-one

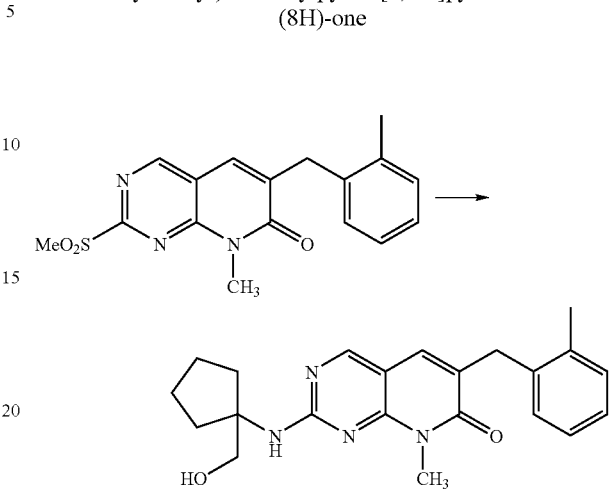

A mixture of sulfone (prepared in similar fashion to sulfone 8) (0.05 g, 0.146 mmol), (1-aminocyclopentyl)methanol (0.033 g, 0.291 mmol) in 2 ml $CHCl_3$ was heated to 65° C. for 18 hours. The cooled reaction mixture was evaporated, followed by addition of 1 mL MeOH. The resulting precipitate was collected and purified via Supelco Supelclean™ LC-Si SPE tube, 6 mL (1 g) ($CH_2Cl_2$ to 4% MeOH/$CH_2Cl_2$) and MS/HPLC (0.0155 g, mass spec. M+1=379).

Example 106

6-Benzyl-2-{[1-(hydroxymethyl)cyclopentyl]amino}-8-methylpyrido[2,3-d]pyrimidin-7(8H)-one

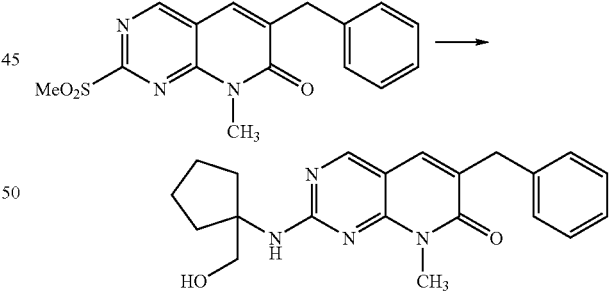

A mixture of sulfone (prepared in similar fashion to sulfone 8) (0.05 g, 0.152 mmol), (1-aminocyclopentyl)methanol (0.033 g, 0.291 mmol) in 1 ml $CHCl_3$ was heated to 65° C. for 18 hours. Another 0.020 g of (1-aminocyclopentyl)methanol was added and the mixture heated at 65° C. for 18 hours. The cooled reaction mixture was evaporated, followed by addition of 1 mL MeOH. The resulting precipitate was collected and purified via Supelco Supelclean™ LC-Si SPE tube, 6 mL (1 g) ($CH_2Cl_2$ to 1% MeOH/$CH_2Cl_2$) and MS/HPLC (0.0345 g, mass spec. M+1=365).

Example 107

N-[6-(2,4-Difluoro-phenoxy)-8-methyl-7-oxo-4a,7,8, 8a-tetrahydro-pyrido[2,3 d]pyrimidin-2-yl]-N-(tetrahydro-pyran-4-yl)-acetamide

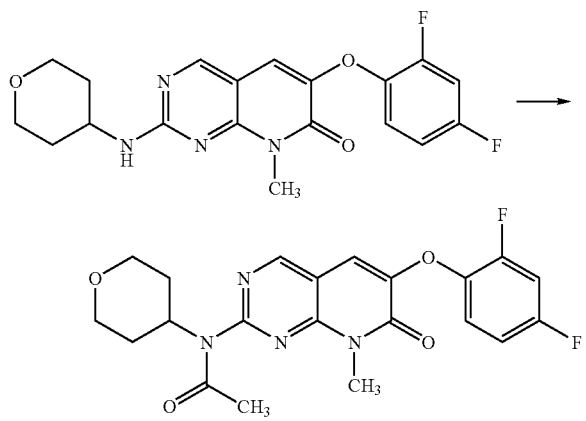

A mixture of 6-(2,4-difluorophenoxy)-8-methyl-2-(tetrahydro-2H-pyran-4-ylamino)pyrido[2,3-d]pyrimidin-7 (8H)-one (Example 23) (1.0 g, 2.57 mmol), N,N-diisopropylethylamine (0.498 g, 0.67 mL, 3.86 mmol) in acetic anhydride (1.42 g, 1.02 mL, 13.9 mmol) was heated to 123-127° C. for 2 hours. The volatiles were evaporated at 60° C. to provide a thick residue which was dissolved in 4 mL of acetone at 67-70° C. To the resulting solution was added 5 mL of hexane maintaining a temperature of 53-55° C. This mixture was allowed to cool to ambient temperature over 18 hours. The resulting solid was filtered and washed with 3×3 mL of 1:2 acetone:hexane. The rinsed solid was suspended in 5 mL of hexane and heated to reflux for 45 minutes. After cooling to ambient temperature, the slurry was filtered and the solid washed with hexane and dried under vacuum. (0.903 g, mass spec. M+1=431, MP=185.3-186.9° C.).

Example 108

Preparation of ethyl 4-{[6-(2-fluorophenoxy)-8-methyl-7-oxo-7,8-dihydropyrido[2,3-d]pyrimidin-2-yl]amino}piperidine-1-carboxylate

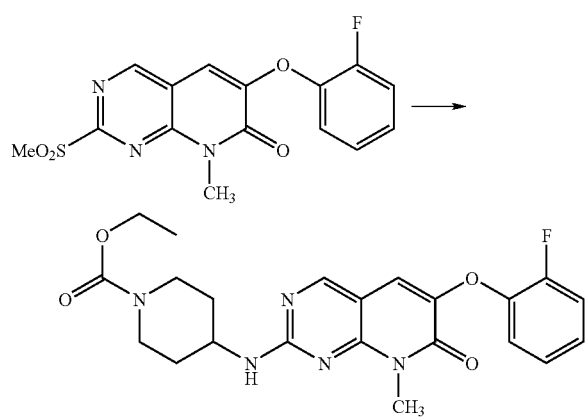

A mixture of sulfone 2 (1.0 g, 2.86 mmol). and ethyl 4-amino-1-piperidinecarboxylate (0.98 mL, 5.73 mmol) in 5 mL of 1-methyl-2-pyrrolidinone was stirred at 120° C. for 2 hours and then poured into water (200 mL) and stirred at room temperature for 1 hour. Filtration followed by drying provided the free amine. A portion of this product (0.050 g, 0.113 mmol) was dissolved in methanol (1-2 mL) and hydrochloric acid in ether (1M, 1 eq) was added. Isolation of the solid via filtration, followed by rinsing with ether and drying provided 0.038 g of the desired product as the hydrochloride salt (MP=171.2-183.5° C.).

Example 109

Preparation of 6-(2-fluorophenoxy)-8-methyl-2-{[(1-benzylsulfonyl)piperidin-4-yl]amino}pyrido[2,3-d]pyrimidin-7(8H)-one Step A: Preparation of 6-(2-fluorophenoxy)-8-methyl-2-(4-piperidylamino)pyrido[2,3-d]pyrimidin-7(8H)-one

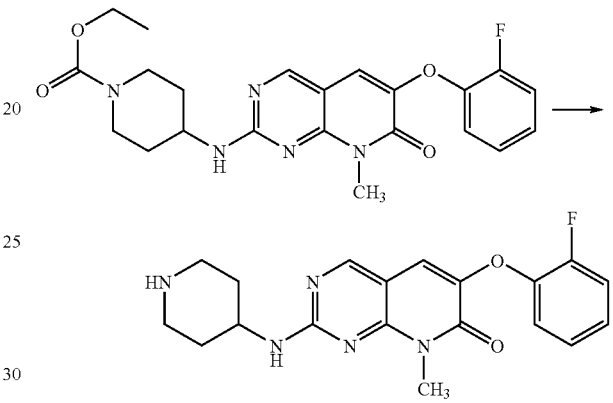

A mixture of the free base of ethyl 4-{[6-(2-fluorophenoxy)-8-methyl-7-oxo-7,8-dihydropyrido[2,3-d]pyrimidin-2-yl]amino}piperidine-1-carboxylate (0.500 g, 1.13 mmol) and iodotrimethylsilane (0.32 mL, 2.27 mmol) in 5 mL dichloromethane was refluxed. After 4 hours, additional iodotrimethylsilane (0.32 mL, 2.27 mmol) was added and the reaction stirred at room temperature for 3 days. The reaction was diluted with methanol and evaporated, with the residue taken up in a methanolic solution of sodium methoxide (0.5 M, 9.1 mL) and re-evaporated.

The resulting solids were washed with dichloromethane and dried in vacuo to yield 540 mg of the desired free aminopiperidine.

Step B: Preparation of 6-(2-fluorophenoxy)-8-methyl-2-{ [(1-benzylsulfonyl)piperidiny-4-yl]amino}pyrido[2,3-d]pyrimidin-7(8H)-one

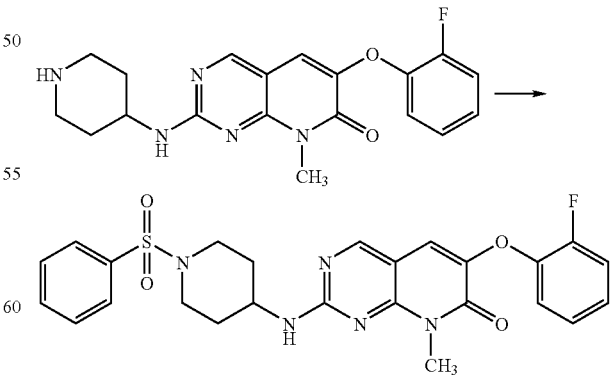

A mixture of aminopiperidine (0.125 g, 0.338 mmol), sodium carbonate (0.072 g, 0.677 mmol), and benzenesulfonyl chloride (0.052 mL, 0.406 mmol) in 4 ml dichloromethane was stirred at room temperature for four days. The reaction mixture was purified by column chromatography (SiO2, CH₂Cl₂/MeOH/NH₃OH—95/4/1). The column fractions were combined and concentrated under reduced pressure to provide the free amine. This free amine (0.040 g, 0.078 mmol) was dissolved in ethyl acetate (1-2 mL) and hydrochloric acid in ether (1M, 1 eq) was added. Isolation of the solid via filtration, followed by rinsing with ether and drying provided 0.032 g of the desired product as the hydrochloride salt (MP=130.0-135.0° C.).

Example 110

Preparation of 6-(2-ethoxy-4-fluorophenoxy)-8-methyl-2-{[(1-benzylsulfonyl)piperidiny-4-yl]amino}pyrido[2,3-d]pyrimidin-7(8H)-one Step A: Preparation of 6-(2-ethoxy-4-fluorophenoxy)-8-methyl-2-(4-piperidylamino)pyrido[2,3-d]pyrimidin-7(8H)-one:

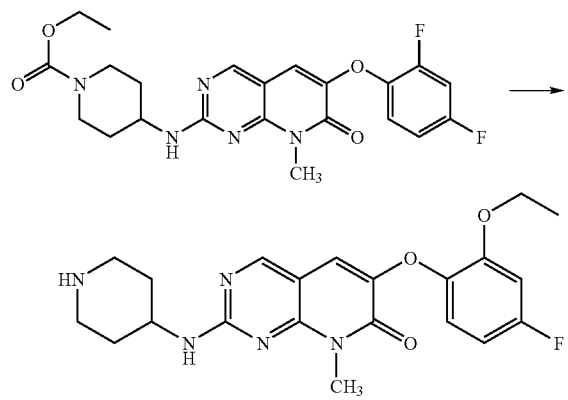

A mixture of ethyl 4-{[6-(2,4-difluorophenoxy)-8-methyl-7-oxo-7,8-dihydropyrido[2,3-d]pyrimidin-2-yl]amino}piperidine-1-carboxylate (Example 70, 1.0 g, 2.16 mmol) and potassium hydroxide (2.43 g, 43.2 mmol) in 20 mL of ethanol was refluxed for 17 hours, after which 0.5 mL water was added and reflux continued for another 20 hours before evaporating the reaction volume under reduced pressure. The residue was taken up in 100 ml water and chilled in an ice bath before acidifying with dropwise concentrated HCl. The acidic aqueous solution was extracted with dichloromethane (2×) before being re-alkalized with sodium hydroxide and re-extracted with dichloromethane (2×). The organic extracts from the alkaline aqueous solution were combined, dried with magnesium sulfate, and dried in vacuo to yield the aminopiperidine (M+1=414.1).

Step B: Preparation of 6-(2-ethoxy-4-fluorophenoxy)-8-methyl-2-{[(1-benzylsulfonyl)piperidiny-4-yl]amino}pyrido[2,3-d]pyrimidin-7(8H)-one

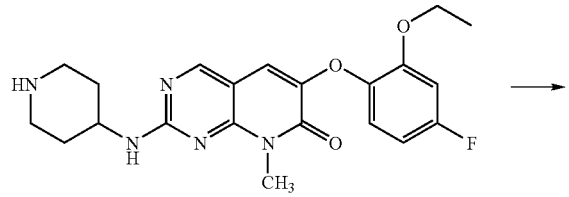

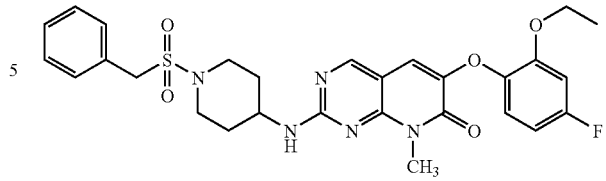

A portion of the above piperidine (0.150 g, 0.387 mmol) was taken up in 2 mL dichloromethane with sodium carbonate (0.082 g, 0.774 mmol) and α-toluenesulfonyl chloride (0.085 mL, 0.465 mmol) and stirred at room temperature for 17 hours. The reaction mixture was purified by column chromatography (SiO₂, CH₂Cl₂/MeOH—95/5). The column fractions were combined and concentrated under reduced pressure to provide the free amine. This free amine (0.076 g, 0.140 mmol) was dissolved in methanol (1-2 mL) and hydrochloric acid in ether (1M, 1 eq) was added before evaporation under reduced pressure Isolation of the solid by rinsing with ether, filtration, and drying in vacuo provided 0.031 g of the desired product as the hydrochloride salt (MP=134.6-187.3° C.).

Example 111

Preparation of 6-(2-methyl-4-fluorophenoxy)-8-methyl-2-{[(1-benzylsulfonyl)piperidiny-4-yl]amino}pyrido[2,3-d]pyrimidin-7(8H)-one Step A: Preparation of 6-(2-methyl-4-fluorophenoxy)-8-methyl-2-methylthio)pyrido[2,3-d]pyrimidin-7(8H)-one

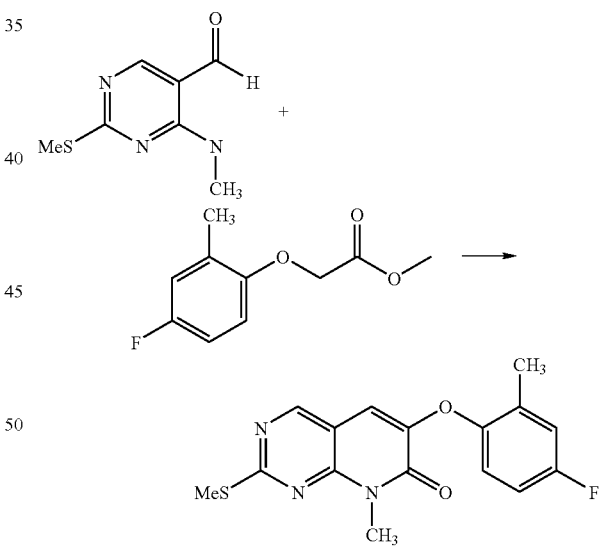

To a mixture of 4-methylamino-2-methylthiopyrimidine-5-carboxaldehyde (preparation described in Example 1) (7.3 g, 39.6 mmol) and methyl 2-methyl-4-fluorophenoxyacetate (prepared as in Example 4 substituting 2-methyl-4-fluorophenol for 2-fluorophenol), (11.8 g, 59.4 mmol) in 80 mL of 1-methyl-2-pyrrolidinone was added potassium carbonate (11.0 g, 79.3 mmol). The reaction mixture was heated to 120° C. and after 3 days, additional phenoxyacetate (15.0 g, 75.7 mmol) was added. After 18 hours of stirring at 120° C., the reaction was cooled to room temperature and water (1 L) was added. The suspension was stirred for 2 hours then extracted with ethyl acetate (2×). The combined extracts were washed with water (3×) and saturated brine, dried with magnesium sulfate, and evaporated in vacuo. The crude solid (10.1 g) was washed with ethyl ether and ethyl acetate, then dried in vacuo, yielding 2.3 g of the pure sulfide (mass spec. M+1=332).

Step B: Preparation of 6-(2-methyl-4-fluorophenoxy)-8-methyl-2-(methylsulfonyl)pyrido[2,3-d]pyrimidin-7(8H)-one

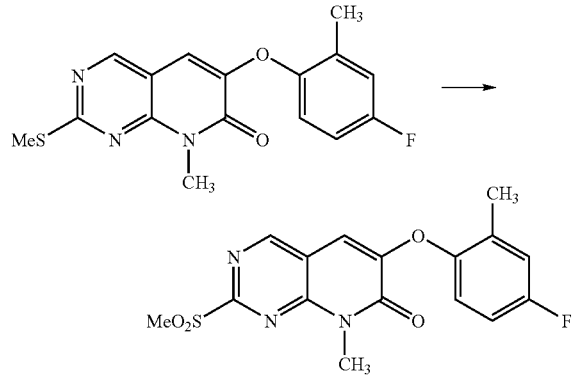

The sulfide (2.3 g, 6.9 mmol) was dissolved in 100 mL of methylene chloride and 3-chloroperbenzoic acid (77%, 3.6 g, 20.6 mmol) was added. The mixture was stirred at room temperature for 2 hours, then poured into aqueous sodium sulfite solution (10%, 100 mL) and stirred for 2 hours at room temperature before partitioning. The organic layer was washed with half-saturated aqueous sodium bicarbonate solution (3×, 100 mL), dried with magnesium sulfate, and evaporated. The resultant solid was stirred with ether for 1 hour and filtered to yield the sulfone.

Step C: Preparation of 6-(2-methyl-4-fluorophenoxy)-8-methyl-2-(4-piperidylamino)pyrido[2,3-d]pyrimidin-7(8H)-one:

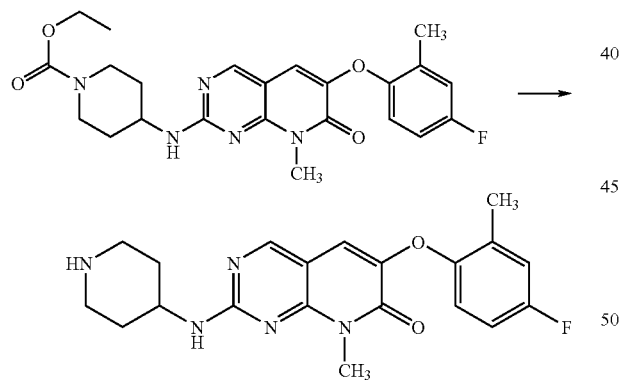

The piperidine ethyl carboxylate (prepared from the sulfone described in Step B and ethyl 4-amino-1-piperidine carboxylate in similar fashion as described in example 70). was isolated as the hydrochloride salt (mp 184.0-210.3° C.). 1.03 g of this ethyl carbamate (2.26 mmol) and potassium hydroxide (4.81 g, 85.7 mmol) in 60 ml ethanol was refluxed for 3 days and evaporated in vacuo. The residue was dissolved in aqueous hydrochloric acid (2M) and extracted with dichloromethane (2×), then chilled in an ice bath and re-alkalized with solid sodium hydroxide. The resultant oily precipitate was decanted and washed with methanol and dichloromethane, dried with sodium carbonate, and evaporated in vacuo to yield 0.550 g of the desired piperidine.

Step D: Preparation of 6-(2-methyl-4-fluorophenoxy)-8-methyl-2-{[(1-benzylsulfonyl)piperidiny-4-yl]amino}pyrido[2,3-d]pyrimidin-7(8H)-one

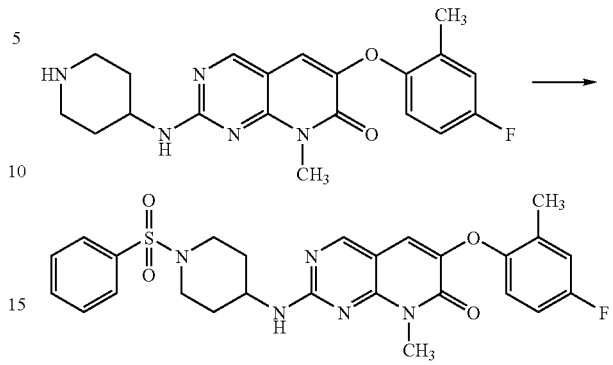

A mixture of the piperidine (0.125 g, 0.326 mmol), sodium carbonate (0.069 g, 0.652 mmol), and benzenesulfonyl chloride (0.050 ml, 0.391 mmol) in 2 ml dichloromethane was stirred at room temperature for 5 days and purified by column chromatography (SiO$_2$, CH$_2$Cl$_2$/MeOH—95/5). The column fractions were combined and concentrated under reduced pressure to provide the free amine. This free amine (0.185 g, 0.353 mmol) was dissolved in ethyl acetate (1-2 mL) and hydrochloric acid in ether (1M, 1 eq) was added. Isolation of the solid by filtration, rinsing with ether, and drying in vacuo provided 0.156 g of the hydrochloride salt (MP=115.2-122.9° C.).

Example 112

Preparation of 6-(2,4-difluorophenoxy)-8-methyl-2-(N$^1$-methylsulfonyl)-1,3-diaminopentane)pyrido[2,3-d]pyrimidin-7(8H)-one Step A: Preparation of 6-(2,4-difluorophenoxy)-8-methyl-2-(N$^1$-(carbobenzyloxy)-1,3-diaminopentane)pyrido[2,3-d]pyrimidin-7(8H)-one

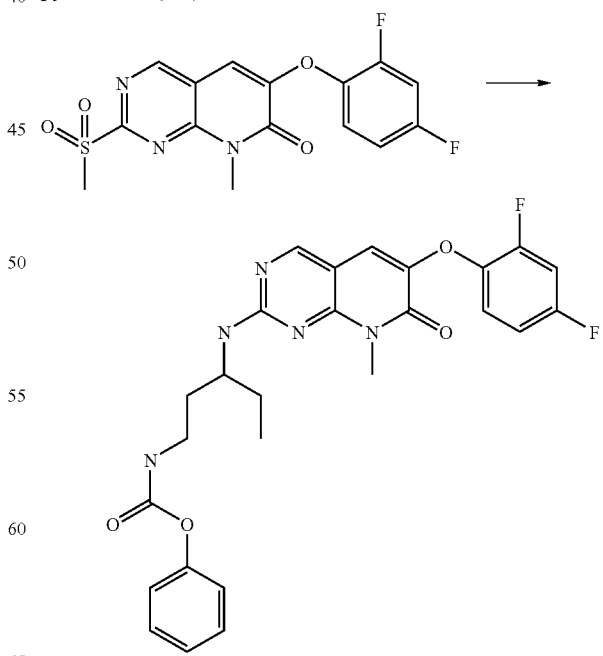

Sulfone 5 (0.47 g, 6.4 mmol) was dissolved in anhydrous THF to which was added N$^1$-(carbobenzyloxy)-1,3-diaminopentane (Org. Prep. and Proceed. Int., 30(3), 339-348 (1998)), (1.52 g, 6.4 mmol) and stirred overnight at 23° under nitrogen. Concentrated under vacuum to give crude oil that was dissolved up with dichloromethane washed with saturated sodium bicarbonate, washed with brine and dried (MgSO$_4$). Filtered and concentrated to give crude oil which was chromatographed on silica gel eluding with 2% methanol in dichloromethane to give 0.657 g 6-(2,4-difluorophenoxy)-8-methyl-2-(N$^1$-(carbobenzyloxy)-1,3-diaminopentane)pyrido[2,3-d]pyrimidin-7(8H)-one (mass spec. M+1=524)

Step B: Preparation of 6-(2,4-difluorophenoxy)-8-methyl-2-(N$^1$-methylsulfonyl)-1,3-diaminopentane)pyrido[2,3-d]pyrimidin-7(8H)-one

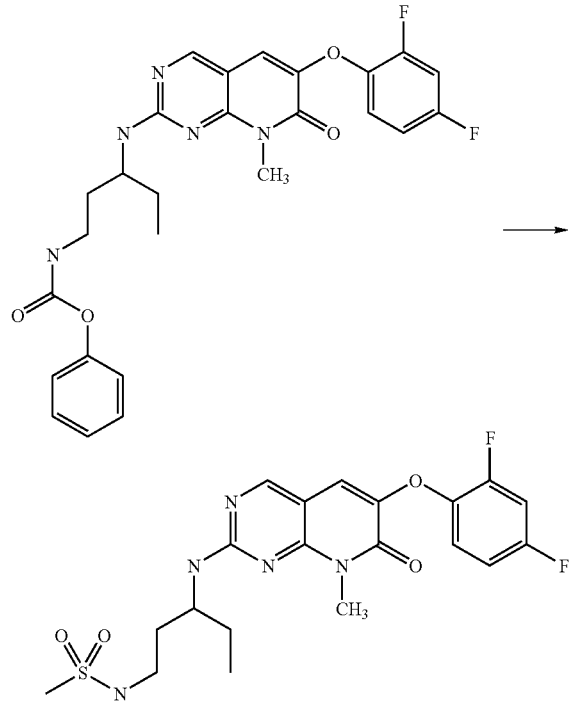

To a THF solution of 6-(2,4-difluorophenoxy)-8-methyl-2-(N$^1$-(carbobenzyloxy)-1,3-diaminopentane)pyrido[2,3-d]pyrimidin-7(8H)-one (0.65 g, 1.2 mmol) was added 10% Pd—C (0.13 g) and stirred for 4 hrs at 23° C. under hydrogen gas. Filtered and concentrated under vacuum. Residue dissolved up with 10 ml dichloromethane and cooled to −10° C.; added pyridine (5 ml, 62 mmol) and methanesulfony chloride (0.070 ml, 0.86 mmol) and stirred. Concentrated under vacuum and chromatographed on silica gel eluding with 1% methanol in dicloromethane to give 0.121 g 6-(2,4-difluorophenoxy)-8-methyl-2-(N$^1$-methylsulfonyl)-1,3-diaminopentane)pyrido[2,3-d]pyrimidin-7(8H)-one which was dissolved in anhydrous ether and converted to hydrochloride salt (mass spec. M+1=468, m.p. 178.6-181.2° C.)

Example 113

Preparation of 4-Amino-2-methylthiopyrimidine-5-carbaldehyde

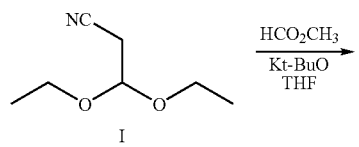

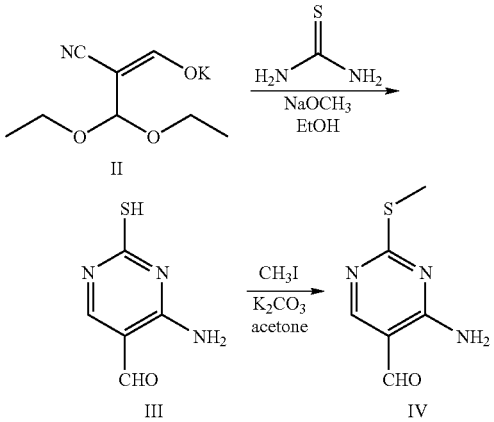

Preparation of 3,3-Diethoxy-2-formylpropionitrile Potassium Salt (II)

To a stirred solution of 3,3-diethoxypropane-nitrile (I, 283.80 g, 1.98 moles) and methyl formate (148.80 g, 2.48 moles) in anhydrous THF (1.1 L) at 10° C. was added 1.0 M potassium tert-butoxide in THF (2.2 L, 2.2 moles). Temperature was maintained in the range of 10° C. to 15° C. throughout the 45 minute addition. Following the addition, the resulting slurry was stirred 2 hours at ambient room temperature. Hexane (400 mL) was then added and stirring was continued for another 20 min. The slurry was filtered and the cake washed with 1/1 hexanes/THF and dried overnight at 60° C. in a vacuum oven. The yield of pale tan powder was 302.5 grams (73.0%). $^1$H-NMR (CD$_3$OD) was consistent with the desired structure II.

Preparation of 4-Amino-2-sulfanylpyrimidine-5-carbaldehyde (III)

A slurry of thiourea (92.8 g, 1.22 moles) in ethanol (90 mL) was heated under reflux and vigorously stirred. To this slurry was added a suspension of 3,3-diethoxy-2-formylpropionitrile potassium salt II (222.20 g, 1.06 moles) in 25% sodium methoxide/methanol (85.5 mL, 0.37 mole) and ethanol (285 mL) in five aliquots over a 10 minute period while maintaining reflux conditions (alternatively, the latter slurry may be heated to 50° C. to give a homogenous solution for the addition). An additional portion of ethanol (150 mL) was added to facilitate stirring. The thick slurry became a bright yellow color following the addition and was held under reflux for an additional 1 hour. The mixture was then cooled and evaporated to near dryness on a rotoevaporator. The residue was dissolved in water (940 mL). Crude product was precipitated from solution by the addition of 30% acetic acid (280 mL) and isolated via filtration using a medium frit sintered glass filtration funnel. The cake was washed with water (800 mL). Purification via trituration in hot water (1 L) for 30 minutes, followed by cooling and filtration gave 118.9 grams (72.3%) of product as a bright yellow solid after drying overnight at 60° C. in a vacuum oven (subsequent preparations have demonstrated that this trituration is unnecessary). An HPLC gave purity as 98.67%. $^1$H-NMR (DMSO-d$_6$) was consistent with desired structure III.

Preparation of 4-Amino-2-methylthiopyrimidine-5-carbaldehyde (IV)

To a solution of 4-amino-2-sulfanyl-pyrimidine-5-carbaldehyde III (100.00 g, 644.4 mmoles) and 325 mesh potassium carbonate (178.10 g, 1.29 moles) in acetone (1.5 L) was added iodomethane (128.10 g, 902.2 mmoles) dropwise over 20 minutes with mild cooling. The mixture was stirred at ambient room temperature over the weekend. TLC showed remaining III and an additional aliquot of iodomethane was added (8 mL) and stirring was continued overnight. TLC again showed some III remaining and an addition portion of iodomethane was added (8 mL) and stirring was continued another 24 hour period. An HPLC showed 95.9% S-alkylated product and 3.7% of compound III. The reaction mixture was stripped to near dryness on a rotoevaporator. Water (1 L) was added to the residue and the product was collected via filtration and washed with water (200 mL). The product was dried overnight in a vacuum oven at 60° C. Yield was 103.37 grams (94.8%). An HPLC showed 95.8% IV and 4.2% III.

Example 114

This example illustrates a p38 (MAP) kinase in vitro assay useful for evaluating the compounds of the present invention.

The p-38 MAP kinase inhibitory activity of compounds of this invention in vitro was determined by measuring the transfer of the γ-phosphate from γ-$^{33}$P-ATP by p-38 kinase to Myelin Basic Protein (MBP), using a minor modification of the method described in Ahn, et al., *J. Biol. Chem.* 266:4220-4227 (1991).

The phosphorylated form of the recombinant p38 MAP kinase was co-expressed with SEK-1 and MEKK in *E. Coli* (see, Khokhlatchev, et al., *J. Biol. Chem.* 272:11057-11062 (1997)) and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis (beta-aminoethyl ether)-N,N,N',N'-tetraacetic acid, 1 mM sodium ortho-vanadate, 1 mM dithiothreitol, 40 mM magnesium chloride). Test compound dissolved in DMSO or only DMSO (control) was added and the samples were incubated for 10 min at 30° C. The kinase reaction was initiated by the addition of a substrate cocktail containing MBP and γ-$^{33}$P-ATP. After incubating for an additional 20 min at 30° C., the reaction was terminated by adding 0.75% phosphoric acid. The phosphorylated MBP was then separated from the residual γ-$^{33}$P-ATP using a phosphocellulose membrane (Millipore, Bedfrod, Mass.) and quantitated using a scintillation counter (Packard, Meriden, Conn.).

Example 115

This example illustrates an in vitro assay to evaluate the inhibition of LPS-induced TNF-α production in THP 1 cells.

The ability of the compounds of this invention to inhibit the TNF-α release was determined using a minor modification of the methods described in Blifeld, et al. *Transplantation*, 51:498-503 (1991).

(a) Induction of TNF Biosynthesis:

THP-1 cells were suspended in culture medium [RPMI (Gibco-BRL, Gailthersburg, Md.) containing 15% fetal bovine serum, 0.02 mM 2-mercaptoethanol], at a concentration of 2.5×10$^6$ cells/mL and then plated in 96 well plate (0.2 mL aliquots in each well). Test compounds were dissolved in DMSO and then diluted with the culture medium such that the final DMSO concentration was 5%. Twenty five μL aliquots of test solution or only medium with DMSO (control) were added to each well. The cells were incubated for 30 min., at 37° C. LPS (Sigma, St. Louis, Mo.) was added to the wells at a final concentration of 0.5 μg/ml, and cells were incubated for an additional 2 h. At the end of the incubation period, culture supernatants were collected and the amount of TNF-α present was determined using an ELISA assay as described below.

(b) ELISA Assay:

The amount of human TNF-α present was determined by a specific trapping ELISA assay using two anti-TNF-α antibodies (2TNF-H12 and 2TNF-H34) described in Reimund, J. M., et al. *GUT*. Vol. 39(5), 684-689 (1996).

Polystyrene 96-well plates were coated with 50 μl per well of antibody 2TNF-H12 in PBS (10 μg/mL) and incubated in a humidified chamber at 4° C. overnight. The plates were washed with PBS and then blocked with 5% nonfat-dry milk in PBS for 1 hour at room temperature and washed with 0.1% BSA (bovine serum albumin) in PBS.

TNF standards were prepared from a stock solution of human recombinant TNF-α (R&D Systems, Minneapolis, Minn.). The concentration of the standards in the assay began at 10 ng/mL followed by 6 half log serial dilutions.

Twenty five μL aliquots of the above culture supernatants or TNF standards or only medium (control) were mixed with 25 μl aliquots of biotinylated monoclonal antibody 2TNF-H34 (2 μg/mL in PBS containing 0.1% BSA) and then added to each well. The samples were incubated for 2 hr at room temperature with gentle shaking and then washed 3 times with 0.1% BSA in PBS. 50 μl of peroxidase-streptavidin (Zymed, S. San Francisco, Calif.) solution containing 0.416 μg/mL of peroxidase-streptavidin and 0.1% BSA in PBS was added to each well. The samples were incubated for an additional 1 hr at room temperature and then washed 4 times with 0.1% BSA in PBS. Fifty μL of O-phenylenediamine solution (1 μg/1 L O-phenylenediamine and 0.03% hydrogen peroxide in 0.2M citrate buffer pH 4.5) was added to each well and the samples were incubated in the dark for 30 min., at room temperature. Optical density of the sample and the reference were read at 450 nm and 650 nm, respectively. TNF-α levels were determined from a graph relating the optical density at 450 nm to the concentration used.

The IC$_{50}$ value was defined as the concentration of the test compound corresponding to half-maximal reduction in 450 nm absorbance.

Example 116

This example illustrates an in vivo assay to evaluate the inhibition of LPS-induced TNF-α production in mice (or rats).

The ability of the compounds of this invention to inhibit the TNF-α release, in vivo, was determined using a minor modification of the methods described in described in Zanetti, et. al., *J. Immunol.*, 148:1890 (1992) and Sekut, et. al., *J. Lab. Clin. Med.*, 124:813 (1994).

Female BALB/c mice weighing 18-21 grams (Charles River, Hollister, Calif.) were acclimated for one week. Groups containing 8 mice each were dosed orally either with the test compounds suspended or dissolved in an aqueous vehicle containing 0.9% sodium chloride, 0.5% sodium carboxymethyl-cellulose, 0.4% polysorbate 80, 0.9% benzyl alcohol (CMC vehicle) or only vehicle (control group). After 30 min., the mice were injected intraperitoneally with 20 μg of LPS (Sigma, St. Louis, Mo.). After 1.5 h, the mice were sacrificed by $CO_2$ inhalation and blood was harvested by cardiocentesis. Blood was clarified by centrifugation at 15,600×g for 5 min., and sera were transferred to clean tubes and frozen at −20° C. until analyzed for TNF-α by ELISA assay (Biosource International, Camarillo, Calif.) following the manufacturer's protocol.

Representative compounds of the present invention are shown in Table 1 below. Compounds of Table 1 have $IC_{50}$ activity against p38 kinase in the range of from about 0.1 to 5000 nM, with the majority being between 1 to 1000 nM and are surprisingly selective for p38 kinase relative to cyclin-dependent kinases and tyrosine kinase.

TABLE 1

Representative compounds of Formula I.

| MOL STRUCTURE | M. Pt. | Mass Spec | Example |
|---|---|---|---|
| I-1 | 182.1-183.8 | | |
| I-2 | | | |
| I-3 | | | |

TABLE 1-continued

Representative compounds of Formula I.

| MOL STRUCTURE | M. Pt. | Mass Spec | Example |
|---|---|---|---|
| I-4 | | | |
| I-5 | | | |
| I-6 | 200.9 to 201.6 | | |
| I-7 | 197-197.4 | | |

TABLE 1-continued

Representative compounds of Formula I.

| MOL STRUCTURE | M. Pt. | Mass Spec | Example |
|---|---|---|---|
| I-8 | 197.0 to 197.4 | | |
| I-9 | | | |
| I-10 | 210.4-231.5 | | |
| I-11 | 235-253 | | |

TABLE 1-continued
Representative compounds of Formula I.
| MOL STRUCTURE | M. Pt. | Mass Spec | Example |
|---|---|---|---|
| I-12 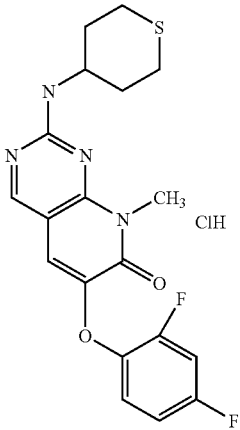 | 230.7-232.8 | | 57 |
| I-13 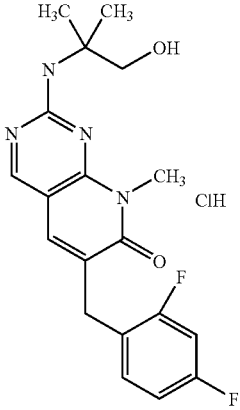 | 224.2-225 | | |
| I-14 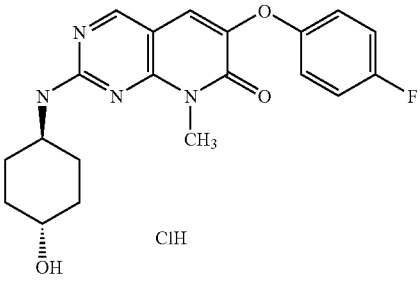 | 253.2-253.9 | M + 1 = 385 | 26 |
| I-15 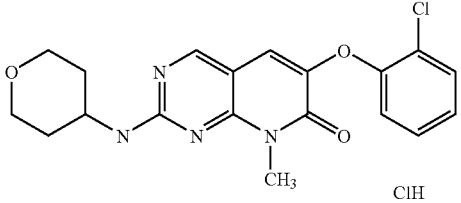 | 253.8-254.7 | | |

TABLE 1-continued

Representative compounds of Formula I.

| MOL STRUCTURE | M. Pt. | Mass Spec | Example |
|---|---|---|---|
| I-16 | | M + 1 = 387 | |
| I-17 | | 387 | |
| I-18 | | M + 1 = 353 | 21 |
| I-19 | | M + 1 = 465 | 33 |
| I-20 | | M + 1 = 371 | 22 |
| I-21 | 183-191 | M + 1 = 370 | |
| I-22 | 208-211 | M + 1 = 389 | 23 |

TABLE 1-continued

Representative compounds of Formula I.

| MOL STRUCTURE | M. Pt. | Mass Spec | Example |
|---|---|---|---|
| I-23 | | M + 1 = 430 | |
| I-24 | | M + 1 = 465 | 32 |
| I-25 | | M + 1 = 448 | 29 |
| I-26 | | M + 1 = 448 | |
| I-27 | | M + 1 = 371 | |
| I-28 | | M + 1 = 448 | |
| I-29 | | M + 1 = 466 | |

TABLE 1-continued

Representative compounds of Formula I.

| MOL STRUCTURE | M. Pt. | Mass Spec | Example |
|---|---|---|---|
| I-30 | | M + 1 = 337 | |
| I-31 | | M + 1 = 371 | |
| I-32 | | M + 1 = 371 | |
| I-33 | | M + 1 = 355 | |
| I-34 | | M + 1 = 355 | 35 |
| I-35 | | M + 1 = 373 | |
| I-36 | | M + 1 = 355 | 36 |

TABLE 1-continued

Representative compounds of Formula I.

| MOL STRUCTURE | M. Pt. | Mass Spec | Example |
|---|---|---|---|
| I-37 | | M + 1 = 389 | 52 |
| I-38 | | M + 1 = 403 | |
| I-39 | | M + 1 = 375 | |
| I-40 | | M + 1 = 380 | 80 |
| I-41 | | M + 1 = 373 | 40 |
| I-42 | 245.2–246.1 | M + 1 = 478 | 79 |

TABLE 1-continued

Representative compounds of Formula I.

| MOL STRUCTURE | M. Pt. | Mass Spec | Example |
|---|---|---|---|
| I-43 | 203.2-204 | M + 1 = 377 | 63 |
| I-44 | 245.2-246.1 | | |
| I-45 | 214.7-226.8 | | |
| I-46 | | M + 1 = 343 | 37 |
| I-47 | | M + 1 = 456 | |
| I-48 | | M + 1 = 331 | 38 |

TABLE 1-continued

Representative compounds of Formula I.

| MOL STRUCTURE | M. Pt. | Mass Spec | Example |
|---|---|---|---|
| I-49 | | M + 1 = 356 | |
| I-50 | | M + 1 = 343 | 39 |
| I-51 | 255.5-261.4 | M + 1 = 494 | 78 |
| I-52 | 249-.4-251.2 | | |
| I-53 | 215.2-218.1 | | |

TABLE 1-continued

Representative compounds of Formula I.

| MOL STRUCTURE | M. Pt. | Mass Spec | Example |
|---|---|---|---|
| I-54 | | M + 1 = 361 | 41 |
| I-55 | | M + 1 = 345 | |
| I-56 | | M + 1 = 371 | |
| I-57 | 122.1-161.2 | | |
| I-58 | | M + 1 = 378 | 66 |
| I-59 | | M + 1 = 400 | |

TABLE 1-continued

Representative compounds of Formula I.

| MOL STRUCTURE | M. Pt. | Mass Spec | Example |
|---|---|---|---|
| I-60 | | M + 1 = 398 | 42 |
| I-61 | | M + 1 = 383 | 43 |
| I-62 | 210.4-211.2 | | |
| I-63 | 207.2-207.5 | | |
| I-64 | | M + 1 = 341 | 44 |
| I-65 | | M + 1 = 345 | 45 |

TABLE 1-continued

Representative compounds of Formula I.

| MOL STRUCTURE | M. Pt. | Mass Spec | Example |
|---|---|---|---|
| I-66 | | M + 1 = 372 | 46 |
| I-67 | | M + 1 = 329 | |
| I-68 | | M + 1 = 301 | |
| I-69 | | M + 1 = 477 | |
| I-70 | | M + 1 = 367 | 67 |
| I-71 | 188.8-189.7 | M + 1 = 403 | 55 |

TABLE 1-continued
Representative compounds of Formula I.
| MOL STRUCTURE | M. Pt. | Mass Spec | Example |
|---|---|---|---|
| I-72 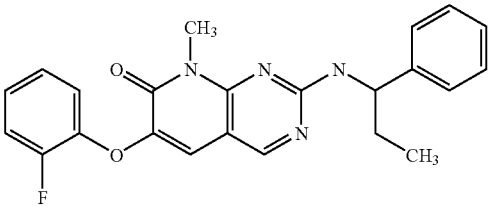 | 109.4-111.3 | M + 1 = 405 | 65 |
| I-73 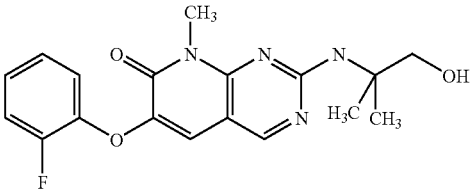 | 180.2-183.9 | M + 1 = 359 | |
| I-74 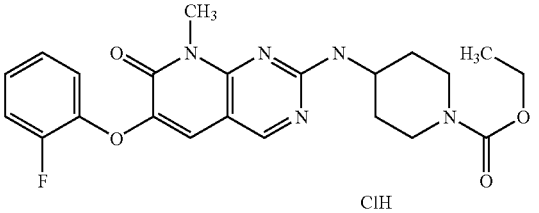 | | M + 1 = 442 | |
| I-75 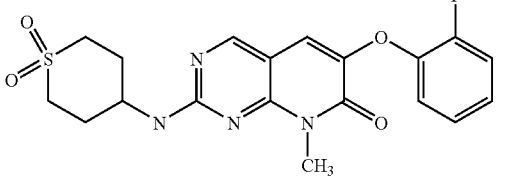 | | M + 1 = 419 | 56 |
| I-76 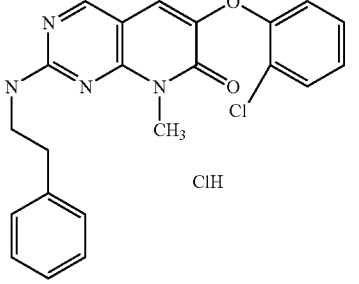 | 210-211 | M + 1 = 407 | 69 |

TABLE 1-continued
Representative compounds of Formula I.
| MOL STRUCTURE | M. Pt. | Mass Spec | Example |
|---|---|---|---|
| I-77 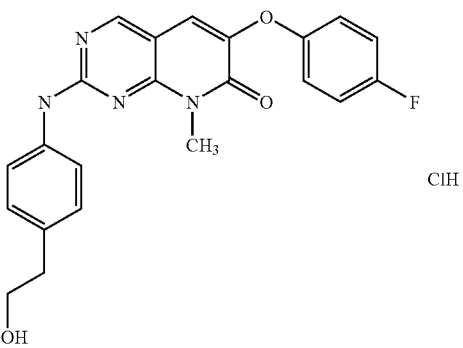 | 222.7-224.8 | M+ = 407 | |
| I-78 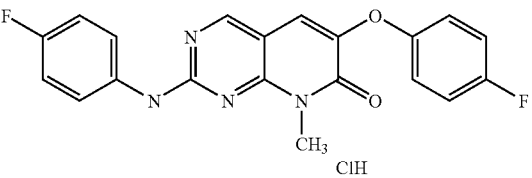 | 242.3-242.6 | M + 1 = 381 | 74 |
| I-79 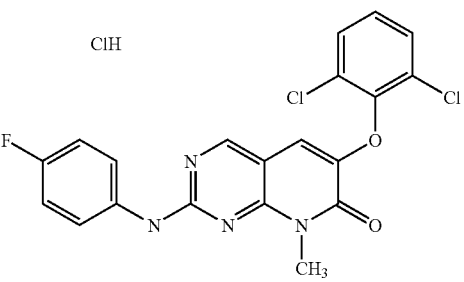 | 248.2-249.1 | M + 1 = 430 | 75 |
| I-80 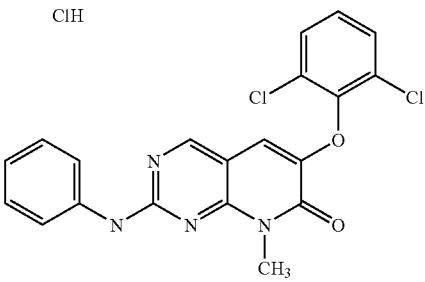 | 239.3-240.5 | | |
| I-81 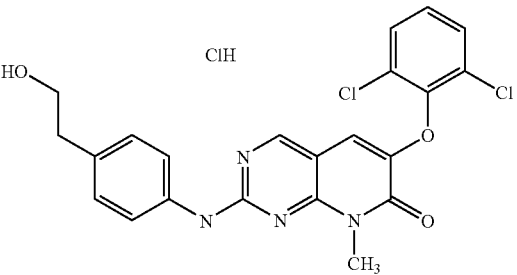 | 266-268 | M+ = 457 | |

TABLE 1-continued

Representative compounds of Formula I.

| MOL STRUCTURE | M. Pt. | Mass Spec | Example |
|---|---|---|---|
| I-82 | 234.9-236.1 | | |
| I-83 | 233.9-235.5 | M + 1 = 443 | 72 |
| I-84 | 239.7-240.4 | | |
| I-85 | 188-196 | | |
| I-86 | 243.6-244.7 | | |

TABLE 1-continued
Representative compounds of Formula I.
| MOL STRUCTURE | M. Pt. | Mass Spec | Example |
|---|---|---|---|
| I-87 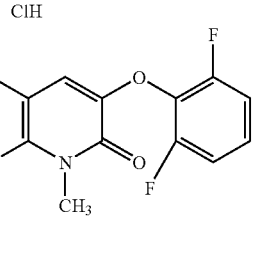 | 212.8-213.5 | M + 1 = 377 | 60 |
| I-88 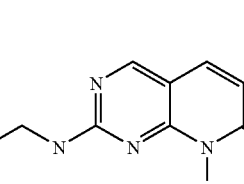 | | M + 1 = 359 | |
| I-89 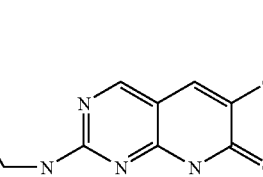 | | M + 1 = 414 | |
| I-90 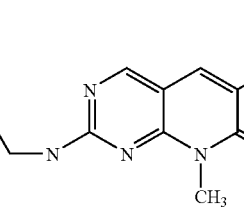 | | M + 1 = 412 | 47 |
| I-91 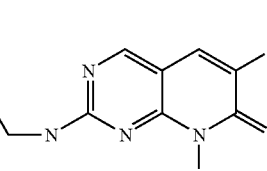 | | M + 1 = 373 | 48 |
| I-92 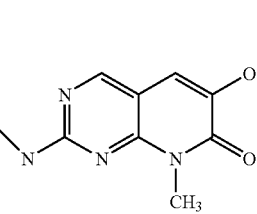 | | M + 1 = 392 | |

TABLE 1-continued
Representative compounds of Formula I.
| MOL STRUCTURE | M. Pt. | Mass Spec | Example |
|---|---|---|---|
| I-93 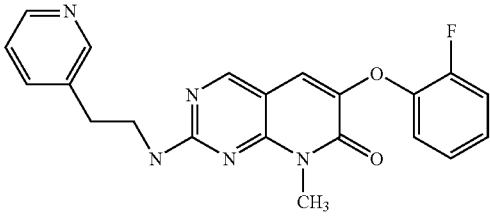 | | M + 1 = 392 | 49 |
| I-94 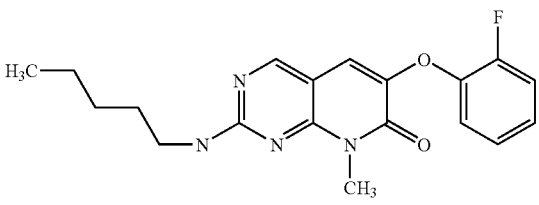 | | M + 1 = 357 | |
| I-95 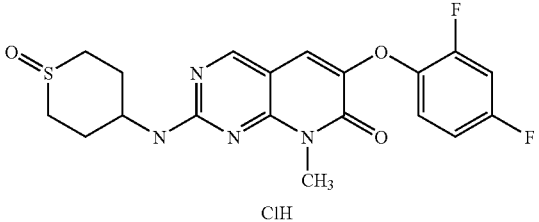 | 201.8-202.5 | M + 1 = 421 | 57 |
| I-96 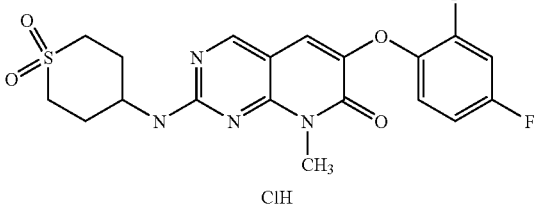 | 251.7-254.9 | M + 1 = 437 | 58 |
| I-97 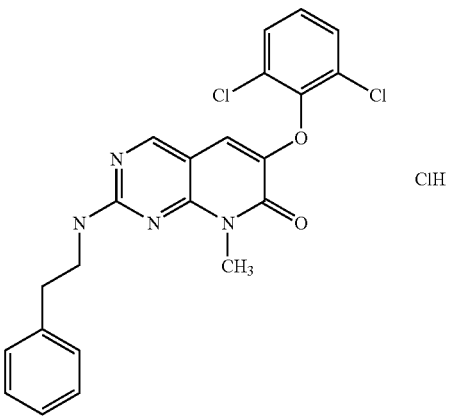 | 216.3-218.1 | M+ = 441 | |

TABLE 1-continued

Representative compounds of Formula I.

| MOL STRUCTURE | M. Pt. | Mass Spec | Example |
|---|---|---|---|
| I-98 | 253.4-257.8 | M+ = 363 | |
| I-99 | | M+ = 389 | |
| I-100 | 227.9-228.8 | M + 1 = 389 | 77 |
| I-101 | | | |
| I-102 | 210.8-211.8 | M + 1 = 391 | |

TABLE 1-continued

Representative compounds of Formula I.

| MOL STRUCTURE | M. Pt. | Mass Spec | Example |
|---|---|---|---|
| I-103 | | M + 1 = 474 | 31 |
| I-104 | | M + 1 = 358 | |
| I-105 | | M + 1 = 384 | |
| I-106 | | M + 1 = 398 | |
| I-107 | | M + 1 = 315 | |
| I-108 | | M + 1 = 378 | 81 |

TABLE 1-continued
Representative compounds of Formula I.
| MOL STRUCTURE | M. Pt. | Mass Spec | Example |
|---|---|---|---|
| I-109 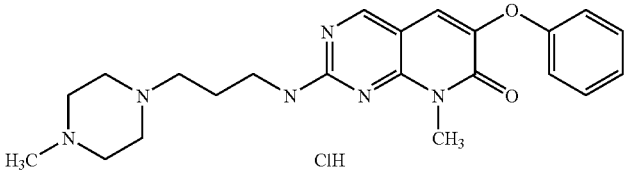 | 180.2-182.2 | M + 1 = 409 | 71 |
| I-110 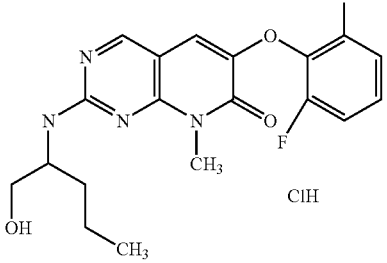 | 176.7-177.7 | M + 1 = 391 | 59 |
| I-111 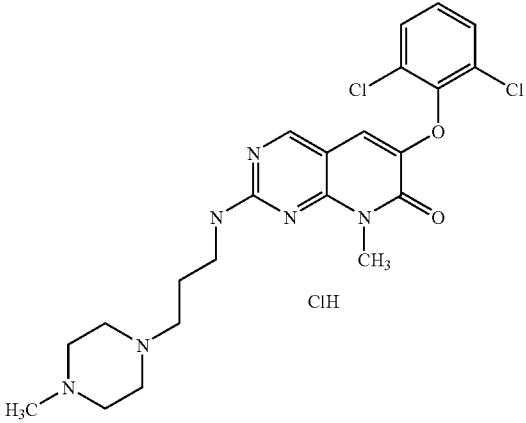 | 208.7-212.4 | | |
| I-112 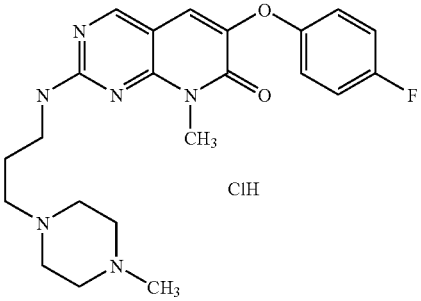 | 242.7-243.1 | | |
| I-113 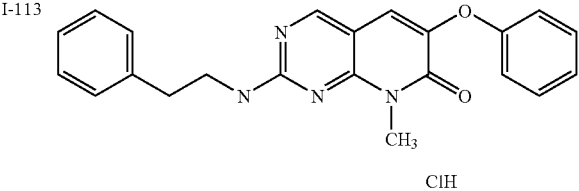 | 211.8-213 | M + 1 = 373 | 68 |

TABLE 1-continued

Representative compounds of Formula I.

| MOL STRUCTURE | M. Pt. | Mass Spec | Example |
|---|---|---|---|
| I-114 | 193.7-194.3 | | |
| I-115 | 207.3-207.6 | M + 1 = 421 | |
| I-116 | | M + 1 = 329 | |
| I-117 | 222.1-222.8 | M + 1 = 437 | |
| I-118 | 174.6-175.2 | M + 1 = 391 | |

TABLE 1-continued
Representative compounds of Formula I.
| MOL STRUCTURE | M. Pt. | Mass Spec | Example |
|---|---|---|---|
| I-119 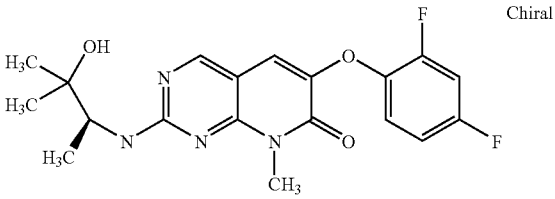 | 104.3-107.5 | M + 1 = 391 | 53 |
| I-120 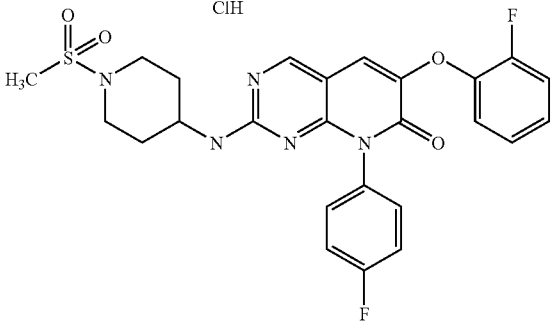 | 223.4-225 | M + 1 = 528 | 30 |
| I-121 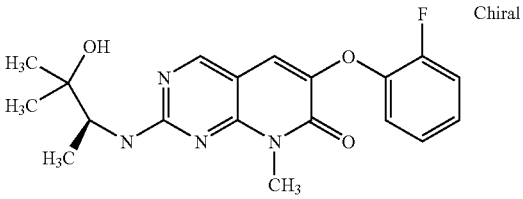 | 107.2-111.4 | M + 1 = 373 | |
| I-122 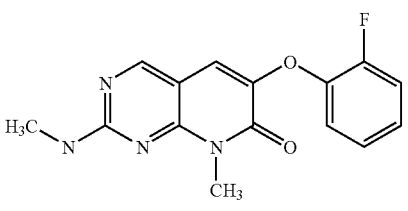 | 250.5-253.7 | | |
| I-123 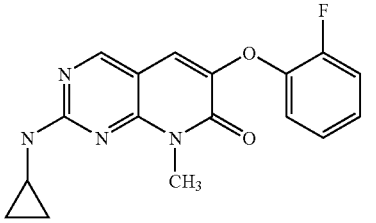 | 178.2-179.6 | M + 1 = 327 | 34 |

TABLE 1-continued
Representative compounds of Formula I.
| MOL STRUCTURE | M. Pt. | Mass Spec | Example |
|---|---|---|---|
| I-124 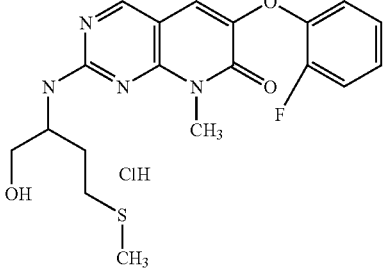 | 130.6-132.2 | M + 1 = 405 | 62 |
| I-125 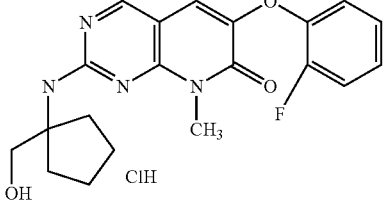 | 198.6-200.3 | M + 1 = 385 | 61 |
| I-126 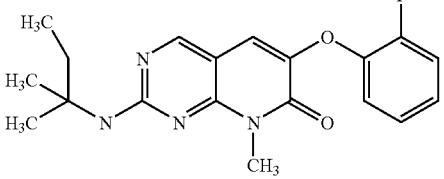 | | M + 1 = 357 | |
| I-127 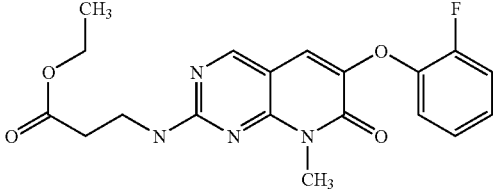 | | M + 1 = 387 | 50 |
| I-128 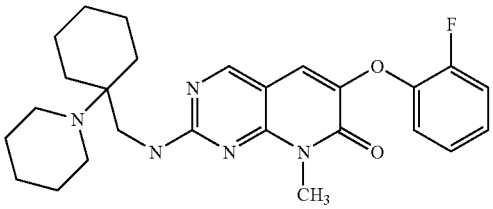 | | M + 1 = 466 | |
| I-129 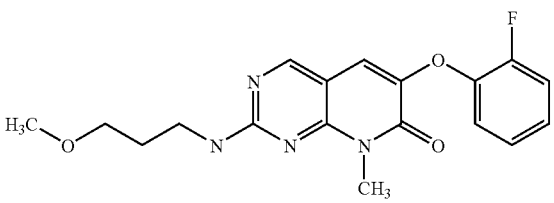 | | M + 1 = 359 | 51 |

TABLE 1-continued

Representative compounds of Formula I.

| MOL STRUCTURE | M. Pt. | Mass Spec | Example |
|---|---|---|---|
| I-130 | 203.6-207.5 | | |
| I-131 | 224-224.9 | | |
| I-132 | 232.4-233.7 | | |
| I-133 | 197-204 | M + 1 = 462 | 70 |
| I-134 | 197.0-204.0 | | |
| I-135 | mp = 135-145 | M + 1 = 399 | 28 |

TABLE 1-continued

Representative compounds of Formula I.

| MOL STRUCTURE | M. Pt. | Mass Spec | Example |
|---|---|---|---|
| I-136 | | M + 1 = 397 | |
| I-137 | | M + 1 = 398 | |
| I-138 (Chiral, ClH) | 205.0-207.0 | | |
| I-139 | | M + 1 = 427 | |
| I-140 | | M + 1 = 423 | |

TABLE 1-continued
Representative compounds of Formula I.
| MOL STRUCTURE | M. Pt. | Mass Spec | Example |
|---|---|---|---|
| I-141 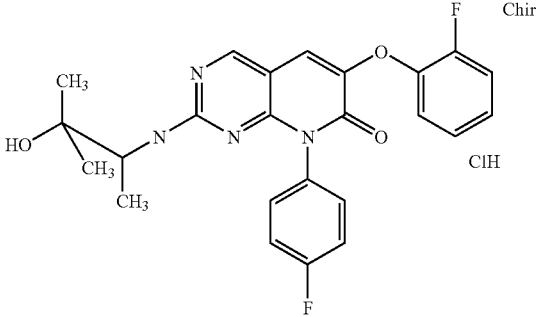 | 149-180 | M + 1 = 453 | |
| I-142 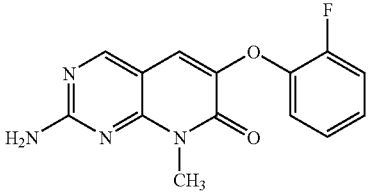 | 240.8-242.6 | M + 1 = 287 | 20 |
| I-143 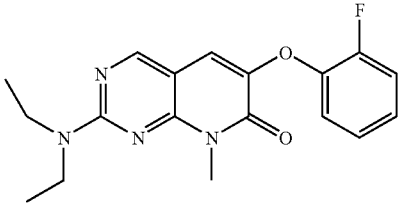 | | | |
| I-144 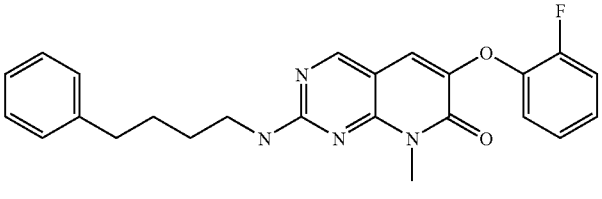 | | | |
| I-145 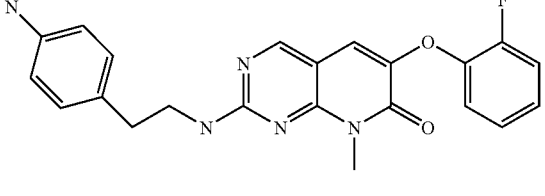 | | | |
| I-146 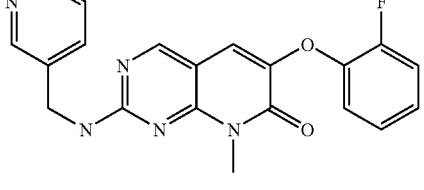 | | | |

TABLE 1-continued
Representative compounds of Formula I.
| MOL STRUCTURE | M. Pt. | Mass Spec | Example |
|---|---|---|---|
| I-147 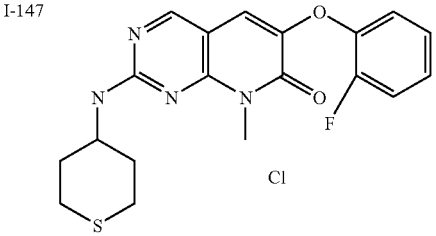 | 60.3-61.4 | (M + H)+ = 387 | 55 |
| I-148 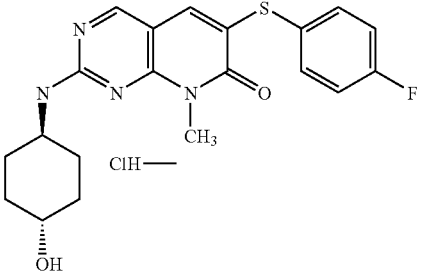 | 246-247.5 | M + 1 = 401 | 25 |
| I-149 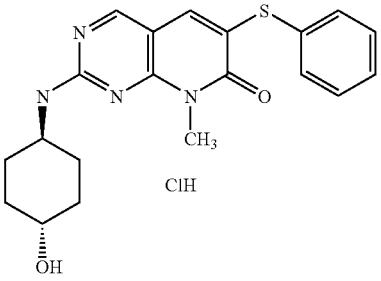 | 233-235.7 | | |
| I-150 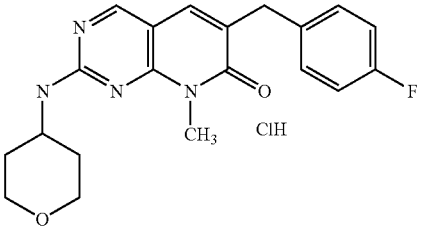 | 209-211.2 | | |
| I-151 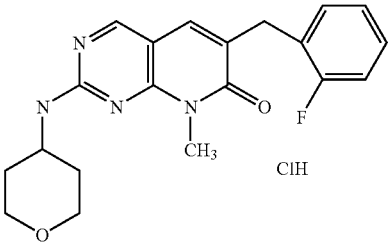 | 198.4-201.6 | M + 1 = 369 | 24 |

TABLE 1-continued
Representative compounds of Formula I.
| MOL STRUCTURE | M. Pt. | Mass Spec | Example |
|---|---|---|---|
| I-152 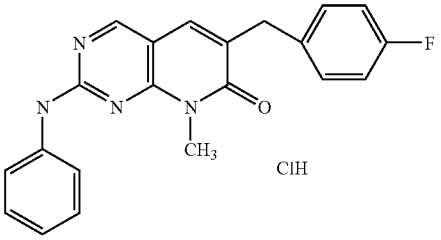 | 243.1-246.3 | M + 1 = 361 | 73 |
| I-153 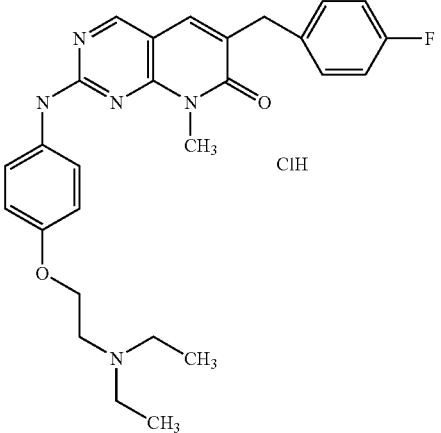 | 254.5-256.1 | | |
| I-154 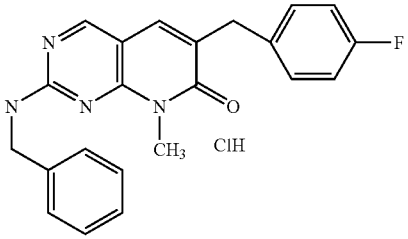 | 154-175 | M + 1 = 375 | 64 |
| I-155 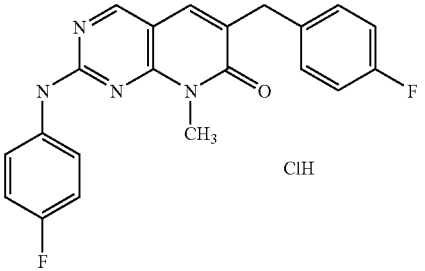 | 246-250 | M + 1 = 379 | 76 |
| I-156 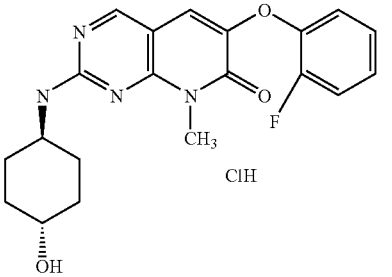 | 229.5-230.2 | M + 1 = 383 | 27 |

TABLE 1-continued
Representative compounds of Formula I.
| MOL STRUCTURE | M. Pt. | Mass Spec | Example |
|---|---|---|---|
| I-157 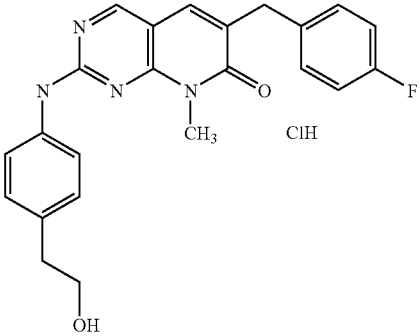 | 243.2-243.8 | | |
| I-158 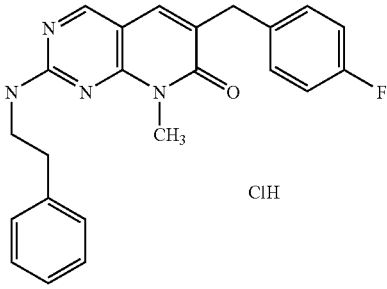 | 179.6-182.7 | | |
| I-159 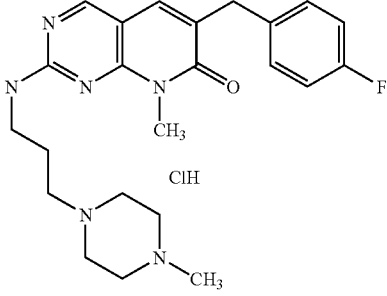 | 254.4-255.7 | | |
| I-160 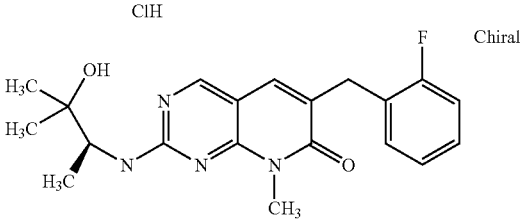 | 162.9-170.5 | M + 1 = 371 | 54 |
| I-161 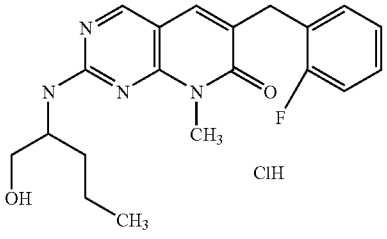 | 178.3-179.3 | | |

TABLE 1-continued
Representative compounds of Formula I.
| MOL STRUCTURE | M. Pt. | Mass Spec | Example |
|---|---|---|---|
| I-162 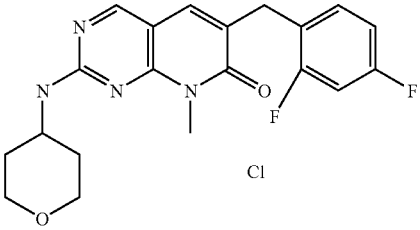 | 233.8-234.6 | | |
| I-163 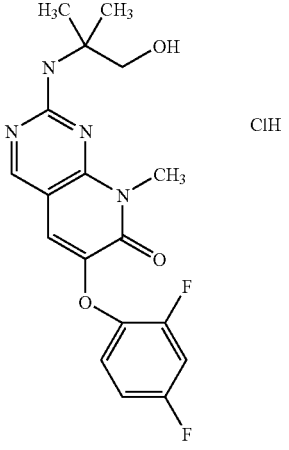 | 215.2-218.1 | | |
| I-164 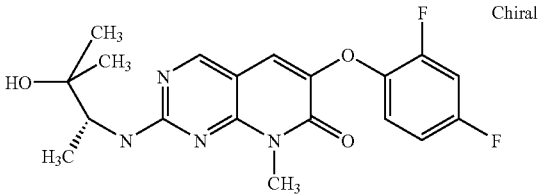 Chiral | 85.0-89.0 | | |
| I-165 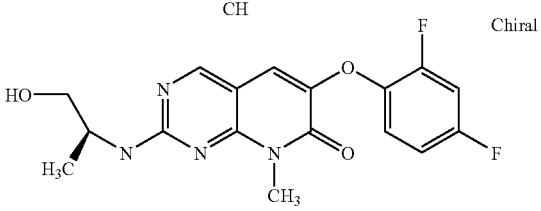 Chiral | 201.5-203.0 | | |
| I-166 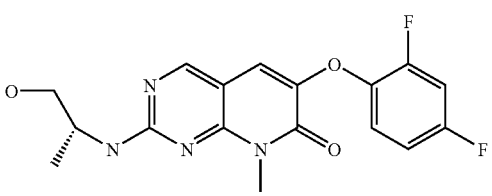 | | | |

TABLE 2

Additional representative compounds of Formula I

| | Structure | MS | MP | Example |
|---|---|---|---|---|
| 2-1 | 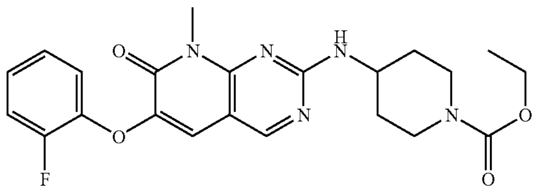 | | 171.2-183.5 | 108 |
| 2-2 | 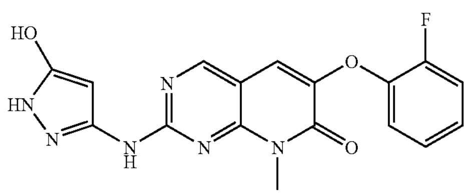 | M + 1 = 369 | | 99 |
| 2-3 | 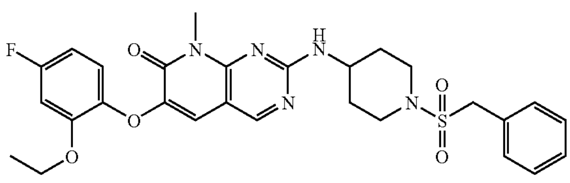 | | 134.6-187.3 | 110 |
| 2-4 | 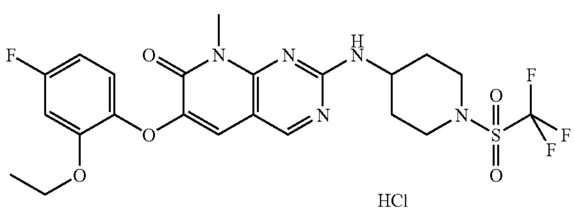 | | 155.0-185.8 | |
| 2-5 | 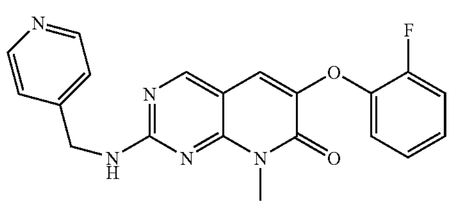 | M + 1 = 378 | | 100 |
| 2-6 | 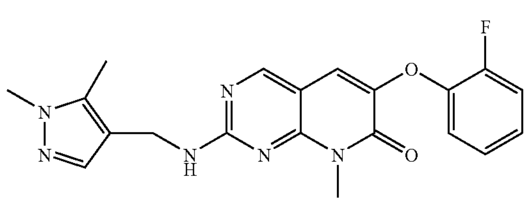 | M + 1 = 395 | | 101 |
| 2-7 | 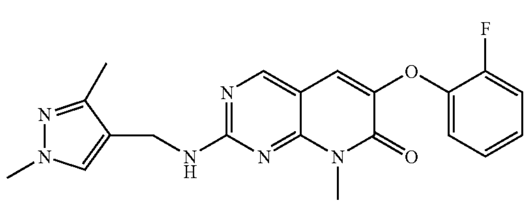 | M + 1 = 395 | | 102 |

TABLE 2-continued

Additional representative compounds of Formula I

| Structure | MS | MP | Example |
|---|---|---|---|
| 2-8 | M + 1 = 382 | | 103 |
| 2-9 | | 115.2-122.9 | 111 |
| 2-10 | | 136.0-140.0 | |
| 2-11 | | 194.0-197.0 | |
| 2-12 | | 150.5-153.0 | |
| 2-13 | | 130.0-135.0 | 109 |
| 2-14 | | 130.0-135.0 | |

TABLE 2-continued

Additional representative compounds of Formula I

| | Structure | MS | MP | Example |
|---|---|---|---|---|
| 2-15 | 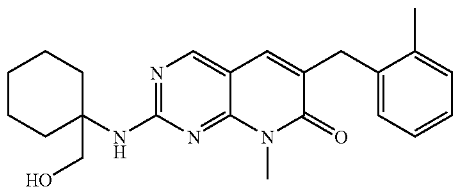 | M + 1 = 393 | | 104 |
| 2-16 | 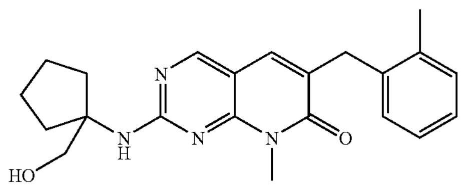 | M + 1 = 379 | | 105 |
| 2-17 | 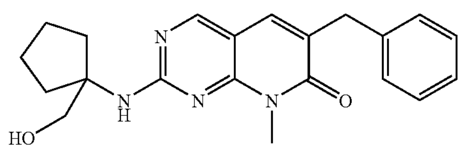 | M + 1 = 365 | | 106 |
| 2-18 | 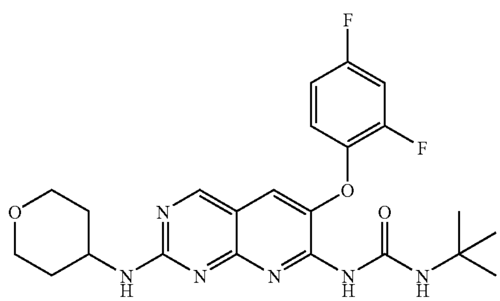 | (M + H) + 416 | 195-201 | 84 |
| 2-19 | HCl | 419.1MH+ | 200-202 | 87 |
| 2-20 | HCl | 393MH+ | 196-197.2 | 86 |
| 2-21 | 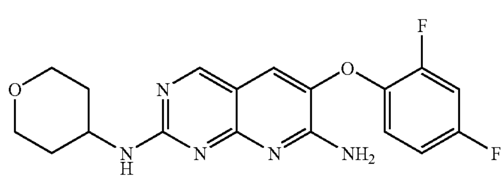 | (M + H) + 374 | | |

TABLE 2-continued
Additional representative compounds of Formula I
| Structure | MS | MP | Example |
|---|---|---|---|
| 2-22 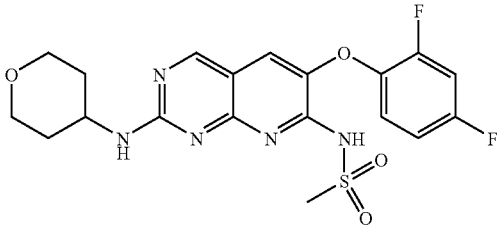 | (M + H) + 452 | 199-204 | |
| 2-23 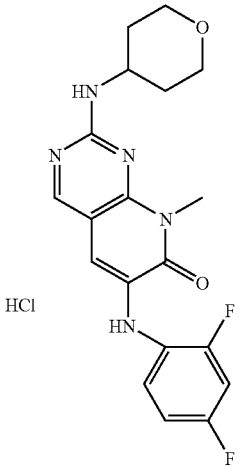 | (M + H) + 388 | 257.1-257.8 | |
| 2-24 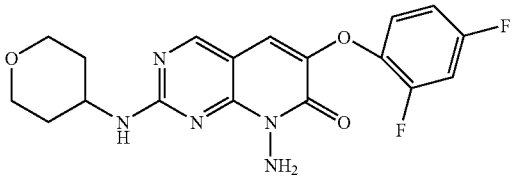 | (M + H) = 390 | | 89 |
| 2-25 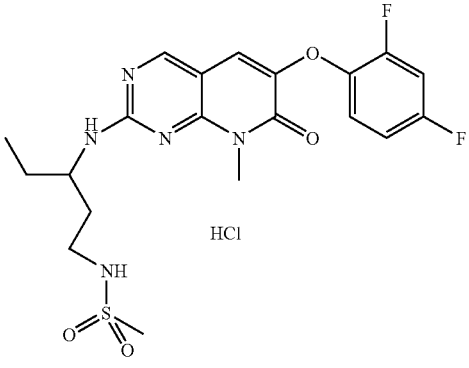 | 467 | 178.6-181.2 | 112 |

TABLE 2-continued
Additional representative compounds of Formula I
| Structure | MS | MP | Example |
|---|---|---|---|
| 2-26 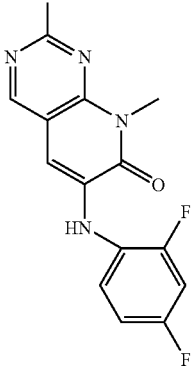 | (M + H) + 376 | 216-217.9 | 93 |
| 2-27 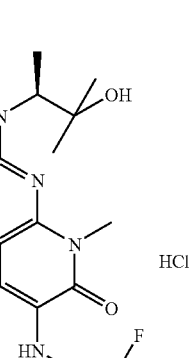 | (M + H) + 389 | 200.9-206.7 | |
| 2-28 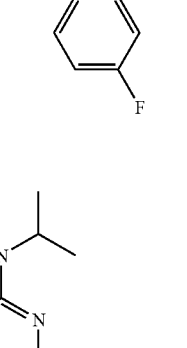 | (M + H) + 346 | 222-230.6 | |

TABLE 2-continued

Additional representative compounds of Formula I

| | Structure | MS | MP | Example |
|---|---|---|---|---|
| 2-29 | 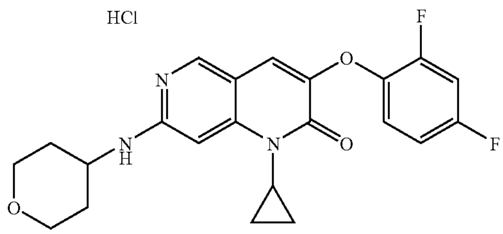 | 414.43MH | 239-244 | |
| 2-30 | 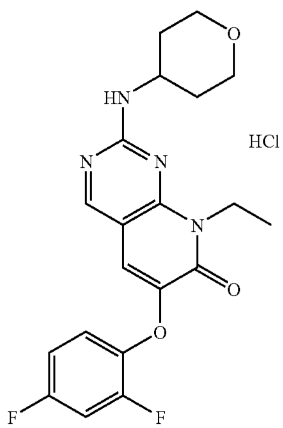 | (M + H) + 403 | 199.1-205.9 | 95 |
| 2-31 | 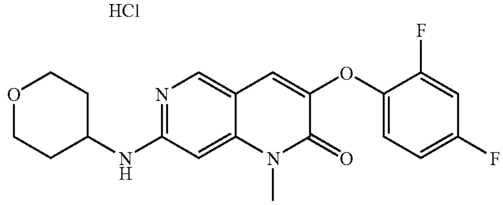 | 388MH | 237.5-239 | 88 |
| 2-32 | 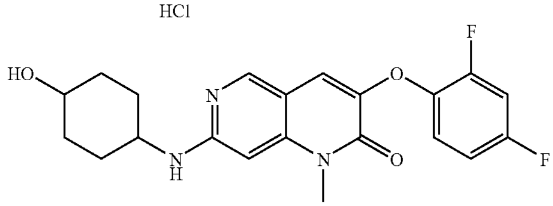 | 402MH | 151-164.8 | |
| 2-33 | 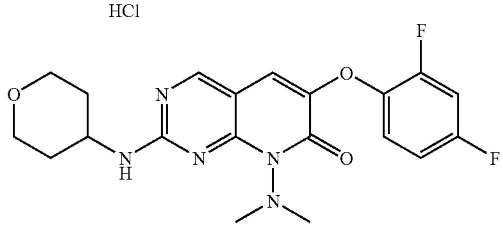 | (M + H) = 418 | 136.4-131.0 | 92 |

TABLE 2-continued

Additional representative compounds of Formula I

| | Structure | MS | MP | Example |
|---|---|---|---|---|
| 2-34 | 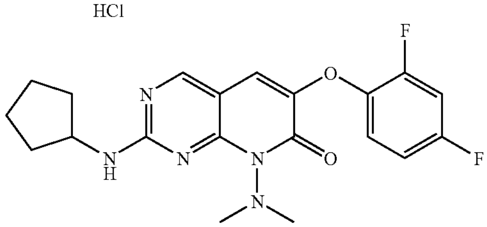 | (M + H) = 402 | 198.1-199.7 | |
| 2-35 | 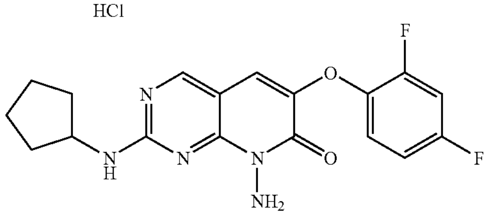 | (M + H) = 374 | 212.2-214.0 | |
| 2-36 | 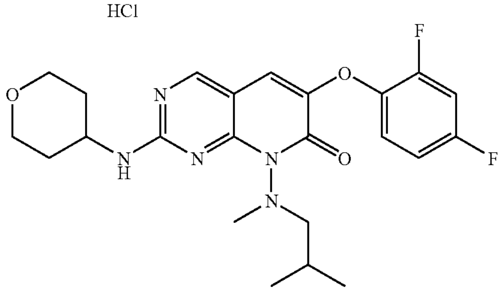 | (M + H) = 460 | | 91 |
| 2-37 | 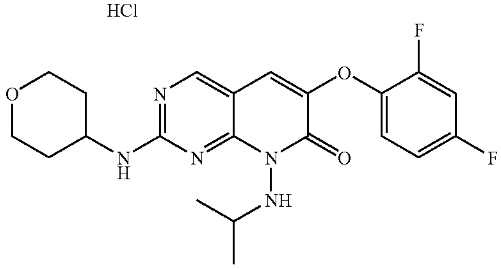 | (M + H) = 432 | | 90 |
| 2-38 | 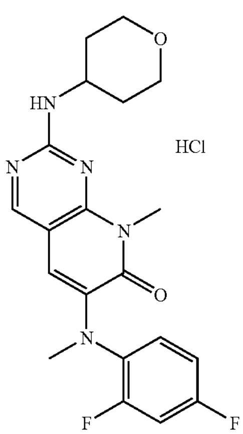 | (M + H) + 402 | 197-198.5 | 94 |

TABLE 2-continued

Additional representative compounds of Formula I

| Structure | MS | MP | Example |
|---|---|---|---|
| 2-39 | (M + H) + 405 | 154.5-156.0 | 97 |
| 2-40 | M + H = 405 | 226.4-227.7 | 98 |
| 2-41 | (M + H) + 386 | 210.3-219.8 | |
| 2-42 | M + 1 = 417 | 175.3°-176.9° | |

TABLE 2-continued

Additional representative compounds of Formula I

| Structure | MS | MP | Example |
|---|---|---|---|
| 2-43 | | | |
| 2-44 | | 239.5 to 249.7 | |
| 2-45 | (M + H) = 419 | 174.9-176.3 | 96 |
| 2-46 | | 148-152 | |

TABLE 2-continued

Additional representative compounds of Formula I

| Structure | MS | MP | Example |
|---|---|---|---|
| 2-47 | | 185.3-186.9 | 107 |
| 2-48 | (M + H) = 452 | 199-204 | 85 |
| 2-49 | | | |
| 2-50 | | | |
| 2-51 | | | |

TABLE 2-continued

Additional representative compounds of Formula I

| Structure | MS | MP | Example |
|---|---|---|---|
| 2-52 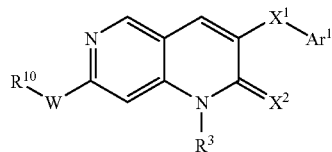 | | | |

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All publications, patents, and patent applications cited herein are hereby incorporated by reference in their entirety for all purposes.

What is claimed is:

1. A compound of Formula I

Formula I' wherein:

W is S, S(O), S(O)$_2$ or O;

$X^1$ is O, $NR^4$ (where $R^4$ is hydrogen or alkyl), S, or $CR^5R^6$ (where $R^5$ and $R^6$ are independently hydrogen or alkyl) or C=O;

$X^2$ is O or $NR^7$;

$Ar^1$ is aryl or heteroaryl;

$R^{10}$ is alkyl, aryl, aralkyl, cycloalkyl or cycloalkylalkyl, or $R^{10}W$ together form a leaving group or hydroxy;

$R^3$ is hydrogen, alkyl, cycloalkyl, cycloalkylalkyl, aryl, aralkyl, haloalkyl, heteroalkyl, cyanoalkyl, alkylene—C(O)—$R^{31}$ (where $R^{31}$ is hydrogen, alkyl, hydroxy, alkoxy, amino, monoalkylamino or dialkylamino), amino, monoalkylamino, dialkylamino or $NR^{32}$—$Y^3$—$R^{33}$ (where $Y^3$ is —C(O), —C(O)O—, —C(O)$NR^{34}$, S(O)$_2$, or S(O)$_2NR^{35}$; $R^{32}$, $R^{34}$ and $R^{35}$ are independently hydrogen or alkyl; and $R^{33}$ is hydrogen, alkyl, cycloalkyl, cycloalkylalkyl, heteroalkyl or optionally substituted phenyl) or acyl;

$R^7$ is hydrogen or alkyl.

* * * * *